US012710817B1

(12) United States Patent
Sugimura

(10) Patent No.: US 12,710,817 B1
(45) Date of Patent: Aug. 18, 2026

(54) SYSTEM

(71) Applicant: Softbank Group Corp., Tokyo (JP)

(72) Inventor: Sota Sugimura, Tokyo (JP)

(73) Assignee: SoftBank Group Corp., Tokyo (JP)

( * ) Notice: Subject to any disclaimer, the term of this patent is extended or adjusted under 35 U.S.C. 154(b) by 0 days.

(21) Appl. No.: 19/083,607

(22) Filed: Mar. 19, 2025

(51) Int. Cl.
*G06F 21/32* (2013.01)
*A61B 5/16* (2006.01)
*G06F 3/01* (2006.01)
*G16H 10/60* (2018.01)

(52) U.S. Cl.
CPC .............. *G06F 3/015* (2013.01); *A61B 5/165* (2013.01); *G06F 21/32* (2013.01); *G16H 10/60* (2018.01)

(58) Field of Classification Search
CPC ......... G06F 3/015; G06F 21/32; A61B 5/165; G16H 10/60
See application file for complete search history.

(56) References Cited

U.S. PATENT DOCUMENTS

2021/0141820 A1* 5/2021 Vora ...................... G06F 16/337
2023/0071994 A1* 3/2023 Day ....................... G16H 50/20
2023/0306726 A1* 9/2023 Jelveh .................... G06N 20/00
2024/0050003 A1* 2/2024 Day ..................... A61B 5/7267
2024/0416067 A1* 12/2024 Fox ....................... A61M 21/02

FOREIGN PATENT DOCUMENTS

JP 2022-180282 A 12/2022

OTHER PUBLICATIONS

Taichiro Sunaga, "Nenriki" to operate home appliances, etc., Nikkei Business, Nikkei Business publications, Jul. 25, 2016,No. 1851,pp. 66-68.
Emotion x Brain AI, [online], MACNICA, Inc., Jun. 30, 2022, Internet,<URL:https://www.macnica.co.jp/business/ai/manufacturers/innereye/seminar_brain_ai_sense_plus.html >, [Searched May 8, 2025].
New edition of detailed illustration, [online], Faculty of Science and Technology, Keio University, 2009.12, No. 1 , Internet, <URL:https://www.st.keio.ac.jp/education/kyurizukai/files/2018/2/13/kyurizukai01_j.pdf>, [retrieval date May 8, 2025].
May 20, 2025 (JP) Office Action Application No. 2024-16182.

* cited by examiner

*Primary Examiner* — Jeff Piziali
(74) *Attorney, Agent, or Firm* — Banner & Witcoff, Ltd.

(57) ABSTRACT

A system including means for acquiring EEG data of a user in real time, means for analyzing said acquired EEG data and extracting the intention of said user, means for analyzing the emotional state of said user, and means for executing output using a generative AI based on the extracted intention of said user and the prompt sentence according to the analyzed emotional state of said user.

4 Claims, 22 Drawing Sheets

3/22

14/22

Brainwave Data Processing and Metaverse Integration

SYSTEM

TECHNICAL FIELD

The technology of this disclosure relates to a system.

BACKGROUND TECHNOLOGY

JP 2022-180282 discloses a persona chatbot control method, carried out by at least one processor, comprising the steps of: receiving a user utterance; adding said user utterance to a prompt containing a description of the chatbot character and associated instructions The method is disclosed, including the steps of adding the prompt to a prompt, encoding said prompt, and inputting said encoded prompt into a language model to generate a chatbot utterance in response to said user utterance.

The conventional brain-machine interface (BMI) has been limited in its widespread use by the dilemma between accuracy and invasiveness. There were also limitations in the provision of new services utilizing BMI.

SUMMARY

This invention provides a means to generate minimally invasive and highly accurate BMI by combining EEG and generative AI, and a means to provide a platform for the dissemination of this BMI in society. Furthermore, the platform will also provide a means to provide new services such as intuitive communication services using brain activity, metaverse interface, health management services, and biometric authentication services. This will enable the diffusion of BMI and the provision of new services.

BRIEF DESCRIPTION OF THE DRAWINGS

Exemplary embodiments of the present disclosure will be described in detail based on the following figures.

DETAILED DESCRIPTION

The following is an example of an exemplary embodiment of a system for the technology of the present disclosure according to the accompanying drawings.

First, let us explain the wording used in the following description.

In the following exemplary embodiments, a signed processor (hereinafter simply referred to as "processor") may be one arithmetic device or a combination of multiple arithmetic devices. The processor may be one type of computing device or a combination of multiple types of computing devices. An example of an arithmetic device is a CPU (Central Processing Unit), GPU (Graphics Processing Unit), GPGPU (General-Purpose computing on Graphics Processing Units), APU (Accelerated Processing Unit), or TPU (Tensor PROCESSING UNIT (registered trademark)), etc.

In the following exemplary embodiment, signed RAM (Random Access Memory) is a memory in which information is temporarily stored and is used by the processor as work memory.

In the following exemplary embodiments, the signed storage is one or more non-volatile storage devices that store various programs and various parameters, etc. Examples of non-volatile storage devices include flash memory (SSD (Solid State Drive)), magnetic disks (e.g., hard disks), or magnetic tape.

In the following exemplary embodiment, a signed communication I/F (Interface) is an interface that includes a communication processor and antenna, etc. The communication I/F is responsible for communication between multiple computers. Examples of communication standards applicable to the communication I/F include wireless communication standards including 5G (5th Generation Mobile Communication System), Wi-Fi (registered trademark), or Bluetooth (registered trademark).

In the following exemplary embodiments, "A and/or B" is synonymous with "at least one of A and B". In other words, "A and/or B" means that it may be only A, only B, or a combination of A and B. The same concept as "A and/or B" also applies when three or more matters are expressed in this document by linking them together with "and/or".

First Exemplary Embodiment

Figure 1:
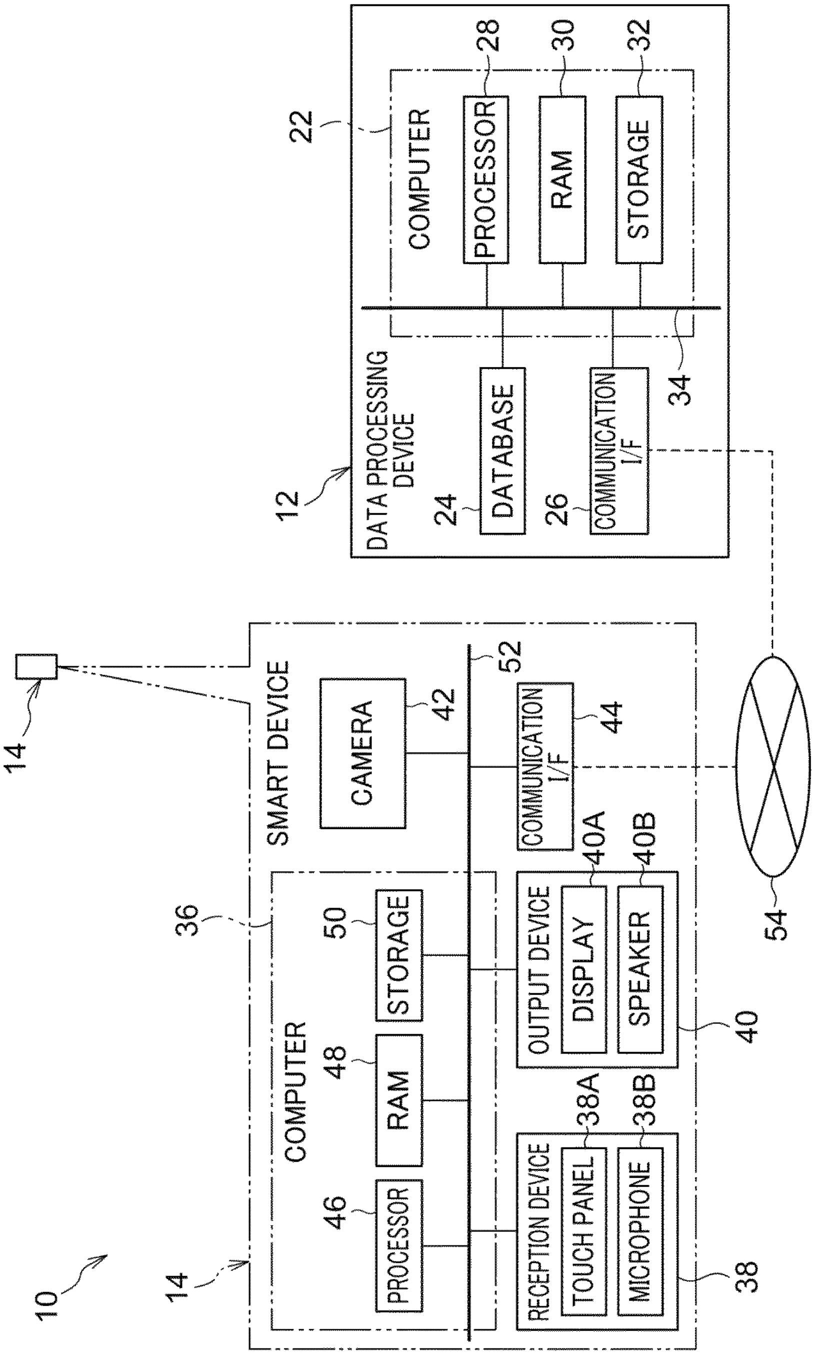
FIG. 1 is a conceptual diagram showing an example of implement of a data processing system.

FIG. 1 shows an example of implement of a data processing system 10.

As shown in FIG. 1, data processing system 10 has data processing device 12 and smart device 14. An example of the data processing device 12 is a server.

The data processing device 12 has a computer 22, a database 24, and a communication I/F 26. Computer 22 is an example of a "computer" in the context of the present disclosure. Computer 22 has a processor 28, RAM 30, and storage 32. The processor 28, RAM 30, and storage 32 are connected to a bus 34. The database 24 and the communication I/F 26 are also connected to the bus 34. The communication I/F 26 is connected to a network 54. An example of a network 54 is a Wide Area Network (WAN) and/or a Local Area Network (LAN).

Smart device 14 has a computer 36, reception device 38, output device 40, camera 42, and communication I/F 44. The computer 36 has a processor 46, RAM 48, and storage 50. The processor 46, RAM 48, and storage 50 are connected to a bus 52. The reception device 38, output device 40, and camera 42 are also connected to the bus 52.

The reception device 38 is equipped with a touch panel 38A and a microphone 38B, etc., to accept user input. The touch panel 38A detects the touch of an indicating body (e.g., a pen or a finger, etc.), thereby accepting user input by the touch of the indicating body. The microphone 38B detects the user's voice, thereby accepting user input by voice. The control unit 46A transmits data indicating the user input accepted by the touch panel 38A and microphone 38B to the data processing device 12. In the data processing device 12, the specific processing unit 290 acquires the data indicating the user input.

The output device 40 is equipped with a display 40A and a speaker 40B, etc., and presents data to the user 20 by outputting the data in a form of representation (e.g., audio and/or text) that can be perceived by the user 20. Display 40A displays text, images, and other visible information in accordance with instructions from processor 46. Speaker 40B outputs audio in accordance with instructions from processor 46. Camera 42 is a compact digital camera equipped with an optical system, such as a lens, aperture, and shutter, and an image sensor, such as a CMOS (Complementary Metal-Oxide-Semiconductor) image sensor or CCD (Charge Coupled Device) image sensor. The camera is a compact digital camera.

The communication I/F 44 is connected to the network 54. The communication I/F 44 and 26 are responsible for transferring and receiving various types of information between the processor 46 and the processor 28 via the network 54.

Figure 2:
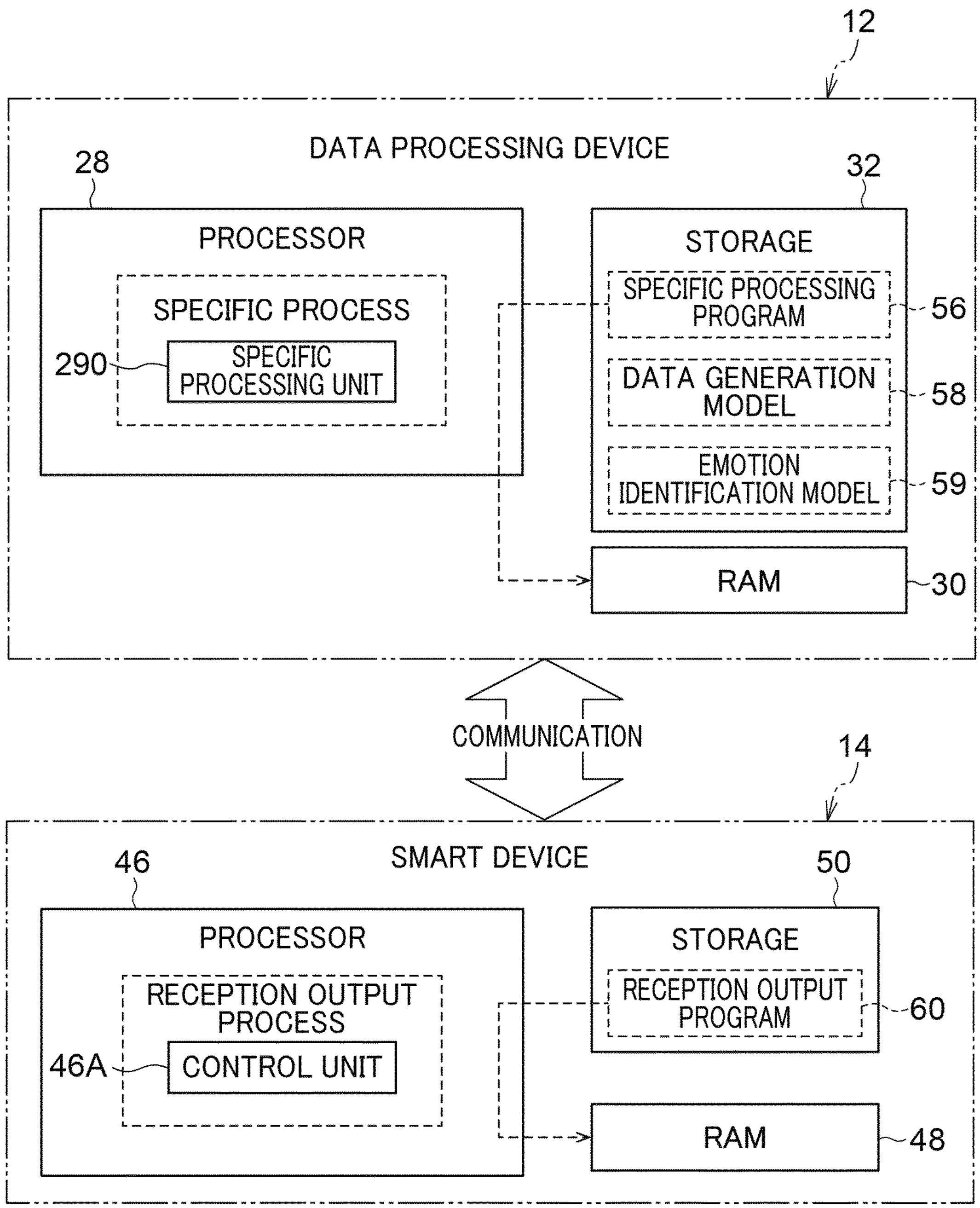
FIG. 2 is a conceptual diagram showing an example of the key functions of the data processing device and smart device of the first exemplary embodiment.

FIG. 2 shows an example of the key functions of data processing device 12 and smart device 14.

As shown in FIG. 2, specific processing is performed by processor 28 in data processing device 12. The specific processing program 56 is stored in the storage 32. The specific processing program 56 is an example of a "program" for the technology of the present disclosure. The processor 28 reads the specific processing program 56 from the storage 32 and executes the read specific processing program 56 on the RAM 30. The specific processing is realized by the processor 28 operating as the specific processing unit 290 according to the specific processing program 56 executing on the RAM 30.

The data generation model 58 and emotion identification model 59 are stored in storage 32. The data generation model 58 and emotion identification model 59 are used by the specific processing unit 290.

In smart device 14, the reception output process is performed by processor 46. The reception output program 60 is stored in storage 50. The reception output program 60 is used by the data processing system 10 in conjunction with the specific processing program 56. Processor 46 reads reception output program 60 from storage 50 and executes the read reception output program 60 on RAM 48. The reception output process is realized by the processor 46 operating as the control unit 46A according to the reception output program 60 executing on RAM 48.

Next, the specific processing by the specific processing unit 290 of the data processing device 12 is described.

Example of Implement 1

One exemplary embodiment of this invention is a system that combines brain waves with a generative AI to generate a brain-machine interface (BMI). This system uses the user's brain waves as a real-time The results are analyzed by the brainwave data and input to the generative AI. Based on this brain wave data, the generative AI understands the user's intention and generates output based on it. For example, when a user wants a cup of coffee, the brain waves are analyzed, and the generative AI understands the user's intention and can take action such as "making coffee.

Example of Implement 2

Another exemplary embodiment of this invention is a platform to promote BMI in society. This platform has a function that allows users to manage their own EEG data and share it with third parties as needed. For example, users can manage their own EEG data on the platform and share it with medical and research institutions to obtain more accurate medical services and research results.

Example of Implement 3

A further exemplary embodiment of the invention are the new services offered through the platform. These services include intuitive communication services using brain activity, metaverse interface, health management services, and biometric authentication services. For example, intuitive communication services analyze a user's brain waves to understand their emotions and intentions, and communicate based on this information. Also, in metaverse interfaces, the user's brain waves are analyzed to control their behavior in VR and AR worlds. The health management service analyzes the user's brain waves to understand their stress level, sleep state, etc., and proposes health management based on this information. The biometric authentication service analyzes the user's brain wave patterns to perform personal authentication.

The following is a description of the process flow for each example of implement.

Example of Implement 1

Step 1: The user has a specific thought or intention.

Step 2: The system captures and analyzes the user's brain waves in real time.

Step 3: Input the analysis results to the generative AI.

Step 4: The generative AI understands the user's intentions based on the brain wave data and generates output based on it. For example, it will perform an action such as "make coffee.

Example of Implement 2

Step 1: Users access the platform and upload their own EEG data.

Step 2: The platform manages the user's EEG data and shares it with third parties as needed. For example, sharing with medical and research institutions will enable more accurate medical services and research results.

Example of Implement 3

Step 1: The user selects a specific service through the platform. For example, intuitive communication services, metaverse interface, health care services, biometric services, etc.

Step 2: The selected service analyzes the user's brain waves and provides services based on them. For example, an intuitive communication service analyzes the user's brain waves to understand his/her feelings and intentions and communicates based on them.

Example 1

The following is an example of exemplary embodiment of implement. In the following description, data processing device 12 is referred to as the "server" and smart device 14 is referred to as the "terminal.

Conventional brain-machine interfaces (BMIs) are inaccurate in analyzing the user's brain waves, making it difficult to understand the user's intentions in real time. In addition, these systems were highly invasive and burdensome to users. Furthermore, the management and sharing of EEG data is not easy, which has hindered its widespread use in society.

The specific processing by the specific processing unit 290 of the data processing device 12 in Example 1 is realized by the following means.

In this invention, the server provides a means for collecting brain waves of a user in real time, a means for analyzing the collected brain wave data, a means for inputting the analyzed brain wave data into a generative AI model, a means for the generative AI model to understand the intent of the user and generate outputs based thereon, a means for providing feedback of the generated means to provide a platform for the dissemination of the brain-machine interface (BMI) to society, and to provide intuitive communication services, virtual space services, biometric authentication services, and other services using brain activity that are provided through the platform. interface, health management services, and biometric authentication services provided through the platform. This enables highly accurate and minimally invasive analysis of users' brain waves and real-time understanding of their intentions. It will also facilitate the management and sharing of EEG data and promote its widespread use in society.

The term "user" refers to the individual who uses the brain-machine interface (BMI).

Brain waves" refer to the electrical signals generated by the user's brain.

Real-time" means that data is processed and analyzed as soon as it is generated.

The term "means of collection" refers to devices and methods used to detect and acquire data on the user's brain waves.

Means of analysis" refers to methods and devices used to process the collected EEG data and infer user intent.

The term "generative AI model" refers to an artificial intelligence model that understands the user's intent based on the input data and generates output based on that intent.

The term "means of input" refers to the methods and devices used to provide the analyzed EEG data to the generative AI model.

Output" refers to the results and suggestions generated by the generative AI model based on its understanding of the user's intentions.

The term "means of feedback" refers to the methods and devices used to communicate the generated output to the user.

The term "platform" refers to the systems and services that serve as the foundation for the diffusion of brain-machine interfaces (BMIs) in society.

The term "communication service" refers to a service that uses brain waves to allow users to intuitively exchange information with others.

The term "virtual space interface" refers to an interface that uses brain waves to allow users to operate and move within a virtual space.

The term "health management service" refers to a service that uses users' brain wave data to monitor and manage their health.

The term "biometric service" refers to a service that uses a user's brain wave data to authenticate an individual.

This invention is a brain-machine interface (BMI) system that analyzes a user's brain waves in real time and inputs the results into a generative AI model to understand the user's intentions and generate output based on them. The system is implemented using the following hardware and software Hardware and Software Configuration EEG Sensor The user wears an EEG sensor on the head. This sensor detects the user's brain waves in real time and collects the data as electrical signals.

Server

The server receives EEG data transmitted from the EEG sensor. The received data is sent to the terminal for analysis.

Terminal

The terminal analyzes the EEG data sent from the server. An EEG analysis library using Python (registered trademark) is used for the analysis. The terminal sends the analysis results to the server.

Generative AI Model

The server inputs the analyzed EEG data into a generative AI model (e.g., GPT-4 (registered trademark) of OpenAI (registered trademark)). The generative AI model understands the user's intention based on the input data and generates output based on it.

Feedback

The generated output is sent to the terminal through the server, which feeds it back to the user. The user can then take the suggested action.

Concrete Example

For example, consider the case where a user wants to listen to music. An EEG sensor collects the user's EEG data, and the terminal analyzes the data. If the analysis results indicate the intention to "listen to music," the following prompt statement is entered into the generative AI model:

The user's EEG data has detected the intention to listen to music. Please suggest actions to play appropriate music.

The generative AI model generates an output "play music" based on this prompt sentence and feeds it back to the user through the terminal. The user can then play the music according to the suggested action.

In this way, the system can analyze the user's EEG with high accuracy and minimally invasive, and understand their intentions in real time. In addition, the system will facilitate the management and sharing of EEG data and promote its widespread use in society.

Figure 11:
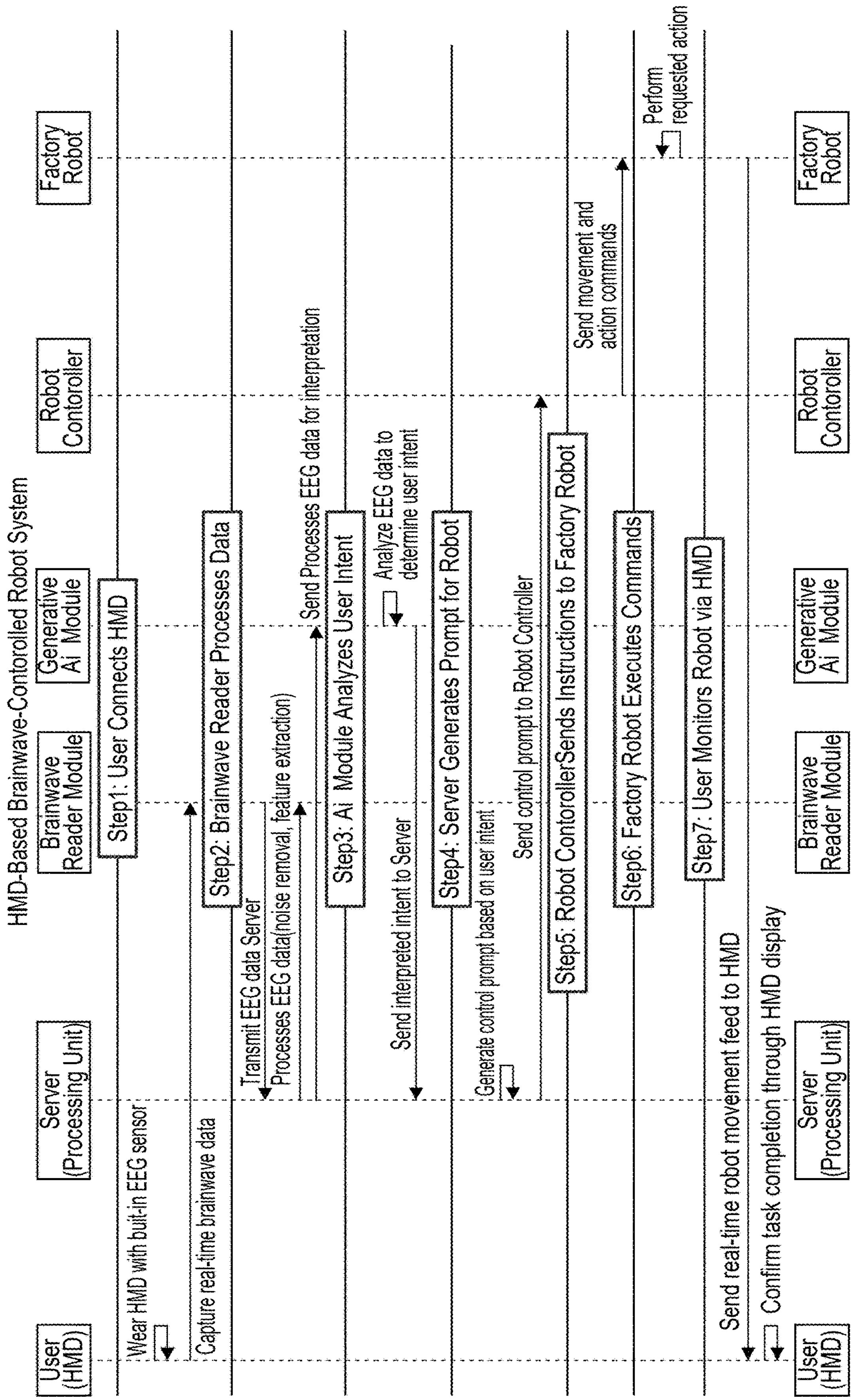
FIG. 11 is a sequence diagram showing the flow of data processing system processing in Example 1 of implement example.

The flow of the identification process in Example 1 is described in FIG. 11.

Step 1:

The user wears an EEG sensor on his/her head. The EEG sensor detects the user's brain waves in real time and collects the data as electrical signals. The collected EEG data is transmitted to a server.

Input: User's brain waves

Output: EEG data (electrical signals)

Step 2:

The server receives the EEG data transmitted from the EEG sensor. The received EEG data is sent to the terminal for analysis.

Input: EEG data (electrical signals)

Output: EEG data (transfer from server to terminal)

Step 3:

The terminal receives the EEG data sent from the server. The terminal analyzes the EEG data using a Python-based EEG analysis library. In the process of analysis, specific brain wave patterns are detected and the intention of the user is inferred. The analysis results are sent to the server.

Input: EEG data (transferred from server)

Output: Analysis results (user intent)

Step 4:

The server receives the analysis results sent from the terminal. The server generates prompt sentences based on the analysis results and inputs them into the generative AI model.

Input: Analysis results (user intent)

Output: Prompt statement

Step 5:

The generative AI model receives prompt sentences sent from the server. The generative AI model understands the user's intention based on the prompt sentences and generates output based on it. The generated output is sent to the server.

Input: Prompt statement

Output: Output

Step 6:

The server receives the output sent from the generative AI model. The server sends the output to the terminal.

Input: Output (transfer from generative AI model)

Output: Output (transfer from server to terminal)

Step 7:

The terminal receives the output sent from the server. The terminal feeds back the output to the user. The user can perform the suggested action.

Input: Output (transfer from server)

Output: Feedback to user

Example of Application 1

Next, example of application 1 of example of implement 1 will be described. In the following description, data processing device 12 will be referred to as the "server" and smart device 14 will be referred to as the "terminal.

Conventional control methods for factory robots are mainly manual operation or programmed control, which is difficult to operate intuitively. In addition, more intuitive and quicker control methods are required to improve work efficiency. Furthermore, brain-machine interface (BMI) using brain waves has been applied in the medical and entertainment fields, but has not yet been fully utilized in factory automation and robot control. To solve these problems, a system that can intuitively control factory robots using brain waves is needed The specific processing by the specific processing unit 290 of the data processing device 12 in example of application 1 is realized by the following means.

In this invention, the server provides means to generate a minimally invasive and highly accurate brain-machine interface (BMI) that combines brain waves and generative AI, means to provide a platform for disseminating the BMI in society, means to provide intuitive brain activity-based means to provide communication services, metaverse interface, health management services, and biometric authentication services using brain activity, means for factory workers to wear head-mounted displays and control factory robots using brain waves, and means for analyzing users' brain wave data in real time and inputting the results into a generative system AI, including means to understand the user's intentions and generate output based on them by inputting the results into the AI, and means to control the factory robot based on the user's intentions. This allows factory workers to intuitively control factory robots using brain waves.

Brain waves" are electrical signals generated by neural activity in the brain.

Generative AI" is a type of artificial intelligence that generates new data and outputs based on input data.

A "brain-machine interface" (BMI) is an interface that uses brain waves to control a machine or computer.

The term "minimally invasive" refers to less burden or damage to the body.

The term "high precision" refers to extreme accuracy.

A "platform" is the underlying system or environment that provides a specific service or function.

An "intuitive communication service" is one that allows users to operate and communicate intuitively.

A "metaverse interface" is an interface for performing activities and operations in a virtual space.

A "health management service" is a service designed to manage and improve a user's health status.

Biometric services" are services that authenticate individuals using biometric information such as fingerprints and facial recognition.

A "factory worker" is a worker engaged in production activities in a factory.

A "head-mounted display" is a display device worn on the head.

A "factory robot" is a robot used to automate production tasks in a factory.

Real-time" means immediate processing and reaction without delay.

User intent" is the intention or purpose of what the user wants to do or think.

Output" is the result or behavior output from a system or device.

The following system configuration and program are required to implement this invention.

System Configuration

1. Hardware

Head-mounted display (HMD): Built-in EEG sensor to collect EEG data in real time.

Factory robots: robots that are designed to perform actions based on the user's intentions.

Server: analyzes EEG data and executes generative AI models.

2. Software

BrainwaveReader: module for collecting EEG data.

GenerativeAIModel: A generative AI model that analyzes brain wave data to understand user intent.

RobotController: Module for controlling robots based on user intent.

Explanation of Program Processing

The server first collects brain wave data from the head-mounted display (HMD); the BrainwaveReader module analyzes this data in real time and inputs it to a generative AI model (GenerativeAIModel). The generative AI model interprets the user's intentions based on the brainwave data and passes the intentions to the RobotController, which controls the factory robot based on the interpreted intentions and performs the corresponding actions.

Concrete Example

For example, if a factory worker thinks "assemble parts," the following prompt sentence is entered into the generative AI model.

Example of a Prompt Statement:

Based on the analysis of the user's brain wave data, the user believes that the user is "assembling parts". Based on this intention, instruct the robot to perform an action to assemble the parts.

Based on this prompt sentence, the generative AI model interprets the user's intention and instructs the RobotController to perform the "assemble parts" operation. As a result, the factory robot automatically starts assembling the parts.

This system allows factory workers to intuitively control factory robots using brain waves, greatly improving work efficiency.

Figure 12:
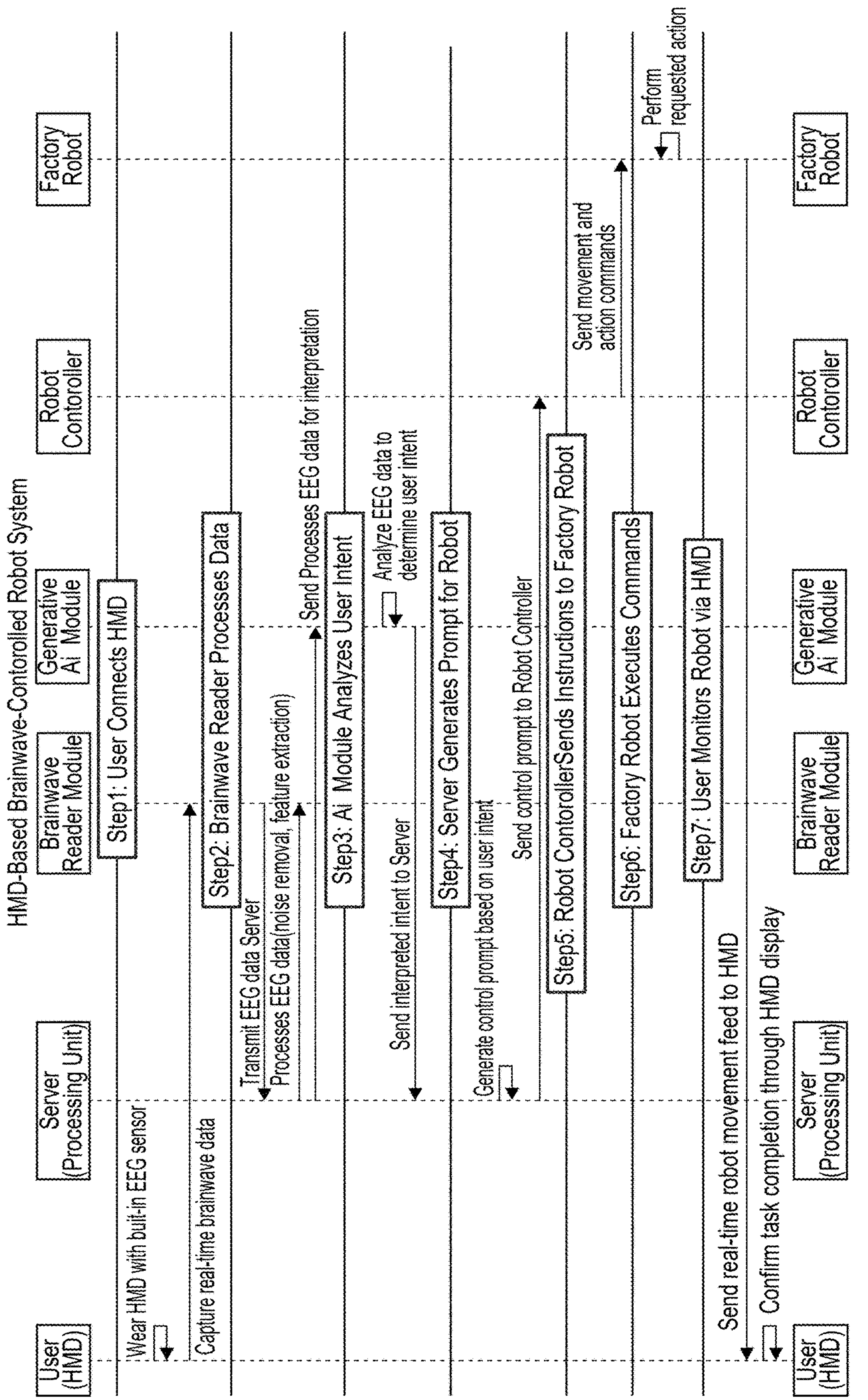
FIG. 12 is a sequence diagram showing the flow of data processing system processing in example of application 1 of example of implement.

The flow of the identification process in Example of Application 1 is described in FIG. 12.

Step 1:

A user wears a head-mounted display (HMD); the HMD has a built-in EEG sensor that collects the user's EEG data in real time. The input is the user's EEG and the output is the collected EEG data.

Step 2:

The server receives the EEG data sent from the HMD using the BrainwaveReader module; BrainwaveReader analyzes this data in real time, performing noise removal and feature extraction. The input is the EEG data from the HMD and the output is the analyzed EEG data.

Step 3:

The server inputs the analyzed EEG data to GenerativeAIModel, which is a generative AI model for interpreting user intentions based on the EEG data. The input is the analyzed EEG data and the output is the data indicating the user's intention.

Step 4:

Based on the server's interpretation of the user's intent, a prompt statement is generated. This prompt sentence is a specific description of the user's intent. The input is the data indicating the user's intent, and the output is the prompt sentence.

Step 5:

The server passes the generated prompt sentence to the RobotController, which generates specific instructions for the factory robot based on this prompt sentence. The input is the prompt sentence and the output is the instructions to the robot.

Step 6:

RobotController sends instructions to the factory robot. The factory robot executes the corresponding action based on these instructions. The input is the instruction to the robot and the output is the robot's action.

Step 7:

The user checks the operation of the factory robot through the HMD; the HMD displays the robot's operating status in real time to confirm that the robot is operating as intended by the user. The input is the operating status of the robot and the output is the image displayed on the HMD.

Example 2

Next, example 2 of exemplary embodiment of implement will be described. In the following description, data processing device 12 is referred to as the "server" and smart device 14 is referred to as the "terminal.

Conventional brain-machine interfaces (BMIs) lack a platform for effectively managing users' EEG data and securely sharing it with third parties. They also lacked real-time analysis of EEG data and linkage with generative AI, making it difficult to accurately understand user intentions and generate appropriate outputs. Furthermore, encryption of EEG data and management of access privileges were insufficient, and data security was not ensured.

The specific processing by the specific processing unit 290 of the data processing device 12 in Example 2 is realized by the following means. In this invention, the server is equipped with the following means: a means by which the user uploads brain wave data acquired by using a dedicated measurement device from the terminal to the server; a means by which the server stores the received brain wave data in a database; a means by which the user accesses the platform and manages the data; a means by which the user encrypts the data and grants access to a third party and means to configure the data to be shared, and the server encrypts the data and grants access to the third party. This allows users to effectively manage their own EEG data and securely share it with third parties. In addition, in conjunction with the generative AI, the system can accurately understand the user's intentions and generate appropriate output.

A "brain-machine interface (BMI)" is an interface that uses brain waves to communicate a user's intentions to a machine.

Generative AI" is artificial intelligence that analyzes a user's brain wave data and generates appropriate output based on the results.

A "platform" is a system that allows users to manage their EEG data and share it with third parties as needed.

EEG data" is data that measures the user's brain activity and is obtained using an EEG measurement device.

A "measurement device" is a device used to measure a user's brain waves in real time.

A "terminal" is a computer, smart device, or other device used by a user to upload EEG data acquired using the measurement device to a server.

A "server" is a computer system used to store and manage EEG data received from users.

A "database" is a system for efficiently storing and accessing EEG data received by the server.

Encryption" is a technique for converting data into a format that cannot be deciphered by a third party.

Access privileges" is the ability to set the rights of a specific user or third party to access data.

Output" is the output generated by the generative AI based on the results of analyzing the user's EEG data.

Exemplary Embodiment of the Invention

This invention is a system that provides a platform for users to manage EEG data acquired using specialized measurement devices and share it with third parties as needed. Specific exemplary embodiments of this system are described below.

Hardware and Software Configuration

The user uses a dedicated EEG measurement device to obtain EEG data. This measurement device measures the user's brain waves in real time and transmits the data to a terminal (PC or smartphone).

The terminal uploads the acquired EEG data to the server through a dedicated application. The application converts the data into the appropriate format (e.g., CSV or JSON) and sends it securely to the server using the HTTPS protocol.

The server stores the received EEG data in a database (e.g., MySQL (registered trademark) or PostgreSQL). The database organizes the data by user and indexes it for efficient access.

Users access the platform through a web browser or mobile application. The platform authenticates the user (e.g., OAuth or JWT) and provides an interface that allows users to view, edit, and delete their own EEG data.

Data Sharing and Encryption

If the user wants to share data with a third party, he/she selects the third party (e.g., a medical or research institution) with whom he/she wants to share the data on the platform. The user sets the scope and duration of the data to be shared and submits a sharing request.

The server receives the user's sharing request and encrypts the data to be shared. Encryption uses a strong encryption algorithm such as AES-256. The server grants access privileges to designated third parties and creates a secure access link to the shared data.

Concrete Example

For example, when a user shares his/her EEG data with a medical institution, the following steps are taken 1. the user wears the EEG sensor and launches the dedicated application.
2. the terminal converts the acquired EEG data into CSV format and uploads it to the server using HTTPS.

The server stores the received data in a MySQL database.

4. the user logs into the platform with a web browser and checks his/her EEG data.

The user selects a medical institution and sets the scope and duration of the data to be shared.

6. the server encrypts the data with AES-256 and grants access privileges to the medical institution.

Example of Prompt Sentences to be Entered into a Generative AI Model:

Describe the steps a user would take to use an EEG sensor to obtain EEG data and share it with their healthcare provider."

By inputting this prompt statement into the data generation AI model, the specific procedure for the user to obtain EEG data and share it with the healthcare provider is output.

Figure 13:
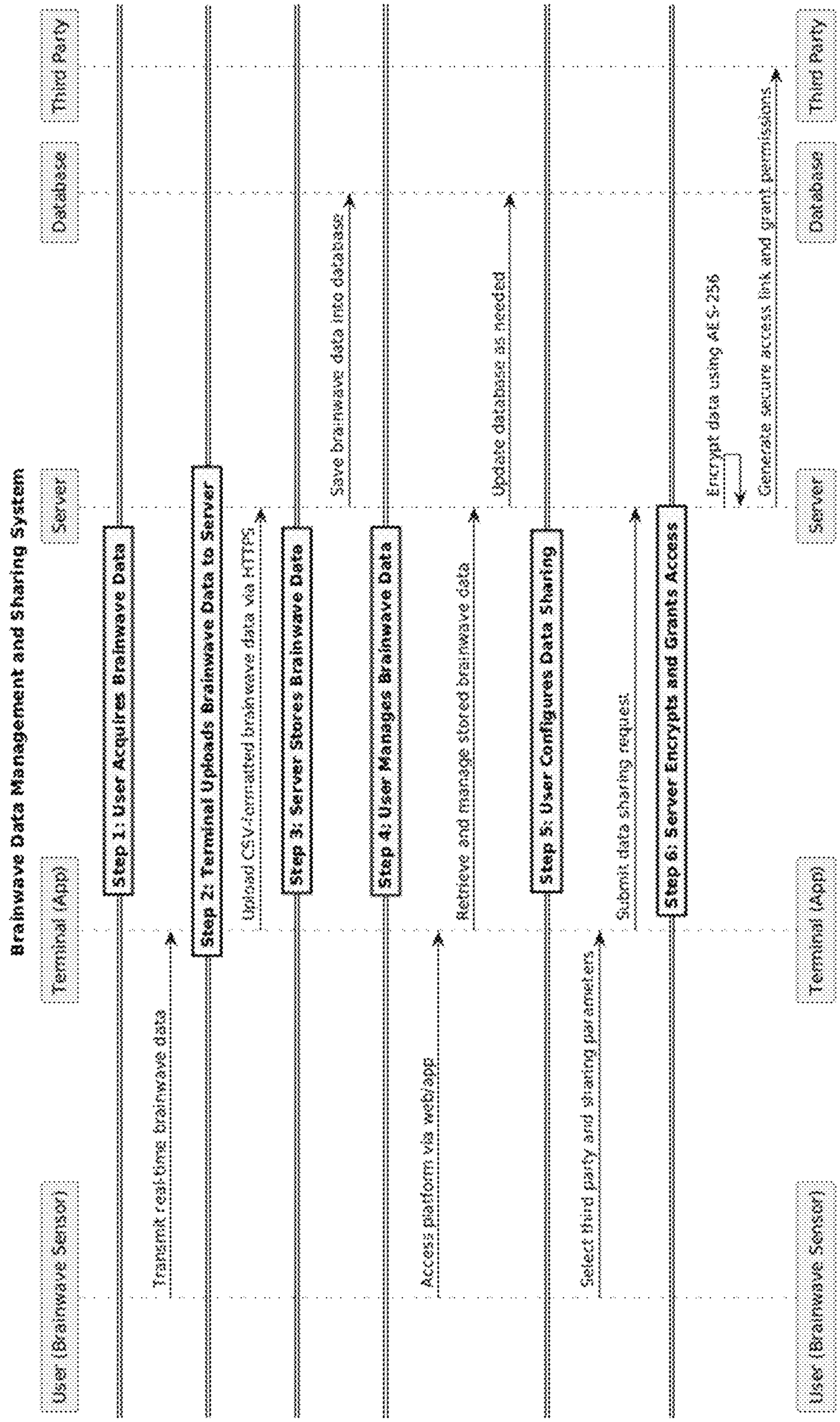
FIG. 13 is a sequence diagram showing the flow of data processing system processing in Example 2 of implement example.

The flow of the identification process in Example 2 is described in FIG. 13.

Step 1:

The user uses a dedicated EEG measurement device to acquire EEG data. The user wears the measurement device and starts the dedicated application. The measurement device measures the user's brain waves in real time and transmits the data to the terminal. The input is the user's EEG and the output is the EEG data transmitted to the terminal.

Step 2:

The terminal uploads the EEG data to the server. The terminal converts the acquired EEG data into CSV format through a dedicated application and sends it to the server using the HTTPS protocol. The input is the EEG data sent from the measurement device and the output is the EEG data in CSV format uploaded to the server.

Step 3:

The server stores the received EEG data in a database. The server imports the received EEG data in CSV format into the database and organizes the data for each user. The input is the EEG data in CSV format sent from the terminal, and the output is the EEG data stored in the database.

Step 4:

Users access the platform and manage their data. The user logs into the platform through a web browser or mobile application to view, edit, and delete his/her EEG data. The input is the user's login information and the EEG data stored in the database, and the output is the EEG data that the user has viewed, edited, or deleted.

Step 5:

The user sets up the sharing of data with third parties. The user selects the third party they wish to share with on the platform and sets the scope and duration of the data to be shared. The input is the user's sharing configuration information and the output is the sharing request sent to the server.

Step 6:

Server encrypts data and grants access to third parties. The server receives the user's share request and encrypts the data to be shared with AES-256. The server grants access privileges to the designated third party and generates a secure access link to the shared data. The input is the user's sharing request and the EEG data stored in the database, and the output is the encrypted data and the access rights granted to the third party.

Example of Application 2

Next, example of application 2 of example of implement 2 will be described. In the following description, data processing device 12 is referred to as the "server" and smart device 14 is referred to as the "terminal.

Conventional brain-machine interfaces (BMIs) lack a platform for effectively managing users' EEG data and sharing it with third parties as needed. In addition, they lacked sufficient management of EEG data security and sharing history, which prevented smooth data sharing with medical and research institutions. Furthermore, the lack of a function to collect users' EEG data in real time, encrypt it, and upload it to the cloud did not ensure the security and convenience of the data The specific processing by the specific processing unit 290 of the data processing device 12 in example of application 2 is realized by the following means. In this invention, the server provides means to generate a minimally invasive and highly accurate brain-machine interface (BMI) that combines brain waves and generative AI, means to provide a platform to disseminate the BMI to society, means to provide intuitive communication services, metaverse interface, health management services, and biometric authentication services provided through the platform; means for collecting users' brain wave data in real time, encrypting and uploading the data to the cloud; and means for sharing the data with medical institutions and research organizations and managing data sharing history. The means to share the data with medical and research institutions, and to manage the data sharing history. This allows users' EEG data to be managed securely and efficiently and shared with third parties as needed.

Brain waves" are electrical signals generated by neural activity in the brain.

Generative AI" is a type of artificial intelligence, a system that has the ability to generate new data and information based on input data.

Minimally invasive" means less stressful or damaging to the body.

High precision" means extremely accurate.

A "brain-machine interface" (BMI) is an interface that uses brain waves to operate a machine or computer.

A "platform" is the underlying system or environment that provides a specific function or service.

An "intuitive communication service" is one that allows users to interact with information in a natural way.

A "metaverse interface" is an interface that allows users to operate and experience things in a virtual space.

A "health management service" is a service that monitors and manages a user's health status.

Biometric services" are services that use a user's biometric information to verify identity.

Real-time" means that data and information are processed immediately.

Encryption" means that data is converted using a specific algorithm to a form that cannot be easily understood by a third party.

The "cloud" is a collection of computer resources and services provided via the Internet.

A "sharing history" is a record of how, when, and by whom data was shared.

A "medical institution" is a facility that provides medical services, such as a hospital or clinic.

A "research institution" is an organization or facility for conducting scientific research.

The following system configuration is an exemplary embodiment of this invention.

System Configuration

The system has the ability to collect users' EEG data in real time, encrypt it, and upload it to the cloud. It also has the ability to share data with medical and research institutions and manage data sharing history.

Hardware Used

Smart device: a device that allows users to manage their EEG data and upload it to the cloud.

EEG sensors: devices (e.g., Muse, Emotiv) to collect EEG data on users.

Software to be Used

Python: A programming language for performing the main processing of a program.

NeuroKit2: A library for simulation and analysis of EEG data.

Requests: Library for sending HTTP requests.

Cryptography: Library for data encryption.

Process Flow

1. EEG data collection: EEG sensors are used to collect the user's EEG data in real time. The collected data is stored on the smartphone.

Data encryption: The EEG data collected will be encrypted using the Cryptography library. This ensures data security.

Data upload: Encrypted data is uploaded to the cloud using the Requests library. Data is stored securely in the cloud.

Data sharing: Users can share data with medical institutions and research organizations as needed. Sharing history is stored locally, allowing users to see who accessed what data and when.

Concrete Example

The user wears the EEG sensor and launches the NeuroGuard app. The app collects the EEG data, encrypts it, and uploads it to the cloud. With the user's permission, a medical institution retrieves the data from the cloud and uses it for diagnosis.

Example of Prompt Text

The user wears the EEG sensor and launches the NeuroGuard app. The app collects EEG data, encrypts it, and uploads it to the cloud. With the user's permission, a healthcare provider retrieves the data from the cloud and uses it for diagnosis.

This system will allow users' EEG data to be managed securely and efficiently and shared with third parties as needed.

Figure 14:
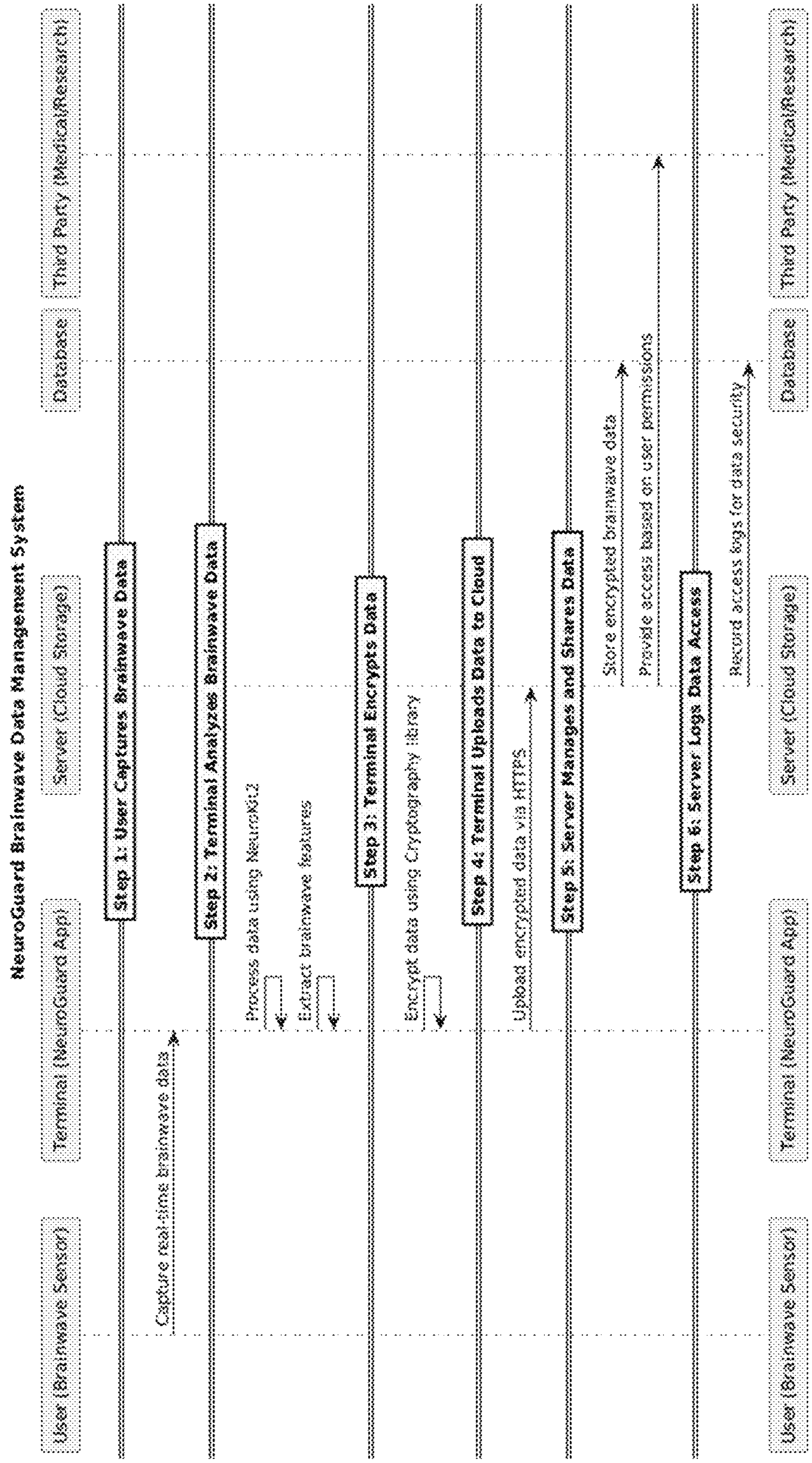
FIG. 14 is a sequence diagram showing the flow of data processing system processing in example of application 2 of example of implement.

The flow of the identification process in example of application 2 is described in FIG. 14.

Step 1:

The user wears the EEG sensor and launches the NeuroGuard application on the smartphone. The EEG sensor collects the user's EEG data in real time and transmits it to the smartphone. The input is the EEG data from the EEG sensor and the output is the raw EEG data stored on the smartphone.

Step 2:

The terminal (smartphone) analyzes the EEG data collected using the NeuroKit2 library. This analysis extracts the features of the EEG data. The input is the raw EEG data and the output is the features of the analyzed EEG data. Specifically, NeuroKit2 functions are invoked to analyze the EEG data and extract the features.

Step 3:

The terminal encrypts the analyzed EEG data using the Cryptography library. The input is the features of the analyzed EEG data and the output is the encrypted EEG data. The specific operation is to generate an encryption key and encrypt the EEG data using the key.

Step 4:

The terminal uploads encrypted EEG data to the cloud using the Requests library. The input is the encrypted EEG data and the output is the encrypted data stored on the cloud. The specific operation is to send an HTTP POST request and upload the data to the cloud server.

Step 5:

The server manages the encrypted data stored on the cloud and shares the data with medical and research institutions as needed. The input is the encrypted data on the cloud and the output is the shared data. The specific operation is to decrypt the data and provide it to the designated third party with the user's permission.

Step 6:

The server maintains a data sharing history, recording who accessed what data and when. The input is the data access request information and the output is the shared history log. The specific operation is to generate an access log and store it locally or in the cloud.

In this way, the user's EEG data can be managed securely and efficiently and shared with third parties as needed.

Example 3

Next, example 3 of exemplary embodiment of implement will be described. In the following description, data processing device 12 is referred to as the "server" and smart device 14 is referred to as the "terminal.

Conventional brain-machine interfaces (BMIs) have had difficulty effectively analyzing users' brain wave data and identifying their emotions and intentions in real time. They also lacked a platform for intuitive communication, health management, biometric authentication, and other services based on these data. Furthermore, users lacked the ability to manage their own EEG data and share it with third parties as needed. To solve these problems, a system that provides highly accurate analysis of EEG data and a variety of services based on this data is needed.

The specific processing by the specific processing unit 290 of the data processing device 12 in Example 3 is realized by the following means.

In this invention, the server has means for the user to wear an EEG measurement device and connect it to the terminal; the terminal collects EEG data from the EEG measurement device and transmits it to the server; the server receives the EEG data and performs pre-processing; the server analyzes the pre-processed data to identify emotions and intentions, means for the server to transmit the analysis results to the terminal, the terminal to display the analysis results and provide feedback to the user, means for providing a platform for disseminating the system to society, and means for providing intuitive communication using brain activity provided through the platform. services, virtual reality interface, health management services, and biometric authentication services provided through the platform. This makes it possible to analyze users' brain wave data with high precision and provide a variety of services based on such data in real time.

The term "user" refers to the individual who wears the EEG measurement device and uses the system.

The term "EEG measurement device" refers to a device used to measure a user's EEG data.

The term "terminal" refers to an electronic device that transmits the data collected from the EEG measurement device to the server and displays the analysis results to the user.

The term "server" refers to a computer system that receives EEG data, performs pre-processing and analysis, and transmits the results to the terminal.

Pre-processing" refers to data cleansing operations performed on EEG data prior to analysis, such as noise removal and filtering.

The term "analysis" refers to the processing of data to identify the user's emotions and intentions based on the preprocessed EEG data.

The term "generative AI model" refers to a machine learning model used to analyze brain wave data to identify a user's emotions and intentions.

The term "platform" refers to the infrastructure that will allow the system to be disseminated to society and for users to manage their EEG data and share it with third parties as needed.

The term "intuitive communication service" refers to a service that uses brain wave data from users to understand their emotions and intentions and communicate accordingly.

The term "virtual reality interface" refers to an interface that controls behavior in a virtual or augmented reality world based on the user's brain wave data.

The term "health management service" refers to a service that uses brain wave data to determine a user's stress level, sleep status, etc., and suggests health management based on this information.

The term "biometric authentication service" refers to a service that analyzes a user's brain wave patterns for personal authentication.

The invention begins with the user wearing an EEG measurement device and connecting it to a terminal. The user wears the EEG measurement device (e.g. EEG device) on his/her head and connects it to a terminal (e.g. smart phone or PC) using Bluetooth or USB cable.

The terminal collects EEG data from the EEG device in real time using a dedicated application. The collected data is sent to the server via the Internet. The server receives the EEG data sent from the terminal and performs pre-processing. Pre-processing includes noise removal and filtering, and uses the Python MNE library for data cleansing.

The preprocessed data is input to a machine learning model on the server (e.g., using TENSORFLOW (registered trademark) or PyTorch) to analyze the emotions and intentions. The analysis results are used to identify the user's emotion (e.g., joy, sadness, surprise, etc.) or intention (e.g., the intention to perform a specific action).

The analysis results are sent from the server to the terminal. The terminal displays the analysis results received from the server to the user. For example, a chat application displays a message that the user is happy. The metaverse interface also controls actions in the VR and AR worlds based on the user's intentions.

As a concrete example, consider an intuitive communication service. A user wears an EEG device and connects it to a smart phone. The smart device collects brain wave data from the EEG device in real time and sends it to the server. The server preprocesses the received data and analyzes emotions using TensorFlow. If the analysis shows that the user is "happy," this information is reflected in the smartphone's chat application and a message is sent to the other party saying that the user is happy.

Example of a Prompt Statement:

The user wears the EEG device and connects it to a smart phone. The smartphone collects EEG data in real-time and sends it to the server. The server preprocesses the data and analyzes the emotions using TensorFlow. If the analysis shows that the user is "happy," the information is reflected in the chat application and a message is sent to the other party saying that the user is happy.

Figure 15:
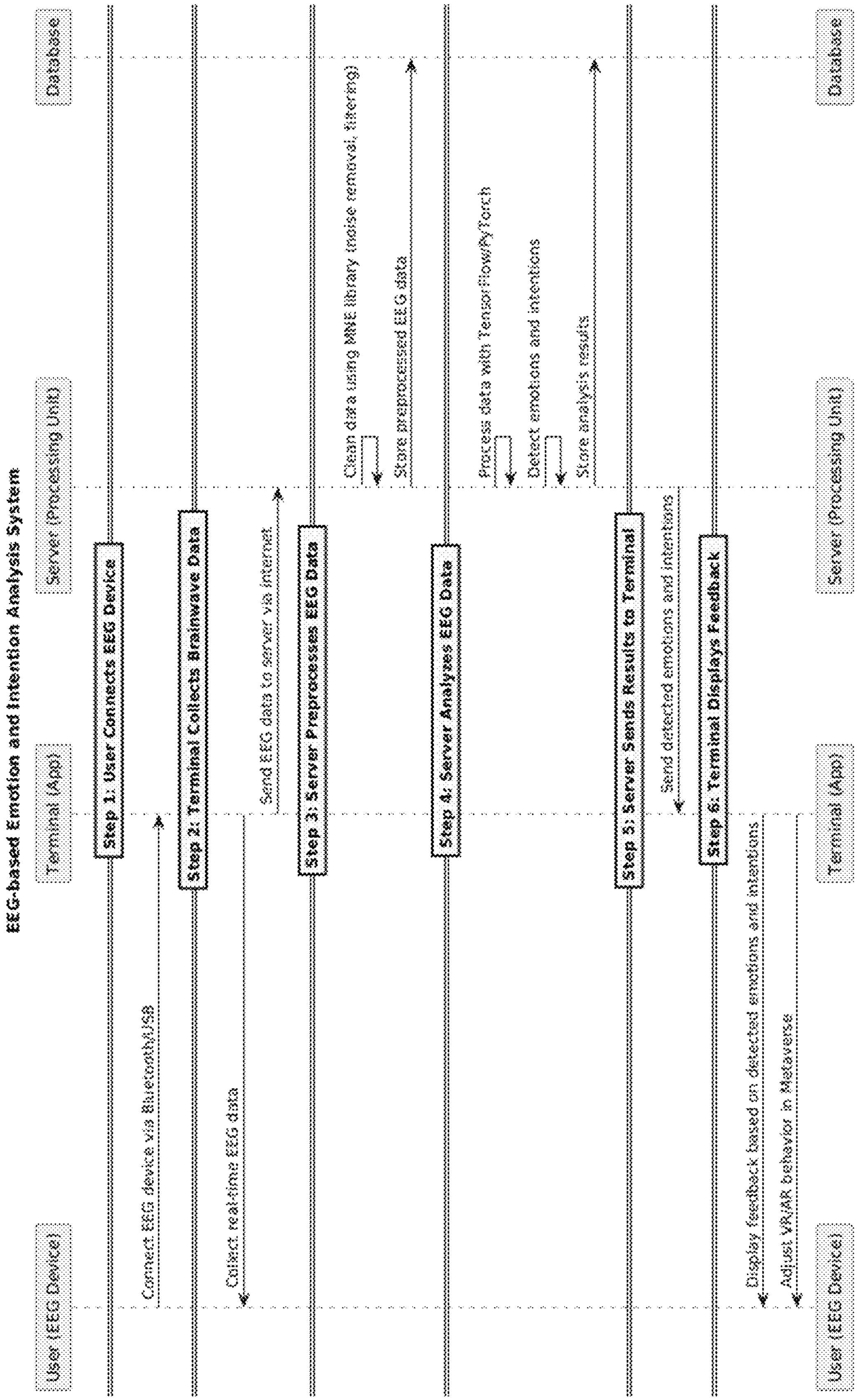
FIG. 15 is a sequence diagram showing the flow of data processing system processing in Example 3 of implement example.

In this way, the server, terminal, and user work together to realize a system that provides new services using EEG data. The flow of the identification process in Example 3 is described using FIG. 15.

Step 1:

The user wears the EEG measurement device and connects it to the terminal.

Specifically, the user wears an EEG measurement device (e.g., EEG device) on his/her head and connects it to a terminal (e.g., smart phone or PC) using Bluetooth or USB cable. The input is the user's EEG and the output device is the EEG measurement device connected to the terminal.

Step 2:

The terminal collects EEG data from the EEG measurement device and sends it to the server.

Specifically, the terminal uses a dedicated application to collect EEG data from the EEG device in real time. The collected data is sent to the server via the Internet. The input is the EEG data from the EEG measurement device and the output is the EEG data sent to the server.

Step 3:

The server receives the EEG data and performs preprocessing.

Specifically, the server receives EEG data sent from the terminal. The received data is preprocessed, including noise removal and filtering; data cleansing is performed using Python's MNE library. The input is the EEG data transmitted from the terminal and the output is the preprocessed EEG data.

Step 4:

The server analyzes the preprocessed data to identify emotions and intentions.

Specifically, the server inputs the preprocessed data into a machine learning model (e.g., using TensorFlow or PyTorch). The model identifies the user's emotions and intentions from the EEG data. The input is the preprocessed EEG data and the output is the emotion and intention information as the result of the analysis.

Step 5:

The server sends the analysis results to the terminal.

As a specific action, the server sends the analysis results to the terminal. The analysis results include the user's emotions (e.g., joy, sadness, surprise, etc.) and intentions (e.g., intention to perform a specific action). The input is the analysis result and the output is the analysis result sent to the terminal.

Step 6:

The terminal displays the analysis results and provides feedback to the user.

As a specific action, the terminal displays the analysis results received from the server to the user. For example, a chat application displays a message that the user is happy. In addition, the metaverse interface controls actions in the VR and AR worlds based on the user's intentions. The input is the analysis results received from the server and the output is the feedback displayed to the user.

Example of Application 3

Next, example 3 of application of example of implement 3 will be described. In the following description, data processing device 12 is referred to as the "server" and smart device 14 is referred to as the "terminal.

Conventional brain-machine interfaces (BMIs) have limited technology for analyzing a user's brain waves, making it difficult to perform highly accurate analysis in real time. They also lacked intuitive means of navigation and interaction within the metaverse, making it difficult to perform actions that reflect the user's intentions and emotions. Furthermore, functions related to the management and sharing of EEG data were inadequate, making it less convenient for users.

The specific processing by the specific processing unit 290 of the data processing device 12 in example of application 3 is realized by the following means.

In this invention, the server provides means for generating a minimally invasive and highly accurate brain-machine interface (BMI) that combines brain waves and generative AI, means for providing a platform for disseminating the BMI in society, means for providing, through the platform, brain activity-based intuitive communication services, metaverse interface, health management services, and biometric authentication services provided through the platform; means for controlling navigation and interaction in the metaverse by analyzing the user's brain waves in real time; and means for performing actions in the metaverse based on the user's intentions and emotions. means to perform actions. This allows users to intuitively navigate and interact within the metaverse using brain waves.

EEG" is a recording of the brain's electrical activity, data that can be used to analyze a user's intentions and emotions.

Generative AI" is a type of artificial intelligence that generates new information and output based on input data.

A "brain-machine interface" (BMI) is an interface that analyzes brain waves to control machines and computers.

A "platform" is a system that serves as the foundation for providing a particular service or function.

Intuitive Communication Service" is a service that analyzes a user's brain waves to understand their emotions and intentions, and communicates accordingly.

A "metaverse interface" is an interface for user interaction in a virtual or augmented reality world.

The "Health Management Service" is a service that analyzes users' brain waves to determine their stress levels and sleep conditions, and suggests health management based on this information.

Biometric authentication service" is a personal authentication service that analyzes a user's brain wave patterns.

The term "navigation" refers to the instructions and operations that users use to navigate within a virtual space.

Interaction" refers to the user's interaction with other objects or characters in the virtual space.

Intent" is the user's intention to perform a particular action or operation.

Emotion" refers to the psychological state or feeling of a user.

An "action" is an action or reaction performed in the virtual space based on a user's intention or emotion.

A system for implementing this invention includes means to generate a minimally invasive, highly accurate brain-machine interface (BMI) that combines electroencephalograms and generative AI; means to provide a platform for popularizing the BMI in society; means to provide intuitive communication utilizing brain activity provided through the platform, metaverse interface, health management services, and biometric authentication services using brain activity provided through the platform; means to control navigation and interaction in the metaverse by analyzing the user's brain waves in real time; and means to execute actions in the metaverse based on the user's intentions and emotions. The system includes means to execute actions in the metaverse based on the user's intentions and emotions.

System Configuration

This system uses the following hardware and software

Hardware: Brainwave sensor, head-mounted display

Software: Python, EEG sensor API, Metaverse controller API

Explanation of Program Processing

The server analyzes the EEG data acquired from the EEG sensor in real time and inputs it to the generative AI. The generative AI analyzes the user's intentions and emotions based on the input EEG data and generates output based on them. Specifically, if the user wants to move forward, the brain wave sensor detects this intention and the avatar moves forward. Also, if the user feels happy, the emotion is detected and the avatar smiles.

Concrete Example

For example, if the user wants to move forward in the metaverse, the brainwave sensor will detect that intention and the avatar will move forward. Also, if the user feels happy, the emotion will be detected and the avatar will smile.

Example of Prompt Text

Examples of prompt sentences to be input into the generative AI model are as follows If the user wants to move forward, the brainwave sensor should detect that intention and generate a program that causes the avatar to move forward. Also, if the user feels happy, the emotion should be detected and the avatar should smile.

Figure 16:
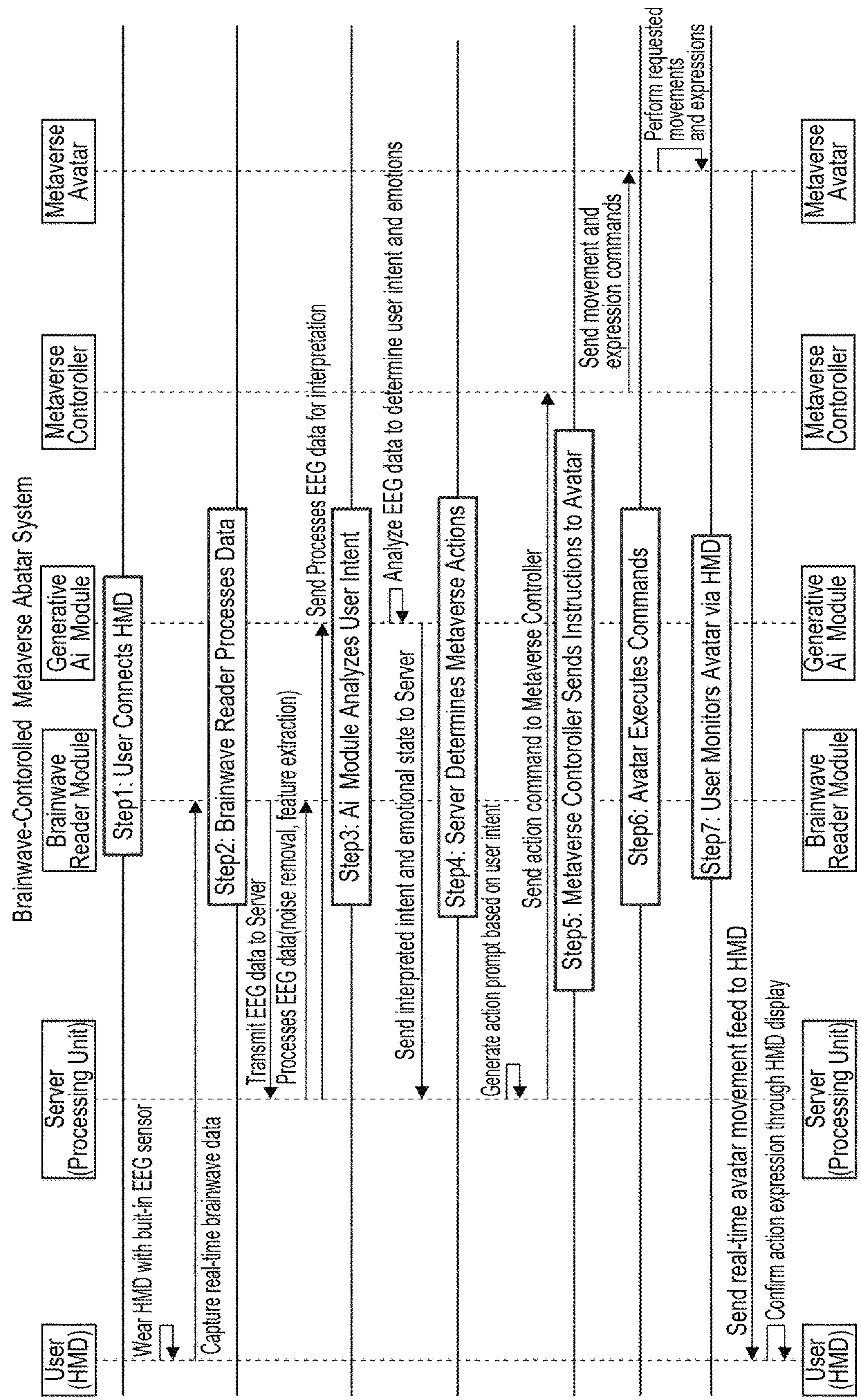
FIG. 16 is a sequence diagram showing the flow of data processing system processing in example of application 3 of implement.

The flow of the identification process in example of application 3 is described in FIG. 16.

Step 1:

The server acquires EEG data from the EEG sensor.

Input: Raw data from EEG sensor

Output: Acquired EEG data

Specific operation: An EEG sensor measures the user's brain waves in real time and sends the data to the server.

Step 2:

The server preprocesses the acquired EEG data.

Input: EEG data acquired

Output: preprocessed EEG data

Specific operation: Pre-processing such as noise removal and filtering is performed, and the data is converted into a format suitable for analysis.

Step 3:

The server inputs the preprocessed EEG data to the generator system AI.

Input: preprocessed EEG data

Output: Data input to the generative AI

Specific operation: Pre-processed EEG data is input into a generative AI model to analyze the user's intentions and emotions.

Step 4:

The generative AI analyzes the user's intentions and emotions based on the input brain wave data.

Input: Data input to the generative AI

Output: parsed intentions and feelings

Specific behavior: A generative AI model analyzes brain wave data to identify what the user intends and what emotion identification model the user has.

Step 5:

The server determines actions in the metaverse based on the analysis results.

Input: parsed intentions and feelings

Output: Actions performed in the metaverse

Specific actions: If the user's intention is "forward", the avatar determines the action of moving forward; if the emotion is "happy", the avatar determines the action of smiling.

Step 6:

The server sends the determined action to the Metaverse Controller.

Input: Actions to be performed in the metaverse

Output: Action instructions sent to the Metaverse Controller

Specific actions: The determined actions are sent through the Metaverse Controller's API to instruct the avatar to actually perform the action.

Step 7:

The Metaverse Controller controls the avatar based on the action instructions received.

Input: Action instructions sent to the Metaverse Controller

Output: Avatar behavior

Specific actions: The metaverse controller controls the avatar to perform actions based on the user's intentions and emotions. For example, the avatar moves forward or smiles.

Furthermore, an emotion engine that estimates the user's emotion may be combined. In other words, the specific processing unit 290 may use the emotion identification model 59 to estimate the user's emotion and perform specific processing using the user's emotion.

Example of Implement 1

In one exemplary embodiment, the brain-machine interface (BMI) analyzes the user's brain waves in real time and inputs the results to the generative AI. In addition, by combining an emotion engine, the user's emotional state is also analyzed simultaneously. Based on the results of this analysis, the system understands the user's intentions and emotional state, and generates output based on them. For example, if a user thinks of "making coffee" with an emotion of joy, the system recognizes that joyful emotion and takes action to make coffee accordingly.

Example of Implement 2

In another exemplary embodiment of the invention, the platform has a function that allows users to manage their own EEG data and emotional states and share them with third parties as needed. For example, users can share their EEG data with medical and research institutions when they are feeling joyful emotions to obtain more accurate medical services and research results.

Example of Implement 3

In a further exemplary embodiment of the invention, the services provided through the platform have the ability to provide services that utilize the emotional state of the user. For example, an intuitive communication service analyzes the user's brain waves to understand their emotions and intentions, and communicates with them based on this information. If the user has a joyful emotion, the service recognizes that joyful emotion and provides communication accordingly.

The following is a description of the process flow for each example of implement.

Example of Implement 1

Step 1: The user thinks of a specific action. For example, think "make coffee".

Step 2: The brain-machine interface (BMI) analyzes the user's brain waves in real time.

Step 3: The emotion engine analyzes the user's emotional state. In this example, it analyzes that the user has the emotion of joy.

Step 4: Based on the analysis results, understand the user's intentions and emotional state and generate output based on them. In this example, the coffee-making action is tailored to the emotion of joy.

Example of Implement 2

Step 1: The user feels a specific emotion. For example, feel the emotion of joy.
Step 2: The platform manages the user's EEG data and emotional state.
Step 3: The user shares his/her EEG data and emotional state with third parties as needed. In this example, it is shared with a medical or research institution.

Example of Implement 3

Step 1: The user uses the service through the platform. For example, use intuitive communication services.
Step 2: The service analyzes the user's brain waves to understand their emotions and intentions.
Step 3: The service provides communication tailored to the user's emotional state based on the analysis results. In this example, if the user has a joyful emotion, the service provides communication tailored to that joyful emotion.

Example 1

The following is an example of exemplary embodiment of implement. In the following description, data processing device 12 is referred to as the "server" and smart device 14 is referred to as the "terminal.

Conventional brain-machine interfaces (BMI) only analyze the user's brain waves and fail to take into account the user's emotional state. This made it difficult to accurately understand the user's intentions and generate appropriate output. It also lacked a platform for managing users' EEG data and sharing it with third parties. This prevented the social diffusion of BMI and made it difficult to provide intuitive communication services, health management services, and biometric authentication services The specific processing by the specific processing unit 290 of the data processing device 12 in Example 1 is realized by the following means.

In this invention, the server includes means for acquiring the user's brain waves in real time, analyzing the acquired brain wave data to extract the user's intentions, analyzing the user's emotional state, generating and inputting prompt sentences to a generative AI based on the analysis results, and executing the output generated by the generative AI The system also includes means to execute the outputs generated by the generative AI. This enables the system to accurately understand the user's intentions and emotional state and generate appropriate outputs. The system can also provide a platform for disseminating the system in society, and provide intuitive communication services, virtual space interface, health management services, and biometric authentication services using brain activity.

A "user" is an individual who uses the system.

Brain waves" are electrical signals generated by neural activity in the brain.

Real-time" means that data is processed as soon as it is generated.

Means of acquisition" refers to devices and methods for collecting data.

Means to analyze" refers to devices and methods used to analyze acquired data and extract meaningful information.

Intent" refers to information that indicates what the user wants or is thinking about.

The term "emotional state" refers to information that indicates a user's feelings or mood.

Generative AI" refers to artificial intelligence that generates new information and output based on given data.

A "prompt sentence" is an input sentence used to give instructions or ask questions to the generative AI.

Output" refers to the results or responses generated by the generative AI based on the prompted statements.

Means of execution" refers to devices and methods used to convert output generated by the generative AI into concrete actions and operations.

The term "platform" refers to the infrastructure used to operate the system and provide services to users.

An "intuitive communication service" is one that allows users to exchange information with others in a natural way.

The term "virtual space interface" refers to an interface that allows users to operate and experience things within a virtual environment.

The term "health management services" refers to services for monitoring and managing the health status of users.

The term "biometric authentication service" refers to a service that uses a user's biometric information to verify his or her identity.

This invention is a system that analyzes a user's brain waves in real time and inputs the results to a generative AI to understand the user's intentions and emotional state and generate output based on the results. The system includes an EEG measurement device to acquire the user's EEG, software to analyze the EEG data, an emotion engine to analyze the emotional state, a generative AI, and hardware to execute the generated output.

Hardware and Software Used

1. Brain Wave Measurement Device

The user wears a special EEG measurement device. This device acquires the user's brain waves in real time.

2. Brain Wave Analysis Software

EEG analysis software (e.g., OpenBCI) is used by the terminal to analyze the EEG data acquired from the EEG measurement device. This software analyzes the EEG data and extracts the user's intentions.

3. Emotion Engine:

The terminal uses an emotion engine to analyze the user's emotional state. This engine acquires emotional data through facial recognition cameras and voice analysis to understand the user's emotional state.

4. Generative AI: The

The server generates and inputs prompt sentences to the generative AI (e.g. OpenAI GPT-4) based on the analysis results. The generative AI generates appropriate outputs based on the prompt sentences.

Output Execution Hardware: 5.

The server receives output from the generative AI and manipulates hardware (e.g., IoT devices) to perform specific actions.

Concrete Example

The user wakes up in the morning and puts on the EEG measurement device.

The terminal receives data from the EEG measurement device and begins analyzing it in real time.

The terminal detects the intention to "drink coffee" from brain wave data.

The terminal confirms that the user has a feeling of "joy" through the facial recognition camera.

The terminal says, "The user wants to 'have a cup of coffee' with an emotion of pleasure. Please suggest an appropriate action." The terminal generates the prompt sentence "The user wants to have a cup of coffee.

The server sends a prompt sentence to the generative AI, and the generative AI generates an output that "instructs the coffee maker to make coffee.

The server operates the coffee maker through an IoT device to make coffee.

Example of Prompt Text

EEG data of user: [data].

User's emotional state: joy

User Intent: I want a cup of coffee

Prompt for generative AI: A user wants to 'have a cup of coffee' with a joyful emotion. Please suggest an appropriate action.

In this way, the system can analyze the user's brain waves and emotional state, generate output based on the user's intentions using generative AI, and execute specific actions.

Figure 17:
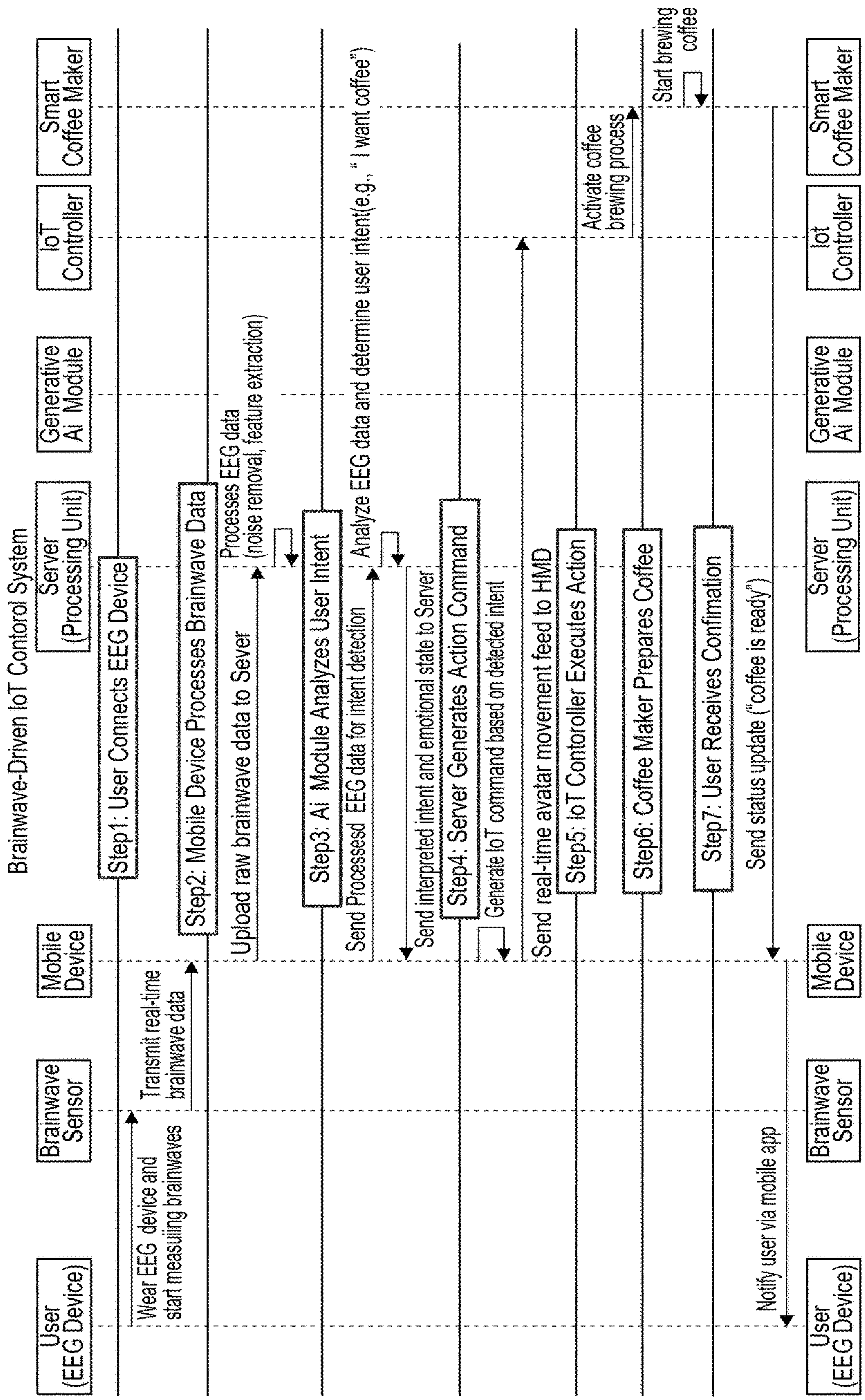
FIG. 17 is a sequence diagram showing the flow of data processing system processing in Example 1 of embodiment when the emotional engine is combined.

The flow of the identification process in Example 1 is described in FIG. 17.

Step 1:

The user wears a special EEG measurement device.

Input: User's brain waves

Output: Real-time EEG data

Specific operation: The user wears the EEG measurement device on his/her head and the device begins to measure brain waves. The device transmits EEG data to the terminal in real time via Bluetooth or USB connection.

Step 2:

The terminal acquires EEG data from the EEG measurement device in real time.

Input: Real-time EEG data

Output: Acquired EEG data

Specific operation: The terminal receives EEG data transmitted from the EEG measurement device and stores it in a database.

Step 3:

The EEG data acquired by the terminal is analyzed to extract the user's intention.

Input: EEG data acquired

Output: User intent

Specific operation: The terminal uses EEG analysis software (e.g. OpenBCI) to analyze EEG data. It detects specific brain wave patterns and extracts the user's intentions based on them. For example, the intention of "I want a cup of coffee" is detected.

Step 4:

The terminal analyzes the user's emotional state.

Input: User's face image and voice data

Output: User's emotional state

Specific operation: The terminal uses the emotion engine to acquire emotion data through facial recognition camera and voice analysis. As a result of the analysis, the user identifies an emotional state such as "joy" or "sadness".

Step 5:

The terminal generates and inputs prompt sentences to the generative AI based on the analysis results.

Input: user intent and emotional state

Output: Prompt statement to generative AI

Specific action: The terminal integrates the user's intention and emotional state and says, "The user wants to 'have a cup of coffee' with a feeling of joy. Please suggest an appropriate action." The prompt sentence "The user wants to drink a cup of coffee" is generated.

Step 6:

The server sends prompt sentences to the generative AI, and the generative AI generates output.

Input: Prompt statement to generative AI

Output: Output from generative AI

Specific behavior: The server sends a prompt sentence to the generative AI (e.g., OpenAI GPT-4), and the generative AI generates an output "instructing the coffee maker to make coffee" based on the prompt sentence.

Step 7:

The server receives output from the generative AI and executes specific actions.

Input: Output from generative AI

Output: Actions performed

Specific operation: The server operates the coffee maker through the IoT device to make coffee. Specifically, "make coffee" instructions are sent to the coffee maker, and coffee is actually made.

Example of Application 1

Next, example of application 1 of example of implement 1 will be described. In the following description, data processing device 12 will be referred to as the "server" and smart device 14 will be referred to as the "terminal.

Conventional brain-machine interface (BMI) technology exists that analyzes the brain waves of users to understand their intentions, but its application is limited and has not been fully utilized, especially in supporting work in factories. In addition, the lack of a system that understands the intentions of workers in real time and automatically performs appropriate tasks has not sufficiently improved work efficiency or enabled human-machine collaboration.

The specific processing by the specific processing unit 290 of the data processing device 12 in example of application 1 is realized by the following means. In this invention, the server provides means to generate a minimally invasive and highly accurate brain-machine interface (BMI) that combines brain waves and generative AI, means to provide a platform to disseminate the BMI in society, means to provide intuitive communication services, metaverse interface, health management services, and biometric authentication services, and means to be installed in a robot performing work in a factory to analyze the worker's brain waves in real time, understand the worker's intentions, and automatically perform appropriate tasks. This makes it possible to understand the worker's intentions in real time and automatically perform appropriate tasks.

Brain waves" are electrical signals generated by neural activity in the brain.

Generative AI" is an artificial intelligence technology that generates new data and outputs based on input data.

Brain Machine Interface (BMI) is an interface technology that analyzes brain waves and uses the results to control machines and computers.

Minimally invasive" means less stressful or damaging to the body.

High precision" means extremely accurate.

A "platform" is the underlying system or environment that provides a specific service or function.

An "intuitive communication service" is one that allows users to interact with information in a natural way.

The term "metaverse interface" refers to the user interface within the virtual space.

A "health management service" is a service that monitors and manages a user's health status.

Biometric authentication service" is a service that uses an individual's biometric information for authentication.

A "robot that works in a factory" is a machine that is designed to automatically perform a specific task in a factory.

A "worker" is a person who performs work in a factory.

Real-time" means that processing and analysis occur almost simultaneously.

Intent" refers to the purpose or idea of what the user wants to do.

Output" refers to the results or actions produced by a system or machine.

The system for implementing this invention uses a minimally invasive and highly accurate brain-machine interface (BMI) that combines EEG and generative AI. The server analyzes the user's brain waves in real time and inputs the results to the generative AI, which understands the user's intentions and generates output based on them. In addition, by combining an emotion engine, the emotional state of the user is analyzed at the same time to understand the user's intentions and emotional state to generate output.

The system is installed on a robot performing a task in the factory and analyzes the worker's brain waves in real time. When a worker wants to perform a specific task, the robot understands his/her intention and automatically performs the appropriate task. For example, if the worker wants to assemble a part, the robot understands his/her intention and starts assembling the part.

The server uses EEG sensors to acquire EEG data. EEG data is analyzed in real-time using a Python library. An emotional engine is used to analyze emotional states. A generative AI model (e.g., OpenAI GPT-3 (registered trademark)) understands the user's intentions based on the analyzed EEG data and emotional state and generates appropriate output.

As a concrete example, here is a prompt sentence for a worker who wants to "assemble a part".

Example of a prompt statement: "I am a member of the EEG data of user: [0.1, 0.2, 0.3, . . . ].

User's emotional state: joy

User Intent: To assemble parts

By inputting this prompt sentence into the generative AI model, it understands the user's intention and generates appropriate actions. For example, a specific output is obtained, such as a robot starting to assemble a part.

This system enables the system to understand the intentions of workers in real time and automatically perform appropriate tasks. This improves work efficiency in the factory and realizes collaboration between man and machine.

Figure 18:
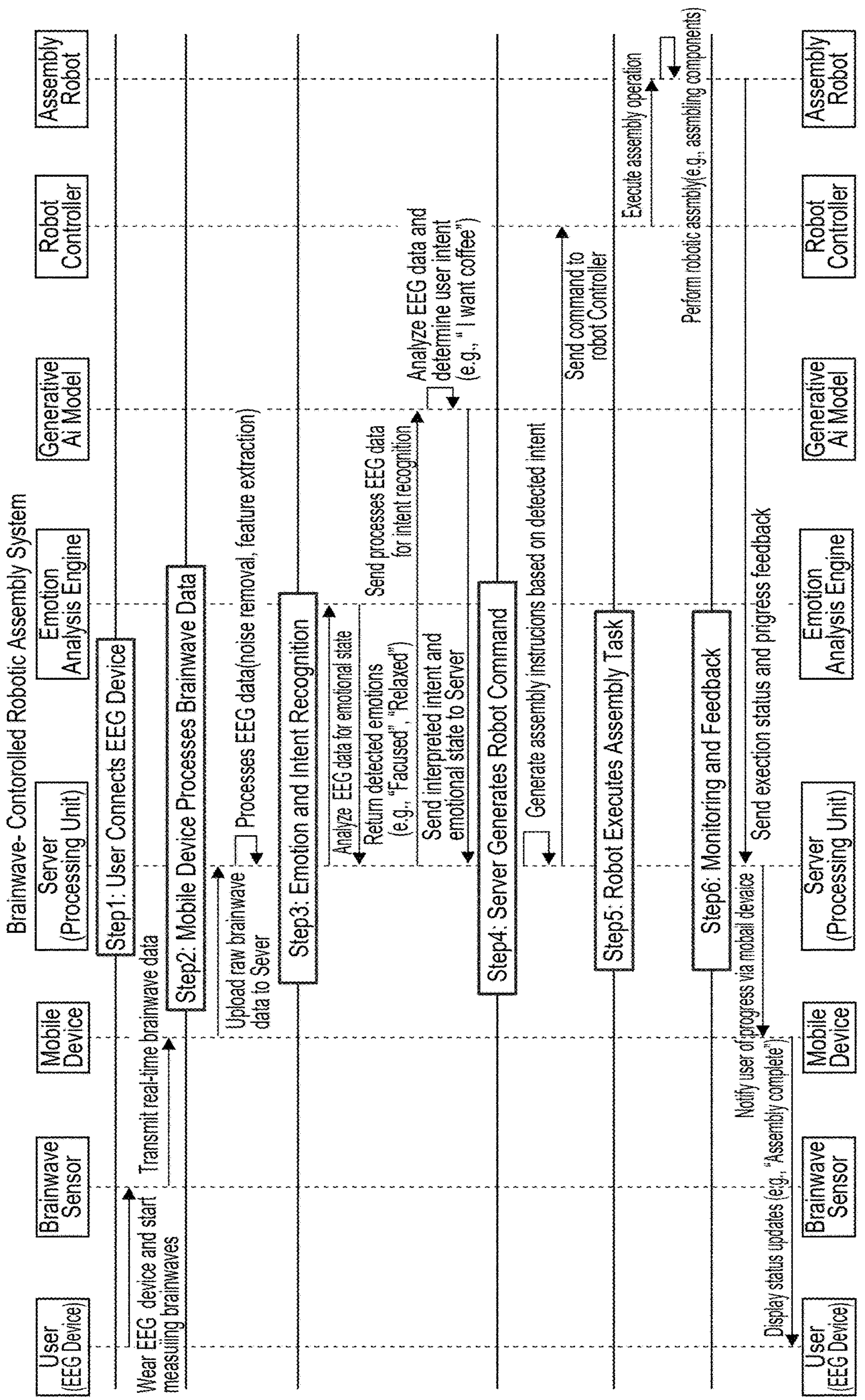
FIG. 18 is a sequence diagram showing the flow of data processing system processing in example of application 1 of example of implement when combined with an emotion engine.

The flow of the identification process in Example of Application 1 is described in FIG. 18.

Step 1:

The server acquires the user's EEG data in real time using EEG sensors. The input is the user's EEG signal and the output is the EEG data acquired. This data is transmitted from the EEG sensor to the server.

Step 2:

The server analyzes the acquired EEG data in real time using a Python library. The input is the acquired EEG data and the output is the analyzed EEG data. Through this analysis, EEG features and patterns are extracted.

Step 3:

The server uses the emotion engine to analyze the user's emotional state from the analyzed EEG data. The input is the analyzed EEG data and the output is the user's emotional state. This analysis determines whether the user is happy, sad, angry, etc.

Step 4:

The server uses a generative AI model (e.g., OpenAI GPT-3) to understand user intentions based on parsed EEG data and emotional states. The input is the parsed EEG data and emotional state, and the output is the user's intention. The data generation AI model inputs these data as prompts and infers what the user wants to do.

Step 5:

The server generates appropriate outputs based on user intent. The input is the user's intention and the output is a specific action. For example, if the user intends to assemble a part, the server instructs the robot to begin the process of assembling the part.

Step 6:

The robot receives instructions from the server and executes specific tasks. The input is the instructions from the server and the output is the work performed. For example, this includes a series of operations in which the robot starts and completes the assembly of a part.

Step 7:

The server monitors work progress and provides feedback as needed. The input is work progress data from the robot and the output is feedback information. This improves the accuracy and efficiency of the work.

Example 2

Next, example 2 of exemplary embodiment of implement will be described. In the following description, data processing device 12 is referred to as the "server" and smart device 14 is referred to as the "terminal.

Conventional brain-machine interfaces (BMIs) lack the ability to effectively manage users' EEG data and share it with third parties as needed. In addition, the accuracy and real-time nature of EEG data analysis was low, making it difficult to accurately understand the user's intentions. Furthermore, the acquisition and management of EEG data was complicated, making it difficult for ordinary users to use the system.

The specific processing by the specific processing unit 290 of the data processing device 12 in Example 2 is realized by the following means. In this invention, the server includes means by which the user acquires EEG data using a dedicated EEG measurement device and uploads it to the platform through a terminal, the server receives the EEG data and stores it in a database, and the server preprocesses and analyzes the EEG data. This allows users to effectively manage their own EEG data and share it with third parties as needed. It also improves the accuracy of the analysis of the EEG data and allows for an accurate understanding of the user's intentions in real time. Furthermore, the system simplifies the acquisition and management of EEG data, providing an easy-to-use system for the general user.

Brain Machine Interface (BMI) is a technology that uses brain wave data to understand the user's intentions and intuitively interact with machines and computers.

Generative AI is an artificial intelligence technology that analyzes a user's brain wave data and generates output based on the results.

The "platform" is the system infrastructure that allows users to manage their EEG data and share it with third parties as needed.

An "EEG measurement device" is a device worn on the user's head to acquire EEG data.

A "terminal" is a device that allows users to input and upload their EEG data to the platform.

A "server" is a computer system that receives EEG data, stores it in a database, and performs preprocessing and analysis.

A "database" is an information management system for storing received EEG data.

Pre-processing" refers to data cleaning operations performed on EEG data prior to analysis, such as noise removal and completion of missing values.

Analysis" is the process of classifying and understanding the user's emotional state and intentions based on the preprocessed EEG data.

The "third party" is the party with whom the user shares the EEG data, such as a medical or research institution.

Exemplary Embodiment of the Invention

This invention is a system in which users acquire EEG data using a dedicated EEG measurement device and upload it to the platform through a terminal. The server stores the received EEG data in a database for pre-processing and analysis. This allows users to effectively manage their own EEG data and share it with third parties as needed.

Hardware and Software Used

Hardware: (1)

EEG measurement device: The user uses a dedicated EEG measurement device (e.g., a common EEG measuring device) to obtain EEG data. This device is worn on the user's head and collects EEG data in real time.

Software: C

Terminal application: The terminal provides an interface for the user to receive and upload the EEG data acquired by the user to the platform. The user uploads the data through the terminal application.

Server: The server performs preprocessing and analysis of EEG data using Python.

Specifically, libraries such as NumPy and Pandas are used to clean and filter the data. It also builds and analyzes machine learning models using libraries such as TensorFlow and PyTorch.

Database: The server uses a relational database such as MySQL or PostgreSQL to store EEG data.

Concrete Example

As a concrete example, consider a scenario in which EEG data is shared with a healthcare provider when a user is experiencing feelings of joy. The user acquires the data using an EEG measurement device and uploads it to the platform through a terminal. The server receives the data, analyzes it, and then sends the data to the medical institution.

Example of Prompt Sentences to be Entered into a Generative AI Model:

Describe the steps you would take to share EEG data with a medical provider when a user is experiencing feelings of joy."

Using this prompt statement, the generated AI model can provide detailed descriptions of specific procedures and necessary hardware and software.

In this way, users can effectively manage their own EEG data and share it with third parties as needed. In addition, the accuracy of EEG data analysis is improved, allowing the system to accurately understand the user's intentions in real time. Furthermore, the system simplifies the acquisition and management of EEG data, providing an easy-to-use system for the general user.

Figure 19:
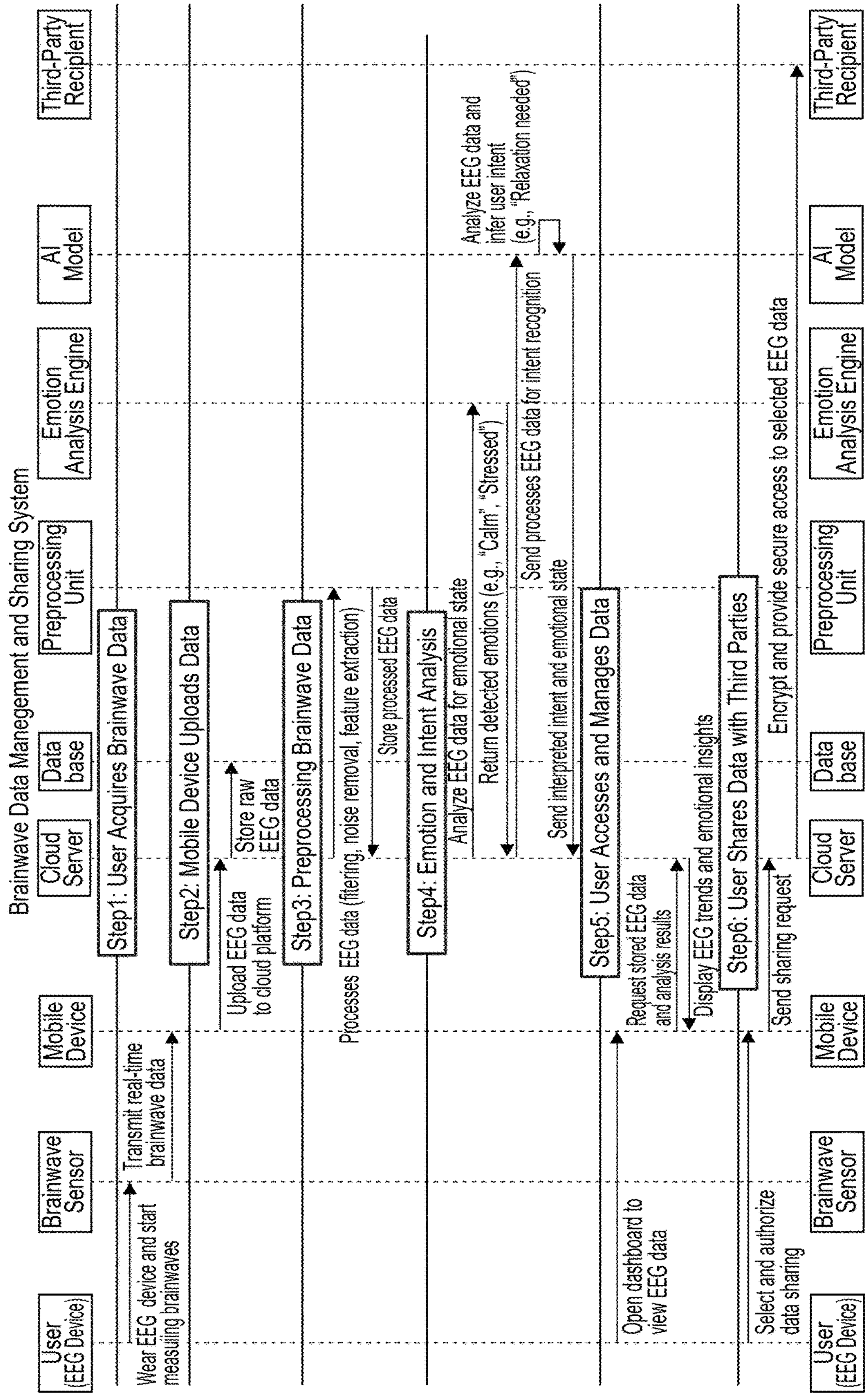
FIG. 19 is a sequence diagram showing the flow of data processing system processing in Example 2 of exemplary embodiment when the emotional engine is combined.

The flow of the identification process in Example 2 is described in FIG. 19.

Program Processing Flow

Step 1:

User Obtains EEG Data

Input: User's brain waves

Output: EEG data

Specific Operation: The user wears a dedicated EEG measurement device on the head to acquire EEG data in real time. The device detects the user's brain waves with sensors and stores them as digital data.

Step 2:

The terminal uploads EEG data to the platform

Input: EEG data

Output: Data uploaded to the platform

Specific operation: The user opens the application on the terminal, selects the EEG data acquired and presses the "Upload" button. The terminal sends the data to the platform.

Step 3:

Server Receives EEG Data and Stores it in a Database

Input: Uploaded EEG data

Output: Data stored in database

Specific Operation: The server receives EEG data sent from the terminal and stores it in a relational database such as MySQL or PostgreSQL. The database also stores metadata such as user IDs and time stamps.

Step 4:

Server Preprocesses EEG Data

Input: EEG data stored in database

Output: preprocessed data

Specifics: The server runs Python scripts and uses libraries such as NumPy and Pandas to clean and filter data. Specifically, it performs noise removal and missing value completion.

Step 5:

Server analyzes EEG data

Input: preprocessed data

Output: Analysis results (e.g. classification of emotional states)

Specific operation: The server runs machine learning models using libraries such as TensorFlow and PyTorch to classify emotional states from EEG data. The analysis results are output as data indicating the user's emotional state and intentions.

Step 6:

User Manages EEG Data

Input: Analysis results and original EEG data

Output: Controlled data (e.g. filtered data display)

Specific behavior: users access the platform's dashboard to review analysis results. Data can be filtered and displayed for specific time periods.

Step 7:

Users Share EEG Data with Third Parties

Input: Managed data

Output: Shared data

How it specifically works: The user presses the "Share" button on the dashboard, enters the contact information of a third party (e.g., a medical institution), and gives permission to share. The server encrypts the data and sends it to the third party using HTTPS.

Thus, by performing specific actions in each step, users can effectively manage their own EEG data and share it with third parties as needed.

Example of Application 2

Next, example of application 2 of example of implement 2 will be described. In the following description, data processing device 12 is referred to as the "server" and smart device 14 is referred to as the "terminal.

Conventional brain-machine interfaces (BMIs) can collect and analyze users' brain wave data, but lacked a means to share that data with third parties in a secure and efficient manner. In addition, no system existed to analyze the user's emotional state in real time and take appropriate action when abnormalities were detected. This made it difficult to share data with medical and research institutions, and prevented users from improving the accuracy of their health management and biometric identification.

The specific processing by the specific processing unit 290 of the data processing device 12 in example of application 2 is realized by the following means.

In this invention, the server provides means for generating a minimally invasive and highly accurate brain-machine interface (BMI) that combines brain waves and generative AI, means for providing a platform for disseminating the BMI to society, means for providing intuitive brain activity-based communication services, metaverse interface, health management services, and biometric authentication services provided through the platform; collecting users' brain wave data in real time, encrypting it, and sharing it with third parties; analyzing users' emotional states and alerting them if any abnormality is detected. The system includes the following. This enables the secure and efficient sharing of the user's EEG data and strengthens cooperation with medical and research institutions. In addition, the user's emotional state can be monitored in real time, and if an abnormality is detected, a quick response can be made to improve the accuracy of health management and biometric authentication.

Brain waves" are electrical signals generated by neural activity in the brain.

Generative AI" is a type of artificial intelligence, a system that has the ability to generate new data and information based on input data.

The term "minimally invasive" refers to less burden or damage to the body.

A "brain-machine interface" (BMI) is an interface that uses brain waves to operate a machine or computer.

A "platform" is the underlying system or environment that provides a specific function or service.

An "intuitive communication service" is one that allows users to interact with information in a natural way.

A "metaverse interface" is an interface that allows users to operate and experience things in a virtual space.

Health Management Service" is a service that monitors the health status of users and provides appropriate advice and support.

Biometric services" are services that use a user's biometric information to verify identity.

Encryption" is a technique whereby data is converted using a specific algorithm so that it cannot be easily deciphered by a third party.

An "emotional state" is the emotional state a user is feeling at a particular moment in time.

An "alert" is a notification or warning of an abnormality or emergency.

The following system configuration is an exemplary embodiment of this invention.

System Configuration

The system will include hardware and software to collect the user's EEG data and analyze it using a generative AI. Specifically, the system will include the following elements.

1. EEG sensor: A device that collects the user's brain waves in real time. The EEG sensor is worn on the user's head and measures the electrical activity of the brain.
2. smart device: a device used to receive, encrypt, and analyze data from the EEG sensor. A dedicated application is installed on the smartphone.
3. server: provides a platform for receiving encrypted EEG data and sharing it with third parties (medical and research institutions) as needed. The server shall include software to manage and share the data.

Program Processing

The server will perform the following processes

1. EEG data collection: EEG sensors collect the user's EEG data in real time and transmit it to the smartphone.
2. data encryption: The smartphone encrypts the received EEG data. Fernet, a cryptography library, is used for encryption.
3. data sharing: encrypted data is sent from the smartphone to the server. The server shares the received data with a designated third party (medical or research institution).
4. emotional state analysis: Smartphones analyze brain wave data to identify the user's emotional state. If an abnormality is detected, the smart phone will send out an alert.

Hardware and Software Used

EEG sensor: a device that collects the user's brain waves.

Smart devices: devices that receive, encrypt, parse, and share data.

Server: A platform for managing and sharing data.

Cryptography library: Software used to encrypt data.

Requests library: Software used to transmit data.

Concrete Example

For example, consider a case where brain wave data is collected when a user is stressed and sent to a medical facility. An EEG sensor collects the user's brain waves and transmits them to a smart phone. The smartphone encrypts the received data and sends it to the server. The server shares the encrypted data with the medical institution. The medical institution analyzes the received data and evaluates the user's stress state.

Example of Prompt Text

Create a Python program that collects the user's EEG data, encrypts it, and sends it to a designated health care provider. The EEG data can be virtual data. Use the cryptography library Fernet for encryption and the requests library to send the data."

The above is an exemplary embodiment of this invention.

Figure 20:
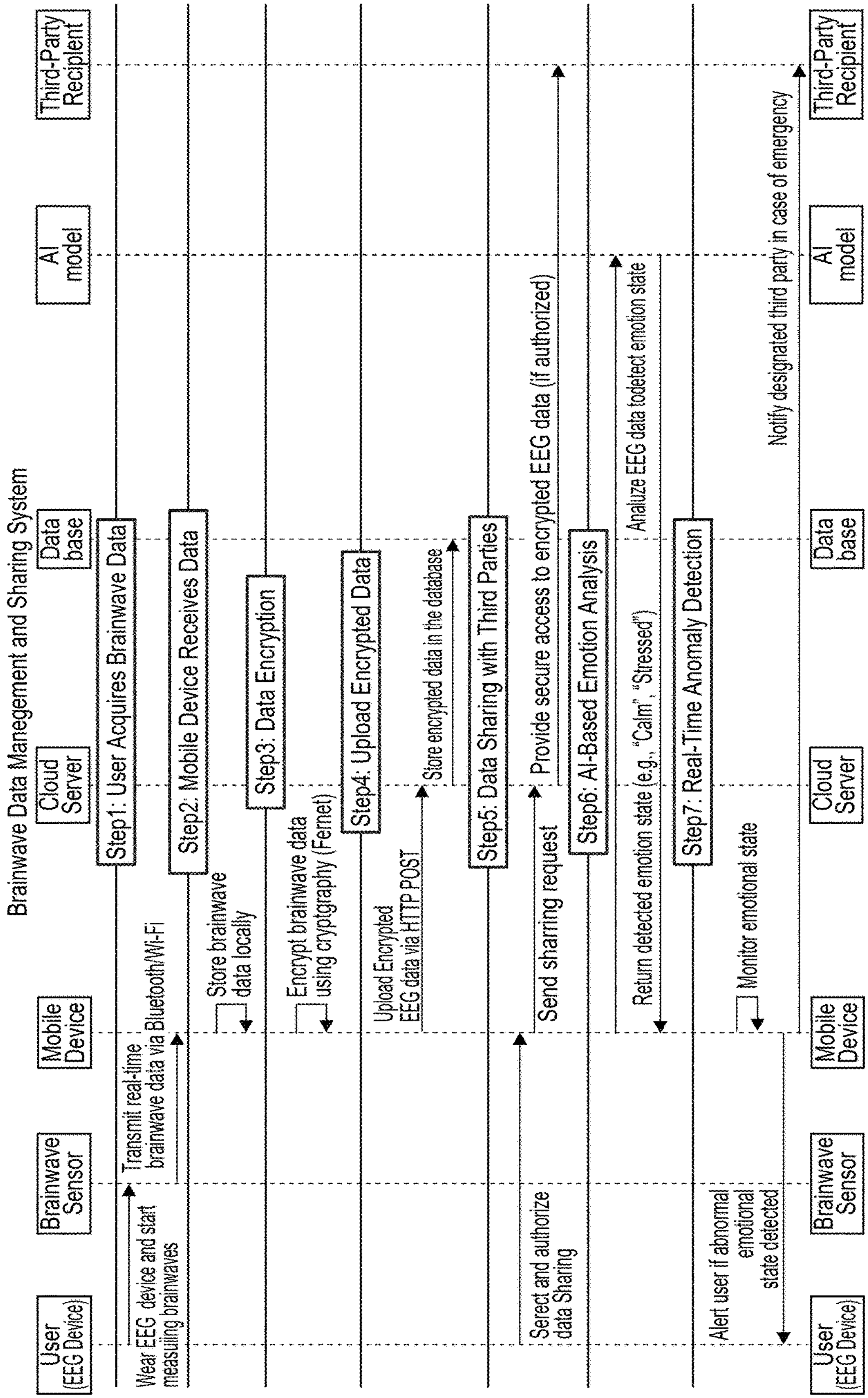
FIG. 20 is a sequence diagram showing the flow of data processing system processing in example of application 2 of example of implement when combined with an emotion engine.

The flow of the identification process in example of application 2 is described in FIG. 20.

Step 1:

The user wears an EEG sensor. The EEG sensor collects the user's EEG data in real time. The input is the user's EEG signal and the output is the raw data collected by the EEG sensor.

Step 2:

The terminal (smartphone) receives EEG data from the EEG sensor. The terminal acquires the data using wireless communication such as Bluetooth or Wi-Fi. The input is the raw data transmitted from the EEG sensor and the output is the EEG data stored in the terminal.

Step 3:

Encrypt the EEG data received by the terminal. Fernet from the cryptography library is used for encryption. The input is the EEG data stored in the terminal and the output is the encrypted EEG data. The specific operation is to generate an encryption key and encrypt the EEG data with the key.

Step 4:

The terminal sends encrypted EEG data to the server. The requests library is used for transmission. The input is the encrypted EEG data and the output is the data sent to the server. The specific operation is to send the data using an HTTP POST request.

Step 5:

The server stores the encrypted EEG data received. The server manages the data using a database. The input is the encrypted data sent from the terminal and the output is the encrypted data stored in the database.

Step 6:

The server shares encrypted EEG data with third parties (medical and research institutions) as needed. Secure communication protocols are used for sharing. The input is the encrypted data stored in the database and the output is the data sent to the third party. The specific operation is to authenticate the third party and send the data if the authentication is successful.

Step 7:

The terminal analyzes EEG data to identify the user's emotional state. A generative AI model is used for the analysis. The input is the EEG data stored in the terminal and the output is the emotional state as the result of the analysis. Specifically, the EEG data is input to the AI generation model, and the emotional state is estimated.

Step 8:

The terminal monitors the emotional state and sends out an alert when an abnormality is detected. The input is the emotional state as an analysis result, and the output is an alert when an abnormality is detected. Specifically, when the emotional state exceeds a predefined threshold, a notification is sent to the user or a designated third party.

Example 3

Next, example 3 of exemplary embodiment of implement will be described. In the following description, data processing device 12 is referred to as the "server" and smart device 14 is referred to as the "terminal.

Conventional brain-machine interfaces (BMI) require high accuracy in analyzing a user's brain waves, but it has been difficult to achieve high accuracy in a minimally invasive manner. In addition, there was a lack of a system to provide real-time feedback of the analysis results to the user, which could not immediately reflect the user's intentions or emotional state. Furthermore, users lacked the ability to manage their own EEG data and share it with third parties as needed.

The specific processing by the specific processing unit 290 of the data processing device 12 in Example 3 is realized by the following means. In this invention, the server includes the following means: the server measures the user's EEG data and transmits it to the server in real time; the server analyzes the EEG data and identifies the user's emotional state and intentions; and the server stores the analysis results in a database and transmits them to the terminal. This enables minimally invasive and highly accurate EEG analysis, which can reflect the user's intentions and emotional state in real time. It also allows users to manage their own EEG data and share it with third parties as needed.

Brain Machine Interface (BMI) is a technology that uses brain waves to control computers and other devices.

Generative AI" is a type of artificial intelligence that has the ability to generate new data and information based on input data.

A "platform" is the underlying system or environment that provides a specific service or function.

EEG data" is data that electrically measures the user's brain activity and reflects emotional states and intentions.

Real-time" means that data is measured and processed immediately.

Analysis" is the process of processing measured data to extract specific information or patterns.

The "emotional state" is a state that indicates the user's current emotion or mood.

Intent is what the user is trying to do or wants.

A "database" is a system that stores data in an organized manner and can be retrieved and updated as needed.

Feedback" is the response or information provided by the system to the user.

Minimally invasive" means less physical strain or discomfort to the user.

High precision" means that the measurement and analysis of data is extremely accurate.

A "virtual reality interface" is a means by which a user interacts with a virtual reality environment.

Health Management Service" is a service that monitors the user's health status and provides appropriate advice and support.

A "biometric service" is a service that uses a user's biometric information to authenticate an individual.

This invention is a system that provides a minimally invasive and highly accurate brain-machine interface (BMI) that combines EEG and generative AI. The system measures and analyzes the user's EEG data in real time to identify the user's emotional state and intentions, and provides feedback based on them.

Hardware and Software Used

Hardware (esp. Computer)

- EEG measurement devices: Devices to measure the user's brain waves (e.g., EEG headsets)
- Terminal: Device (e.g., smart device, tablet, PC) that connects to the EEG measurement device and sends data to the server
- Server: Computer system for receiving and analyzing EEG data Software

- Data transmission program: A program installed in the terminal to transmit EEG data to the server
- Data analysis programs: Programs installed on the server to analyze EEG data (e.g., FFT analysis using Python)
- Database management system: A system for storing analysis results and retrieving and updating them as needed.
- Feedback program: A program installed on the terminal to display the results of the analysis to the user.

Specific System Operation

User Behavior

The user wears an EEG measurement device (e.g., EEG headset) and connects it to the terminal. The user performs certain actions to generate EEG data. For example, if the user is relaxed, the EEG data has a specific frequency component.

Terminal Operation

The terminal measures the user's brain waves in real time and transmits them to the server using a data transmission program. The terminal waits for a response from the server to confirm that the data transmission was successful.

Server Operation

The server receives the EEG data sent from the terminal. The received data is analyzed using a data analysis program. Specifically, the FFT (Fast Fourier Transform) is used to break down the EEG data into its frequency components and extract specific patterns. For example, the intensity of alpha and beta waves is calculated to identify the user's emotional state.

Save and Send Analysis Results

The server stores the analysis results in a database. The stored data includes user ID, measurement date and time, and analysis results (emotional state and intention). This makes it possible to refer to the data later. The server sends the analysis results to the terminal. Secure communication protocols (e.g. HTTPS) are used for transmission.

Terminal Feedback

The terminal displays the analysis results received from the server to the user. The display uses a graphical user interface (GUI). For example, if the user is relaxed, the terminal displays "relaxed state" and suggests appropriate actions (e.g., playing relaxing music).

Examples of Specific Examples and Prompt Sentences

Concrete Example

For example, when a user uses an intuitive communication service, the following steps are taken 1. the user puts on the EEG headset and connects it to the terminal.

The terminal measures EEG data in real time and sends it to the server.

3. the server receives the EEG data and analyzes it using FFT. For example, if the intensity of alpha waves is high, the server determines that the user is relaxed.

The results of the analysis are stored in a database. For example, data such as "User ID: 12345, Date: 2023 Oct. 1 10:00, State: Relaxed" will be saved.

The server sends the analysis results to the terminal. The terminal displays "Relaxed" and suggests playing relaxing music.

6. the user relaxes by playing relaxing music as suggested by the terminal.

Example of Prompt Text

You will generate a program that analyzes the user's EEG data to identify their emotional state and communicate intuitively with them. The hardware used is an EEG headset and the software is Python. Specifically, the program will analyze EEG data using FFT and calculate the intensity of alpha and beta waves to identify emotional states."

Figure 21:
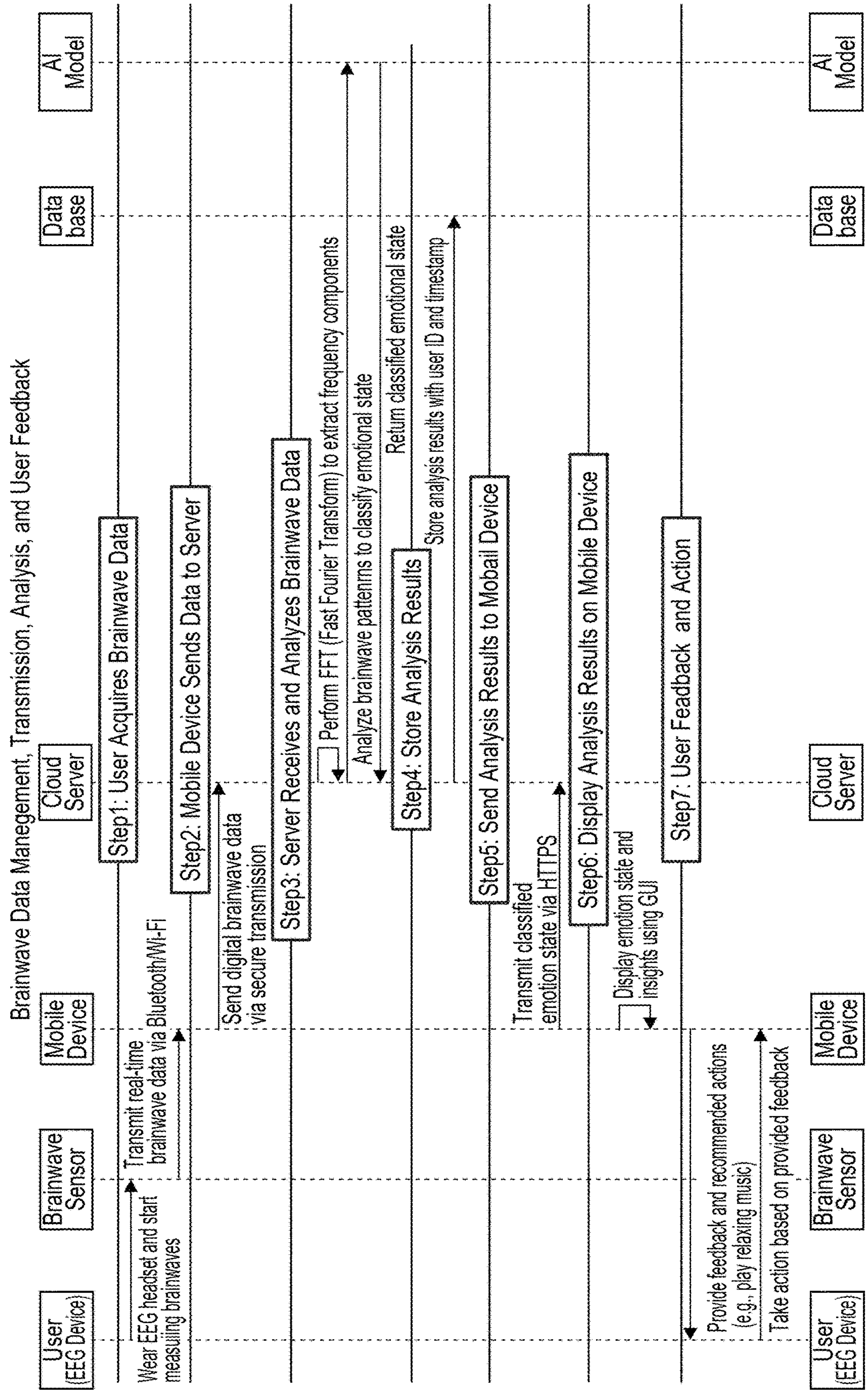
FIG. 21 is a sequence diagram showing the flow of data processing system processing in Example 3 of exemplary embodiment when the emotional engine is combined.

This specific description of the operation of the entire system clearly shows the exemplary embodiment of the invention. The flow of the specific process in Example 3 is explained using FIG. 21.

Step 1: Measure the User's EEG Data

The user wears an EEG measurement device (e.g., EEG headset). The device measures the user's EEG in real time and converts it into a digital signal. The input is the user's EEG and the output is the digitized EEG data. Specifically, the device contacts the user's scalp and detects the electrical signals.

Step 2: Transmission of EEG Data

The terminal transmits the measured EEG data to the server via Bluetooth or Wi-Fi. The input is the digitized EEG data and the output is the data sent to the server. Specifically, the terminal executes a data transmission program and sends the data to the IP address of the server.

Step 3: Receive and Analyze EEG Data by Server

The server receives the EEG data sent from the terminal. The input is the EEG data transmitted from the terminal and the output is the analysis result. The server executes FFT (Fast Fourier Transform) using Python to decompose the EEG data into its frequency components. Specifically, the server runs a data analysis program to calculate the intensity of alpha and beta waves.

Step 4: Save Analysis Results

The server stores the analysis results in a database. The input is the analysis results and the output is the data stored in the database. Specifically, the server uses a database management system to store user IDs, measurement dates and times, and analysis results.

Step 5: Transmission of Analysis Results

The server sends the analysis results to the terminal. The input is the analysis results stored in the database and the output is the analysis results sent to the terminal. As a specific operation, the server sends data using a secure communication protocol (e.g., HTTPS).

Step 6: Display of Analysis Results by Terminal

The terminal displays the analysis results received from the server to the user. The input is the analysis results sent from the server and the output is the information displayed to the user. Specifically, the terminal executes a feedback program and displays the analysis results using a graphical user interface (GUI).

Step 7: Feedback to Users

The user confirms his/her own emotional state and intentions based on the feedback provided by the terminal. The input is the feedback information from the terminal and the output is the user's next action. Specifically, the user takes actions such as playing relaxing music according to the terminal's suggestions.

Example of Application 3

Next, example 3 of application of example of implement 3 will be described. In the following description, data processing device 12 is referred to as the "server" and smart device 14 is referred to as the "terminal.

Conventional brain-machine interfaces (BMI) can understand intentions by analyzing the user's brain waves, but there are issues with their accuracy and real-time performance. In addition, intuitive operation and emotion-based action control within the metaverse were difficult, and there was a need to improve the user experience. Furthermore, there was a lack of a user-friendly system for managing EEG data and sharing it with third parties.

The specific processing by the specific processing unit 290 of the data processing device 12 in example of application 3 is realized by the following means.

In this invention, the server provides means for generating a minimally invasive and highly accurate brain-machine interface (BMI) that combines brain waves and generative AI, means for providing a platform for disseminating the BMI in society, means for providing, through the platform, intuitive communication services, metaverse interface, health management services, and biometric authentication services provided through the platform; means for controlling actions in the metaverse by analyzing brain waves of users in real time and understanding their emotions and intentions; and means for controlling actions in the metaverse based on the emotional state of users. means to control actions in the metaverse based on the user's emotional state. This allows the user to intuitively perform operations in the metaverse using brain waves, thereby enabling action control based on emotions. In addition, EEG data can be easily managed and shared with third parties.

Brain waves" are electrical signals generated by neural activity in the brain.

Generative AI is an artificial intelligence technology that generates new information and content based on data.

A "brain-machine interface" (BMI) is an interface that analyzes brain waves to control machines and computers.

A "platform" is the underlying system or environment that provides a specific service or function.

Intuitive communication service" is a service that analyzes a user's brain waves to understand their emotions and intentions, and communicates accordingly.

A "metaverse interface" is an interface for controlling behavior in virtual reality (VR) and augmented reality (AR) worlds.

The "Health Management Service" is a service that analyzes users' brain waves to determine their stress levels and sleep conditions, and suggests health management based on this information.

Biometric authentication service" is a personal authentication service that analyzes a user's brain wave patterns.

Real-time" refers to immediate processing and reaction without delay.

The "emotional state" is the emotional state analyzed from the user's brain waves.

The term "action control" refers to controlling the behavior of a system or avatar based on a user's intentions or emotions.

The system for implementing this invention includes: means for generating a minimally invasive and highly accurate brain-machine interface (BMI) by combining brain waves and generative AI; means for providing a platform for disseminating the BMI in society; means for providing intuitive communication services, metaverse interface, health management services, and biometric authentication services using brain activity provided through the platform; means for controlling actions in the metaverse based on the user's emotional state by analyzing the user's brain waves in real time and understanding the user's emotions and intentions; and means for controlling actions in the metaverse based on the user's emotional state. means to provide intuitive communication services, metaverse interface, health management services, and biometric authentication services using brain activity provided through the platform; means to control actions in the metaverse by analyzing the user's brain waves in real time and understanding emotions and intentions; means to control actions in the metaverse based on the user's emotional state. Means to control actions in the metaverse based on the user's emotional state, including.

System Configuration

The server will use an EEG sensor, a head-mounted display (HMD), and a generative AI to configure the system. The EEG sensor acquires the user's brain waves in real time, and the HMD provides the user with visual information in the metaverse. The generative AI analyzes the acquired EEG data to understand the user's emotions and intentions.

Program Processing

The server acquires EEG data using the BrainFlow library and filters the data to remove noise. Next, the data is analyzed using a generative AI to detect the user's emotion (e.g., joy). Based on the detected emotion, actions in the metaverse are controlled. Specifically, if the user has the emotion of joy, the avatar is controlled to dance a joyful dance.

Hardware and Software Used

- Hardware: EEG sensor (e.g., BrainFlow-compatible device), head-mounted display (HMD)
- Software: Python, BrainFlow library Concrete Example For example, consider a scene where a user wears an HMD and uses brainwave sensors to control their behavior in the metaverse. If the user has the emotion of joy, the avatar will dance a joyful dance. This allows the user to intuitively operate within the metaverse and control actions based on emotions.

Example of Prompt Text

Example of prompt sentences to be entered into a generative AI model:

Create a Python program that analyzes the user's brain wave data to detect emotions and control actions in the metaverse. If the user has a joyful emotion, have the avatar perform a joyful dance.

In this way, an intuitive metaverse interface can be realized using brain waves.

Figure 22:
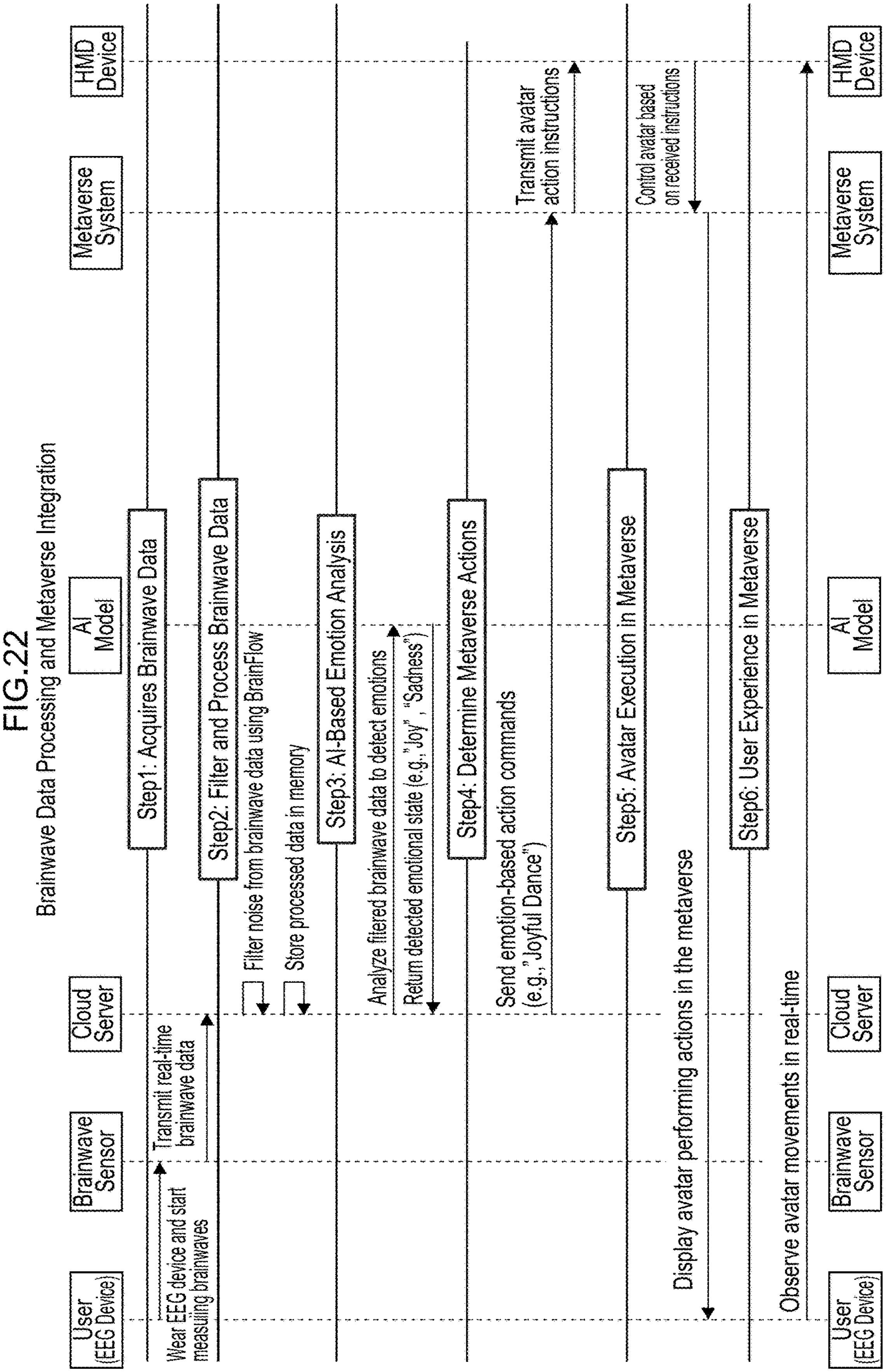
FIG. 22 is a sequence diagram showing the flow of data processing system processing in example of application 3 of example of implement when combined with an emotion engine.

The flow of the identification process in example of application 3 is described in FIG. 22.

Step 1:

The server uses EEG sensors to acquire the user's EEG data in real time.

- Input: User's EEG signal
- Output: Raw EEG data
- Specific operation: The server collects data from EEG sensors using the BrainFlow library and stores this in memory.

Step 2:

The server filters the acquired EEG data to remove noise.

- Input: Raw EEG data
- Output: Filtered EEG data
- Specific operation: The server uses the filtering function of the BrainFlow library to remove noise in specific frequency bands.

Step 3:

The server inputs the filtered EEG data to the generative AI to analyze the user's emotions.

- Input: Filtered EEG data
- Output: User's emotional state (e.g., joy, sadness)
- Specific operation: The server inputs data into the data generation AI model and runs an emotion identification model to identify the user's emotion.

Step 4:

The server determines actions in the metaverse based on the analyzed emotional state.

- Input: User's emotional state
- Output: Action instructions in the metaverse (e.g., Dance of Joy)
- Specific operation: The server determines the action according to the emotional state and sends the instructions to the metaverse system.

Step 5:

The terminal (HMD) controls avatars in the metaverse based on action instructions received from the server.

- Input: Action instructions in the metaverse
- Output: Avatar behavior (e.g., joyful dancing)
- Specific operation: The terminal provides visual information to the user through the HMD and controls the avatar to perform the specified action.

Step 6:

Users visually see the action in the metaverse through the HMD.

- Input: Avatar behavior
- Output: Visual information (e.g., avatar dancing for joy scene)
- Specific behavior: The user wears an HMD to visually confirm the avatar's behavior in the metaverse in real time.

The specific processing unit 290 sends the results of the specific processing to the smart device 14. In smart device 14, control unit 46A causes output device 40 to output the results of the specific processing. Microphone 38B acquires audio indicating user input to the results of the specific processing. The control unit 46A transmits the voice data indicating the user input acquired by the microphone 38B to the data processing device 12. In data processing device 12, specific processing unit 290 acquires the voice data.

The data generation model 58 is a so-called Generative AI (Artificial Intelligence). An example of a data generation model 58 is a generative AI such as ChatGPT (registered trademark) (Internet search <URL: https://openai.com/blog/chatgpt>). The data generation model 58 is obtained by having a neural network perform deep learning. Prompts containing instructions are input to the data generation model 58, as well as data for inference, such as voice data indicating voice, text data indicating text, and image data indicating images. The data generation model 58 infers the input data for inference according to the instructions indicated by the prompts, and outputs the results of the inference in data formats such as voice data and text data. Here, reasoning refers to, for example, analysis, classification, prediction, and/or summarization.

Another example of generative AI is Gemini (registered trademark) (Internet search <URL: https://gemini.google-.com/?hl=ja>).

In the above exemplary embodiment, an example of implement in which the specific processing is performed by the data processing device 12 is given, but the technology of the present disclosure is not limited to this, and the specific processing may be performed by the smart device 14.

Second Exemplary Embodiment

Figure 3:
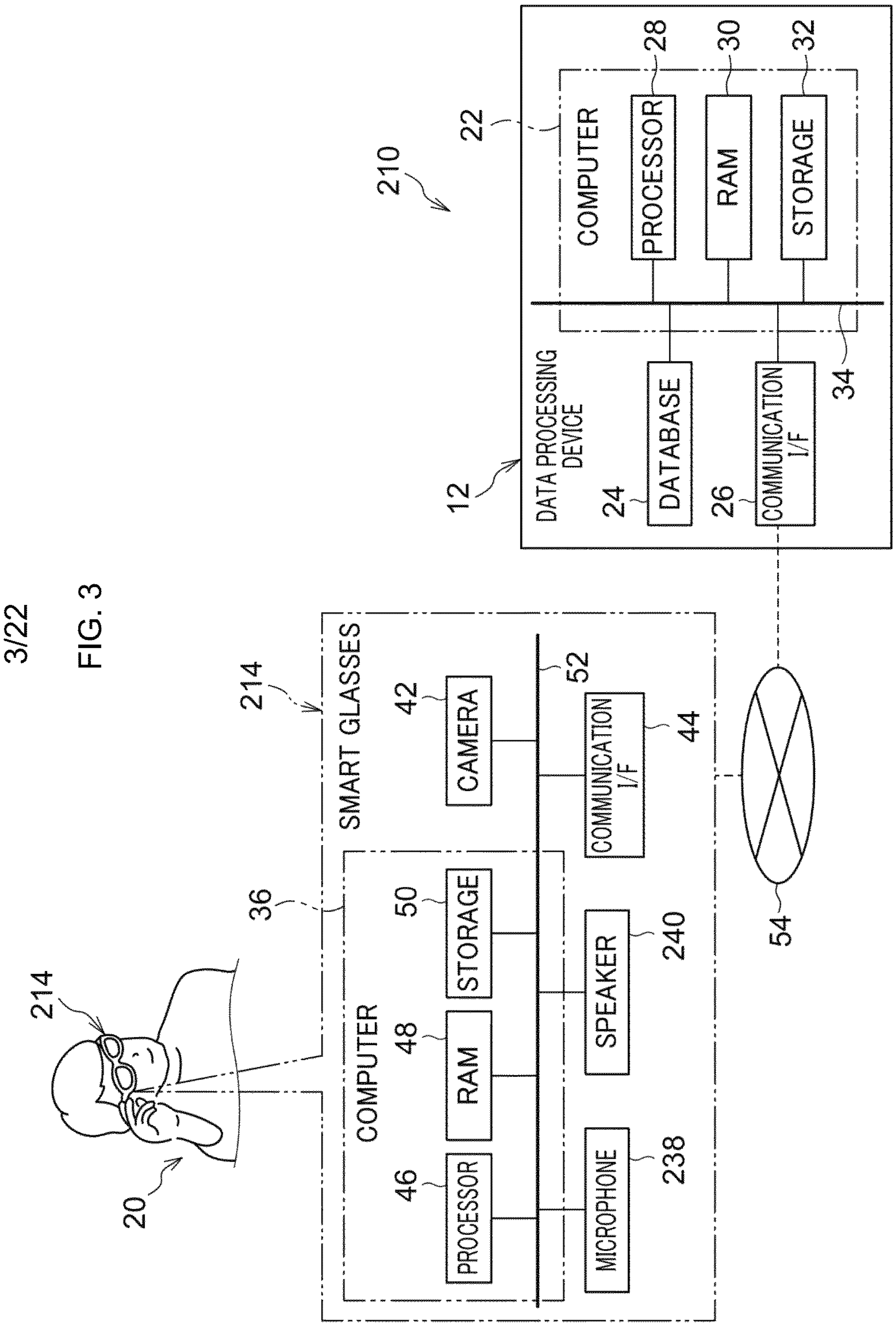
FIG. 3 is a conceptual diagram showing an example of implement of a data processing system for the second exemplary embodiment.

FIG. 3 shows an example of implement of a data processing system 210 for the second exemplary embodiment.

As shown in FIG. 3, data processing system 210 includes data processing device 12 and smart glasses 214. An example of the data processing device 12 is a server.

The data processing device 12 has a computer 22, a database 24, and a communication I/F 26. Computer 22 is an example of a "computer" in the context of the present disclosure. Computer 22 has a processor 28, RAM 30, and storage 32. The processor 28, RAM 30, and storage 32 are connected to a bus 34. The database 24 and the communication I/F 26 are also connected to the bus 34. The communication I/F 26 is connected to a network 54. An example of a network 54 is a Wide Area Network (WAN) and/or a Local Area Network (LAN).

Smart glasses 214 have a computer 36, microphone 238, speaker 240, camera 42, and communication I/F 44. The computer 36 has a processor 46, RAM 48, and storage 50. Processor 46, RAM 48, and storage 50 are connected to bus 52. The microphone 238, speaker 240, and camera 42 are also connected to the bus 52.

Microphone 238 accepts the voice emitted by user 20 and receives instructions, etc., from user 20. The microphone 238 captures the voice emitted by the user 20, converts the captured voice into voice data, and outputs the data to the processor 46. Speaker 240 outputs audio in accordance with instructions from processor 46.

Camera 42 is a compact digital camera equipped with an optical system, such as a lens, aperture, and shutter, and an image sensor, such as a CMOS (Complementary Metal-Oxide-Semiconductor) image sensor or CCD (Charge Coupled Device) image sensor. It is a small digital camera equipped with an image sensor such as a CMOS (Complementary Metal-Oxide-Semiconductor) image sensor or CCD (Charge-Coupled Device) image sensor, and images the surroundings of the user 20 (for example, the imaging range defined by an angle of view equivalent to the field of view of an average healthy person).

The communication I/F 44 is connected to the network 54. The communication I/Fs 44 and 26 are responsible for transferring and receiving various information between the processor 46 and the processor 28 via the network 54. The transfer of various information between the processor 46 and the processor 28 using the communication I/Fs 44 and 26 is performed in a secure manner.

Figure 4:
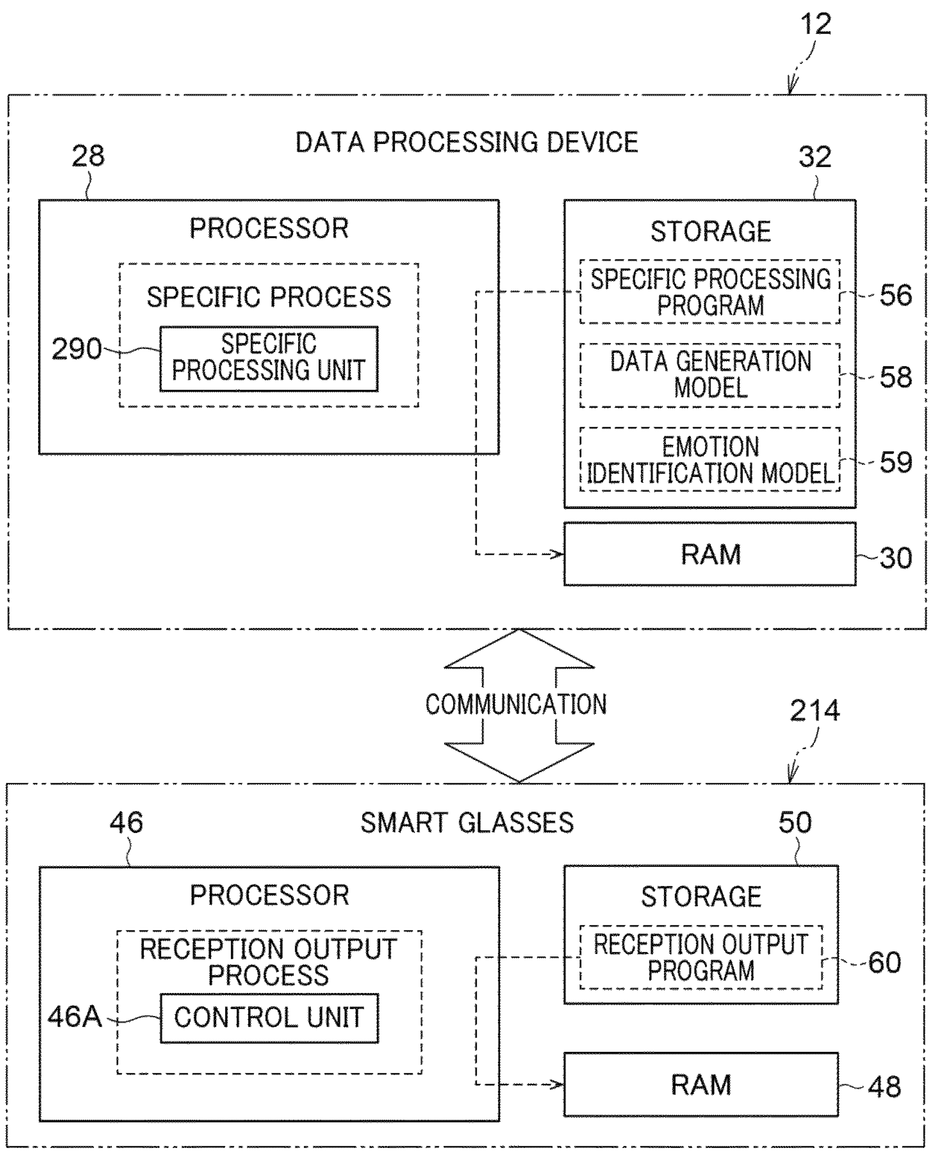
FIG. 4 is a conceptual diagram showing an example of the key functions of the data processing device and smart glasses of the second exemplary embodiment.

FIG. 4 shows an example of the key functions of data processing device 12 and smart glasses 214. As shown in FIG. 4, in data processing device 12, specific processing is performed by processor 28. The storage 32 contains a specific processing program 56.

The specific processing program 56 is an example of a "program" for the technology of the present disclosure. The processor 28 reads the specific processing program 56 from the storage 32 and executes the read specific processing program 56 on the RAM 30. The specific processing is realized by the processor 28 operating as the specific processing unit 290 according to the specific processing program 56 executed on RAM 30.

The data generation model 58 and emotion identification model 59 are stored in storage 32. The data generation model 58 and emotion identification model 59 are used by the specific processing unit 290.

In smart glasses 214, the reception output process is performed by processor 46. The reception output program 60 is stored in storage 50. Processor 46 reads reception output program 60 from storage 50 and executes the read reception output program 60 on RAM 48.

The reception output process is realized by the processor 46 operating as the control unit 46A according to the reception output program 60 executed by the processor 46 on RAM 48.

Next, the specific processing by the specific processing unit 290 of the data processing device 12 is described.

Example of Implement 1

One exemplary embodiment of this invention is a system that combines brain waves and a generative AI to generate a brain-machine interface (BMI). This system analyzes the user's brain waves in real time and inputs the results to the generative AI. The generative AI uses this brain wave data to understand the user's intentions and generates output based on them. For example, when a user wants a cup of coffee, the brain waves are analyzed, and the generative AI understands the user's intention and can take action such as "make coffee. Example of implement 2."

Another exemplary embodiment of this invention is a platform to promote BMI in society. This platform has a function that allows users to manage their own EEG data and share it with third parties as needed. For example, users can manage their own EEG data on the platform and share it with medical and research institutions to obtain more accurate medical services and research results.

Example of Implement 3

In addition, one exemplary embodiment of the invention is new services offered through the platform. These services include intuitive communication services using brain activity, metaverse interface, health management services, and biometric authentication services. For example, intuitive communication services analyze a user's brain waves to understand their emotions and intentions, and communicate based on this information. Also, in metaverse interfaces, the user's brain waves are analyzed to control their behavior in VR and AR worlds. The health management service analyzes the user's brain waves to understand their stress level, sleep state, etc., and proposes health management based on this information. The biometric authentication service analyzes the user's brain wave patterns to perform personal authentication.

The following is a description of the process flow for each example of implement.

Example of Implement 1

Step 1: The user has a specific thought or intention.
Step 2: The system captures and analyzes the user's brain waves in real time.
Step 3: Input the analysis results to the generative AI.
Step 4: The generative AI understands the user's intentions based on the brain wave data and generates output based on it. For example, it will perform an action such as "make coffee.

Example of Implement 2

Step 1: Users access the platform and upload their own EEG data.
Step 2: The platform manages the user's EEG data and shares it with third parties as needed. For example, sharing with medical and research institutions will enable more accurate medical services and research results.

Example of Implement 3

Step 1: The user selects a specific service through the platform. For example, intuitive communication services, metaverse interface, health care services, biometric services, etc.
Step 2: The selected service analyzes the user's brain waves and provides services based on them. For example, an intuitive communication service analyzes the user's brain waves to understand his/her feelings and intentions and communicates based on them.

Example 1

The following is an example of exemplary embodiment of implement. In the following description, the data processing device 12 will be referred to as the "server" and the smart glasses 214 will be referred to as the "terminal".

Conventional brain-machine interfaces (BMIs) are inaccurate in analyzing the user's brain waves, making it difficult to understand the user's intentions in real time. In addition, these systems were highly invasive and burdensome to users. Furthermore, the management and sharing of EEG data is not easy, which has hindered its widespread use in society.

The specific processing by the specific processing unit 290 of the data processing device 12 in Example 1 is realized by the following means.

In this invention, the server provides a means for collecting brain waves of a user in real time, a means for analyzing the collected brain wave data, a means for inputting the analyzed brain wave data into a generative AI model, a means for the generative AI model to understand the intent of the user and generate outputs based thereon, a means for providing feedback of the generated means to provide a platform for the dissemination of the brain-machine interface (BMI) to society, and to provide intuitive communication services, virtual space services, biometric authentication services, and other services using brain activity that are provided through the platform. interface, health management services, and biometric authentication services provided through the platform. This enables highly accurate and minimally invasive analysis of users' brain waves and real-time understanding of their intentions. It will also facilitate the management and sharing of EEG data and promote its widespread use in society.

The term "user" refers to the individual who uses the brain-machine interface (BMI).

Brain waves" are electrical signals generated by the user's brain.

Real-time" means that data is processed and analyzed as soon as it is generated.

The term "means of collection" refers to devices and methods used to detect and acquire data on the user's brain waves.

The term "means of analysis" refers to methods and devices used to process the collected EEG data and infer the user's intent.

The term "generative AI model" refers to an artificial intelligence model that understands the user's intent based on the input data and generates output based on that intent.

The term "means of input" refers to the methods and devices used to provide the analyzed EEG data to the generative AI model.

Output" refers to the results and suggestions generated by the generative AI model based on its understanding of the user's intentions.

The term "means of feedback" refers to the methods and devices used to communicate the generated output to the user.

The term "platform" refers to the systems and services that serve as the foundation for the diffusion of brain-machine interfaces (BMIs) in society.

The term "communication service" refers to a service that uses brain waves to allow users to intuitively exchange information with others.

The term "virtual space interface" refers to an interface that uses brain waves to allow users to operate and move within a virtual space.

The term "health management service" refers to a service that uses users' brain wave data to monitor and manage their health.

The term "biometric service" refers to a service that uses a user's brain wave data to authenticate an individual.

This invention is a brain-machine interface (BMI) system that analyzes a user's brain waves in real time and inputs the results into a generative AI model to understand the user's intentions and generate output based on them. The system is implemented using the following hardware and software Hardware and Software Configuration EEG Sensor The user wears an EEG sensor on the head. This sensor detects the user's brain waves in real time and collects the data as electrical signals.

Server

The server receives EEG data transmitted from the EEG sensor. The received data is sent to the terminal for analysis.

Terminal

The terminal analyzes the EEG data sent from the server. An EEG analysis library using Python is used for the analysis. The terminal sends the analysis results to the server.

Generative AI Model

The server inputs the analyzed brain wave data into a generative AI model (e.g., OpenAI's GPT-4). The generative AI model understands the user's intention based on the input data and generates output based on it.

Feedback

The generated output is sent to the terminal through the server, which then feeds it back to the user. The user can then take the suggested action.

Concrete Example

For example, consider the case where a user wants to listen to music. An EEG sensor collects the user's EEG data, and the terminal analyzes the data. If the analysis results indicate the intention to "listen to music," the following prompt statement is entered into the generative AI model:

The user's EEG data has detected the intention to listen to music. Please suggest actions to play appropriate music.

The generative AI model generates an output "play music" based on this prompt sentence and feeds it back to the user through the terminal. The user can then play the music according to the suggested action.

In this way, the system can analyze the user's EEG with high accuracy and minimally invasive, and understand their intentions in real time. In addition, the system will facilitate the management and sharing of EEG data and promote its widespread use in society.

The flow of the identification process in Example 1 is described in FIG. 11.

Step 1:

The user wears an EEG sensor on his/her head. The EEG sensor detects the user's brain waves in real time and collects the data as electrical signals. The collected EEG data is transmitted to a server.

Input: User's brain waves

Output: EEG data (electrical signals)

Step 2:

The server receives the EEG data transmitted from the EEG sensor. The received EEG data is sent to the terminal for analysis.

Input: EEG data (electrical signals)

Output: EEG data (transfer from server to terminal)

Step 3:

The terminal receives the EEG data sent from the server. The terminal analyzes the EEG data using a Python-based EEG analysis library. In the process of analysis, specific brain wave patterns are detected and the intention of the user is inferred. The analysis results are sent to the server.

Input: EEG data (transferred from server)

Output: Analysis results (user intent)

Step 4:

The server receives the analysis results sent from the terminal. The server generates prompt sentences based on the analysis results and inputs them into the generative AI model.

Input: Analysis results (user intent)

Output: Prompt statement

Step 5:

The generative AI model receives prompt sentences sent from the server. The generative AI model understands the user's intention based on the prompt sentences and generates output based on it. The generated output is sent to the server.

Input: Prompt statement

Output: Output

Step 6:

The server receives the outputs sent from the generative AI model. The server sends the output to the terminal.

Input: Output (transfer from generative AI model)

Output: Output (transfer from server to terminal)

Step 7:

The terminal receives the output sent from the server. The terminal feeds back the output to the user. The user can perform the suggested action.

Input: Output (transfer from server)

Output: Feedback to user

Example of Application 1

Next, example of application 1 of example of implement 1 will be described. In the following description, the data processing device 12 will be referred to as the "server" and the smart glasses 214 will be referred to as the "terminal.

Conventional control methods for factory robots are mainly manual operation or programmed control, which is difficult to operate intuitively. In addition, more intuitive and quicker control methods are required to improve work efficiency. Furthermore, brain-machine interface (BMI) using brain waves has been applied in the medical and entertainment fields, but has not yet been fully utilized in factory automation and robot control. To solve these problems, a system that can intuitively control factory robots using brain waves is needed The specific processing by the specific processing unit 290 of the data processing device 12 in example of application 1 is realized by the following means.

In this invention, the server provides means to generate a minimally invasive and highly accurate brain-machine interface (BMI) that combines brain waves and generative AI, means to provide a platform for disseminating the BMI in society, means to provide intuitive brain activity-based means to provide communication services, metaverse interface, health management services, and biometric authentication services using brain activity, means for factory workers to wear head-mounted displays and control factory robots using brain waves, and means for analyzing users' brain wave data in real time and inputting the results into a generative system AI, including means to understand the user's intentions and generate output based on them by inputting the results into the AI, and means to control the factory robot based on the user's intentions. This allows factory workers to intuitively control factory robots using brain waves.

Brain waves" are electrical signals generated by neural activity in the brain.

Generative AI" is a type of artificial intelligence that generates new data and outputs based on input data.

A "brain-machine interface" (BMI) is an interface that uses brain waves to control a machine or computer.

The term "minimally invasive" refers to less burden or damage to the body.

The term "high precision" refers to extreme accuracy.

A "platform" is the underlying system or environment that provides a specific service or function.

An "intuitive communication service" is one that allows users to operate and communicate intuitively.

A "metaverse interface" is an interface for performing activities and operations in a virtual space.

A "health management service" is a service designed to manage and improve a user's health status.

Biometric services" are services that authenticate individuals using biometric information such as fingerprints and facial recognition.

A "factory worker" is a worker engaged in production activities in a factory.

A "head-mounted display" is a display device worn on the head.

A "factory robot" is a robot used to automate production tasks in a factory.

Real-time" means immediate processing and reaction without delay.

User intent" is the intention or purpose of what the user wants to do or think.

Output" is the result or behavior output from a system or device.

The following system configuration and program are required to implement this invention.

System Configuration 1. hardware
   - Head-mounted displays (HMDs): Built-in EEG sensors to collect EEG data in real time.
   - Factory robots: robots that are designed to perform actions based on the user's intentions.
   - Server: analyzes EEG data and executes generative AI models.
2. Software
   - BrainwaveReader: module for collecting EEG data.
   - GenerativeAIModel: A generative AI model that analyzes brain wave data to understand user intent.
   - RobotController: Module for controlling robots based on user intent.

Explanation of Program Processing

The server first collects brain wave data from the head-mounted display (HMD); the BrainwaveReader module analyzes this data in real time and inputs it to a generative AI model (GenerativeAIModel). The generative AI model interprets the user's intentions based on the brainwave data and passes the intentions to the RobotController, which controls the factory robot based on the interpreted intentions and performs the corresponding actions.

Concrete Example

For example, if a factory worker thinks "assemble parts," the following prompt sentence is entered into the generative AI model.

Example of a Prompt Statement:

Based on the analysis of the user's brain wave data, the user believes that the user is "assembling parts". Based on this intention, instruct the robot to perform an action to assemble the parts.

Based on this prompt sentence, the generative AI model interprets the user's intention and instructs the RobotController to perform the "assemble parts" operation. As a result, the factory robot automatically starts assembling the parts.

This system allows factory workers to intuitively control factory robots using brain waves, greatly improving work efficiency.

The flow of the identification process in Example of Application 1 is described in FIG. 12.

Step 1:

A user wears a head-mounted display (HMD); the HMD has a built-in EEG sensor that collects the user's EEG data in real time. The input is the user's EEG and the output is the collected EEG data.

Step 2:

The server receives the EEG data sent from the HMD using the BrainwaveReader module; BrainwaveReader analyzes this data in real time, performing noise removal and feature extraction. The input is the EEG data from the HMD and the output is the analyzed EEG data.

Step 3:

The server inputs the analyzed EEG data to GenerativeAIModel, which is a generative AI model for interpreting user intentions based on the EEG data. The input is the analyzed EEG data and the output is the data indicating the user's intention.

Step 4:

Based on the server's interpretation of the user's intent, a prompt statement is generated. This prompt sentence is a specific description of the user's intent. The input is the data indicating the user's intent, and the output is the prompt sentence.

Step 5:

The server passes the generated prompt sentence to the RobotController, which generates specific instructions for the factory robot based on this prompt sentence. The input is the prompt sentence and the output is the instructions to the robot.

Step 6:

RobotController sends instructions to the factory robot. The factory robot executes the corresponding action based on these instructions. The input is the instruction to the robot and the output is the robot's action.

Step 7:

The user checks the operation of the factory robot through the HMD; the HMD displays the robot's operating status in real time to confirm that the robot is operating as intended by the user. The input is the operating status of the robot and the output is the image displayed on the HMD.

Example 2

Next, example 2 of exemplary embodiment of implement will be described. In the following description, the data processing device 12 will be referred to as the "server" and the smart glasses 214 will be referred to as the "terminal".

Conventional brain-machine interfaces (BMIs) lack a platform for effectively managing users' EEG data and securely sharing it with third parties. They also lacked real-time analysis of EEG data and linkage with generative AI, making it difficult to accurately understand user intentions and generate appropriate outputs. Furthermore, encryption of EEG data and management of access privileges were insufficient, and data security was not ensured.

The specific processing by the specific processing unit 290 of the data processing device 12 in Example 2 is realized by the following means. In this invention, the server is equipped with the following means: the means by which the user uploads brain wave data acquired by using a dedicated measurement device from the terminal to the server; the means by which the server stores the received brain wave data in a database; the means by which the user accesses the platform and manages the data; the means by which the user encrypts the data and grants access to a third party and the means to configure the data to be shared, and the server encrypts the data and grants access to the third party. This allows users to effectively manage their own EEG data and securely share it with third parties. In addition, in conjunction with the generative AI, the system can accurately understand the user's intentions and generate appropriate output.

A "brain-machine interface (BMI)" is an interface that uses brain waves to communicate a user's intentions to a machine.

Generative AI" is artificial intelligence that analyzes a user's brain wave data and generates appropriate output based on the results.

A "platform" is a system that allows users to manage their EEG data and share it with third parties as needed.

EEG data" is data that measures the user's brain activity and is obtained using an EEG measurement device.

A "measurement device" is a device used to measure a user's brain waves in real time.

A "terminal" is a computer, smart device, or other device used by a user to upload EEG data acquired using the measurement device to a server.

A "server" is a computer system used to store and manage EEG data received from users.

A "database" is a system for efficiently storing and accessing EEG data received by the server.

Encryption" is a technique for converting data into a format that cannot be deciphered by a third party.

Access privileges" is the ability to set the rights of a specific user or third party to access data.

Output" is the output generated by the generative AI based on the results of analyzing the user's EEG data.

Exemplary Embodiment of the Invention

This invention is a system that provides a platform for users to manage EEG data acquired using specialized measurement devices and share it with third parties as needed.

Specific exemplary embodiments of this system are described below.

Hardware and Software Configuration

The user uses a dedicated EEG measurement device to obtain EEG data. This measurement device measures the user's brain waves in real time and transmits the data to a terminal (PC or smartphone).

The terminal uploads the acquired EEG data to the server through a dedicated application. The application converts the data into the appropriate format (e.g., CSV or JSON) and sends it securely to the server using the HTTPS protocol.

The server stores the received EEG data in a database (e.g., MySQL or PostgreSQL). The database organizes the data by user and indexes it for efficient access.

Users access the platform through a web browser or mobile application. The platform authenticates the user (e.g., OAuth or JWT) and provides an interface that allows users to view, edit, and delete their own EEG data.

Data Sharing and Encryption

If the user wants to share data with a third party, he/she selects the third party (e.g., a medical or research institution) with whom he/she wants to share the data on the platform. The user sets the scope and duration of the data to be shared and submits a sharing request.

The server receives the user's sharing request and encrypts the data to be shared. Encryption uses a strong encryption algorithm such as AES-256. The server grants access privileges to designated third parties and creates a secure access link to the shared data.

Concrete Example

For example, when a user shares his/her EEG data with a medical institution, the following steps are taken 1. the user wears the EEG sensor and launches the dedicated application.
2. the terminal converts the acquired EEG data into CSV format and uploads it to the server using HTTPS.

The server stores the received data in a MySQL database.

4. the user logs into the platform with a web browser and checks his/her EEG data.

The user selects a medical institution and sets the scope and duration of the data to be shared.

6. the server encrypts the data with AES-256 and grants access privileges to the medical institution.

Example of Prompt Sentences to be Entered into a Generative AI Model:

Describe the steps a user would take to use an EEG sensor to obtain EEG data and share it with their healthcare provider."

By inputting this prompt statement into the data generation AI model, the specific procedure for the user to obtain EEG data and share it with the healthcare provider is output.

The flow of the identification process in Example 2 is described in FIG. 13.

Step 1:

The user uses a dedicated EEG measurement device to acquire EEG data. The user wears the measurement device and starts the dedicated application. The measurement device measures the user's brain waves in real time and transmits the data to the terminal. The input is the user's EEG and the output is the EEG data transmitted to the terminal.

Step 2:

The terminal uploads the EEG data to the server. The terminal converts the acquired EEG data into CSV format through a dedicated application and sends it to the server using the HTTPS protocol. The input is the EEG data sent from the measurement device and the output is the EEG data in CSV format uploaded to the server.

Step 3:

The server stores the received EEG data in a database. The server imports the received EEG data in CSV format into the database and organizes the data for each user. The input is the EEG data in CSV format sent from the terminal, and the output is the EEG data stored in the database.

Step 4:

Users access the platform and manage their data. The user logs into the platform through a web browser or mobile application to view, edit, and delete his/her EEG data. The input is the user's login information and the EEG data stored in the database, and the output is the EEG data that the user has viewed, edited, or deleted.

Step 5:

The user sets up the sharing of data with third parties. The user selects the third party they wish to share with on the platform and sets the scope and duration of the data to be shared. The input is the user's sharing configuration information and the output is the sharing request sent to the server.

Step 6:

Server encrypts data and grants access to third parties. The server receives the user's share request and encrypts the data to be shared with AES-256. The server grants access privileges to the designated third party and generates a secure access link to the shared data. The input is the user's sharing request and the EEG data stored in the database, and the output is the encrypted data and the access rights granted to the third party.

Example of Application 2

Next, example of application 2 of example of implement 2 will be described. In the following description, data processing device 12 will be referred to as the "server" and smart glasses 214 will be referred to as the "terminal.

Conventional brain-machine interfaces (BMIs) lack a platform for effectively managing users' EEG data and sharing it with third parties as needed. In addition, they lacked sufficient management of EEG data security and sharing history, which prevented smooth data sharing with medical and research institutions. Furthermore, the lack of a function to collect users' EEG data in real time, encrypt it, and upload it to the cloud did not ensure the security and convenience of the data The specific processing by the specific processing unit 290 of the data processing device 12 in example of application 2 is realized by the following means. In this invention, the server provides means to generate a minimally invasive and highly accurate brain-machine interface (BMI) that combines brain waves and generative AI, means to provide a platform to disseminate the BMI to society, means to provide intuitive communication services, metaverse interface, health management services, and biometric authentication services provided through the platform; means for collecting users' brain wave data in real time, encrypting and uploading the data to the cloud; and means for sharing the data with medical institutions and research organizations and managing data sharing history. The means to share the data with medical and research institutions, and to manage the data sharing history. This allows users' EEG data to be managed securely and efficiently and shared with third parties as needed.

Brain waves" are electrical signals generated by neural activity in the brain.

Generative AI" is a type of artificial intelligence, a system that has the ability to generate new data and information based on input data.

Minimally invasive" means less stressful or damaging to the body.

High precision" means extremely accurate.

A "brain-machine interface" (BMI) is an interface that uses brain waves to operate a machine or computer.

A "platform" is the underlying system or environment that provides a specific function or service.

An "intuitive communication service" is one that allows users to interact with information in a natural way.

A "metaverse interface" is an interface that allows users to operate and experience things in a virtual space.

A "health management service" is a service that monitors and manages a user's health status.

Biometric services" are services that use a user's biometric information to verify identity.

Real-time" means that data and information are processed immediately.

Encryption" means that data is converted using a specific algorithm to a form that cannot be easily understood by a third party.

The "cloud" is a collection of computer resources and services provided through the Internet.

A "sharing history" is a record of how, when, and by whom data was shared.

A "medical institution" is a facility that provides medical services, such as a hospital or clinic.

A "research institution" is an organization or facility for conducting scientific research.

The following system configuration is an exemplary embodiment of this invention.

System Configuration

The system has the ability to collect users' EEG data in real time, encrypt it, and upload it to the cloud. It also has the ability to share data with medical and research institutions and manage data sharing history.

Hardware Used

Smart device: a device that allows users to manage their EEG data and upload it to the cloud.

EEG sensors: devices (e.g., Muse, Emotiv) to collect EEG data on users.

Software to be Used

Python: A programming language for performing the main processing of a program.

NeuroKit2: A library for simulation and analysis of EEG data.

Requests: Library for sending HTTP requests.

Cryptography: Library for data encryption.

Process Flow

1. EEG data collection: EEG sensors are used to collect the user's EEG data in real time. The collected data is stored on the smartphone.

Data encryption: The EEG data collected will be encrypted using the Cryptography library. This ensures data security.

Data upload: Encrypted data is uploaded to the cloud using the Requests library. Data is stored securely in the cloud.

Data sharing: Users can share data with medical institutions and research organizations as needed. Sharing history is stored locally, allowing users to see who accessed what data and when.

Concrete Example

The user wears the EEG sensor and launches the NeuroGuard app. The app collects the EEG data, encrypts it, and uploads it to the cloud. With the user's permission, a medical institution retrieves the data from the cloud and uses it for diagnosis.

Example of Prompt Text

The user wears the EEG sensor and launches the NeuroGuard app. The app collects EEG data, encrypts it, and uploads it to the cloud. With the user's permission, a healthcare provider retrieves the data from the cloud and uses it for diagnosis.

This system will allow users' EEG data to be managed securely and efficiently and shared with third parties as needed.

The flow of the identification process in example of application 2 is described in FIG. 14.

Step 1:

The user wears the EEG sensor and launches the NeuroGuard application on the smartphone. The EEG sensor collects the user's EEG data in real time and transmits it to the smartphone. The input is the EEG data from the EEG sensor and the output is the raw EEG data stored on the smartphone.

Step 2:

The terminal (smartphone) analyzes the EEG data collected using the NeuroKit2 library. This analysis extracts the features of the EEG data. The input is the raw EEG data and the output is the features of the analyzed EEG data. Specifically, NeuroKit2 functions are invoked to analyze the EEG data and extract the features.

Step 3:

The terminal encrypts the analyzed EEG data using the Cryptography library. The input is the features of the analyzed EEG data and the output is the encrypted EEG data. The specific operation is to generate an encryption key and encrypt the EEG data using the key.

Step 4:

The terminal uploads encrypted EEG data to the cloud using the Requests library. The input is the encrypted EEG data and the output is the encrypted data stored on the cloud.

The specific operation is to send an HTTP POST request and upload the data to the cloud server.

Step 5:

The server manages the encrypted data stored on the cloud and shares the data with medical and research institutions as needed. The input is the encrypted data on the cloud and the output is the shared data. The specific operation is to decrypt the data and provide it to the designated third party with the user's permission.

Step 6:

The server maintains a data sharing history, recording who accessed what data and when. The input is the data access request information and the output is the shared history log. The specific operation is to generate an access log and store it locally or in the cloud.

In this way, the user's EEG data can be managed securely and efficiently and shared with third parties as needed.

Example 3

Next, example 3 of exemplary embodiment of implement will be described. In the following description, the data processing device 12 will be referred to as the "server" and the smart glasses 214 will be referred to as the "terminal".

Conventional brain-machine interfaces (BMIs) have had difficulty effectively analyzing users' brain wave data and identifying their emotions and intentions in real time. They also lacked a platform for intuitive communication, health management, biometric authentication, and other services based on these data. Furthermore, users lacked the ability to manage their own EEG data and share it with third parties as needed. To solve these problems, a system that provides highly accurate analysis of EEG data and a variety of services based on this data is needed.

The specific processing unit 290 of the data processing device 12 in Example 3 is realized by the following means.

In this invention, the server has means for the user to wear an EEG measurement device and connect it to the terminal; the terminal collects EEG data from the EEG measurement device and transmits it to the server; the server receives the EEG data and performs pre-processing; the server analyzes the pre-processed data to identify emotions and intentions, means for the server to transmit the analysis results to the terminal, the terminal to display the analysis results and provide feedback to the user, means for providing a platform for disseminating the system to society, and means for providing intuitive communication using brain activity provided through the platform. services, virtual reality interface, health management services, and biometric authentication services provided through the platform. This makes it possible to analyze users' brain wave data with high precision and provide a variety of services based on such data in real time.

The term "user" refers to the individual who wears the EEG measurement device and uses the system.

The term "EEG measurement device" refers to a device used to measure a user's EEG data.

The term "terminal" refers to an electronic device that transmits the data collected from the EEG measurement device to the server and displays the analysis results to the user.

The term "server" refers to a computer system that receives EEG data, performs pre-processing and analysis, and transmits the results to the terminal.

Pre-processing" refers to data cleansing operations performed on EEG data prior to analysis, such as noise removal and filtering.

The term "analysis" refers to the processing of data to identify the user's emotions and intentions based on the preprocessed EEG data.

The term "generative AI model" refers to a machine learning model used to analyze brain wave data to identify a user's emotions and intentions.

The term "platform" refers to the infrastructure that will allow the system to be disseminated to society and for users to manage their EEG data and share it with third parties as needed.

The term "intuitive communication service" refers to a service that uses brain wave data from users to understand their emotions and intentions and communicate accordingly.

The term "virtual reality interface" refers to an interface that controls behavior in a virtual or augmented reality world based on the user's brain wave data.

The term "health management service" refers to a service that uses brain wave data to determine a user's stress level, sleep status, etc., and suggests health management based on this information.

The term "biometric authentication service" refers to a service that analyzes a user's brain wave patterns for personal authentication.

The invention begins with the user wearing an EEG measurement device and connecting it to a terminal. The user wears the EEG measurement device (e.g. EEG device) on his/her head and connects it to a terminal (e.g. smart phone or PC) using Bluetooth or USB cable.

The terminal collects EEG data from the EEG device in real time using a dedicated application. The collected data is sent to the server via the Internet. The server receives the EEG data sent from the terminal and performs pre-processing. Pre-processing includes noise removal and filtering, and uses the Python MNE library for data cleansing.

The preprocessed data is input to a machine learning model on the server (e.g., using TensorFlow or PyTorch) to analyze emotions and intentions. The analysis results are used to identify the user's emotion (e.g., joy, sadness, surprise, etc.) or intention (e.g., the intention to perform a specific action).

The analysis results are sent from the server to the terminal. The terminal displays the analysis results received from the server to the user. For example, a chat application displays a message that the user is happy. The metaverse interface also controls actions in the VR and AR worlds based on the user's intentions.

As a concrete example, consider an intuitive communication service. A user wears an EEG device and connects it to a smart phone. The smart device collects brain wave data from the EEG device in real time and sends it to the server. The server preprocesses the received data and analyzes emotions using TensorFlow. If the analysis shows that the user is "happy," this information is reflected in the smartphone's chat application and a message is sent to the other party saying that the user is happy.

Example of a Prompt Statement:

The user wears the EEG device and connects it to a smart phone. The smartphone collects EEG data in real-time and sends it to the server. The server preprocesses the data and analyzes the emotions using TensorFlow. If the analysis shows that the user is "happy," the information is reflected in the chat application and a message is sent to the other party saying that the user is happy.

In this way, the server, terminal, and user work together to realize a system that provides new services using EEG data. The flow of the identification process in Example 3 is described using FIG. 15.

Step 1:

The user wears the EEG measurement device and connects it to the terminal.

Specifically, the user wears an EEG measurement device (e.g., EEG device) on his/her head and connects it to a terminal (e.g., smart phone or PC) using Bluetooth or USB cable. The input is the user's EEG and the output device is the EEG measurement device connected to the terminal.

Step 2:

The terminal collects EEG data from the EEG measurement device and sends it to the server.

Specifically, the terminal uses a dedicated application to collect EEG data from the EEG device in real time. The collected data is sent to the server via the Internet. The input is the EEG data from the EEG measurement device and the output is the EEG data sent to the server.

Step 3:

The server receives the EEG data and performs preprocessing.

Specifically, the server receives EEG data sent from the terminal. The received data is preprocessed by noise removal, filtering, etc. Data cleansing is performed using the Python MNE library. The input is the EEG data transmitted from the terminal and the output is the preprocessed EEG data.

Step 4:

The server analyzes the preprocessed data to identify emotions and intentions.

Specifically, the server inputs the preprocessed data into a machine learning model (e.g., using TensorFlow or PyTorch). The model identifies the user's emotions and intentions from the EEG data. The input is the preprocessed EEG data and the output is the emotion and intention information as the result of the analysis.

Step 5:

The server sends the analysis results to the terminal.

As a specific action, the server sends the analysis results to the terminal. The analysis results include the user's emotions (e.g., joy, sadness, surprise, etc.) and intentions (e.g., intention to perform a specific action). The input is the analysis result and the output is the analysis result sent to the terminal.

Step 6:

The terminal displays the analysis results and provides feedback to the user.

As a specific action, the terminal displays the analysis results received from the server to the user. For example, a chat application displays a message that the user is happy. In addition, the metaverse interface controls actions in the VR and AR worlds based on the user's intentions. The input is the analysis results received from the server and the output is the feedback displayed to the user.

Example of Application 3

Next, example 3 of application of example of implement 3 will be described. In the following description, the data processing device 12 will be referred to as the "server" and the smart glasses 214 will be referred to as the "terminal".

Conventional brain-machine interfaces (BMIs) have limited technology for analyzing a user's brain waves, making it difficult to perform highly accurate analysis in real time. They also lacked intuitive means of navigation and interaction within the metaverse, making it difficult to perform actions that reflect the user's intentions and emotions. Furthermore, functions related to the management and sharing of EEG data were inadequate, making it less convenient for users.

The specific processing by the specific processing unit 290 of the data processing device 12 in example of application 3 is realized by the following means.

In this invention, the server provides means for generating a minimally invasive and highly accurate brain-machine interface (BMI) that combines brain waves and generative AI, means for providing a platform for disseminating the BMI in society, means for providing, through the platform, brain activity-based intuitive communication services, metaverse interface, health management services, and biometric authentication services provided through the platform; means for controlling navigation and interaction in the metaverse by analyzing the user's brain waves in real time; and means for performing actions in the metaverse based on the user's intentions and emotions. means to perform actions. This allows users to intuitively navigate and interact within the metaverse using brain waves.

EEG" is a recording of the brain's electrical activity, data that can be used to analyze a user's intentions and emotions.

Generative AI" is a type of artificial intelligence that generates new information and output based on input data.

A "brain-machine interface" (BMI) is an interface that analyzes brain waves to control machines and computers.

A "platform" is a system that serves as the foundation for providing a particular service or function.

Intuitive communication service" is a service that analyzes a user's brain waves to understand their emotions and intentions, and communicates accordingly.

A "metaverse interface" is an interface for user interaction in a virtual or augmented reality world.

The "Health Management Service" is a service that analyzes users' brain waves to determine their stress levels and sleep conditions, and suggests health management based on this information.

Biometric authentication service" is a personal authentication service that analyzes a user's brain wave patterns.

The term "navigation" refers to the instructions and operations that users use to navigate within a virtual space.

Interaction" refers to the user's interaction with other objects or characters in the virtual space.

Intent" is the user's intention to perform a particular action or operation.

Emotion" refers to the psychological state or feeling of a user.

An "action" is an action or reaction performed in the virtual space based on a user's intention or emotion.

A system for implementing this invention includes means to generate a minimally invasive, highly accurate brain-machine interface (BMI) that combines electroencephalograms and generative AI, means to provide a platform for popularizing the BMI in society, means to provide intuitive communication services utilizing brain activity provided through the platform, metaverse interface, health management services, and biometric authentication services using brain activity provided through the platform; means to control navigation and interaction in the metaverse by analyzing the user's brain waves in real time; and means to execute actions in the metaverse based on the user's intentions and emotions. means to execute actions in the metaverse based on the user's intentions and emotions.

System Configuration

This system uses the following hardware and software

Hardware: Brainwave sensor, head-mounted display

Software: Python, EEG sensor API, Metaverse controller API

Explanation of Program Processing

The server analyzes the EEG data acquired from the EEG sensor in real time and inputs it to the generative AI. The generative AI analyzes the user's intentions and emotions based on the input EEG data and generates output based on them. Specifically, if the user wants to move forward, the brain wave sensor detects this intention and the avatar moves forward. Also, if the user feels happy, the emotion is detected and the avatar smiles.

Concrete Example

For example, if the user wants to move forward in the metaverse, the brainwave sensor will detect that intention and the avatar will move forward. Also, if the user feels happy, the emotion will be detected and the avatar will smile.

Example of Prompt Text

Examples of prompt sentences to be input into the generative AI model are as follows If the user wants to move forward, the brainwave sensor should detect that intention and generate a program that causes the avatar to move forward. Also, if the user feels happy, the emotion should be detected and the avatar should smile.

The flow of the identification process in example of application 3 is described in FIG. 16.

Step 1:

The server acquires EEG data from the EEG sensor.

Input: Raw data from EEG sensor

Output: Acquired EEG data

Specific operation: An EEG sensor measures the user's brain waves in real time and sends the data to the server.

Step 2:

The server preprocesses the acquired EEG data.

Input: EEG data acquired

Output: preprocessed EEG data

Specific operation: Pre-processing such as noise removal and filtering is performed, and the data is converted into a format suitable for analysis.

Step 3:

The server inputs the preprocessed EEG data to the generator system AI.

Input: preprocessed EEG data

Output: Data input to the generative AI

Specific operation: Pre-processed EEG data is input into a generative AI model to analyze the user's intentions and emotions.

Step 4:

The generative AI analyzes the user's intentions and emotions based on the input brain wave data.

Input: Data input to the generative AI

Output: parsed intentions and feelings

Specific behavior: A generative AI model analyzes brain wave data to identify what the user intends and what emotion identification model the user has.

Step 5:

The server determines actions in the metaverse based on the analysis results.

Input: parsed intentions and feelings

Output: Actions performed in the metaverse

Specific actions: If the user's intention is "forward", the avatar determines the action of moving forward; if the emotion is "happy", the avatar determines the action of smiling.

Step 6:

The server sends the determined action to the Metaverse Controller.

Input: Actions to be performed in the metaverse

Output: Action instructions sent to the Metaverse Controller

Specific actions: The determined actions are sent through the Metaverse Controller's API to instruct the avatar to actually perform the action.

Step 7:

The Metaverse Controller controls the avatar based on the action instructions received.

Input: Action instructions sent to the Metaverse Controller

Output: Avatar behavior

Specific actions: The metaverse controller controls the avatar to perform actions based on the user's intentions and emotions. For example, the avatar moves forward or smiles.

Further, an emotion engine that estimates the user's emotion may be combined. In other words, the specific processing unit 290 may use the emotion identification model 59 to estimate the user's emotion and perform specific processing using the user's emotion.

Example of Implement 1

In one exemplary embodiment, the brain-machine interface (BMI) analyzes the user's brain waves in real time and inputs the results to the generative AI. In addition, by combining an emotion engine, the user's emotional state is also analyzed simultaneously. Based on the results of this analysis, the system understands the user's intentions and emotional state, and generates output based on this understanding. For example, if a user thinks of "making coffee" with an emotion of joy, the system recognizes that joyful emotion and takes action to make coffee accordingly.

Example of Implement 2

In another exemplary embodiment of the invention, the platform has a function that allows users to manage their own EEG data and emotional states and share them with third parties as needed. For example, users can share their EEG data with medical and research institutions when they are feeling joyful emotions to obtain more accurate medical services and research results.

Example of Implement 3

In a further exemplary embodiment of the invention, the services provided through the platform have the ability to provide services that utilize the emotional state of the user. For example, an intuitive communication service analyzes the user's brain waves to understand their emotions and intentions, and communicates with them based on this information. If the user has a joyful emotion, the service recognizes that joyful emotion and provides communication accordingly.

The following is a description of the process flow for each example of implement.

Example of Implement 1

Step 1: The user thinks of a specific action. For example, think "make coffee".

Step 2: The brain-machine interface (BMI) analyzes the user's brain waves in real time.

Step 3: The emotion engine analyzes the user's emotional state. In this example, it analyzes that the user has the emotion of joy.

Step 4: Based on the analysis results, understand the user's intentions and emotional state and generate output based on them. In this example, coffee-making actions are generated according to the emotion of joy Rub.

Example of Implement 2

Step 1: The user feels a specific emotion. For example, feel the emotion of joy.

Step 2: The platform manages the user's EEG data and emotional state.

Step 3: The user shares his/her EEG data and emotional state with third parties as needed. In this example, it is shared with a medical or research institution.

Example of Implement 3

Step 1: The user uses the service through the platform. For example, use intuitive communication services.

Step 2: The service analyzes the user's brain waves to understand their emotions and intentions.

Step 3: The service provides communication tailored to the user's emotional state based on the analysis results. In this example, if the user has a joyful emotion, the service provides communication tailored to that joyful emotion.

Example 1

The following is an example of exemplary embodiment of implement. In the following description, the data processing device 12 will be referred to as the "server" and the smart glasses 214 will be referred to as the "terminal".

Conventional brain-machine interfaces (BMI) only analyze the user's brain waves and fail to take into account the user's emotional state. This made it difficult to accurately understand the user's intentions and generate appropriate output. It also lacked a platform for managing users' EEG data and sharing it with third parties. This prevented the social diffusion of BMI and made it difficult to provide intuitive communication services, health management services, and biometric authentication services The specific processing by the specific processing unit 290 of the data processing device 12 in Example 1 is realized by the following means.

In this invention, the server includes means for acquiring the user's brain waves in real time, analyzing the acquired brain wave data to extract the user's intentions, analyzing the user's emotional state, generating and inputting prompt sentences to a generative AI based on the analysis results, and executing the output generated by the generative AI The system also includes means to execute the outputs generated by the generative AI. This enables the system to accurately understand the user's intentions and emotional state and generate appropriate outputs. The system can also provide a platform for disseminating the system in society, and provide intuitive communication services, virtual space interface, health management services, and biometric authentication services using brain activity.

A "user" is an individual who uses the system.

Brain waves" are electrical signals generated by neural activity in the brain.

Real-time" means that data is processed as soon as it is generated.

Means of acquisition" refers to devices and methods for collecting data.

Means to analyze" refers to devices and methods used to analyze acquired data and extract meaningful information.

Intent" refers to information that indicates what the user wants or is thinking about.

The term "emotional state" refers to information that indicates a user's feelings or mood.

Generative AI" refers to artificial intelligence that generates new information and output based on given data.

A "prompt sentence" is an input sentence used to give instructions or ask questions to the generative AI.

Output" refers to the results or responses generated by the generative AI based on the prompted statements.

Means of execution" refers to devices and methods used to convert output generated by the generative AI into concrete actions and operations.

The term "platform" refers to the infrastructure used to operate the system and provide services to users.

An "intuitive communication service" is one that allows users to exchange information with others in a natural way.

The term "virtual space interface" refers to an interface that allows users to operate and experience things within a virtual environment.

The term "health management services" refers to services for monitoring and managing the health status of users.

The term "biometric authentication service" refers to a service that uses a user's biometric information to verify his or her identity.

This invention is a system that analyzes a user's brain waves in real time and inputs the results to a generative AI to understand the user's intentions and emotional state and generate output based on the results. The system includes an EEG measurement device to acquire the user's EEG, software to analyze the EEG data, an emotion engine to analyze the emotional state, a generative AI, and hardware to execute the generated output.

Hardware and Software Used

1. Brain Wave Measurement Device

The user wears a special EEG measurement device. This device acquires the user's brain waves in real time.

2. Brain Wave Analysis Software

EEG analysis software (e.g., OpenBCI) is used by the terminal to analyze the EEG data acquired from the EEG measurement device. This software analyzes the EEG data and extracts the user's intentions.

3. Emotion Engine:

The terminal uses an emotion engine to analyze the user's emotional state. This engine acquires emotional data through facial recognition cameras and voice analysis to understand the user's emotional state.

4. Generative AI: The

The server generates and inputs prompt sentences to the generative AI (e.g. OpenAI GPT-4) based on the analysis results. The generative AI generates appropriate outputs based on the prompt sentences.

5. Output Execution Hardware

The server receives output from the generative AI and manipulates hardware (e.g., IoT devices) to perform specific actions.

Concrete Example

The user wakes up in the morning and puts on the EEG measurement device.

The terminal receives data from the EEG measurement device and begins analyzing it in real time.

The terminal detects the intention to "drink coffee" from brain wave data.

The terminal confirms that the user has a feeling of "joy" through the facial recognition camera.

The terminal says, "The user wants to 'have a cup of coffee' with an emotion of pleasure. Please suggest an appropriate action." The terminal generates the prompt sentence "The user wants to have a cup of coffee.

The server sends a prompt sentence to the generative AI, and the generative AI generates an output that "instructs the coffee maker to make coffee.

The server operates the coffee maker through an IoT device to make coffee.

Example of Prompt Text

EEG data of user: [data].

User's emotional state: joy

User Intent: I want a cup of coffee

Prompt for generative AI: A user wants to 'have a cup of coffee' with a joyful emotion.

Please suggest an appropriate action.

In this way, the system can analyze the user's brain waves and emotional state, generate output based on the user's intentions using generative AI, and execute specific actions.

The flow of the identification process in Example 1 is described in FIG. 17.

Step 1:

The user wears a special EEG measurement device.

Input: User's brain waves

Output: Real-time EEG data

Specific operation: The user wears the EEG measurement device on his/her head and the device begins to measure brain waves. The device transmits EEG data to the terminal in real time via Bluetooth or USB connection.

Step 2:

The terminal acquires EEG data from the EEG measurement device in real time.

Input: Real-time EEG data

Output: Acquired EEG data

Specific operation: The terminal receives EEG data transmitted from the EEG measurement device and stores it in a database.

Step 3:

The EEG data acquired by the terminal is analyzed to extract the user's intention.

Input: EEG data acquired

Output: User intent

Specific operation: The terminal uses EEG analysis software (e.g. OpenBCI) to analyze EEG data. It detects specific brain wave patterns and extracts the user's intentions based on them. For example, the intention of "I want a cup of coffee" is detected.

Step 4:

The terminal analyzes the user's emotional state.

Input: User's face image and voice data

Output: User's emotional state

Specific operation: The terminal uses the emotion engine to acquire emotion data through facial recognition camera and voice analysis. As a result of the analysis, the user identifies an emotional state such as "joy" or "sadness".

Step 5:

The terminal generates and inputs prompt sentences to the generative AI based on the analysis results.

Input: user intent and emotional state

Output: Prompt statement to generative AI

Specific action: The terminal integrates the user's intention and emotional state and says, "The user wants to 'have a cup of coffee' with a feeling of joy. Please suggest an appropriate action." The prompt sentence "The user wants to drink a cup of coffee" is generated.

Step 6:

The server sends prompt sentences to the generative AI, and the generative AI generates output.

Input: Prompt statement to generative AI

Output: Output from generative AI

Specific behavior: The server sends a prompt sentence to the generative AI (e.g., OpenAI GPT-4), and the generative AI generates an output "instructing the coffee maker to make coffee" based on the prompt sentence.

Step 7:

The server receives output from the generative AI and executes specific actions.

Input: Output from generative AI

Output: Actions performed

Specific operation: The server operates the coffee maker through the IoT device to make coffee. Specifically, "make coffee" instructions are sent to the coffee maker, and coffee is actually made.

Example of Application 1

Next, example of application 1 of example of implement 1 will be described. In the following description, the data processing device 12 will be referred to as the "server" and the smart glasses 214 will be referred to as the "terminal.

Conventional brain-machine interface (BMI) technology exists that analyzes the brain waves of users to understand their intentions, but the scope of its application is limited and has not been fully utilized, especially in work support in factories. In addition, the lack of a system that understands the intentions of workers in real time and automatically performs appropriate tasks has not sufficiently improved work efficiency or enabled human-machine collaboration.

The specific processing by the specific processing unit 290 of the data processing device 12 in example of application 1 is realized by the following means. In this invention, the server provides means to generate a minimally invasive and highly accurate brain-machine interface (BMI) that combines brain waves and generative AI, means to provide a platform to disseminate the BMI in society, means to provide intuitive communication services, metaverse interface, health management services, and biometric authentication services, and means to be installed in a robot performing work in a factory to analyze the worker's brain waves in real time, understand the worker's intentions, and automatically perform appropriate tasks. This makes it possible to understand the worker's intentions in real time and automatically perform appropriate tasks.

Brain waves" are electrical signals generated by neural activity in the brain.

Generative AI" is an artificial intelligence technology that generates new data and outputs based on input data.

Brain Machine Interface (BMI) is an interface technology that analyzes brain waves and uses the results to control machines and computers.

Minimally invasive" means less stressful or damaging to the body.

High precision" means extremely accurate.

A "platform" is the underlying system or environment that provides a specific service or function.

An "intuitive communication service" is one that allows users to interact with information in a natural way.

The term "metaverse interface" refers to the user interface within the virtual space.

A "health management service" is a service that monitors and manages a user's health status.

Biometric authentication service" is a service that uses an individual's biometric information for authentication.

A "robot that works in a factory" is a machine that is designed to automatically perform a specific task in a factory.

A "worker" is a person who performs work in a factory.

Real-time" means that processing and analysis occur almost simultaneously.

Intent" refers to the purpose or idea of what the user wants to do.

Output" refers to the results or actions produced by a system or machine.

The system for implementing this invention uses a minimally invasive and highly accurate brain-machine interface (BMI) that combines EEG and generative AI. The server analyzes the user's brain waves in real time and inputs the results to the generative AI, which understands the user's intentions and generates output based on them. In addition, by combining an emotion engine, the emotional state of the user is analyzed at the same time to understand the user's intentions and emotional state to generate output.

The system is installed on a robot performing a task in the factory and analyzes the worker's brain waves in real time. When a worker wants to perform a specific task, the robot understands his/her intention and automatically performs the appropriate task. For example, if the worker wants to assemble a part, the robot understands his/her intention and starts assembling the part.

The server uses EEG sensors to acquire EEG data. EEG data is analyzed in real-time using a Python library. An emotional engine will be used to analyze emotional states. A generative AI model (e.g., OpenAI GPT-3) understands the user's intentions based on the analyzed EEG data and emotional state, and generates appropriate output.

As a concrete example, here is a prompt sentence for a worker who wants to "assemble a part".

Example of a prompt statement: "I am a member of the User's EEG data: [0.1, 0.2, 0.3, . . . ].

User's emotional state: joy

User Intent: To assemble parts

By inputting this prompt sentence into the generative AI model, it understands the user's intention and generates appropriate actions. For example, a specific output is obtained, such as a robot starting to assemble a part.

This system enables the system to understand the intentions of workers in real time and automatically perform appropriate tasks. This improves work efficiency in the factory and realizes collaboration between man and machine.

The flow of the identification process in Example of Application 1 is described in FIG. 18.

Step 1:

The server acquires the user's EEG data in real time using EEG sensors. The input is the user's EEG signal and the output is the EEG data acquired. This data is transmitted from the EEG sensor to the server.

Step 2:

The server analyzes the acquired EEG data in real time using a Python library. The input is the acquired EEG data and the output is the analyzed EEG data. Through this analysis, EEG features and patterns are extracted.

Step 3:

The server uses the emotion engine to analyze the user's emotional state from the analyzed EEG data. The input is the analyzed EEG data and the output is the user's emotional state. This analysis determines whether the user is happy, sad, angry, etc.

Step 4:

The server uses a generative AI model (e.g., OpenAI GPT-3) to understand user intentions based on parsed EEG data and emotional states. The input is the parsed EEG data and emotional state, and the output is the user's intention. The data generation AI model inputs these data as prompts and infers what the user wants to do.

Step 5:

The server generates appropriate outputs based on user intent. The input is the user's intention and the output is a specific action. For example, if the user intends to assemble a part, the server instructs the robot to begin the process of assembling the part.

Step 6:

The robot receives instructions from the server and executes specific tasks. The input is the instructions from the server and the output is the work performed. For example, this includes a series of operations in which the robot starts and completes the assembly of a part.

Step 7:

The server monitors work progress and provides feedback as needed. The input is work progress data from the robot and the output is feedback information. This improves the accuracy and efficiency of the work.

Example 2

Next, example 2 of exemplary embodiment of implement will be described. In the following description, data processing device 12 will be referred to as the "server" and smart glasses 214 will be referred to as the "terminal.

Conventional brain-machine interfaces (BMIs) lack the ability to effectively manage users' EEG data and share it with third parties as needed. In addition, the accuracy and real-time nature of EEG data analysis was low, making it difficult to accurately understand the user's intentions. Furthermore, the acquisition and management of EEG data was complicated, making it difficult for ordinary users to use the system.

The specific processing by the specific processing unit 290 of the data processing device 12 in Example 2 is realized by the following means. In this invention, the server includes means by which the user acquires EEG data using a dedicated EEG measurement device and uploads it to the platform through a terminal, the server receives the EEG data and stores it in a database, and the server preprocesses and analyzes the EEG data. This allows users to effectively manage their own EEG data and share it with third parties as needed. It also improves the accuracy of the analysis of the EEG data and allows for an accurate understanding of the user's intentions in real time. Furthermore, the system simplifies the acquisition and management of EEG data, providing an easy-to-use system for the general user.

Brain Machine Interface (BMI) is a technology that uses brain wave data to understand the user's intentions and intuitively interact with machines and computers.

Generative AI is an artificial intelligence technology that analyzes a user's brain wave data and generates output based on the results.

The "platform" is the system infrastructure that allows users to manage their EEG data and share it with third parties as needed.

An "EEG measurement device" is a device worn on the user's head to acquire EEG data.

A "terminal" is a device that allows users to input and upload their EEG data to the platform.

A "server" is a computer system that receives EEG data, stores it in a database, and performs pre-processing and analysis.

A "database" is an information management system for storing received EEG data.

Pre-processing" refers to data cleaning operations performed on EEG data prior to analysis, such as noise removal and completion of missing values.

Analysis" is the process of classifying and understanding the user's emotional state and intentions based on the preprocessed EEG data.

The "third party" is the party with whom the user shares the EEG data, such as a medical or research institution.

Exemplary Embodiment of the Invention

This invention is a system in which users acquire EEG data using a dedicated EEG measurement device and upload it to the platform through a terminal. The server stores the received EEG data in a database for pre-processing and analysis. This allows users to effectively manage their own EEG data and share it with third parties as needed.

Hardware and Software Used

Hardware: (1)

EEG measurement device: The user uses a dedicated EEG measurement device (e.g., a common EEG measuring device) to obtain EEG data. This device is worn on the user's head and collects EEG data in real time.

Software: C

Terminal application: The terminal provides an interface for the user to receive and upload the EEG data acquired by the user to the platform. The user uploads the data through the terminal application.

Server: The server performs preprocessing and analysis of EEG data using Python. Specifically, libraries such as NumPy and Pandas are used to clean and filter the data. It also builds and analyzes machine learning models using libraries such as TensorFlow and PyTorch.

Database: The server uses a relational database such as MySQL or PostgreSQL to store EEG data.

Concrete Example

As a concrete example, consider a scenario in which EEG data is shared with a healthcare provider when a user is experiencing feelings of joy. The user acquires the data using an EEG measurement device and uploads it to the platform through a terminal. The server receives the data, analyzes it, and then sends the data to the medical institution.

Example of Prompt Sentences to be Entered into a Generative AI Model:

Describe the steps you would take to share EEG data with a health care provider when a user is experiencing feelings of joy."

Using this prompt statement, the generated AI model can provide detailed descriptions of specific procedures and necessary hardware and software.

In this way, users can effectively manage their own EEG data and share it with third parties as needed. In addition, the accuracy of EEG data analysis is improved, allowing the system to accurately understand the user's intentions in real time. Furthermore, the system simplifies the acquisition and management of EEG data, providing an easy-to-use system for the general user.

The flow of the identification process in Example 2 is described in FIG. 19.

Program Processing Flow

Step 1:

User Obtains EEG Data

Input: User's brain waves

Output: EEG data

Specific Operation: The user wears a dedicated EEG measurement device on the head to acquire EEG data in real time. The device detects the user's brain waves with sensors and stores them as digital data.

Step 2:

The Terminal Uploads EEG Data to the Platform

Input: EEG data

Output: Data uploaded to the platform

Specific operation: The user opens the application on the terminal, selects the EEG data acquired and presses the "Upload" button. The terminal sends the data to the platform.

Step 3:

Server Receives EEG Data and Stores it in a Database

Input: Uploaded EEG data

Output: Data stored in database

Specific Operation: The server receives EEG data sent from the terminal and stores it in a relational database such as MySQL or PostgreSQL. The database also stores metadata such as user IDs and time stamps.

Step 4:

Server Preprocesses EEG Data

Input: EEG data stored in database

Output: preprocessed data

Specifics: The server runs Python scripts and uses libraries such as NumPy and Pandas to clean and filter data. Specifically, it performs noise removal and missing value completion.

Step 5:

Server Analyzes EEG Data

Input: preprocessed data

Output: Analysis results (e.g. classification of emotional states)

Specific behavior: The server runs machine learning models using libraries such as TensorFlow and PyTorch to classify emotional states from EEG data. The analysis results are output as data indicating the user's emotional state and intentions.

Step 6:

User Manages EEG Data

Input: Analysis results and original EEG data

Output: Controlled data (e.g. filtered data display)

Specific behavior: users access the platform's dashboard to review analysis results. Data can be filtered and displayed for specific time periods.

Step 7:

Users Share EEG Data with Third Parties

Input: Managed data

Output: Shared data

Specifics: The user presses the "Share" button on the dashboard, enters the contact information of a third party (e.g., a medical institution), and gives permission to share. The server encrypts the data and sends it to the third party using HTTPS.

Thus, by performing specific actions in each step, users can effectively manage their own EEG data and share it with third parties as needed.

Example of Application 2

Next, example of application 2 of example of implement 2 will be described. In the following description, data processing device 12 will be referred to as the "server" and smart glasses 214 will be referred to as the "terminal.

Conventional brain-machine interfaces (BMIs) can collect and analyze users' brain wave data, but lacked a means to share that data with third parties in a secure and efficient manner. In addition, no system existed to analyze the user's emotional state in real time and take appropriate action when abnormalities were detected. This made it difficult to share data with medical and research institutions, and prevented users from improving the accuracy of their health management and biometric identification.

The specific processing by the specific processing unit 290 of the data processing device 12 in example of application 2 is realized by the following means.

In this invention, the server provides means for generating a minimally invasive and highly accurate brain-machine interface (BMI) that combines brain waves and generative AI, means for providing a platform for disseminating the BMI to society, means for providing intuitive brain activity-based communication services, metaverse interface, health management services, and biometric authentication services provided through the platform; collecting users' brain wave data in real time, encrypting it, and sharing it with third parties; analyzing users' emotional states and alerting them if any abnormality is detected. The system includes the following. This enables the secure and efficient sharing of the user's EEG data and strengthens cooperation with medical and research institutions. In addition, the user's emotional state can be monitored in real time, and if an abnormality is detected, a quick response can be made to improve the accuracy of health management and biometric authentication.

Brain waves" are electrical signals generated by neural activity in the brain.

Generative AI" is a type of artificial intelligence, a system that has the ability to generate new data and information based on input data.

The term "minimally invasive" refers to less burden or damage to the body.

A "brain-machine interface" (BMI) is an interface that uses brain waves to operate a machine or computer.

A "platform" is the underlying system or environment that provides a specific function or service.

An "intuitive communication service" is one that allows users to interact with information in a natural way.

A "metaverse interface" is an interface that allows users to operate and experience things in a virtual space.

Health Management Service" is a service that monitors the health status of users and provides them with appropriate advice and support.

Biometric services" are services that use a user's biometric information to verify identity.

Encryption" is a technique whereby data is converted using a specific algorithm so that it cannot be easily deciphered by a third party.

An "emotional state" is the emotional state a user is feeling at a particular moment in time.

An "alert" is a notification or warning of an abnormality or emergency.

The following system configuration is an exemplary embodiment of this invention.

System Configuration

The system will include hardware and software to collect the user's EEG data and analyze it using a generative AI. Specifically, the system will include the following elements.

1. EEG sensor: A device that collects the user's brain waves in real time. The EEG sensor is worn on the user's head and measures the electrical activity of the brain.
2. smart device: a device used to receive, encrypt, and analyze data from the EEG sensor. A dedicated application is installed on the smartphone.
3. server: provides a platform for receiving encrypted EEG data and sharing it with third parties (medical and research institutions) as needed. The server shall include software to manage and share the data.

Program Processing

The Server Will Perform the Following Processes

1. EEG data collection: EEG sensors collect the user's EEG data in real time and transmit it to the smartphone.
2. data encryption: The smartphone encrypts the received EEG data. Fernet, a cryptography library, is used for encryption.
3. data sharing: encrypted data is sent from the smartphone to the server. The server shares the received data with a designated third party (medical or research institution).
4. emotional state analysis: Smartphones analyze brain wave data to identify the user's emotional state. If an abnormality is detected, the smart phone will send out an alert.

Hardware and Software Used

EEG sensor: a device that collects the user's brain waves.

Smart devices: devices that receive, encrypt, parse, and share data.

Server: A platform for managing and sharing data.

cryptography library: Software used to encrypt data.

requests library: Software used to transmit data.

Concrete Example

For example, consider a case where brain wave data is collected when a user is stressed and sent to a medical facility. An EEG sensor collects the user's brain waves and transmits them to a smart phone. The smartphone encrypts the received data and sends it to the server. The server shares the encrypted data with the medical institution. The medical institution analyzes the received data and evaluates the user's stress state.

Example of Prompt Text

Create a Python program that collects the user's EEG data, encrypts it, and sends it to a designated medical facility. The EEG data can be virtual data. Use the cryptography library Fernet for encryption and the requests library to send the data."

The above is an exemplary embodiment of this invention.

The flow of the identification process in example of application 2 is described in FIG. 20.

Step 1:

The user wears an EEG sensor. The EEG sensor collects the user's EEG data in real time. The input is the user's EEG signal and the output is the raw data collected by the EEG sensor.

Step 2:

The terminal (smartphone) receives EEG data from the EEG sensor. The terminal acquires the data using wireless communication such as Bluetooth or Wi-Fi. The input is the raw data transmitted from the EEG sensor and the output is the EEG data stored in the terminal.

Step 3:

Encrypt the EEG data received by the terminal. The cryptography library Fernet is used for encryption. The input is the EEG data stored in the terminal and the output is the encrypted EEG data. The specific operation is to generate an encryption key and encrypt the EEG data with the key.

Step 4:

The terminal sends encrypted EEG data to the server. The requests library is used for transmission. The input is the encrypted EEG data and the output is the data sent to the server. The specific operation is to send the data using an HTTP POST request.

Step 5:

The server stores the encrypted EEG data received. The server manages the data using a database. The input is the encrypted data sent from the terminal and the output is the encrypted data stored in the database.

Step 6:

The server shares encrypted EEG data with third parties (medical and research institutions) as needed. Secure communication protocols are used for sharing. The input is the encrypted data stored in the database and the output is the data sent to the third party. The specific operation is to authenticate the third party and send the data if the authentication is successful.

Step 7:

The terminal analyzes EEG data to identify the user's emotional state. A generative AI model is used for the analysis. The input is the EEG data stored in the terminal and the output is the emotional state as the result of the analysis. Specifically, the EEG data is input to the AI generation model, and the emotional state is estimated.

Step 8:

The terminal monitors the emotional state and sends out an alert when an abnormality is detected. The input is the emotional state as an analysis result, and the output is an alert when an abnormality is detected. Specifically, when the emotional state exceeds a predefined threshold, a notification is sent to the user or a designated third party.

Example 3

Next, example 3 of exemplary embodiment of implement will be described. In the following description, the data processing device 12 will be referred to as the "server" and the smart glasses 214 will be referred to as the "terminal".

Conventional brain-machine interfaces (BMI) require high accuracy in analyzing a user's brain waves, but it has been difficult to achieve high accuracy in a minimally invasive manner. In addition, there was a lack of a system to provide real-time feedback of the analysis results to the user, which could not immediately reflect the user's intentions or emotional state. Furthermore, users lacked the ability to manage their own EEG data and share it with third parties as needed.

The specific processing by the specific processing unit 290 of the data processing device 12 in Example 3 is realized by the following means. In this invention, the server includes the following means: the server measures the user's EEG data and transmits it to the server in real time; the server analyzes the EEG data and identifies the user's emotional state and intentions; and the server stores the analysis results in a database and transmits them to the terminal. This enables minimally invasive and highly accurate EEG analysis, which can reflect the user's intentions and emotional state in real time. It also allows users to manage their own EEG data and share it with third parties as needed.

Brain Machine Interface (BMI) is a technology that uses brain waves to control computers and other devices.

Generative AI" is a type of artificial intelligence that has the ability to generate new data and information based on input data.

A "platform" is the underlying system or environment that provides a specific service or function.

EEG data" is data that electrically measures the user's brain activity and reflects emotional states and intentions.

Real-time" means that data is measured and processed immediately.

Analysis" is the process of processing measured data to extract specific information or patterns.

The "emotional state" is a state that indicates the user's current emotion or mood.

Intent Is what the user is trying to do or wants.

A "database" is a system that stores data in an organized manner and can be retrieved and updated as needed.

Feedback" is the response or information provided by the system to the user.

Minimally invasive" means less physical strain or discomfort to the user.

High precision" means that the measurement and analysis of data is extremely accurate.

A "virtual reality interface" is the means by which a user interacts with a virtual reality environment.

Health Management Service" is a service that monitors the user's health status and provides appropriate advice and support.

A "biometric service" is a service that uses a user's biometric information to authenticate an individual.

This invention is a system that provides a minimally invasive and highly accurate brain-machine interface (BMI) that combines EEG and generative AI. The system measures and analyzes the user's EEG data in real time to identify the user's emotional state and intentions, and provides feedback based on them.

Hardware and Software Used

Hardware (esp. Computer)

- EEG measurement devices: Devices to measure the user's brain waves (e.g., EEG headsets)
- Terminal: Device (e.g., smart device, tablet, PC) that connects to the EEG measurement device and sends data to the server
- Server: Computer system for receiving and analyzing EEG data Software

- Data transmission program: A program installed in the terminal to transmit EEG data to the server
- Data analysis programs: Programs installed on the server to analyze EEG data (e.g., FFT analysis using Python)
- Database management system: A system for storing analysis results and retrieving and updating them as needed.
- Feedback program: A program installed on the terminal to display the results of the analysis to the user.

Specific System Operation

User Behavior

The user wears an EEG measurement device (e.g., EEG headset) and connects it to the terminal. The user performs certain actions to generate EEG data. For example, if the user is relaxed, the EEG data has a specific frequency component.

Terminal Operation

The terminal measures the user's brain waves in real time and transmits them to the server using a data transmission program. The terminal waits for a response from the server to confirm that the data transmission was successful.

Server Operation

The server receives the EEG data sent from the terminal. The received data is analyzed using a data analysis program. Specifically, the FFT (Fast Fourier Transform) is used to break down the EEG data into its frequency components and extract specific patterns. For example, the intensity of alpha and beta waves is calculated to identify the user's emotional state.

Save and Send Analysis Results

The server stores the analysis results in a database. The stored data includes user ID, date and time of measurement, and analysis results (emotional state and intention). This makes it possible to refer to the data later. The server sends the analysis results to the terminal. Secure communication protocols (e.g. HTTPS) are used for transmission.

Feedback by Terminal

The terminal displays the analysis results received from the server to the user. The display uses a graphical user interface (GUI). For example, if the user is relaxed, the terminal displays "relaxed state" and suggests appropriate actions (e.g., playing relaxing music).

Examples of Specific Examples and Prompt Sentences

Concrete Example

For example, when a user uses an intuitive communication service, the following steps are taken 1. the user puts on the EEG headset and connects it to the terminal.

The terminal measures EEG data in real time and sends it to the server.

3. the server receives the EEG data and analyzes it using FFT. For example, if the intensity of alpha waves is high, the server determines that the user is relaxed.

The results of the analysis are stored in a database. For example, data such as "User ID: 12345, Date: 2023 Oct. 1 10:00, State: Relaxed" will be saved.

The server sends the analysis results to the terminal. The terminal displays "Relaxed" and suggests playing relaxing music.

6. the user relaxes by playing relaxing music as suggested by the terminal.

Example of Prompt Text

The program should analyze the user's EEG data to identify their emotional state and generate a program for intuitive communication. The hardware used is an EEG headset and the software is Python. Specifically, the program will analyze EEG data using FFT and calculate the intensity of alpha and beta waves to identify emotional states."

This specific description of the operation of the entire system clearly shows the exemplary embodiment of the invention. The flow of the specific process in Example 3 is explained using FIG. 21.

Step 1: Measure the User's EEG Data

The user wears an EEG measurement device (e.g., EEG headset). The device measures the user's EEG in real time and converts it into a digital signal. The input is the user's EEG and the output is the digitized EEG data. Specifically, the device contacts the user's scalp and detects the electrical signals.

Step 2: Transmission of EEG Data

The terminal transmits the measured EEG data to the server via Bluetooth or Wi-Fi. The input is the digitized EEG data and the output is the data sent to the server. Specifically, the terminal executes a data transmission program and sends the data to the IP address of the server.

Step 3: Receive and Analyze EEG Data by Server

The server receives the EEG data sent from the terminal. The input is the EEG data transmitted from the terminal and the output is the analysis result. The server executes FFT (Fast Fourier Transform) using Python to decompose the EEG data into its frequency components. Specifically, the server runs a data analysis program to calculate the intensity of alpha and beta waves.

Step 4: Save Analysis Results

The server stores the analysis results in a database. The input is the analysis results and the output is the data stored in the database. Specifically, the server uses a database management system to store user IDs, measurement dates and times, and analysis results.

Step 5: Transmission of Analysis Results

The server sends the analysis results to the terminal. The input is the analysis results stored in the database and the output is the analysis results sent to the terminal. As a specific operation, the server sends data using a secure communication protocol (e.g., HTTPS).

Step 6: Display of Analysis Results by Terminal

The terminal displays the analysis results received from the server to the user. The input is the analysis results sent from the server and the output is the information displayed to the user. Specifically, the terminal executes a feedback program and displays the analysis results using a graphical user interface (GUI).

Step 7: Feedback to Users

The user confirms his/her own emotional state and intentions based on the feedback provided by the terminal. The input is the feedback information from the terminal and the output is the user's next action. Specifically, the user takes actions such as playing relaxing music according to the terminal's suggestions.

Example of Application 3

Next, example 3 of application of example of implement 3 will be described. In the following description, the data processing device 12 will be referred to as the "server" and the smart glasses 214 will be referred to as the "terminal".

Conventional brain-machine interfaces (BMI) can understand intentions by analyzing the user's brain waves, but there are issues with their accuracy and real-time performance. In addition, intuitive operation and emotion-based action control within the metaverse were difficult, and there was a need to improve the user experience. Furthermore, there was a lack of a user-friendly system for managing EEG data and sharing it with third parties.

The specific processing by the specific processing unit 290 of the data processing device 12 in example of application 3 is realized by the following means.

In this invention, the server provides means for generating a minimally invasive and highly accurate brain-machine interface (BMI) that combines brain waves and generative AI, means for providing a platform for disseminating the BMI in society, means for providing, through the platform, intuitive communication services, metaverse interface, health management services, and biometric authentication services provided through the platform; means for controlling actions in the metaverse by analyzing brain waves of users in real time and understanding their emotions and intentions; and means for controlling actions in the metaverse based on the emotional state of users. means to control actions in the metaverse based on the user's emotional state.

This allows the user to intuitively perform operations in the metaverse using brain waves, thereby enabling action control based on emotions. In addition, EEG data can be easily managed and shared with third parties.

Brain waves" are electrical signals generated by neural activity in the brain.

Generative AI is an artificial intelligence technology that generates new information and content based on data.

A "brain-machine interface" (BMI) is an interface that analyzes brain waves to control machines and computers.

A "platform" is the underlying system or environment that provides a specific service or function.

Intuitive communication service" is a service that analyzes a user's brain waves to understand their emotions and intentions, and communicates accordingly.

A "metaverse interface" is an interface for controlling behavior in virtual reality (VR) and augmented reality (AR) worlds.

The "Health Management Service" is a service that analyzes users' brain waves to determine their stress levels and sleep conditions, and suggests health management based on this information.

Biometric authentication service" is a personal authentication service that analyzes a user's brain wave patterns.

Real-time" means immediate processing and reaction without delay.

The "emotional state" is the emotional state analyzed from the user's brain waves.

The term "action control" refers to controlling the behavior of a system or avatar based on a user's intentions or emotions.

The system for implementing this invention includes: means for generating a minimally invasive and highly accurate brain-machine interface (BMI) by combining brain waves and generative AI; means for providing a platform for disseminating the BMI in society; means for providing intuitive communication services, metaverse interface, health management services, and biometric authentication services using brain activity provided through the platform; means for controlling actions in the metaverse based on the user's emotional state by analyzing the user's brain waves in real time and understanding the user's emotions and intentions; and means for controlling actions in the metaverse based on the user's emotional state. means to provide intuitive communication services, metaverse interface, health management services, and biometric authentication services using brain activity provided through the platform; means to control actions in the metaverse by analyzing the user's brain waves in real time and understanding emotions and intentions; means to control actions in the metaverse based on the user's emotional state. Means to control actions in the metaverse based on the user's emotional state, including.

System Configuration

The server will use an EEG sensor, a head-mounted display (HMD), and a generative AI to configure the system. The EEG sensor acquires the user's brain waves in real time, and the HMD provides the user with visual information in the metaverse. The generative AI analyzes the acquired EEG data to understand the user's emotions and intentions.

Program Processing

The server acquires EEG data using the BrainFlow library and filters the data to remove noise. Next, the data is analyzed using a generative AI to detect the user's emotion (e.g., joy). Based on the detected emotion, actions in the metaverse are controlled. Specifically, if the user has the emotion of joy, the avatar is controlled to dance a joyful dance.

Hardware and Software Used

- Hardware: EEG sensor (e.g., BrainFlow-compatible device), head-mounted display (HMD)
- Software: Python, BrainFlow library Concrete Example For example, consider a scene where a user wears an HMD and uses brainwave sensors to control their behavior in the metaverse. If the user has a joyful emotion, the avatar will dance a joyful dance. This allows the user to intuitively operate within the metaverse and control actions based on emotions.

Example of Prompt Text

Example of prompt sentences to be entered into a generative AI model:

Create a Python program that analyzes the user's brain wave data to detect emotions and control actions in the metaverse. If the user has a joyful emotion, have the avatar perform a joyful dance.

In this way, an intuitive metaverse interface can be realized using brain waves.

The flow of the identification process in example of application 3 is described in FIG. 22.

Step 1:

The server uses EEG sensors to acquire the user's EEG data in real time.

- Input: User's EEG signal
- Output: Raw EEG data
- Specific operation: The server collects data from EEG sensors using the BrainFlow library and stores this in memory.

Step 2:

The server filters the acquired EEG data to remove noise.

- Input: Raw EEG data
- Output: Filtered EEG data
- Specific operation: The server uses the filtering function of the BrainFlow library to remove noise in specific frequency bands.

Step 3:

The server inputs the filtered EEG data to the generative AI to analyze the user's emotions.

- Input: Filtered EEG data
- Output: User's emotional state (e.g., joy, sadness)
- Specific operation: The server inputs data into the data generation AI model and runs an emotion identification algorithm to identify the user's emotion.

Step 4:

The server determines actions in the metaverse based on the analyzed emotional state.

- Input: User's emotional state
- Output: Action instructions in the metaverse (e.g., Dance of Joy)
- Specific operation: The server determines actions according to the emotional state and sends the instructions to the metaverse system.

Step 5:

The terminal (HMD) controls avatars in the metaverse based on action instructions received from the server.

- Input: Action instructions in the metaverse
- Output: Avatar behavior (e.g., joyful dancing)
- Specific operation: The terminal provides visual information to the user through the HMD and controls the avatar to perform the specified action.

Step 6:

Users visually see the action in the metaverse through the HMD.

Input: Avatar behavior

Output: Visual information (e.g., avatar dancing for joy scene)

Specific behavior: The user wears an HMD to visually confirm the avatar's behavior in the metaverse in real time.

The specific processing unit 290 sends the results of the specific processing to the smart glasses 214. In smart glasses 214, control unit 46A causes speaker 240 to output the results of the specific processing. Microphone 238 acquires audio indicating user input to the results of the specific processing. The control unit 46A transmits the voice data indicating the user input acquired by the microphone 238 to the data processing device 12. In data processing device 12, specific processing unit 290 acquires the voice data.

The data generation model 58 is a so-called Generative AI (Artificial Intelligence). An example of a data generation model 58 is a generative AI such as ChatGPT (Internet Search <URL: https://openai.com/blog/chatgpt>). The data generation model 58 is obtained by having a neural network perform deep learning. Prompts containing instructions are input to the data generation model 58, as well as data for inference, such as voice data indicating audio, text data indicating text, and image data indicating images. The data generation model 58 infers the input data for inference according to the instructions indicated by the prompts, and outputs the results of the inference in data formats such as voice data and text data. Here, reasoning refers to, for example, analysis, classification, prediction, and/or summarization.

Another example of generative AI is Gemini (Internet search <URL: https://gemini.google.com/?hl=ja>).

In the above exemplary embodiment, an example of implement in which the specific processing is performed by the data processing device 12 is given, but the technology of the present disclosure is not limited to this, and the specific processing may be performed by the smart glasses 214.

Third Exemplary Embodiment

Figure 5:
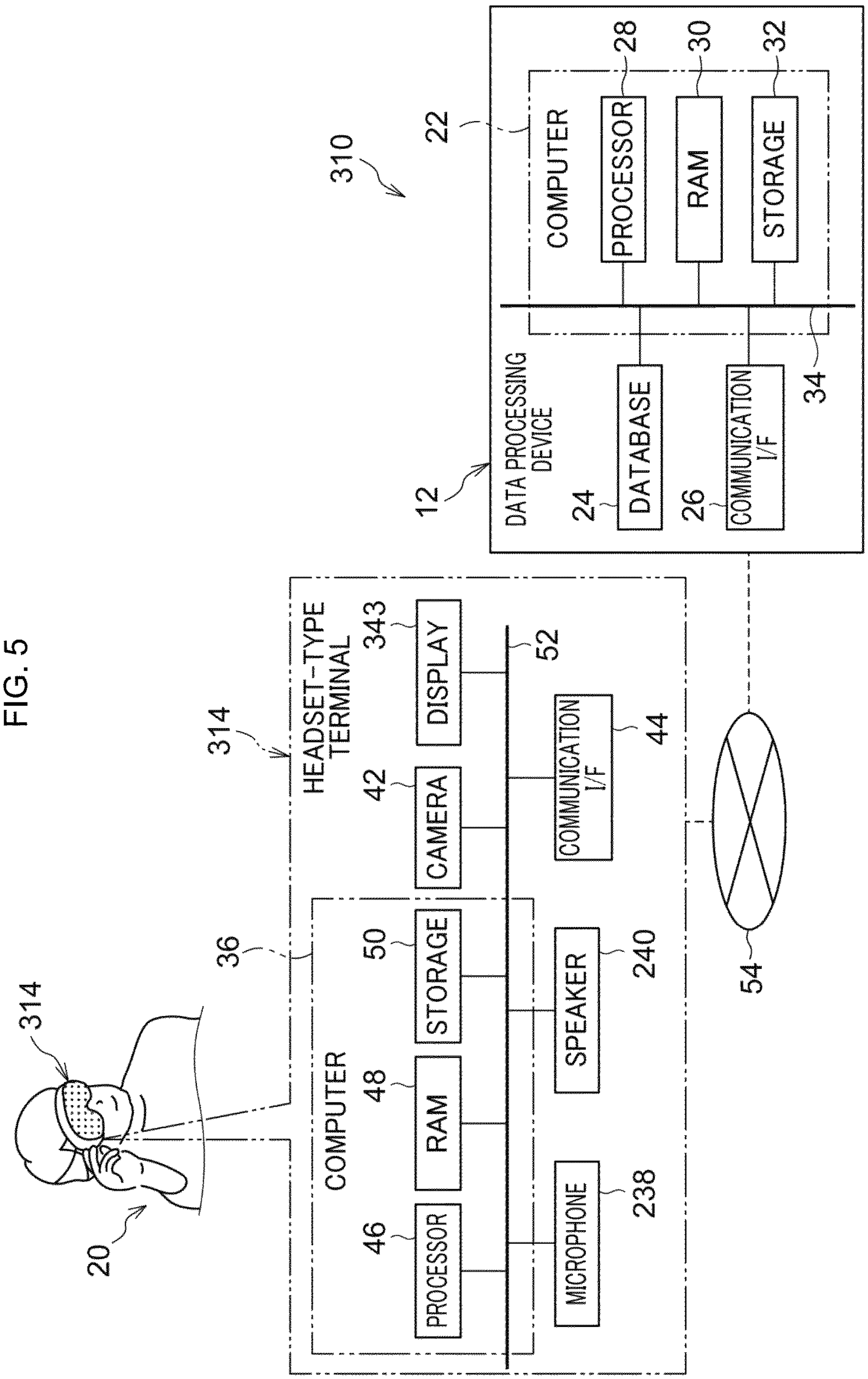
FIG. 5 is a conceptual diagram showing an example of implement of a data processing system for the third exemplary embodiment.

FIG. 5 shows an example of implement of a data processing system 310 for the third exemplary embodiment.

As shown in FIG. 5, data processing system 310 has data processing device 12 and headset-type terminal 314. An example of the data processing device 12 is a server.

The data processing device 12 has a computer 22, a database 24, and a communication I/F 26. Computer 22 is an example of a "computer" in the context of the present disclosure.

Computer 22 has a processor 28, RAM 30, and storage 32. The processor 28, RAM 30, and storage 32 are connected to a bus 34. The database 24 and the communication I/F 26 are also connected to the bus 34. The communication I/F 26 is connected to a network 54. An example of a network 54 is a Wide Area Network (WAN) and/or a Local Area Network (LAN).

The headset-type terminal 314 has a computer 36, microphone 238, speaker 240, camera 42, communication I/F 44, and display 343. The computer 36 has a processor 46, RAM 48, and storage 50. Processor 46, RAM 48, and storage 50 are connected to bus 52. The microphone 238, speaker 240, camera 42, and display 343 are also connected to the bus 52.

Microphone 238 accepts the voice emitted by user 20 and receives instructions, etc., from user 20. The microphone 238 captures the voice emitted by the user 20, converts the captured voice into voice data, and outputs the data to the processor 46. Speaker 240 outputs audio in accordance with instructions from processor 46.

Camera 42 is a compact digital camera equipped with an optical system, such as a lens, aperture, and shutter, and an image sensor, such as a CMOS (Complementary Metal-Oxide-Semiconductor) image sensor or CCD (Charge Coupled Device) image sensor. It is a small digital camera equipped with an image sensor such as a CMOS (Complementary Metal-Oxide-Semiconductor) image sensor or CCD (Charge-Coupled Device) image sensor, and captures images of the surroundings of the user 20 (for example, an image range defined by an angle of view equivalent to the field of view of a typical healthy person).

The communication I/F 44 is connected to the network 54. The communication I/Fs 44 and 26 are responsible for transferring and receiving various information between the processor 46 and the processor 28 via the network 54. The transfer of various information between the processor 46 and the processor 28 using the communication I/Fs 44 and 26 is performed in a secure manner.

Figure 6:
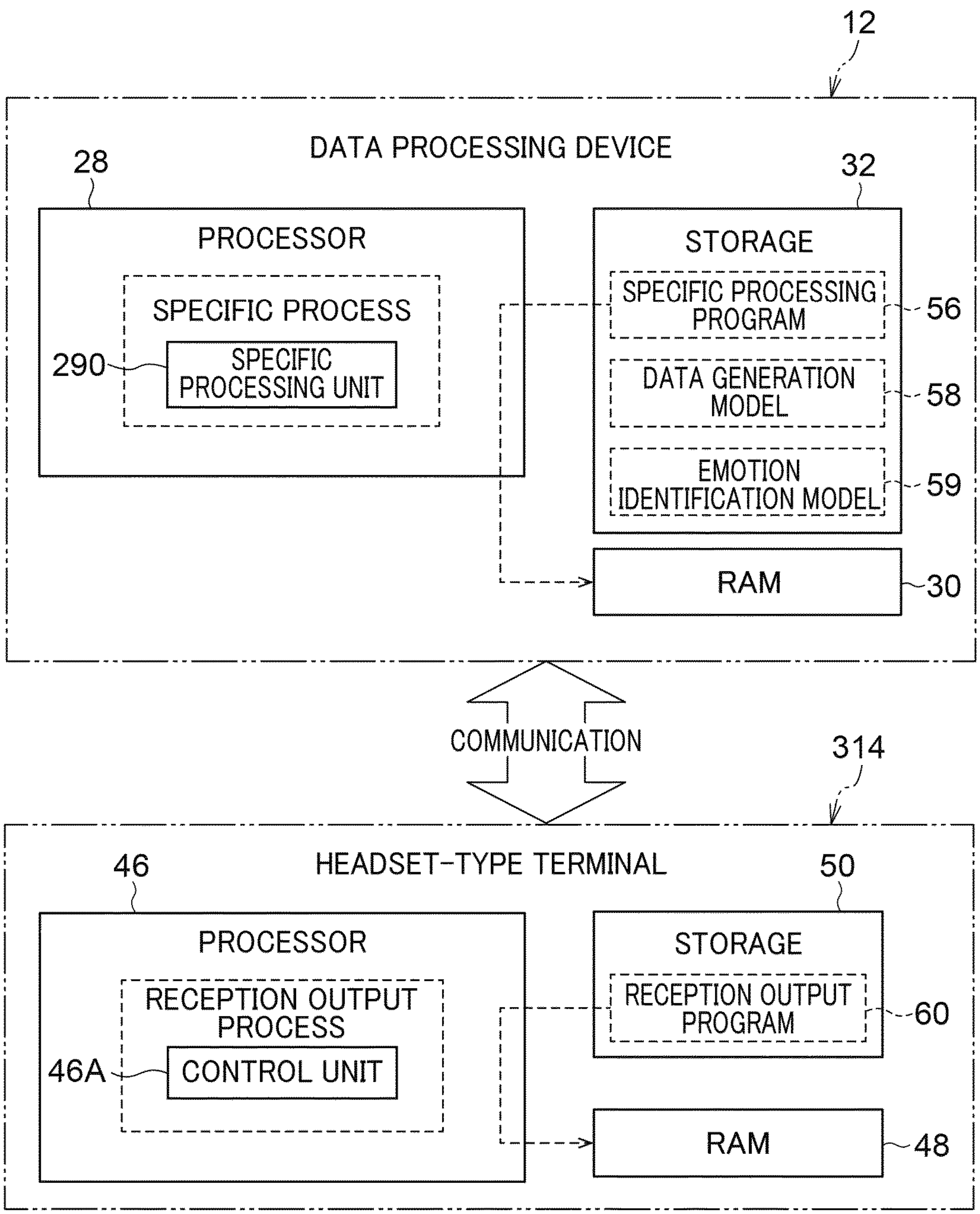
FIG. 6 is a conceptual diagram showing an example of the key functions of the data processing device and headset-type terminal for the third exemplary embodiment.

FIG. 6 shows an example of the key functions of data processing device 12 and headset-type terminal 314. As shown in FIG. 6, in data processing device 12, specific processing is performed by processor 28. The storage 32 contains a specific processing program 56.

The specific processing program 56 is an example of a "program" for the technology of the present disclosure. The processor 28 reads the specific processing program 56 from the storage 32 and executes the read specific processing program 56 on the RAM 30. The specific processing is realized by the processor 28 operating as the specific processing unit 290 according to the specific processing program 56 executed on RAM 30.

The data generation model 58 and emotion identification model 59 are stored in storage 32. The data generation model 58 and emotion identification model 59 are used by the specific processing unit 290.

At the headset-type terminal 314, the reception output process is performed by processor 46. The reception output program 60 is stored in the storage 50. Processor 46 reads reception output program 60 from storage 50 and executes the read reception output program 60 on RAM 48. The reception output process is realized by the processor 46 operating as the control unit 46A according to the reception output program 60 executed by the processor 46 on RAM 48.

Next, the specific processing by the specific processing unit 290 of the data processing device 12 is described.

Example of Implement 1

One exemplary embodiment of the invention is a brain-machine interface that combines brain waves and generative AI.

There is a system that generates a BMI. This system analyzes the user's brain waves in real time and inputs the results to a generative AI. The generative AI understands the user's intention based on the brain wave data and generates output based on it. For example, when a user wants a cup of coffee, the brain waves are analyzed, and the generative AI understands the user's intention and can take action such as "make coffee.

Example of Implement 2

Another exemplary embodiment of this invention is a platform to promote BMI in society. This platform has a function that allows users to manage their own EEG data and share it with third parties as needed. For example, users can manage their own EEG data on the platform and share it with medical and research institutions to obtain more accurate medical services and research results.

Example of Implement 3

A further exemplary embodiment of the invention are the new services offered through the platform. These services include intuitive communication services using brain activity, metaverse interface, health management services, and biometric authentication services. For example, intuitive communication services analyze a user's brain waves to understand their emotions and intentions, and communicate based on this information. Also, in metaverse interfaces, the user's brain waves are analyzed to control their behavior in VR and AR worlds. The health management service analyzes the user's brain waves to understand their stress level, sleep state, etc., and proposes health management based on this information. The biometric authentication service analyzes the user's brain wave patterns to perform personal authentication.

The process flow for each example of implement is described below.

Example of Implement 1

Step 1: The user has a specific thought or intention.
Step 2: The system captures and analyzes the user's brain waves in real time.
Step 3: Input the analysis results to the generative AI.
Step 4: The generative AI understands the user's intentions based on the brain wave data and generates output based on it. For example, it will perform an action such as "make coffee.

Example of Implement 2

Step 1: Users access the platform and upload their own EEG data.
Step 2: The platform manages the user's EEG data and shares it with third parties as needed. For example, sharing with medical and research institutions will enable more accurate medical services and research results.

Example of Implement 3

Step 1: The user selects a specific service through the platform. For example, intuitive communication services, metaverse interface, health care services, biometric services, etc.
Step 2: The selected service analyzes the user's brain waves and provides services based on them. For example, an intuitive communication service analyzes the user's brain waves to understand his/her feelings and intentions and communicates based on them.

Example 1

Next, example 1 of exemplary embodiment of implement will be described. In the following description, data processing device 12 is referred to as the "server" and headset-type terminal 314 is referred to as the "terminal.

Conventional brain-machine interfaces (BMIs) are inaccurate in analyzing the user's brain waves, making it difficult to understand the user's intentions in real time. In addition, these systems were highly invasive and burdensome to users. Furthermore, the management and sharing of EEG data is not easy, which has hindered its widespread use in society.

The specific processing by the specific processing unit 290 of the data processing device 12 in Example 1 is realized by the following means.

In this invention, the server provides a means for collecting brain waves of a user in real time, a means for analyzing the collected brain wave data, a means for inputting the analyzed brain wave data into a generative AI model, a means for the generative AI model to understand the intent of the user and generate outputs based thereon, a means for providing feedback of the generated means to provide a platform for the dissemination of the brain-machine interface (BMI) to society, and to provide intuitive communication services, virtual space services, biometric authentication services, and other services using brain activity that are provided through the platform. interface, health management services, and biometric authentication services provided through the platform. This enables highly accurate and minimally invasive analysis of users' brain waves and real-time understanding of their intentions. It will also facilitate the management and sharing of EEG data and promote its widespread use in society.

The term "user" refers to the individual who uses the brain-machine interface (BMI).

Brain waves" are electrical signals generated by the user's brain.

Real-time" means that data is processed and analyzed as soon as it is generated.

The term "means of collection" refers to devices and methods used to detect and acquire data on the user's brain waves.

The term "means of analysis" refers to methods and devices used to process the collected EEG data and infer the user's intent.

The term "generative AI model" refers to an artificial intelligence model that understands the user's intent based on the input data and generates output based on that intent.

The term "means of input" refers to the methods and devices used to provide the analyzed EEG data to the generative AI model.

Output" refers to the results and suggestions generated by the generative AI model based on its understanding of the user's intentions.

The term "means of feedback" refers to the methods and devices used to communicate the generated output to the user.

The term "platform" refers to the systems and services that serve as the foundation for the diffusion of brain-machine interfaces (BMIs) in society.

The term "communication service" refers to a service that uses brain waves to allow users to intuitively exchange information with others.

The term "virtual space interface" refers to an interface that uses brain waves to allow users to operate and move within a virtual space.

The term "health management service" refers to a service that uses users' brain wave data to monitor and manage their health.

The term "biometric service" refers to a service that uses a user's brain wave data to authenticate an individual.

This invention is a brain-machine interface (BMI) system that analyzes a user's brain waves in real time and inputs the results into a generative AI model to understand the user's intentions and generate output based on them. The system is implemented using the following hardware and software Hardware and Software Configuration EEG Sensor The user wears an EEG sensor on the head. This sensor detects the user's brain waves in real time and collects the data as electrical signals.

Server

The server receives EEG data transmitted from the EEG sensor. The received data is sent to the terminal for analysis.

Terminal

The terminal analyzes the EEG data sent from the server. An EEG analysis library using Python is used for the analysis. The terminal sends the analysis results to the server.

Generative AI Model

The server inputs the analyzed brain wave data into a generative AI model (e.g., OpenAI's GPT-4). The generative AI model understands the user's intention based on the input data and generates output based on it.

Feedback

The generated output is sent to the terminal through the server, which then feeds it back to the user. The user can then take the suggested action.

Concrete Example

For example, consider the case where a user wants to listen to music. An EEG sensor collects the user's EEG data, and the terminal analyzes the data. If the analysis results indicate the intention to "listen to music," the following prompt statement is entered into the generative AI model:

The user's EEG data has detected the intention to listen to music. Please suggest actions to play appropriate music.

The generative AI model generates an output "play music" based on this prompt sentence and feeds it back to the user through the terminal. The user can then play the music according to the suggested action.

In this way, the system can analyze the user's EEG with high accuracy and minimally invasive, and understand their intentions in real time. In addition, the system will facilitate the management and sharing of EEG data and promote its widespread use in society.

The flow of the identification process in Example 1 is described in FIG. 11.

Step 1:

The user wears an EEG sensor on his/her head. The EEG sensor detects the user's brain waves in real time and collects the data as electrical signals. The collected EEG data is transmitted to a server.

Input: User's brain waves

Output: EEG data (electrical signals)

Step 2:

The server receives the EEG data transmitted from the EEG sensor. The received EEG data is sent to the terminal for analysis.

Input: EEG data (electrical signals)

Output: EEG data (transfer from server to terminal)

Step 3:

The terminal receives the EEG data sent from the server. The terminal analyzes the EEG data using a Python-based EEG analysis library. In the process of analysis, specific brain wave patterns are detected and the intention of the user is inferred. The analysis results are sent to the server.

Input: EEG data (transferred from server)

Output: Analysis results (user intent)

Step 4:

The server receives the analysis results sent from the terminal. The server generates prompt sentences based on the analysis results and inputs them into the generative AI model.

Input: Analysis results (user intent)

Output: Prompt statement

Step 5:

The generative AI model receives prompt sentences sent from the server. The generative AI model understands the user's intention based on the prompt sentences and generates output based on it. The generated output is sent to the server.

Input: Prompt statement

Output: Output

Step 6:

The server receives the output sent from the generative AI model. The server sends the output to the terminal.

Input: Output (transfer from generative AI model)

Output: Output (transfer from server to terminal)

Step 7:

The terminal receives the output sent from the server. The terminal feeds back the output to the user. The user can perform the suggested action.

Input: Output (transfer from server)

Output: Feedback to user

Example of Application 1

Next, example of application 1 of example of implement 1 will be described. In the following description, data processing device 12 is referred to as the "server" and headset-type terminal 314 is referred to as the "terminal.

Conventional control methods for factory robots are mainly manual operation or programmed control, which is difficult to operate intuitively. In addition, more intuitive and quicker control methods are required to improve work efficiency. Furthermore, brain-machine interface (BMI) using brain waves has been applied in the medical and entertainment fields, but has not yet been fully utilized in factory automation and robot control. To solve these problems, a system that can intuitively control factory robots using brain waves is needed The specific processing by the specific processing unit 290 of the data processing device 12 in example of application 1 is realized by the following means.

In this invention, the server provides means to generate a minimally invasive and highly accurate brain-machine interface (BMI) that combines brain waves and generative AI, means to provide a platform for disseminating the BMI in society, means to provide intuitive brain activity-based means to provide communication services, metaverse interface, health management services, and biometric authentication services using brain activity, means for factory workers to wear head-mounted displays and control factory robots using brain waves, and means for analyzing users' brain wave data in real time and inputting the results into a generative system AI, including means to understand the user's intentions and generate output based on them by inputting the results into the AI, and means to control the factory robot based on the user's intentions. This allows factory workers to intuitively control factory robots using brain waves.

Brain waves" are electrical signals generated by neural activity in the brain.

Generative AI" is a type of artificial intelligence that generates new data and outputs based on input data.

A "brain-machine interface" (BMI) is an interface that uses brain waves to control a machine or computer.

The term "minimally invasive" refers to less burden or damage to the body.

The term "high precision" refers to extreme accuracy.

A "platform" is the underlying system or environment that provides a specific service or function.

An "intuitive communication service" is one that allows users to operate and communicate intuitively.

A "metaverse interface" is an interface for performing activities and operations in a virtual space.

A "health management service" is a service designed to manage and improve a user's health status.

Biometric services" are services that authenticate individuals using biometric information such as fingerprints and facial recognition.

A "factory worker" is a worker engaged in production activities in a factory.

A "head-mounted display" is a display device worn on the head.

A "factory robot" is a robot used to automate production tasks in a factory.

Real-time" refers to immediate processing and reaction without delay.

User intent" is the intention or purpose of what the user wants to do or think.

Output" is the result or behavior output from a system or device.

The following system configuration and program are required to implement this invention.

System Configuration 1. hardware
   - Head-mounted displays (HMDs): Built-in EEG sensors to collect EEG data in real time.
   - Factory robots: robots that are designed to perform actions based on the user's intentions.
   - Server: analyzes EEG data and executes generative AI models.
2. Software
   - BrainwaveReader: module for collecting EEG data.
   - GenerativeAIModel: A generative AI model that analyzes brain wave data to understand user intent.
   - RobotController: Module for controlling robots based on user intent.

Explanation of Program Processing

The server first collects brain wave data from the head-mounted display (HMD); the BrainwaveReader module analyzes this data in real time and inputs it to the Generative AI model (GenerativeAIModel). The generative AI model interprets the user's intentions based on the brainwave data and passes the intentions to the RobotController, which controls the factory robot based on the interpreted intentions and performs the corresponding actions.

Concrete Example

For example, if a factory worker thinks "assemble parts," the following prompt sentence is entered into the generative AI model.

Example of a Prompt Statement:

Based on the analysis of the user's brain wave data, the user believes that the user is "assembling parts". Based on this intention, instruct the robot to perform an action to assemble the parts.

Based on this prompt sentence, the generative AI model interprets the user's intention and instructs the RobotController to perform the "assemble parts" operation. As a result, the factory robot automatically starts assembling the parts.

This system allows factory workers to intuitively control factory robots using brain waves, greatly improving work efficiency.

The flow of the identification process in Example of Application 1 is described in FIG. 12.

Step 1:

A user wears a head-mounted display (HMD); the HMD has a built-in EEG sensor that collects the user's EEG data in real time. The input is the user's EEG and the output is the collected EEG data.

Step 2:

The server receives the EEG data sent from the HMD using the BrainwaveReader module; BrainwaveReader analyzes this data in real time, performing noise removal and feature extraction. The input is the EEG data from the HMD and the output is the analyzed EEG data.

Step 3:

The server inputs the analyzed EEG data to GenerativeAIModel, which is a generative AI model for interpreting user intentions based on the EEG data. The input is the analyzed EEG data and the output is the data indicating the user's intention.

Step 4:

Based on the server's interpretation of the user's intent, a prompt statement is generated. This prompt sentence is a specific description of the user's intent. The input is the data indicating the user's intent, and the output is the prompt sentence.

Step 5:

The server passes the generated prompt sentence to the RobotController, which generates specific instructions for the factory robot based on this prompt sentence. The input is the prompt sentence and the output is the instructions to the robot.

Step 6:

RobotController sends instructions to the factory robot. The factory robot executes the corresponding action based on these instructions. The input is the instruction to the robot and the output is the robot's action.

Step 7:

The user checks the operation of the factory robot through the HMD; the HMD displays the robot's operating status in real time to confirm that the robot is operating as intended by the user. The input is the operating status of the robot and the output is the image displayed on the HMD.

Example 2

Next, example 2 of exemplary embodiment of implement will be described. In the following description, data processing device 12 is referred to as the "server" and headset-type terminal 314 is referred to as the "terminal.

Conventional brain-machine interfaces (BMIs) lack a platform for effectively managing users' EEG data and securely sharing it with third parties. They also lacked real-time analysis of EEG data and linkage with generative AI, making it difficult to accurately understand user intentions and generate appropriate outputs. Furthermore, encryption of EEG data and management of access privileges were insufficient, and data security was not ensured.

The specific processing by the specific processing unit 290 of the data processing device 12 in Example 2 is realized by the following means. In this invention, the server is equipped with the following means: a means by which the user uploads brain wave data acquired by using a dedicated measurement device from the terminal to the server; a means by which the server stores the received brain wave data in a database; a means by which the user accesses the platform and manages the data; a means by which the user encrypts the data and grants access to a third party and means to configure the data to be shared, and the server encrypts the data and grants access to the third party. This allows users to effectively manage their own EEG data and securely share it with third parties. In addition, in conjunction with the generative AI, the system can accurately understand the user's intentions and generate appropriate output.

A "brain-machine interface (BMI)" is an interface that uses brain waves to communicate a user's intentions to a machine.

Generative AI" is artificial intelligence that analyzes a user's brain wave data and generates appropriate output based on the results.

A "platform" is a system that allows users to manage their EEG data and share it with third parties as needed.

EEG data" is data that measures the user's brain activity and is obtained using an EEG measurement device.

A "measurement device" is a device used to measure a user's brain waves in real time.

A "terminal" is a computer, smart device, or other device used by a user to upload EEG data acquired using the measurement device to a server.

A "server" is a computer system used to store and manage EEG data received from users.

A "database" is a system for efficiently storing and accessing EEG data received by the server.

Encryption" is a technique for converting data into a format that cannot be deciphered by a third party.

Access privileges" is the ability to set the rights of a specific user or third party to access data.

Output" is the output generated by the generative AI based on the results of analyzing the user's EEG data.

Exemplary Embodiment of the Invention

This invention is a system that provides a platform for users to manage EEG data acquired using specialized measurement devices and share it with third parties as needed. Specific exemplary embodiments of this system are described below.

Hardware and Software Configuration

The user uses a dedicated EEG measurement device to obtain EEG data. This measurement device measures the user's brain waves in real time and transmits the data to a terminal (PC or smartphone).

The terminal uploads the acquired EEG data to the server through a dedicated application. The application converts the data into the appropriate format (e.g., CSV or JSON) and sends it securely to the server using the HTTPS protocol.

The server stores the received EEG data in a database (e.g., MySQL or PostgreSQL). The database organizes the data by user and indexes it for efficient access.

Users access the platform through a web browser or mobile application. The platform authenticates the user (e.g., OAuth or JWT) and provides an interface that allows users to view, edit, and delete their own EEG data.

Data Sharing and Encryption

If the user wants to share data with a third party, he/she selects the third party (e.g., a medical or research institution) with whom he/she wants to share the data on the platform. The user sets the scope and duration of the data to be shared and submits a sharing request.

The server receives the user's sharing request and encrypts the data to be shared. Encryption uses a strong encryption algorithm such as AES-256. The server grants access privileges to designated third parties and creates a secure access link to the shared data.

Concrete Example

For example, when a user shares his/her EEG data with a medical institution, the following steps are taken 1. the user wears the EEG sensor and launches the dedicated application.
2. the terminal converts the acquired EEG data into CSV format and uploads it to the server using HTTPS.

The server stores the received data in a MySQL database.

4. the user logs into the platform with a web browser and checks his/her EEG data.

The user selects a medical institution and sets the scope and duration of the data to be shared.

6. the server encrypts the data with AES-256 and grants access privileges to the medical institution.

Example of Prompt Sentences to be Entered into a Generative AI Model:

Describe the steps a user would take to use an EEG sensor to obtain EEG data and share it with their healthcare provider."

By inputting this prompt statement into the data generation AI model, the specific procedure for the user to obtain EEG data and share it with the healthcare provider is output.

The flow of the identification process in Example 2 is described in FIG. 13.

Step 1:

The user uses a dedicated EEG measurement device to acquire EEG data. The user wears the measurement device and starts the dedicated application. The measurement device measures the user's brain waves in real time and transmits the data to the terminal. The input is the user's EEG and the output is the EEG data transmitted to the terminal.

Step 2:

The terminal uploads the EEG data to the server. The terminal converts the acquired EEG data into CSV format through a dedicated application and sends it to the server using the HTTPS protocol. The input is the EEG data sent from the measurement device and the output is the EEG data in CSV format uploaded to the server.

Step 3:

The server stores the received EEG data in a database. The server imports the received EEG data in CSV format into the database and organizes the data for each user. The input is the EEG data in CSV format sent from the terminal, and the output is the EEG data stored in the database.

Step 4:

Users access the platform and manage their data. The user logs into the platform through a web browser or mobile application to view, edit, and delete his/her EEG data. The input is the user's login information and the EEG data stored in the database, and the output is the EEG data that the user has viewed, edited, or deleted.

Step 5:

The user sets up the sharing of data with third parties. The user selects the third party they wish to share with on the platform and sets the scope and duration of the data to be shared. The input is the user's sharing configuration information and the output is the sharing request sent to the server.

Step 6:

Server encrypts data and grants access to third parties. The server receives the user's share request and encrypts the data to be shared with AES-256. The server grants access privileges to the designated third party and generates a secure access link to the shared data. The input is the user's sharing request and the EEG data stored in the database, and the output is the encrypted data and the access rights granted to the third party.

Example of Application 2

Next, example of application 2 of example of implement 2 will be described. In the following description, data processing device 12 is referred to as the "server" and headset-type terminal 314 is referred to as the "terminal.

Conventional brain-machine interfaces (BMIs) lack a platform for effectively managing users' EEG data and sharing it with third parties as needed. In addition, they lacked sufficient management of EEG data security and sharing history, which prevented smooth data sharing with medical and research institutions. Furthermore, the lack of a function to collect users' EEG data in real time, encrypt it, and upload it to the cloud did not ensure the security and convenience of the data The specific processing by the specific processing unit 290 of the data processing device 12 in example of application 2 is realized by the following means. In this invention, the server provides means for generating a minimally invasive and highly accurate brain-machine interface (BMI) that combines brain waves and generative AI, means for providing a platform for disseminating the BMI in society, means for providing intuitive communication services, metaverse interface, health management services, and biometric authentication services provided through the platform; means for collecting users' brain wave data in real time, encrypting and uploading the data to the cloud; and means for sharing the data with medical institutions and research organizations and managing data sharing history. The means to share the data with medical and research institutions, and to manage the data sharing history. This allows users' EEG data to be managed securely and efficiently and shared with third parties as needed.

Brain waves" are electrical signals generated by neural activity in the brain.

Generative AI" is a type of artificial intelligence, a system that has the ability to generate new data and information based on input data.

Minimally invasive" means less stressful or damaging to the body.

High precision" means extremely accurate.

A "brain-machine interface" (BMI) is an interface that uses brain waves to operate a machine or computer.

A "platform" is the underlying system or environment that provides a specific function or service.

An "intuitive communication service" is one that allows users to interact with information in a natural way.

A "metaverse interface" is an interface that allows users to operate and experience things in a virtual space.

A "health management service" is a service that monitors and manages a user's health status.

Biometric services" are services that use a user's biometric information to verify identity.

Real-time" means that data and information are processed immediately.

Encryption" means that data is converted using a specific algorithm to a form that cannot be easily understood by a third party.

The "cloud" is a collection of computer resources and services provided via the Internet.

A "sharing history" is a record of how, when, and by whom data was shared.

A "medical institution" is a facility that provides medical services, such as a hospital or clinic.

A "research institution" is an organization or facility for conducting scientific research.

The following system configuration is an exemplary embodiment of this invention.

System Configuration

The system has the ability to collect users' EEG data in real time, encrypt it, and upload it to the cloud. It also has the ability to share data with medical and research institutions and manage data sharing history.

Hardware Used

Smart device: a device that allows users to manage their EEG data and upload it to the cloud.

EEG sensors: devices (e.g., Muse, Emotiv) to collect EEG data on users.

Software to be Used

Python: A programming language for performing the main processing of a program.

NeuroKit2: A library for simulation and analysis of EEG data.

Requests: Library for sending HTTP requests.

Cryptography: Library for data encryption.

Process Flow

1. EEG data collection: EEG sensors are used to collect the user's EEG data in real time. The collected data is stored on the smartphone.

Data encryption: The EEG data collected will be encrypted using the Cryptography library. This ensures data security.

Data upload: Encrypted data is uploaded to the cloud using the Requests library. Data is stored securely in the cloud.

Data sharing: Users can share data with medical institutions and research organizations as needed. Sharing history is stored locally, allowing users to see who accessed what data and when.

Concrete Example

The user wears the EEG sensor and launches the NeuroGuard app. The app collects the EEG data, encrypts it, and uploads it to the cloud. With the user's permission, a medical institution retrieves the data from the cloud and uses it for diagnosis.

Example of Prompt Text

The user wears the EEG sensor and launches the NeuroGuard app. The app collects EEG data, encrypts it, and uploads it to the cloud. With the user's permission, a healthcare provider retrieves the data from the cloud and uses it for diagnosis.

This system will allow users' EEG data to be managed securely and efficiently and shared with third parties as needed.

The flow of the identification process in example of application 2 is described in FIG. 14.

Step 1:

The user wears the EEG sensor and launches the NeuroGuard application on the smartphone. The EEG sensor collects the user's EEG data in real time and transmits it to the smartphone. The input is the EEG data from the EEG sensor and the output is the raw EEG data stored on the smartphone.

Step 2:

The terminal (smartphone) analyzes the EEG data collected using the NeuroKit2 library. This analysis extracts the features of the EEG data. The input is the raw EEG data and the output is the features of the analyzed EEG data. Specifically, NeuroKit2 functions are invoked to analyze the EEG data and extract the features.

Step 3:

The terminal encrypts the analyzed EEG data using the Cryptography library. The input is the features of the analyzed EEG data and the output is the encrypted EEG data. The specific operation is to generate an encryption key and encrypt the EEG data using the key.

Step 4:

The terminal uploads encrypted EEG data to the cloud using the Requests library. The input is the encrypted EEG data and the output is the encrypted data stored on the cloud. The specific operation is to send an HTTP POST request and upload the data to the cloud server.

Step 5:

The server manages the encrypted data stored on the cloud and shares the data with medical and research institutions as needed. The input is the encrypted data on the cloud and the output is the shared data. The specific operation is to decrypt the data and provide it to the designated third party with the user's permission.

Step 6:

The server maintains a data sharing history, recording who accessed what data and when. The input is the data access request information and the output is the shared history log. The specific operation is to generate an access log and store it locally or in the cloud.

In this way, the user's EEG data can be managed securely and efficiently and shared with third parties as needed.

Example 3

Next, example 3 of exemplary embodiment of implement will be described. In the following description, data processing device 12 is referred to as the "server" and headset-type terminal 314 is referred to as the "terminal.

Conventional brain-machine interfaces (BMIs) have had difficulty effectively analyzing users' brain wave data and identifying their emotions and intentions in real time. They also lacked a platform for intuitive communication, health management, biometric authentication, and other services based on these data. Furthermore, users lacked the ability to manage their own EEG data and share it with third parties as needed. To solve these problems, a system that provides highly accurate analysis of EEG data and a variety of services based on this data is needed.

The specific processing by the specific processing unit 290 of the data processing device 12 in Example 3 is realized by the following means.

In this invention, the server has means for the user to wear an EEG measurement device and connect it to the terminal; the terminal collects EEG data from the EEG measurement device and transmits it to the server; the server receives the EEG data and performs pre-processing; the server analyzes the pre-processed data to identify emotions and intentions, means for the server to transmit the analysis results to the terminal, the terminal to display the analysis results and provide feedback to the user, means for providing a platform for disseminating the system to society, and means for providing intuitive communication using brain activity provided through the platform. services, virtual reality interface, health management services, and biometric authentication services provided through the platform. This makes it possible to analyze users' brain wave data with high precision and provide a variety of services based on such data in real time.

The term "user" refers to the individual who wears the EEG measurement device and uses the system.

The term "EEG measurement device" refers to a device used to measure a user's EEG data.

The term "terminal" refers to an electronic device that transmits the data collected from the EEG measurement device to the server and displays the analysis results to the user.

The term "server" refers to a computer system that receives EEG data, performs pre-processing and analysis, and transmits the results to the terminal.

Pre-processing" refers to data cleansing operations performed on EEG data prior to analysis, such as noise removal and filtering.

The term "analysis" refers to the processing of data to identify the user's emotions and intentions based on the preprocessed EEG data.

The term "generative AI model" refers to a machine learning model used to analyze brain wave data to identify a user's emotions and intentions.

The term "platform" refers to the infrastructure that will allow the system to be disseminated to society and for users to manage their EEG data and share it with third parties as needed.

The term "intuitive communication service" refers to a service that uses brain wave data from users to understand their emotions and intentions and communicate accordingly.

The term "virtual reality interface" refers to an interface that controls behavior in a virtual or augmented reality world based on the user's brain wave data.

The term "health management service" refers to a service that uses brain wave data to determine a user's stress level, sleep status, etc., and suggests health management based on this information.

The term "biometric authentication service" refers to a service that analyzes a user's brain wave patterns for personal authentication.

The invention begins with the user wearing an EEG measurement device and connecting it to a terminal. The user wears the EEG measurement device (e.g. EEG device) on his/her head and connects it to a terminal (e.g. smart phone or PC) using Bluetooth or USB cable.

The terminal collects EEG data from the EEG device in real time using a dedicated application. The collected data is sent to the server via the Internet. The server receives the EEG data sent from the terminal and performs pre-processing. Pre-processing includes noise removal and filtering, and uses the Python MNE library for data cleansing.

The preprocessed data is input to a machine learning model on the server (e.g., using TensorFlow or PyTorch) to analyze emotions and intentions. The analysis results are used to identify the user's emotion (e.g., joy, sadness, surprise, etc.) or intention (e.g., the intention to perform a specific action).

The analysis results are sent from the server to the terminal. The terminal displays the analysis results received from the server to the user. For example, a chat application displays a message that the user is happy. The metaverse interface also controls actions in the VR and AR worlds based on the user's intentions.

As a concrete example, consider an intuitive communication service. A user wears an EEG device and connects it to a smart phone. The smart device collects brain wave data from the EEG device in real time and sends it to the server. The server preprocesses the received data and analyzes emotions using TensorFlow. If the analysis shows that the user is "happy," this information is reflected in the smartphone's chat application and a message is sent to the other party saying that the user is happy.

Example of a Prompt Statement:

The user wears the EEG device and connects it to a smart phone. The smartphone collects EEG data in real-time and sends it to the server. The server preprocesses the data and analyzes the emotions using TensorFlow. If the analysis shows that the user is "happy," the information is reflected in the chat application and a message is sent to the other party saying that the user is happy.

In this way, the server, terminal, and user work together to realize a system that provides new services using EEG data. The flow of the identification process in Example 3 is described using FIG. 15.

Step 1:

The user wears the EEG measurement device and connects it to the terminal.

Specifically, the user wears an EEG measurement device (e.g., EEG device) on his/her head and connects it to a terminal (e.g., smart phone or PC) using Bluetooth or USB cable. The input is the user's EEG and the output device is the EEG measurement device connected to the terminal.

Step 2:

The terminal collects EEG data from the EEG measurement device and sends it to the server.

Specifically, the terminal uses a dedicated application to collect EEG data from the EEG device in real time. The collected data is sent to the server via the Internet. The input is the EEG data from the EEG measurement device and the output is the EEG data sent to the server.

Step 3:

The server receives the EEG data and performs preprocessing.

Specifically, the server receives EEG data sent from the terminal. The received data is preprocessed by noise removal, filtering, etc. Data cleansing is performed using the Python MNE library. The input is the EEG data transmitted from the terminal and the output is the preprocessed EEG data.

Step 4:

The server analyzes the preprocessed data to identify emotions and intentions.

Specifically, the server inputs the preprocessed data into a machine learning model (e.g., using TensorFlow or PyTorch). The model identifies the user's emotions and intentions from the EEG data. The input is the preprocessed EEG data and the output is the emotion and intention information as the result of the analysis.

Step 5:

The server sends the analysis results to the terminal.

As a specific action, the server sends the analysis results to the terminal. The analysis results include the user's emotions (e.g., joy, sadness, surprise, etc.) and intentions (e.g., intention to perform a specific action). The input is the analysis result and the output is the analysis result sent to the terminal.

Step 6:

The terminal displays the analysis results and provides feedback to the user.

As a specific action, the terminal displays the analysis results received from the server to the user. For example, a chat application displays a message that the user is happy. In addition, the metaverse interface controls actions in the VR and AR worlds based on the user's intentions. The input is the analysis results received from the server and the output is the feedback displayed to the user.

Example of Application 3

Next, example 3 of application of example of implement 3 will be described. In the following description, data processing device 12 is referred to as the "server" and headset-type terminal 314 is referred to as the "terminal.

Conventional brain-machine interfaces (BMIs) have limited technology for analyzing a user's brain waves, making it difficult to perform highly accurate analysis in real time. They also lacked intuitive means of navigation and interaction within the metaverse, making it difficult to perform actions that reflect the user's intentions and emotions. Furthermore, functions related to the management and sharing of EEG data were inadequate, making it less convenient for users.

The specific processing by the specific processing unit 290 of the data processing device 12 in example of application 3 is realized by the following means.

In this invention, the server provides means for generating a minimally invasive and highly accurate brain-machine interface (BMI) that combines brain waves and generative AI, means for providing a platform for disseminating the BMI in society, means for providing, through the platform, brain activity-based intuitive communication services, metaverse interface, health management services, and biometric authentication services provided through the platform; means for controlling navigation and interaction in the metaverse by analyzing the user's brain waves in real time; and means for performing actions in the metaverse based on the user's intentions and emotions. means to perform actions. This allows users to intuitively navigate and interact within the metaverse using brain waves.

EEG" is a recording of the brain's electrical activity, data that can be used to analyze a user's intentions and emotions.

Generative AI is a type of artificial intelligence that generates new information and output based on input data.

A "brain-machine interface" (BMI) is an interface that analyzes brain waves to control machines and computers.

A "platform" is a system that serves as the foundation for providing a particular service or function.

Intuitive Communication Service" is a service that analyzes a user's brain waves to understand their emotions and intentions, and communicates accordingly.

A "metaverse interface" is an interface for user interaction in a virtual or augmented reality world.

The "Health Management Service" is a service that analyzes users' brain waves to determine their stress levels and sleep conditions, and suggests health management based on this information.

Biometric authentication service" is a personal authentication service that analyzes a user's brain wave patterns.

The term "navigation" refers to the instructions and operations that users use to navigate within a virtual space.

Interaction" refers to the user's interaction with other objects or characters in the virtual space.

Intent" is the user's intention to perform a particular action or operation.

Emotion" refers to the psychological state or feeling of a user.

An "action" is an action or reaction performed in the virtual space based on a user's intention or emotion.

A system for implementing this invention includes means to generate a minimally invasive, highly accurate brain-machine interface (BMI) that combines electroencephalograms and generative AI; means to provide a platform for popularizing the BMI in society; means to provide intuitive communication utilizing brain activity provided through the platform, metaverse interface, health management services, and biometric authentication services using brain activity provided through the platform; means to control navigation and interaction in the metaverse by analyzing the user's brain waves in real time; and means to execute actions in the metaverse based on the user's intentions and emotions. The system includes means to execute actions in the metaverse based on the user's intentions and emotions.

System Configuration

This System Uses the Following Hardware and Software

Hardware: Brainwave sensor, head-mounted display

Software: Python, EEG sensor API, Metaverse controller API

Explanation of Program Processing

The server analyzes the EEG data acquired from the EEG sensor in real time and inputs it to the generative AI. The generative AI analyzes the user's intentions and emotions based on the input EEG data and generates output based on them. Specifically, if the user wants to move forward, the brain wave sensor detects this intention and the avatar moves forward. Also, if the user feels happy, the emotion is detected and the avatar smiles.

Concrete Example

For example, if the user wants to move forward in the metaverse, the brainwave sensor will detect that intention and the avatar will move forward. Also, if the user feels happy, the emotion will be detected and the avatar will smile.

Example of Prompt Text

Examples of prompt sentences to be input into the generative AI model are as follows If the user wants to move forward, the brainwave sensor should detect that intention and generate a program that causes the avatar to move forward. Also, if the user feels happy, the emotion should be detected and the avatar should smile.

The flow of the identification process in example of application 3 is described in FIG. 16.

Step 1:

The server acquires EEG data from the EEG sensor.

Input: Raw data from EEG sensor

Output: Acquired EEG data

Specific operation: An EEG sensor measures the user's brain waves in real time and sends the data to the server.

Step 2:

The server preprocesses the acquired EEG data.

Input: EEG data acquired

Output: preprocessed EEG data

Specific operation: Pre-processing such as noise removal and filtering is performed, and the data is converted into a format suitable for analysis.

Step 3:

The server inputs the preprocessed EEG data to the generator system AI.

Input: preprocessed EEG data

Output: Data input to the generative AI

Specific operation: Pre-processed EEG data is input into a generative AI model to analyze the user's intentions and emotions.

Step 4:

The generative AI analyzes the user's intentions and emotions based on the input brain wave data.

Input: Data input to the generative AI

Output: parsed intentions and feelings

Specific behavior: A generative AI model analyzes brain wave data to identify what the user intends and what emotion identification model the user has.

Step 5:

The server determines actions in the metaverse based on the analysis results.

Input: parsed intentions and feelings

Output: Actions performed in the metaverse

Specific actions: If the user's intention is "forward", the avatar determines the action of moving forward; if the emotion is "happy", the avatar determines the action of smiling.

Step 6:

The server sends the determined action to the Metaverse Controller.

Input: Actions to be performed in the metaverse

Output: Action instructions sent to the Metaverse Controller

Specific actions: The determined actions are sent through the Metaverse Controller's API to instruct the avatar to actually perform the action.

Step 7:

The Metaverse Controller controls the avatar based on the action instructions received.

Input: Action instructions sent to the Metaverse Controller

Output: Avatar behavior

Specific actions: The metaverse controller controls the avatar to perform actions based on the user's intentions and emotions. For example, the avatar moves forward or smiles.

Further, an emotion engine that estimates the user's emotion may be combined. In other words, the specific processing unit 290 may use the emotion identification model 59 to estimate the user's emotion and perform specific processing using the user's emotion.

Example of Implement 1

In one exemplary embodiment, the brain-machine interface (BMI) analyzes the user's brain waves in real time and inputs the results to the generative AI. In addition, by combining an emotion engine, the user's emotional state is also analyzed simultaneously. Based on the results of this analysis, the system understands the user's intentions and emotional state, and generates output based on them. For example, if a user thinks of "making coffee" with an emotion of joy, the system recognizes that joyful emotion and takes action to make coffee accordingly.

Example of Implement 2

In another exemplary embodiment of the invention, the platform has a function that allows users to manage their own EEG data and emotional states and share them with third parties as needed. For example, users can share their EEG data with medical and research institutions when they are feeling joyful emotions to obtain more accurate medical services and research results.

Example of Implement 3

In a further exemplary embodiment of the invention, the services provided through the platform have the ability to provide services that utilize the emotional state of the user. For example, an intuitive communication service analyzes the user's brain waves to understand their emotions and intentions, and communicates based on this information. If the user has a joyful emotion, the service recognizes that joyful emotion and provides communication accordingly.

The process flow for each example of implement is described below.

Example of Implement 1

Step 1: The user thinks of a specific action. For example, think "make coffee".
Step 2: The brain-machine interface (BMI) analyzes the user's brain waves in real time.
Step 3: The emotion engine analyzes the user's emotional state. In this example, it analyzes that the user has the emotion of joy.
Step 4: Based on the analysis results, understand the user's intentions and emotional state and generate output based on them. In this example, the coffee-making action is tailored to the emotion of joy.

Example of Implement 2

Step 1: The user feels a specific emotion. For example, feel the emotion of joy.
Step 2: The platform manages the user's EEG data and emotional state.
Step 3: The user shares his/her EEG data and emotional state with third parties as needed. In this example, it is shared with a medical or research institution.

Example of Implement 3

Step 1: The user uses the service through the platform. For example, use intuitive communication services.
Step 2: The service analyzes the user's brain waves to understand their emotions and intentions.
Step 3: The service provides communication tailored to the user's emotional state based on the analysis results. In this example, if the user has a joyful emotion, the service provides communication tailored to that joyful emotion.

Example 1

Next, example 1 of exemplary embodiment of implement will be described. In the following description, data processing device 12 is referred to as the "server" and headset-type terminal 314 is referred to as the "terminal.

Conventional brain-machine interfaces (BMI) only analyze the user's brain waves and fail to take into account the user's emotional state. This made it difficult to accurately understand the user's intentions and generate appropriate output. It also lacked a platform for managing users' EEG data and sharing it with third parties. This prevented the social diffusion of BMI and made it difficult to provide intuitive communication services, health management services, and biometric authentication services The specific processing by the specific processing unit 290 of the data processing device 12 in Example 1 is realized by the following means.

In this invention, the server includes means for acquiring the user's brain waves in real time, analyzing the acquired brain wave data to extract the user's intentions, analyzing the user's emotional state, generating and inputting prompt sentences to a generative AI based on the analysis results, and executing the output generated by the generative AI The system also includes means to execute the outputs generated by the generative AI. This enables the system to accurately understand the user's intentions and emotional state and generate appropriate outputs. The system can also provide a platform for disseminating the system in society, and provide intuitive communication services, virtual space interface, health management services, and biometric authentication services using brain activity.

A "user" is an individual who uses the system.

Brain waves" are electrical signals generated by neural activity in the brain.

Real-time" means that data is processed as soon as it is generated.

Means of acquisition" refers to devices and methods for collecting data.

Means to analyze" refers to devices and methods used to analyze acquired data and extract meaningful information.

Intent" refers to information that indicates what the user wants or is thinking about.

The term "emotional state" refers to information that indicates a user's feelings or mood.

Generative AI" refers to artificial intelligence that generates new information and output based on given data.

A "prompt sentence" is an input sentence used to give instructions or ask questions to the generative AI.

Output" refers to the results or responses generated by the generative AI based on the prompted statements.

Means of execution" refers to devices and methods used to convert output generated by the generative AI into concrete actions and operations.

The term "platform" refers to the infrastructure used to operate the system and provide services to users.

An "intuitive communication service" is one that allows users to exchange information with others in a natural way.

The term "virtual space interface" refers to an interface that allows users to operate and experience things within a virtual environment.

The term "health management services" refers to services for monitoring and managing the health status of users.

The term "biometric authentication service" refers to a service that uses a user's biometric information to verify his or her identity.

This invention is a system that analyzes a user's brain waves in real time and inputs the results to a generative AI to understand the user's intentions and emotional state and generate output based on these results. The system includes an EEG measurement device to acquire the user's EEG, software to analyze the EEG data, an emotion engine to analyze the emotional state, a generative AI, and hardware to execute the generated output.

Hardware and Software Used

1. Brain Wave Measurement Device

The user wears a special EEG measurement device. This device acquires the user's brain waves in real time.

2. Brain Wave Analysis Software

EEG analysis software (e.g., OpenBCI) is used by the terminal to analyze the EEG data acquired from the EEG measurement device. This software analyzes the EEG data and extracts the user's intentions.

3. Emotion Engine:

The terminal uses an emotion engine to analyze the user's emotional state. This engine acquires emotional data through facial recognition cameras and voice analysis to understand the user's emotional state.

4. Generative AI: The

The server generates and inputs prompt sentences to the generative AI (e.g. OpenAI GPT-4) based on the analysis results. The generative AI generates appropriate outputs based on the prompt sentences.

Output Execution Hardware: 5.

The server receives output from the generative AI and manipulates hardware (e.g., IoT devices) to perform specific actions.

Concrete Example

The user wakes up in the morning and puts on the EEG measurement device.

The terminal receives data from the EEG measurement device and begins analyzing it in real time.

The terminal detects the intention of "wanting a cup of coffee" from brain wave data.

The terminal confirms that the user has a feeling of "joy" through the facial recognition camera.

The terminal says, "The user wants to 'have a cup of coffee' with an emotion of pleasure. Please suggest an appropriate action." The terminal generates the prompt sentence "The user wants to have a cup of coffee.

The server sends a prompt sentence to the generative AI, and the generative AI generates an output that "instructs the coffee maker to make coffee.

The server operates the coffee maker through an IoT device to make coffee.

Example of Prompt Text

EEG data of user: [data].

User's emotional state: joy

User Intent: I want a cup of coffee

Prompt for generative AI: A user wants to 'have a cup of coffee' with a joyful emotion. Please suggest an appropriate action.

In this way, the system can analyze the user's brain waves and emotional state, generate output based on the user's intentions using generative AI, and execute specific actions.

The flow of the identification process in Example 1 is described in FIG. 17.

Step 1:

The user wears a special EEG measurement device.

Input: User's brain waves

Output: Real-time EEG data

Specific operation: The user wears the EEG measurement device on his/her head and the device begins to measure brain waves. The device transmits EEG data to the terminal in real time via Bluetooth or USB connection.

Step 2:

The terminal acquires EEG data from the EEG measurement device in real time.

Input: Real-time EEG data

Output: Acquired EEG data

Specific operation: The terminal receives EEG data transmitted from the EEG measurement device and stores it in a database.

Step 3:

The EEG data acquired by the terminal is analyzed to extract the user's intention.

Input: EEG data acquired

Output: User intent

Specific operation: The terminal uses EEG analysis software (e.g. OpenBCI) to analyze EEG data. It detects specific brain wave patterns and extracts the user's intentions based on them. For example, the intention of "I want a cup of coffee" is detected.

Step 4:

The terminal analyzes the user's emotional state.

Input: User's face image and voice data

Output: User's emotional state

Specific operation: The terminal uses the emotion engine to acquire emotion data through facial recognition camera and voice analysis. As a result of the analysis, the user identifies an emotional state such as "joy" or "sadness".

Step 5:

The terminal generates and inputs prompt sentences to the generative AI based on the analysis results.

Input: user intent and emotional state

Output: Prompt statement to generative AI

Specific action: The terminal integrates the user's intention and emotional state and says, "The user wants to 'have a cup of coffee' with a feeling of joy. Please suggest an appropriate action." The prompt sentence "The user wants to drink a cup of coffee" is generated.

Step 6:

The server sends prompt sentences to the generative AI, and the generative AI generates output.

Input: Prompt statement to generative AI

Output: Output from generative AI

Specific behavior: The server sends a prompt sentence to the generative AI (e.g., OpenAI GPT-4), and the generative AI generates an output "instructing the coffee maker to make coffee" based on the prompt sentence.

Step 7:

The server receives output from the generative AI and executes specific actions.

Input: Output from generative AI

Output: Actions performed

Specific operation: The server operates the coffee maker through the IoT device to make coffee. Specifically, "make coffee" instructions are sent to the coffee maker, and coffee is actually made.

Example of Application 1

Next, example of application 1 of example of implement 1 will be described. In the following description, data processing device 12 is referred to as the "server" and headset-type terminal 314 is referred to as the "terminal.

Conventional brain-machine interface (BMI) technology exists that analyzes the brain waves of users to understand their intentions, but the scope of its application is limited and has not been fully utilized, especially in work support in factories. In addition, the lack of a system that understands the intentions of workers in real time and automatically performs appropriate tasks has not sufficiently improved work efficiency or enabled human-machine collaboration.

The specific processing by the specific processing unit 290 of the data processing device 12 in example of application 1 is realized by the following means. In this invention, the server provides means to generate a minimally invasive and highly accurate brain-machine interface (BMI) that combines brain waves and generative AI, means to provide a platform to disseminate the BMI in society, means to provide intuitive communication services, metaverse interface, health management services, and biometric authentication services, and means to be installed in a robot performing work in a factory to analyze the worker's brain waves in real time, understand the worker's intentions, and automatically perform appropriate tasks. This makes it possible to understand the worker's intentions in real time and automatically perform appropriate tasks.

Brain waves" are electrical signals generated by neural activity in the brain.

Generative AI" is an artificial intelligence technology that generates new data and outputs based on input data.

Brain Machine Interface (BMI) is an interface technology that analyzes brain waves and uses the results to control machines and computers.

Minimally invasive" means less stressful or damaging to the body.

High precision" means extremely accurate.

A "platform" is the underlying system or environment that provides a specific service or function.

An "intuitive communication service" is one that allows users to interact with information in a natural way.

The term "metaverse interface" refers to the user interface within the virtual space.

A "health management service" is a service that monitors and manages a user's health status.

Biometric authentication service" is a service that uses an individual's biometric information for authentication.

A "robot that works in a factory" is a machine that is designed to automatically perform a specific task in a factory.

A "worker" is a person who performs work in a factory.

Real-time" means that processing and analysis occur almost simultaneously.

Intent" refers to the purpose or idea of what the user wants to do.

Output" refers to the results or actions produced by a system or machine.

The system for implementing this invention uses a minimally invasive and highly accurate brain-machine interface (BMI) that combines EEG and generative AI. The server analyzes the user's brain waves in real time and inputs the results to the generative AI, which understands the user's intentions and generates output based on them. In addition, by combining an emotion engine, the emotional state of the user is analyzed at the same time to understand the user's intentions and emotional state to generate output.

The system is installed on a robot performing a task in the factory and analyzes the worker's brain waves in real time. When a worker wants to perform a specific task, the robot understands his/her intention and automatically performs the appropriate task. For example, if the worker wants to assemble a part, the robot understands his/her intention and starts assembling the part.

The server uses EEG sensors to acquire EEG data. EEG data is analyzed in real-time using a Python library. An emotional engine will be used to analyze emotional states. A generative AI model (e.g., OpenAI GPT-3) understands the user's intentions based on the analyzed EEG data and emotional state, and generates appropriate output.

As a concrete example, here is a prompt sentence for a worker who wants to "assemble a part".

Example of a prompt statement: "I am a member of the User's EEG data: [0.1, 0.2, 0.3, . . . ].

User's emotional state: joy

User Intent: To assemble parts

By inputting this prompt sentence into the generative AI model, it understands the user's intention and generates appropriate actions. For example, a specific output is obtained, such as a robot starting to assemble a part.

This system enables the system to understand the intentions of workers in real time and automatically perform appropriate tasks. This improves work efficiency in the factory and realizes collaboration between man and machine.

The flow of the identification process in Example of Application 1 is described in FIG. 18.

Step 1:

The server acquires the user's EEG data in real time using EEG sensors. The input is the user's EEG signal and the output is the EEG data acquired. This data is transmitted from the EEG sensor to the server.

Step 2:

The server analyzes the acquired EEG data in real time using a Python library. The input is the acquired EEG data and the output is the analyzed EEG data. Through this analysis, EEG features and patterns are extracted.

Step 3:

The server analyzes the emotional state of the user from the analyzed EEG data using the emotion engine. The input is the analyzed EEG data and the output is the user's emotional state. This analysis determines whether the user is happy, sad, angry, etc.

Step 4:

The server uses a generative AI model (e.g., OpenAI GPT-3) to understand user intentions based on parsed EEG data and emotional states. The input is the parsed EEG data and emotional state, and the output is the user's intention. The data generation AI model inputs these data as prompts and infers what the user wants to do.

Step 5:

The server generates appropriate outputs based on user intent. The input is the user's intention and the output is a specific action. For example, if the user intends to assemble a part, the server instructs the robot to begin the process of assembling the part.

Step 6:

The robot receives instructions from the server and executes specific tasks. The input is the instructions from the server and the output is the work performed. For example, this includes a series of operations in which the robot starts and completes the assembly of a part.

Step 7:

The server monitors work progress and provides feedback as needed. The input is work progress data from the robot and the output is feedback information. This improves the accuracy and efficiency of the work.

Example 2

Next, example 2 of exemplary embodiment of implement will be described. In the following description, data processing device 12 is referred to as the "server" and headset-type terminal 314 is referred to as the "terminal.

Conventional brain-machine interfaces (BMIs) lack the ability to effectively manage users' EEG data and share it with third parties as needed. In addition, the accuracy and real-time nature of EEG data analysis was low, making it difficult to accurately understand the user's intentions. Furthermore, the acquisition and management of EEG data was complicated, making it difficult for ordinary users to use the system.

The specific processing by the specific processing unit 290 of the data processing device 12 in Example 2 is realized by the following means. In this invention, the server includes means by which the user acquires EEG data using a dedicated EEG measurement device and uploads it to the platform through a terminal, the server receives the EEG data and stores it in a database, and the server preprocesses and analyzes the EEG data. This allows users to effectively manage their own EEG data and share it with third parties as needed. It also improves the accuracy of the analysis of the EEG data and allows for an accurate understanding of the user's intentions in real time. Furthermore, the system simplifies the acquisition and management of EEG data, providing an easy-to-use system for the general user.

Brain Machine Interface (BMI) is a technology that uses brain wave data to understand the user's intentions and intuitively interact with machines and computers.

Generative AI is an artificial intelligence technology that analyzes a user's brain wave data and generates output based on the results.

The "platform" is the system infrastructure that allows users to manage their EEG data and share it with third parties as needed.

An "EEG measurement device" is a device worn on the user's head to acquire EEG data.

A "terminal" is a device that allows users to input and upload their EEG data to the platform.

A "server" is a computer system that receives EEG data, stores it in a database, and performs preprocessing and analysis.

A "database" is an information management system for storing received EEG data.

Pre-processing" refers to data cleaning operations performed on EEG data prior to analysis, such as noise removal and completion of missing values.

Analysis" is the process of classifying and understanding the user's emotional state and intentions based on the preprocessed EEG data.

The "third party" is the party with whom the user shares the EEG data, such as a medical or research institution.

Exemplary Embodiment of the Invention

This invention is a system in which users acquire EEG data using a dedicated EEG measurement device and upload it to the platform through a terminal. The server stores the received EEG data in a database for pre-processing and analysis. This allows users to effectively manage their own EEG data and share it with third parties as needed.

Hardware and Software Used

Hardware: (1)

EEG measurement device: The user uses a dedicated EEG measurement device (e.g., a common EEG measuring device) to obtain EEG data. This device is worn on the user's head and collects EEG data in real time.

Software: C

Terminal application: The terminal provides an interface for the user to receive and upload the EEG data acquired by the user to the platform. The user uploads the data through the terminal application.

Server: The server performs preprocessing and analysis of EEG data using Python. Specifically, libraries such as NumPy and Pandas are used to clean and filter the data. It also builds and analyzes machine learning models using libraries such as TensorFlow and PyTorch.

Database: The server uses a relational database such as MySQL or PostgreSQL to store EEG data.

Concrete Example

As a concrete example, consider a scenario in which EEG data is shared with a healthcare provider when a user is experiencing feelings of joy. The user uses an EEG measurement device to acquire the data and uploads it to the platform through a terminal. The server receives the data, analyzes it, and then sends the data to the medical institution.

Example of Prompt Sentences to be Entered into a Generative AI Model:

Describe the steps you would take to share EEG data with a medical provider when a user is experiencing feelings of joy."

Using this prompt statement, the generated AI model can provide detailed descriptions of specific procedures and necessary hardware and software.

In this way, users can effectively manage their own EEG data and share it with third parties as needed. In addition, the accuracy of EEG data analysis is improved, allowing the system to accurately understand the user's intentions in real time. Furthermore, the system simplifies the acquisition and management of EEG data, providing an easy-to-use system for the general user.

The flow of the identification process in Example 2 is described in FIG. 19.

Program Processing Flow

Step 1:

User Obtains EEG Data

Input: User's brain waves

Output: EEG data

Specific Operation: The user wears a dedicated EEG measurement device on the head to acquire EEG data in real time. The device detects the user's brain waves with sensors and stores them as digital data.

Step 2:

The Terminal Uploads EEG Data to the Platform

Input: EEG data

Output: Data uploaded to the platform

Specific operation: The user opens the application on the terminal, selects the EEG data acquired and presses the "Upload" button. The terminal sends the data to the platform.

Step 3:

Server Receives EEG Data and Stores it in a Database

Input: Uploaded EEG data

Output: Data stored in database

Specific Operation: The server receives EEG data sent from the terminal and stores it in a relational database such as MySQL or PostgreSQL. The database also stores metadata such as user IDs and time stamps.

Step 4:

Server Preprocesses EEG Data

Input: EEG data stored in database

Output: preprocessed data

Specifics: The server runs Python scripts and uses libraries such as NumPy and Pandas to clean and filter data. Specifically, it performs noise removal and missing value completion.

Step 5:

Server Analyzes EEG Data

Input: preprocessed data

Output: Analysis results (e.g. classification of emotional states)

Specific behavior: The server runs machine learning models using libraries such as TensorFlow and PyTorch to classify emotional states from EEG data. The analysis results are output as data indicating the user's emotional state and intentions.

Step 6:

User Manages EEG Data

Input: Analysis results and original EEG data

Output: Controlled data (e.g. filtered data display)

Specific behavior: users access the platform's dashboard to review analysis results. Data can be filtered and displayed for specific time periods.

Step 7:

Users Share EEG Data with Third Parties

Input: Managed data

Output: Shared data

How it specifically works: The user presses the "Share" button on the dashboard, enters the contact information of a third party (e.g., a medical institution), and gives permission to share. The server encrypts the data and sends it to the third party using HTTPS.

Thus, by performing specific actions in each step, users can effectively manage their own EEG data and share it with third parties as needed.

Example of Application 2

Next, example of application 2 of example of implement 2 will be described. In the following description, data processing device 12 is referred to as the "server" and headset-type terminal 314 is referred to as the "terminal.

Conventional brain-machine interfaces (BMIs) can collect and analyze users' brain wave data, but lacked a means to share that data with third parties in a secure and efficient manner. In addition, no system existed to analyze the user's emotional state in real time and take appropriate action when abnormalities were detected. This made it difficult to share data with medical and research institutions, and prevented users from improving the accuracy of their health management and biometric identification.

The specific processing by the specific processing unit 290 of the data processing device 12 in example of application 2 is realized by the following means.

In this invention, the server provides means for generating a minimally invasive and highly accurate brain-machine interface (BMI) that combines brain waves and generative AI, means for providing a platform for disseminating the BMI to society, means for providing intuitive brain activity-based communication services, metaverse interface, health management services, and biometric authentication services provided through the platform; collecting users' brain wave data in real time, encrypting it, and sharing it with third parties; analyzing users' emotional states and alerting them if any abnormality is detected. The system includes the following. This enables the secure and efficient sharing of the user's EEG data and strengthens cooperation with medical and research institutions. In addition, the user's emotional state can be monitored in real time, and if an abnormality is detected, a quick response can be made to improve the accuracy of health management and biometric authentication.

Brain waves" are electrical signals generated by neural activity in the brain.

Generative AI" is a type of artificial intelligence, a system that has the ability to generate new data and information based on input data.

The term "minimally invasive" refers to less burden or damage to the body.

A "brain-machine interface" (BMI) is an interface that uses brain waves to operate a machine or computer.

A "platform" is the underlying system or environment that provides a specific function or service.

An "intuitive communication service" is one that allows users to interact with information in a natural way.

A "metaverse interface" is an interface that allows users to operate and experience things in a virtual space.

Health Management Service" is a service that monitors the health status of users and provides appropriate advice and support.

Biometric services" are services that use a user's biometric information to verify identity.

Encryption" is a technique whereby data is converted using a specific algorithm so that it cannot be easily deciphered by a third party.

An "emotional state" is the emotional state a user is feeling at a particular moment in time.

An "alert" is a notification or warning of an abnormality or emergency.

The following system configuration is an exemplary embodiment of this invention.

System Configuration

The system will include hardware and software to collect the user's EEG data and analyze it using a generative AI. Specifically, the system will include the following elements.

1. EEG sensor: A device that collects the user's brain waves in real time. The EEG sensor is worn on the user's head and measures the electrical activity of the brain.
2. smart device: a device used to receive, encrypt, and analyze data from the EEG sensor. A dedicated application is installed on the smartphone.
3. server: provides a platform for receiving encrypted EEG data and sharing it with third parties (medical and research institutions) as needed. The server shall include software to manage and share the data.

Program Processing

The Server Will Perform the Following Processes

1. EEG data collection: EEG sensors collect the user's EEG data in real time and transmit it to the smartphone.
2. data encryption: The smartphone encrypts the received EEG data. Fernet, a cryptography library, is used for encryption.
3. data sharing: encrypted data is sent from the smartphone to the server. The server shares the received data with a designated third party (medical or research institution).
4. emotional state analysis: Smartphones analyze brain wave data to identify the user's emotional state. If an abnormality is detected, the smart phone will send out an alert.

Hardware and Software Used

EEG sensor: a device that collects the user's brain waves.

Smart devices: devices that receive, encrypt, parse, and share data.

Server: A platform for managing and sharing data.

Cyptography library: Software used to encrypt data.

Requests library: Software used to transmit data.

Concrete Example

For example, consider a case where brain wave data is collected when a user is stressed and sent to a medical facility. An EEG sensor collects the user's brain waves and transmits them to a smart phone. The smartphone encrypts the received data and sends it to the server.

The server shares the encrypted data with the medical institution. The medical institution analyzes the received data and evaluates the user's stress state.

Example of Prompt Text

Create a Python program that collects the user's EEG data, encrypts it, and sends it to a designated health care provider. The EEG data can be virtual data. Use the cryptography library Fernet for encryption and the requests library to send the data."

The above is an exemplary embodiment of this invention.

The flow of the identification process in example of application 2 is described in FIG. 20.

Step 1:

The user wears an EEG sensor. The EEG sensor collects the user's EEG data in real time. The input is the user's EEG signal and the output is the raw data collected by the EEG sensor.

Step 2:

The terminal (smartphone) receives EEG data from the EEG sensor. The terminal acquires the data using wireless communication such as Bluetooth or Wi-Fi. The input is the raw data transmitted from the EEG sensor and the output is the EEG data stored in the terminal.

Step 3:

Encrypt the EEG data received by the terminal. The cryptography library Fernet is used for encryption. The input is the EEG data stored in the terminal and the output is the encrypted EEG data. The specific operation is to generate an encryption key and encrypt the EEG data with the key.

Step 4:

The terminal sends encrypted EEG data to the server. The requests library is used for transmission. The input is the encrypted EEG data and the output is the data sent to the server. The specific operation is to send the data using an HTTP POST request.

Step 5:

The server stores the encrypted EEG data received. The server manages the data using a database. The input is the encrypted data sent from the terminal and the output is the encrypted data stored in the database.

Step 6:

The server shares encrypted EEG data with third parties (medical and research institutions) as needed. Secure communication protocols are used for sharing. The input is the encrypted data stored in the database and the output is the data sent to the third party. The specific operation is to authenticate the third party and send the data if the authentication is successful.

Step 7:

The terminal analyzes EEG data to identify the user's emotional state. A generative AI model is used for the analysis. The input is the EEG data stored in the terminal and the output is the emotional state as the result of the analysis. Specifically, the EEG data is input to the AI generation model, and the emotional state is estimated.

Step 8:

The terminal monitors the emotional state and sends out an alert when an abnormality is detected. The input is the emotional state as an analysis result, and the output is an alert when an abnormality is detected. Specifically, when the emotional state exceeds a predefined threshold, a notification is sent to the user or a designated third party.

Example 3

Next, example 3 of exemplary embodiment of implement will be described. In the following description, data processing device 12 is referred to as the "server" and headset-type terminal 314 is referred to as the "terminal.

Conventional brain-machine interfaces (BMI) require high accuracy in analyzing a user's brain waves, but it has been difficult to achieve high accuracy in a minimally invasive manner. In addition, there was a lack of a system to provide real-time feedback of the analysis results to the user, which could not immediately reflect the user's intentions or emotional state. Furthermore, users lacked the ability to manage their own EEG data and share it with third parties as needed.

The specific processing by the specific processing unit 290 of the data processing device 12 in Example 3 is realized by the following means. In this invention, the server includes the following means: the server measures the user's EEG data and transmits it to the server in real time; the server analyzes the EEG data and identifies the user's emotional state and intentions; and the server stores the analysis results in a database and transmits them to the terminal. This enables minimally invasive and highly accurate EEG analysis, which can reflect the user's intentions and emotional state in real time. It also allows users to manage their own EEG data and share it with third parties as needed.

Brain Machine Interface (BMI) is a technology that uses brain waves to control computers and other devices.

Generative AI" is a type of artificial intelligence that has the ability to generate new data and information based on input data.

A "platform" is the underlying system or environment that provides a specific service or function.

EEG data" is data that electrically measures the user's brain activity and reflects emotional states and intentions.

Real-time" means that data is measured and processed immediately.

Analysis" is the process of processing measured data to extract specific information or patterns.

The "emotional state" is a state that indicates the user's current emotion or mood.

Intent is what the user is trying to do or wants.

A "database" is a system that stores data in an organized manner and can be retrieved and updated as needed.

Feedback" is the response or information provided by the system to the user.

Minimally invasive" means less physical strain or discomfort to the user.

High precision" means that the measurement and analysis of data is extremely accurate.

A "virtual reality interface" is a means by which a user interacts with a virtual reality environment.

Health Management Service" is a service that monitors the user's health status and provides appropriate advice and support.

A "biometric service" is a service that uses a user's biometric information to authenticate an individual.

This invention is a system that provides a minimally invasive and highly accurate brain-machine interface (BMI) that combines EEG and generative AI. The system measures and analyzes the user's EEG data in real time to identify the user's emotional state and intentions, and provides feedback based on them.

Hardware and Software Used

Hardware (esp. Computer)

- EEG measurement devices: Devices to measure the user's brain waves (e.g., EEG headsets)
- Terminal: Device (e.g., smart device, tablet, PC) that connects to the EEG measurement device and sends data to the server
- Server: Computer system for receiving and analyzing EEG data Software

- Data transmission program: A program installed in the terminal to transmit EEG data to the server
- Data analysis programs: Programs installed on the server to analyze EEG data (e.g., FFT analysis using Python)
- Database management system: A system for storing analysis results and retrieving and updating them as needed.

Feedback program: A program installed on the terminal to display the results of the analysis to the user.

Specific System Operation

User Behavior

The user wears an EEG measurement device (e.g., EEG headset) and connects it to the terminal. The user performs certain actions to generate EEG data. For example, if the user is relaxed, the EEG data has a specific frequency component.

Terminal Operation

The terminal measures the user's brain waves in real time and transmits them to the server using a data transmission program. The terminal waits for a response from the server to confirm that the data transmission was successful.

Server Operation

The server receives the EEG data sent from the terminal. The received data is analyzed using a data analysis program. Specifically, the FFT (Fast Fourier Transform) is used to break down the EEG data into its frequency components and extract specific patterns. For example, the intensity of alpha and beta waves is calculated to identify the user's emotional state.

Save and Send Analysis Results

The server stores the analysis results in a database. The stored data includes user ID, measurement date and time, and analysis results (emotional state and intention). This makes it possible to refer to the data later. The server sends the analysis results to the terminal. Secure communication protocols (e.g. HTTPS) are used for transmission.

Terminal Feedback

The terminal displays the analysis results received from the server to the user. The display uses a graphical user interface (GUI). For example, if the user is relaxed, the terminal displays "relaxed state" and suggests appropriate actions (e.g., playing relaxing music).

Examples of Specific Examples and Prompt Sentences

Concrete Example

For example, when a user uses an intuitive communication service, the following steps are taken 1. the user puts on the EEG headset and connects it to the terminal.

The terminal measures EEG data in real time and sends it to the server.

3. the server receives the EEG data and analyzes it using FFT. For example, if the intensity of alpha waves is high, the server determines that the user is relaxed.

The results of the analysis are stored in a database. For example, data such as "User ID: 12345, Date: 2023 Oct. 1 10:00, State: Relaxed" will be saved.

The server sends the analysis results to the terminal. The terminal displays "Relaxed" and suggests playing relaxing music.

6. the user relaxes by playing relaxing music as suggested by the terminal.

Example of Prompt Text

You will generate a program that analyzes the user's EEG data to identify their emotional state and communicate intuitively with them. The hardware used is an EEG headset and the software is Python. Specifically, the program will analyze EEG data using FFT and calculate the intensity of alpha and beta waves to identify emotional states."

This specific description of the operation of the entire system clearly shows the exemplary embodiment of the invention. The flow of the specific process in Example 3 is explained using FIG. 21.

Step 1: Measure the User's EEG Data

The user wears an EEG measurement device (e.g., EEG headset). The device measures the user's EEG in real time and converts it into a digital signal. The input is the user's EEG and the output is the digitized EEG data. Specifically, the device contacts the user's scalp and detects the electrical signals.

Step 2: Transmission of EEG Data

The terminal transmits the measured EEG data to the server via Bluetooth or Wi-Fi. The input is the digitized EEG data and the output is the data sent to the server. Specifically, the terminal executes a data transmission program and sends the data to the IP address of the server.

Step 3: Receive and Analyze EEG Data by Server

The server receives the EEG data sent from the terminal. The input is the EEG data transmitted from the terminal and the output is the analysis result. The server executes FFT (Fast Fourier Transform) using Python to decompose the EEG data into its frequency components. Specifically, the server runs a data analysis program to calculate the intensity of alpha and beta waves.

Step 4: Save Analysis Results

The server stores the analysis results in a database. The input is the analysis results and the output is the data stored in the database. Specifically, the server uses a database management system to store user IDs, measurement dates and times, and analysis results.

Step 5: Transmission of Analysis Results

The server sends the analysis results to the terminal. The input is the analysis results stored in the database and the output is the analysis results sent to the terminal. As a specific operation, the server sends data using a secure communication protocol (e.g., HTTPS).

Step 6: Display of Analysis Results by Terminal

The terminal displays the analysis results received from the server to the user. The input is the analysis results sent from the server and the output is the information displayed to the user. Specifically, the terminal executes a feedback program and displays the analysis results using a graphical user interface (GUI).

Step 7: Feedback to Users

The user confirms his/her own emotional state and intentions based on the feedback provided by the terminal. The input is the feedback information from the terminal and the output is the user's next action. Specifically, the user takes actions such as playing relaxing music according to the terminal's suggestions.

Example of Application 3

Next, example 3 of application of example of implement 3 will be described. In the following description, data processing device 12 is referred to as the "server" and headset-type terminal 314 is referred to as the "terminal.

Conventional brain-machine interfaces (BMI) can understand intentions by analyzing the user's brain waves, but there are issues with their accuracy and real-time performance. In addition, intuitive operation and emotion-based action control within the metaverse were difficult, and there was a need to improve the user experience. Furthermore, there was a lack of a user-friendly system for managing EEG data and sharing it with third parties.

The specific processing by the specific processing unit 290 of the data processing device 12 in example of application 3 is realized by the following means.

In this invention, the server provides means for generating a minimally invasive and highly accurate brain-machine interface (BMI) that combines brain waves and generative AI, means for providing a platform for disseminating the BMI in society, means for providing, through the platform, intuitive communication services, metaverse interface, health management services, and biometric authentication services provided through the platform; means for controlling actions in the metaverse by analyzing brain waves of users in real time and understanding their emotions and intentions; and means for controlling actions in the metaverse based on the emotional state of users. means to control actions in the metaverse based on the user's emotional state. This allows users to intuitively perform operations in the metaverse using brain waves, and enables emotion-based action control. In addition, EEG data can be easily managed and shared with third parties.

Brain waves" are electrical signals generated by neural activity in the brain.

Generative AI is an artificial intelligence technology that generates new information and content based on data.

A "brain-machine interface" (BMI) is an interface that analyzes brain waves to control machines and computers.

A "platform" is the underlying system or environment that provides a specific service or function.

Intuitive communication service" is a service that analyzes a user's brain waves to understand their emotions and intentions, and communicates accordingly.

A "metaverse interface" is an interface for controlling behavior in virtual reality (VR) and augmented reality (AR) worlds.

The "Health Management Service" is a service that analyzes users' brain waves to determine their stress levels and sleep conditions, and suggests health management based on this information.

Biometric authentication service" is a personal authentication service that analyzes a user's brain wave patterns.

Real-time" means immediate processing and reaction without delay.

The "emotional state" is the emotional state analyzed from the user's brain waves.

The term "action control" refers to controlling the behavior of a system or avatar based on a user's intentions or emotions.

The system for implementing this invention includes: means for generating a minimally invasive and highly accurate brain-machine interface (BMI) by combining brain waves and generative AI; means for providing a platform for disseminating the BMI in society; means for providing intuitive communication services, metaverse interface, health management services, and biometric authentication services using brain activity provided through the platform; means for controlling actions in the metaverse based on the user's emotional state by analyzing the user's brain waves in real time and understanding the user's emotions and intentions; and means for controlling actions in the metaverse based on the user's emotional state. means to provide intuitive communication services, metaverse interface, health management services, and biometric authentication services using brain activity provided through the platform; means to control actions in the metaverse by analyzing the user's brain waves in real time and understanding emotions and intentions; means to control actions in the metaverse based on the user's emotional state. Means to control actions in the metaverse based on the user's emotional state, including.

System Configuration

The server will use an EEG sensor, a head-mounted display (HMD), and a generative AI to configure the system. The EEG sensor acquires the user's brain waves in real time, and the HMD provides the user with visual information in the metaverse. The generative AI analyzes the acquired EEG data to understand the user's emotions and intentions.

Program Processing

The server acquires EEG data using the BrainFlow library and filters the data to remove noise. Next, the data is analyzed using a generative AI to detect the user's emotion (e.g., joy). Based on the detected emotion, actions in the metaverse are controlled. Specifically, if the user has the emotion of joy, the avatar is controlled to dance a joyful dance.

Hardware and Software Used

- Hardware: EEG sensors (e.g., BrainFlow-compatible devices), head-mounted displays (HMDs)
- Software: Python, BrainFlow library Concrete Example For example, consider a scene where a user wears an HMD and uses brainwave sensors to control their behavior in the metaverse. If the user has the emotion of joy, the avatar will dance a joyful dance. This allows the user to intuitively operate within the metaverse and control actions based on emotions.

Example of Prompt Text

Example of Prompt Sentences to be Entered into a Generative AI Model:

Create a Python program that analyzes the user's brain wave data to detect emotions and control actions in the metaverse. If the user has a joyful emotion, have the avatar perform a joyful dance.

In this way, an intuitive metaverse interface can be realized using brain waves.

The flow of the identification process in example of application 3 is described in FIG. 22.

Step 1:

The server uses EEG sensors to acquire the user's EEG data in real time.

- Input: User's EEG signal
- Output: Raw EEG data
- Specific operation: The server collects data from EEG sensors using the BrainFlow library and stores this in memory.

Step 2:

- The server filters the acquired EEG data to remove noise.
- Input: Raw EEG data
- Output: Filtered EEG data
- Specific operation: The server uses the filtering function of the BrainFlow library to remove noise in specific frequency bands.

Step 3:

The server inputs the filtered EEG data to the generative AI to analyze the user's emotions.

- Input: Filtered EEG data
- Output: User's emotional state (e.g., joy, sadness)
- Specific operation: The server inputs data into the data generation AI model and runs an emotion identification algorithm to identify the user's emotion.

Step 4:

- The server determines actions in the metaverse based on the analyzed emotional state.
- Input: User's emotional state
- Output: Action instructions in the metaverse (e.g., Dance of Joy)
- Specific operation: The server determines the action according to the emotional state and sends the instructions to the metaverse system.

Step 5:

The terminal (HMD) controls avatars in the metaverse based on action instructions received from the server.

Input: Action instructions in the metaverse

Output: Avatar behavior (e.g., joyful dancing)

Specific operation: The terminal provides visual information to the user through the HMD and controls the avatar to perform the specified action.

Step 6:

Users visually see the action in the metaverse through the HMD.

Input: Avatar behavior

Output: Visual information (e.g., avatar dancing for joy scene)

Specific behavior: The user wears an HMD to visually confirm the avatar's behavior in the metaverse in real time.

The specific processing unit 290 transmits the results of the specific processing to the headset-type terminal 314. At headset-type terminal 314, control unit 46A causes speaker 240 and display 343 to output the results of the specific processing. Microphone 238 acquires audio indicating user input to the results of the specific processing. The control unit 46A transmits the voice data indicating the user input acquired by the microphone 238 to the data processing device 12. In data processing device 12, specific processing unit 290 acquires the voice data.

The data generation model 58 is a so-called Generative AI (Artificial Intelligence). An example of a data generation model 58 is a generative AI such as ChatGPT (Internet Search <URL: https://openai.com/blog/chatgpt>). The data generation model 58 is obtained by having a neural network perform deep learning. Prompts containing instructions are input to the data generation model 58, as well as data for inference, such as voice data indicating audio, text data indicating text, and image data indicating images. The data generation model 58 infers the input data for inference according to the instructions indicated by the prompts, and outputs the results of the inference in data formats such as voice data and text data. Here, reasoning refers to, for example, analysis, classification, prediction, and/or summarization. Another example of generative AI is Gemini (Internet search <URL: https://gemini.google.com/?hl=ja>).

In the above exemplary embodiment, an example of implement in which the specific processing is performed by the data processing device 12 is given, but the technology of the present disclosure is not limited to this, and the specific processing may be performed by the headset-type terminal 314.

Fourth Exemplary Embodiment

Figure 7:
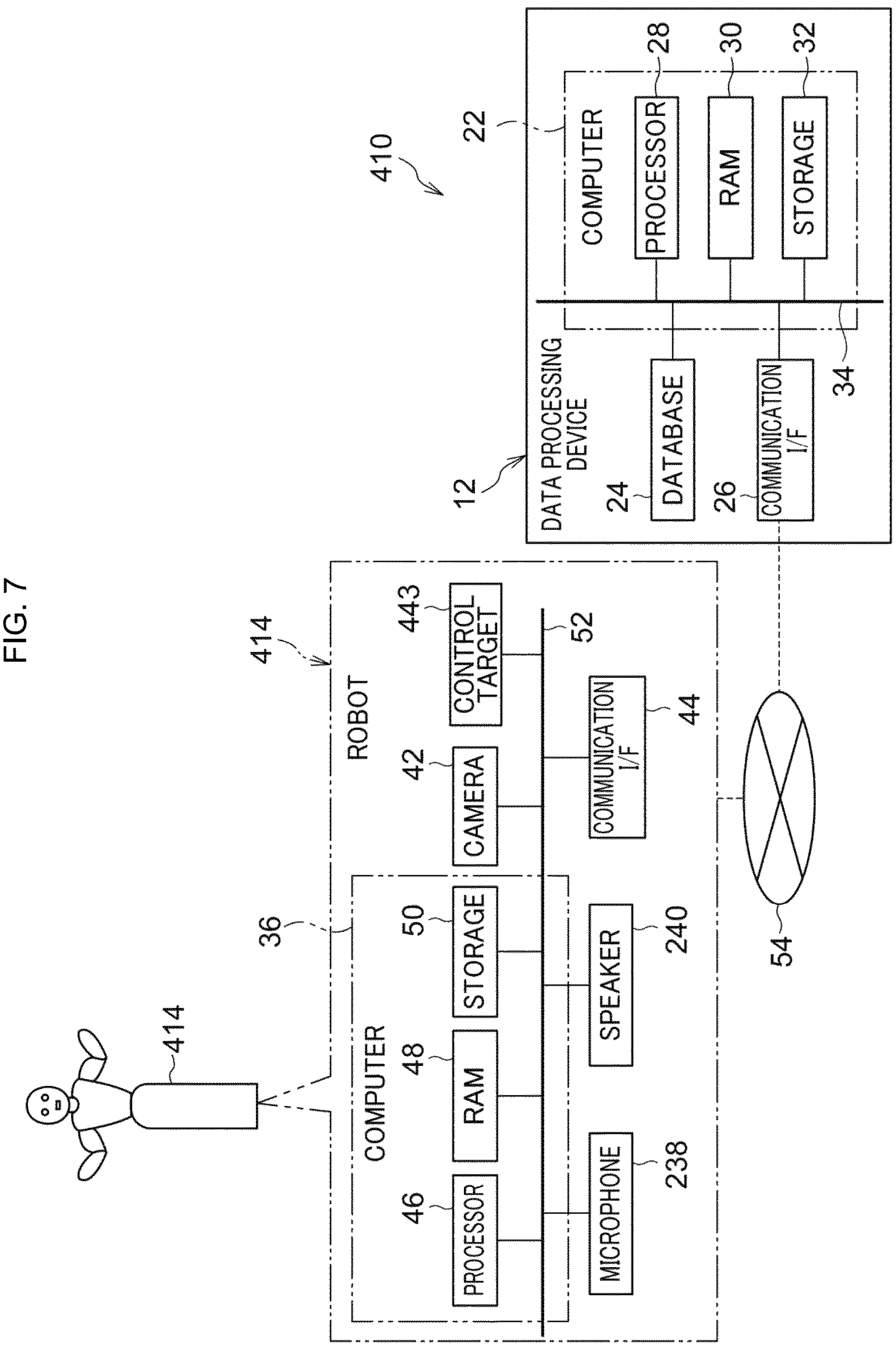
FIG. 7 is a conceptual diagram showing an example of implement of a data processing system for the fourth exemplary embodiment.

FIG. 7 shows an example of implement of a data processing system 410 for the fourth exemplary embodiment.

As shown in FIG. 7, the data processing system 410 has a data processing device 12 and a robot 414. An example of the data processing device 12 is a server.

The data processing device 12 has a computer 22, a database 24, and a communication I/F 26. Computer 22 is an example of a "computer" in the context of the present disclosure. Computer 22 has a processor 28, RAM 30, and storage 32. The processor 28, RAM 30, and storage 32 are connected to a bus 34. The database 24 and the communication I/F 26 are also connected to the bus 34. The communication I/F 26 is connected to a network 54. An example of a network 54 is a Wide Area Network (WAN) and/or a Local Area Network (LAN).

Robot 414 has computer 36, microphone 238, speaker 240, camera 42, communication I/F 44, and control target 443. The computer 36 has a processor 46, RAM 48, and storage 50.

Processor 46, RAM 48, and storage 50 are connected to bus 52. The microphone 238, speaker 240, camera 42, and control target 443 are also connected to the bus 52.

Microphone 238 accepts the voice emitted by user 20 and receives instructions, etc., from user 20. The microphone 238 captures the voice emitted by the user 20, converts the captured voice into voice data, and outputs the data to the processor 46. Speaker 240 outputs audio in accordance with instructions from processor 46.

Camera 42 is a compact digital camera equipped with an optical system, such as a lens, aperture, and shutter, and an image sensor, such as a CMOS (Complementary Metal-Oxide-Semiconductor) image sensor or CCD (Charge Coupled Device) image sensor. It is a small digital camera equipped with an image sensor such as a CMOS (Complementary Metal-Oxide-Semiconductor) image sensor or CCD (Charge-Coupled Device) image sensor, and images the surroundings of the user 20 (for example, the imaging range defined by an angle of view equivalent to the field of view of an average healthy person).

The communication I/F 44 is connected to the network 54. The communication I/Fs 44 and 26 are responsible for transferring and receiving various information between the processor 46 and the processor 28 via the network 54. The transfer of various information between the processor 46 and the processor 28 using the communication I/Fs 44 and 26 is performed in a secure manner.

The control target 443 includes the display unit, the LEDs in the eyes, and the motors that drive the arms, hands, and feet, etc. The posture and gestures of robot 414 are controlled by controlling the motors of the arms, hands, and feet, etc. Some of the emotions of the robot 414 can be expressed by controlling these motors. The facial expressions of the robot 414 can also be expressed by controlling the light emission state of the LEDs in the eyes of the robot 414.

Figure 8:
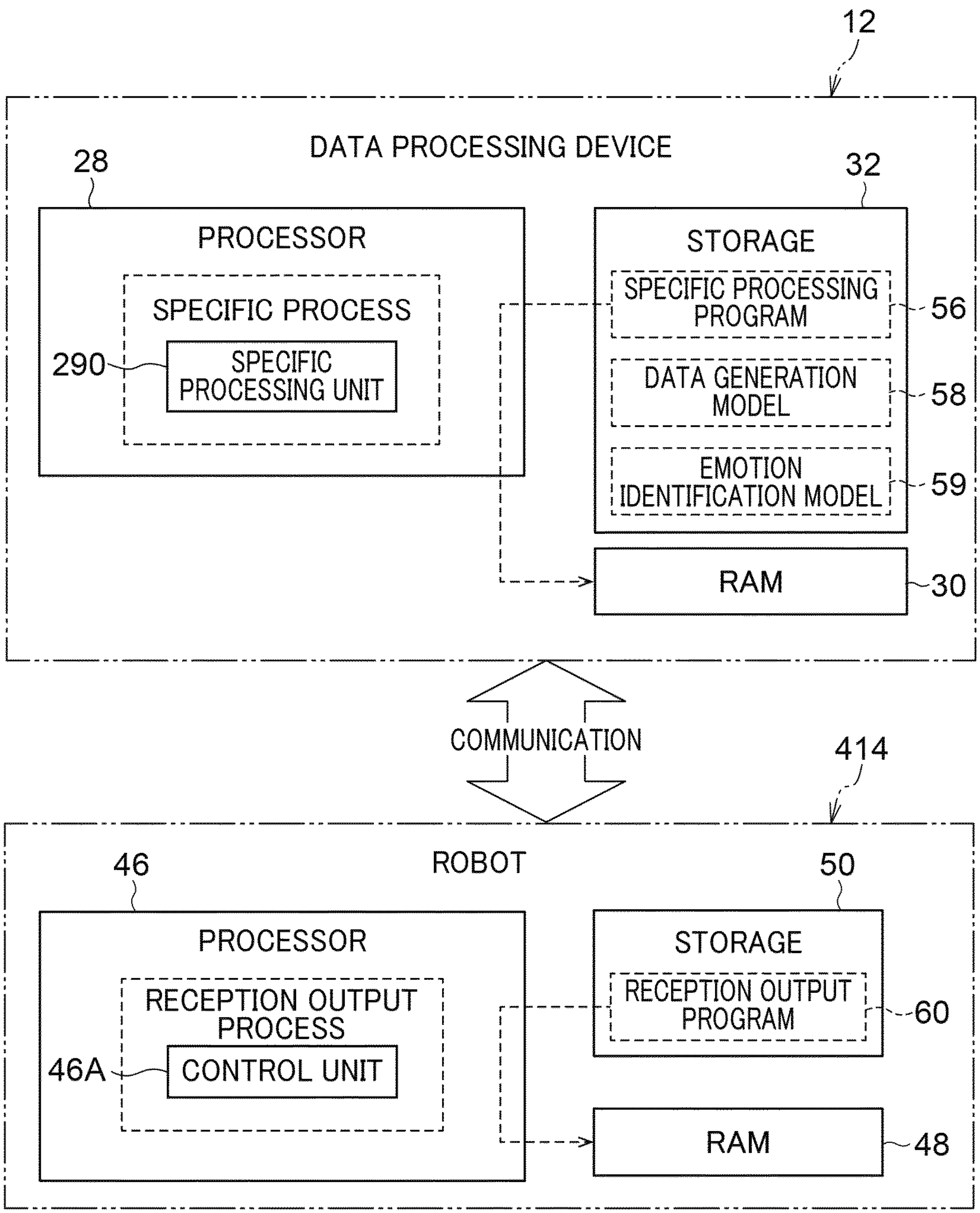
FIG. 8 is a conceptual diagram showing an example of the key functions of the data processing device and robot of the fourth exemplary embodiment.

FIG. 8 shows an example of the key functions of data processing device 12 and robot 414. As shown in FIG. 8, in data processing device 12, specific processing is performed by processor 28. The storage 32 contains a specific processing program 56.

The specific processing program 56 is an example of a "program" for the technology of the present disclosure. The processor 28 reads the specific processing program 56 from the storage 32 and executes the read specific processing program 56 on the RAM 30. The specific processing is realized by the processor 28 operating as the specific processing unit 290 according to the specific processing program 56 executed on RAM 30.

The data generation model 58 and emotion identification model 59 are stored in storage 32. The data generation model 58 and emotion identification model 59 are used by the specific processing unit 290.

In robot 414, the reception output process is performed by processor 46. The reception output program 60 is stored in the storage 50. The processor 46 reads the reception output program 60 from the storage 50 and executes the read reception output program 60 on the RAM 48. The reception output process is realized by the processor 46 operating as the control unit 46A according to the reception output program 60 executed by the processor 46 on RAM 48.

Next, the specific processing by the specific processing unit 290 of the data processing device 12 is described.

Example of Implement 1

One exemplary embodiment of this invention is a system that combines brain waves and a generative AI to generate a brain-machine interface (BMI). This system analyzes the user's brain waves in real time and inputs the results to the generative AI. The generative AI uses this brain wave data to understand the user's intentions and generates output based on them. For example, when a user wants a cup of coffee, the brain waves are analyzed, and the generative AI understands the user's intention and can take action such as "make coffee.

Example of Implement 2

Another exemplary embodiment of this invention is a platform to promote BMI in society. This platform has a function that allows users to manage their own EEG data and share it with third parties as needed. For example, users can manage their own EEG data on the platform and share it with medical and research institutions to obtain more accurate medical services and research results.

Example of Implement 3

In addition, one exemplary embodiment of the invention is new services offered through the platform. These services include intuitive communication services using brain activity, metaverse interface, health management services, and biometric authentication services. For example, intuitive communication services analyze a user's brain waves to understand their emotions and intentions, and communicate based on this information. Also, in metaverse interfaces, the user's brain waves are analyzed to control their behavior in VR and AR worlds. The health management service analyzes the user's brain waves to understand their stress level, sleep state, etc., and proposes health management based on this information. The biometric authentication service analyzes the user's brain wave patterns to perform personal authentication.

The following is a description of the process flow for each example of implement.

Example of Implement 1

Step 1: The user has a specific thought or intention.

Step 2: The system captures and analyzes the user's brain waves in real time.

Step 3: Input the analysis results to the generative AI.

Step 4: The generative AI understands the user's intentions based on the brain wave data and generates output based on it. For example, it will perform an action such as "make coffee.

Example of Implement 2

Step 1: Users access the platform and upload their own EEG data.

Step 2: The platform manages the user's EEG data and shares it with third parties as needed. For example, sharing with medical and research institutions will enable more accurate medical services and research results.

Example of Implement 3

Step 1: The user selects a specific service through the platform. For example, intuitive communication services, metaverse interface, health care services, biometric services, etc.

Step 2: The selected service analyzes the user's brain waves and provides services based on them. For example, an intuitive communication service analyzes the user's brain waves to understand his/her feelings and intentions and communicates based on them.

Example 1

Next, example 1 of exemplary embodiment of implement will be described. In the following description, data processing device 12 is referred to as the "server" and robot 414 is referred to as the "terminal.

Conventional brain-machine interfaces (BMIs) are inaccurate in analyzing the user's brain waves, making it difficult to understand the user's intentions in real time. In addition, these systems were highly invasive and burdensome to users. Furthermore, the management and sharing of EEG data is not easy, which has hindered its widespread use in society.

The specific processing by the specific processing unit 290 of the data processing device 12 in Example 1 is realized by the following means.

In this invention, the server provides a means for collecting brain waves of a user in real time, a means for analyzing the collected brain wave data, a means for inputting the analyzed brain wave data into a generative AI model, a means for the generative AI model to understand the intent of the user and generate outputs based thereon, a means for providing feedback of the generated means to provide a platform for the dissemination of the brain-machine interface (BMI) to society, and to provide intuitive communication services, virtual space services, biometric authentication services, and other services using brain activity that are provided through the platform. interface, health management services, and biometric authentication services provided through the platform. This enables highly accurate and minimally invasive analysis of users' brain waves and real-time understanding of their intentions. It will also facilitate the management and sharing of EEG data and promote its widespread use in society.

The term "user" refers to the individual who uses the brain-machine interface (BMI).

Brain waves" refer to the electrical signals generated by the user's brain.

Real-time" means that data is processed and analyzed as soon as it is generated.

The term "means of collection" refers to devices and methods used to detect and acquire data on the user's brain waves.

Means of analysis" refers to methods and devices used to process the collected EEG data and infer user intent.

The term "generative AI model" refers to an artificial intelligence model that understands the user's intent based on the input data and generates output based on that intent.

The term "means of input" refers to the methods and devices used to provide the analyzed EEG data to the generative AI model.

Output" refers to the results and suggestions generated by the generative AI model based on its understanding of the user's intentions.

The term "means of feedback" refers to the methods and devices used to communicate the generated output to the user.

The term "platform" refers to the systems and services that serve as the foundation for the diffusion of brain-machine interfaces (BMIs) in society.

The term “communication service” refers to a service that uses brain waves to allow users to intuitively exchange information with others.

The term “virtual space interface” refers to an interface that uses brain waves to allow users to operate and move within a virtual space.

The term “health management service” refers to a service that uses users’ brain wave data to monitor and manage their health.

The term “biometric service” refers to a service that uses a user’s brain wave data to authenticate an individual.

This invention is a brain-machine interface (BMI) system that analyzes a user’s brain waves in real time and inputs the results into a generative AI model to understand the user’s intentions and generate output based on them. The system is implemented using the following hardware and software Hardware and Software Configuration EEG Sensor The user wears an EEG sensor on the head. This sensor detects the user’s brain waves in real time and collects the data as electrical signals.

Server

The server receives EEG data transmitted from the EEG sensor. The received data is sent to the terminal for analysis.

Terminal

The terminal analyzes the EEG data sent from the server. An EEG analysis library using Python is used for the analysis. The terminal sends the analysis results to the server.

Generative AI Model

The server inputs the analyzed brain wave data into a generative AI model (e.g., OpenAI’s GPT-4). The generative AI model understands the user’s intention based on the input data and generates output based on it.

Feedback

The generated output is sent to the terminal through the server, which feeds it back to the user. The user can then take the suggested action.

Concrete Example

For example, consider the case where a user wants to listen to music. An EEG sensor collects the user’s EEG data, and the terminal analyzes the data. If the analysis results indicate the intention to “listen to music,” the following prompt statement is entered into the generative AI model:

The user’s EEG data has detected the intention to listen to music. Please suggest actions to play appropriate music.

The generative AI model generates an output “play music” based on this prompt sentence and feeds it back to the user through the terminal. The user can then play the music according to the suggested action.

In this way, the system can analyze the user’s EEG with high accuracy and minimally invasive, and understand their intentions in real time. In addition, the system will facilitate the management and sharing of EEG data and promote its widespread use in society.

The flow of the identification process in Example 1 is described in FIG. 11.

Step 1:

The user wears an EEG sensor on his/her head. The EEG sensor detects the user’s brain waves in real time and collects the data as electrical signals. The collected EEG data is transmitted to a server.

Input: User’s brain waves

Output: EEG data (electrical signals)

Step 2:

The server receives the EEG data transmitted from the EEG sensor. The received EEG data is sent to the terminal for analysis.

Input: EEG data (electrical signals)

Output: EEG data (transfer from server to terminal)

Step 3:

The terminal receives the EEG data sent from the server. The terminal analyzes the EEG data using a Python-based EEG analysis library. In the process of analysis, specific brain wave patterns are detected and the intention of the user is inferred. The analysis results are sent to the server.

Input: EEG data (transferred from server)

Output: Analysis results (user intent)

Step 4:

The server receives the analysis results sent from the terminal. The server generates prompt sentences based on the analysis results and inputs them into the generative AI model.

Input: Analysis results (user intent)

Output: Prompt statement

Step 5:

The generative AI model receives prompt sentences sent from the server. The generative AI model understands the user’s intention based on the prompt sentences and generates output based on it. The generated output is sent to the server.

Input: Prompt statement

Output: Output

Step 6:

The server receives the outputs sent from the generative AI model. The server sends the output to the terminal.

Input: Output (transfer from generative AI model)

Output: Output (transfer from server to terminal)

Step 7:

The terminal receives the output sent from the server. The terminal feeds back the output to the user. The user can perform the suggested action.

Input: Output (transfer from server)

Output: Feedback to user

Example of Application 1

Next, example of application 1 of example of implement 1 will be described. In the following description, the data processing device 12 is referred to as the “server” and the robot 414 is referred to as the “terminal.

Conventional control methods for factory robots are mainly manual operation or programmed control, which is difficult to operate intuitively. In addition, more intuitive and quicker control methods are required to improve work efficiency. Furthermore, brain-machine interface (BMI) using brain waves has been applied in the medical and entertainment fields, but has not yet been fully utilized in factory automation and robot control. To solve these problems, a system that can intuitively control factory robots using brain waves is needed The specific processing by the specific processing unit 290 of the data processing device 12 in example of application 1 is realized by the following means.

In this invention, the server provides means to generate a minimally invasive and highly accurate brain-machine interface (BMI) that combines brain waves and generative AI, means to provide a platform for disseminating the BMI in society, means to provide intuitive brain activity-based means to provide communication services, metaverse interface, health management services, and biometric authentication services using brain activity, means for factory workers to wear head-mounted displays and control factory robots using brain waves, and means for analyzing users' brain wave data in real time and inputting the results into a generative system AI, including means to understand the user's intentions and generate output based on them by inputting the results into the AI, and means to control the factory robot based on the user's intentions. This allows factory workers to intuitively control factory robots using brain waves.

Brain waves" are electrical signals generated by neural activity in the brain.

Generative AI" is a type of artificial intelligence that generates new data and outputs based on input data.

A "brain-machine interface" (BMI) is an interface that uses brain waves to control a machine or computer.

The term "minimally invasive" refers to less burden or damage to the body.

The term "high precision" refers to extreme accuracy.

A "platform" is the underlying system or environment that provides a specific service or function.

An "intuitive communication service" is one that allows users to operate and communicate intuitively.

A "metaverse interface" is an interface for performing activities and operations in a virtual space.

A "health management service" is a service designed to manage and improve a user's health status.

Biometric services" are services that authenticate individuals using biometric information such as fingerprints and facial recognition.

A "factory worker" is a worker engaged in production activities in a factory.

A "head-mounted display" is a display device worn on the head.

A "factory robot" is a robot used to automate production tasks in a factory.

Real-time" means immediate processing and reaction without delay.

User intent" is the intention or purpose of what the user wants to do or think.

Output" is the result or behavior output from a system or device.

The following system configuration and program are required to implement this invention.

System Configuration

1. Hardware
   - Head-mounted displays (HMDs): Built-in EEG sensors to collect EEG data in real time.
   - Factory robots: robots that are designed to perform actions based on the user's intentions.
   - Server: analyzes EEG data and executes generative AI models.
2. Software
   - BrainwaveReader: module for collecting EEG data.
   - GenerativeAIModel: A generative AI model that analyzes brain wave data to understand user intent.
   - RobotController: A module for controlling robots based on user intent.

Explanation of Program Processing

The server first collects brain wave data from the head-mounted display (HMD); the BrainwaveReader module analyzes this data in real time and inputs it to a generative AI model (GenerativeAIModel). The generative AI model interprets the user's intentions based on the brainwave data and passes the intentions to the RobotController, which controls the factory robot based on the interpreted intentions and performs the corresponding actions.

Concrete Example

For example, if a factory worker thinks "assemble parts," the following prompt sentence is entered into the generative AI model.

Example of a Prompt Statement:

Based on the analysis of the user's brain wave data, the user believes that the user is "assembling parts". Based on this intention, instruct the robot to perform an action to assemble the parts.

Based on this prompt sentence, the generative AI model interprets the user's intention and instructs the RobotController to perform the "assemble parts" operation. As a result, the factory robot automatically starts assembling the parts.

This system allows factory workers to intuitively control factory robots using brain waves, greatly improving work efficiency.

The flow of the identification process in Example of Application 1 is described in FIG. 12.

Step 1:

A user wears a head-mounted display (HMD); the HMD has a built-in EEG sensor that collects the user's EEG data in real time. The input is the user's EEG and the output is the collected EEG data.

Step 2:

The server receives the EEG data sent from the HMD using the BrainwaveReader module; BrainwaveReader analyzes this data in real time, performing noise removal and feature extraction. The input is the EEG data from the HMD and the output is the analyzed EEG data.

Step 3:

The server inputs the analyzed EEG data to GenerativeAIModel, which is a generative AI model for interpreting user intentions based on the EEG data. The input is the analyzed EEG data and the output is the data indicating the user's intention.

Step 4:

Based on the server's interpretation of the user's intent, a prompt statement is generated. This prompt sentence is a specific description of the user's intent. The input is the data indicating the user's intent, and the output is the prompt sentence.

Step 5:

The server passes the generated prompt sentence to the RobotController, which generates specific instructions for the factory robot based on this prompt sentence. The input is the prompt sentence and the output is the instructions to the robot.

Step 6:

RobotController sends instructions to the factory robot. The factory robot executes the corresponding action based on these instructions. The input is the instruction to the robot and the output is the robot's action.

Step 7:

The user checks the operation of the factory robot through the HMD; the HMD displays the robot's operating status in real time to confirm that the robot is operating as intended by the user. The input is the operating status of the robot and the output is the image displayed on the HMD.

Example 2

Next, example 2 of exemplary embodiment of implement will be described. In the following description, the data processing device 12 is referred to as the "server" and the robot 414 is referred to as the "terminal.

Conventional brain-machine interfaces (BMIs) lack a platform for effectively managing users' EEG data and securely sharing it with third parties. They also lacked real-time analysis of EEG data and linkage with generative AI, making it difficult to accurately understand user intentions and generate appropriate outputs. Furthermore, encryption of EEG data and management of access privileges were insufficient, and data security was not ensured.

The specific processing by the specific processing unit 290 of the data processing device 12 in Example 2 is realized by the following means. In this invention, the server is equipped with the following means: the means by which the user uploads brain wave data acquired by using a dedicated measurement device from the terminal to the server; the means by which the server stores the received brain wave data in a database; the means by which the user accesses the platform and manages the data; the means by which the user encrypts the data and grants access to a third party and the means to configure the data to be shared, and the server encrypts the data and grants access to the third party. This allows users to effectively manage their own EEG data and securely share it with third parties. In addition, in conjunction with the generative AI, the system can accurately understand the user's intentions and generate appropriate output.

A "brain-machine interface (BMI)" is an interface that uses brain waves to communicate a user's intentions to a machine.

Generative AI" is artificial intelligence that analyzes a user's brain wave data and generates appropriate output based on the results.

A "platform" is a system that allows users to manage their EEG data and share it with third parties as needed.

EEG data" is data that measures the user's brain activity and is obtained using an EEG measurement device.

A "measurement device" is a device used to measure a user's brain waves in real time.

A "terminal" is a computer, smart device, or other device used by a user to upload EEG data acquired using the measurement device to a server.

A "server" is a computer system used to store and manage EEG data received from users.

A "database" is a system for efficiently storing and accessing EEG data received by the server.

Encryption" is a technique for converting data into a format that cannot be deciphered by a third party.

Access privileges" is the ability to set the rights of a specific user or third party to access data.

Output" is the output generated by the generative AI based on the results of analyzing the user's EEG data.

Exemplary Embodiment of the Invention

This invention is a system that provides a platform for users to manage EEG data acquired using specialized measurement devices and share it with third parties as needed. Specific exemplary embodiments of this system are described below.

Hardware and Software Configuration

The user uses a dedicated EEG measurement device to obtain EEG data. This measurement device measures the user's brain waves in real time and transmits the data to a terminal (PC or smartphone).

The terminal uploads the acquired EEG data to the server through a dedicated application. The application converts the data into the appropriate format (e.g., CSV or JSON) and sends it securely to the server using the HTTPS protocol.

The server stores the received EEG data in a database (e.g., MySQL or PostgreSQL). The database organizes the data by user and indexes it for efficient access.

Users access the platform through a web browser or mobile application. The platform authenticates the user (e.g., OAuth or JWT) and provides an interface that allows users to view, edit, and delete their own EEG data.

Data Sharing and Encryption

If the user wants to share data with a third party, he/she selects the third party (e.g., a medical or research institution) with whom he/she wants to share the data on the platform. The user sets the scope and duration of the data to be shared and submits a sharing request.

The server receives the user's sharing request and encrypts the data to be shared. Encryption uses a strong encryption algorithm such as AES-256. The server grants access privileges to designated third parties and creates a secure access link to the shared data.

Concrete Example

For example, when a user shares his/her EEG data with a medical institution, the following steps are taken 1. the user wears the EEG sensor and launches the dedicated application.
2. the terminal converts the acquired EEG data into CSV format and uploads it to the server using HTTPS.

The server stores the received data in a MySQL database.

4. the user logs into the platform with a web browser and checks his/her EEG data.

The user selects a medical institution and sets the scope and duration of the data to be shared.

6. the server encrypts the data with AES-256 and grants access privileges to the medical institution.

Example of Prompt Sentences to be Entered into a Generative AI Model:

Describe the steps a user would take to use an EEG sensor to obtain EEG data and share it with their healthcare provider."

By inputting this prompt statement into the data generation AI model, the specific procedure for the user to obtain EEG data and share it with the healthcare provider is output.

The flow of the identification process in Example 2 is described in FIG. 13.

Step 1:

The user uses a dedicated EEG measurement device to acquire EEG data. The user wears the measurement device and starts the dedicated application. The measurement device measures the user's brain waves in real time and transmits the data to the terminal. The input is the user's EEG and the output is the EEG data transmitted to the terminal.

Step 2:

The terminal uploads the EEG data to the server. The terminal converts the acquired EEG data into CSV format through a dedicated application and sends it to the server using the HTTPS protocol. The input is the EEG data sent from the measurement device and the output is the EEG data in CSV format uploaded to the server.

Step 3:

The server stores the received EEG data in a database. The server imports the received EEG data in CSV format into the database and organizes the data for each user. The input is the EEG data in CSV format sent from the terminal, and the output is the EEG data stored in the database.

Step 4:

Users access the platform and manage their data. The user logs into the platform through a web browser or mobile application to view, edit, and delete his/her EEG data. The input is the user's login information and the EEG data stored in the database, and the output is the EEG data that the user has viewed, edited, or deleted.

Step 5:

The user sets up the sharing of data with third parties. The user selects the third party they wish to share with on the platform and sets the scope and duration of the data to be shared. The input is the user's sharing configuration information and the output is the sharing request sent to the server.

Step 6:

Server encrypts data and grants access to third parties. The server receives the user's share request and encrypts the data to be shared with AES-256. The server grants access privileges to the designated third party and generates a secure access link to the shared data.

The input is the user's sharing request and the EEG data stored in the database, and the output is the encrypted data and the access rights granted to the third party.

Example of Application 2

Next, example of application 2 of example of implement 2 will be described. In the following description, the data processing device 12 is referred to as the "server" and the robot 414 is referred to as the "terminal.

Conventional brain-machine interfaces (BMIs) lack a platform for effectively managing users' EEG data and sharing it with third parties as needed. In addition, they lacked sufficient management of EEG data security and sharing history, which prevented smooth data sharing with medical and research institutions. Furthermore, the lack of a function to collect users' EEG data in real time, encrypt it, and upload it to the cloud did not ensure the security and convenience of the data The specific processing by the specific processing unit 290 of the data processing device 12 in example of application 2 is realized by the following means. In this invention, the server provides means for generating a minimally invasive and highly accurate brain-machine interface (BMI) that combines brain waves and generative AI, means for providing a platform for disseminating the BMI in society, means for providing intuitive communication services, metaverse interface, health management services, and biometric authentication services provided through the platform; means for collecting users' brain wave data in real time, encrypting and uploading the data to the cloud; and means for sharing the data with medical institutions and research organizations and managing data sharing history. The means to share the data with medical and research institutions, and to manage the data sharing history. This allows users' EEG data to be managed securely and efficiently and shared with third parties as needed.

Brain waves" are electrical signals generated by neural activity in the brain.

Generative AI" is a type of artificial intelligence, a system that has the ability to generate new data and information based on input data.

Minimally invasive" means less stressful or damaging to the body.

High precision" means extremely accurate.

A "brain-machine interface" (BMI) is an interface that uses brain waves to operate a machine or computer.

A "platform" is the underlying system or environment that provides a specific function or service.

An "intuitive communication service" is one that allows users to interact with information in a natural way.

A "metaverse interface" is an interface that allows users to operate and experience things in a virtual space.

A "health management service" is a service that monitors and manages a user's health status.

Biometric services" are services that use a user's biometric information to verify identity.

Real-time" means that data and information are processed immediately.

Encryption" means that data is converted using a specific algorithm to a form that cannot be easily understood by a third party.

The "cloud" is a collection of computer resources and services provided through the Internet.

A "sharing history" is a record of how, when, and by whom data was shared.

A "medical institution" is a facility that provides medical services, such as a hospital or clinic.

A "research institution" is an organization or facility for conducting scientific research.

The following system configuration is an exemplary embodiment of this invention.

System Configuration

The system has the ability to collect users' EEG data in real time, encrypt it, and upload it to the cloud. It also has the ability to share data with medical and research institutions and manage data sharing history.

Hardware Used

- Smart device: a device that allows users to manage their EEG data and upload it to the cloud.
- EEG sensors: devices (e.g., Muse, Emotiv) to collect EEG data on users.

Software to be Used

- Python: A programming language for performing the main processing of a program.
- NeuroKit2: A library for simulation and analysis of EEG data.
- Requests: Library for sending HTTP requests.
- Cryptography: Library for data encryption.

Process Flow

1. EEG data collection: EEG sensors are used to collect the user's EEG data in real time. The collected data is stored on the smartphone.

Data encryption: The EEG data collected will be encrypted using the Cryptography library. This ensures data security.

Data upload: Encrypted data is uploaded to the cloud using the Requests library. Data is stored securely in the cloud.

Data sharing: Users can share data with medical institutions and research organizations as needed. Sharing history is stored locally, allowing users to see who accessed what data and when.

Concrete Example

The user wears the EEG sensor and launches the NeuroGuard app. The app collects the EEG data, encrypts it, and uploads it to the cloud. With the user's permission, a medical institution retrieves the data from the cloud and uses it for diagnosis.

Example of Prompt Text

The user wears the EEG sensor and launches the NeuroGuard app. The app collects EEG data, encrypts it, and uploads it to the cloud. With the user's permission, a healthcare provider retrieves the data from the cloud and uses it for diagnosis.

This system will allow users' EEG data to be managed securely and efficiently and shared with third parties as needed.

The flow of the identification process in example of application 2 is described in FIG. 14.

Step 1:

The user wears the EEG sensor and launches the Neuro-Guard application on the smartphone. The EEG sensor collects the user's EEG data in real time and transmits it to the smartphone. The input is the EEG data from the EEG sensor and the output is the raw EEG data stored on the smartphone.

Step 2:

The terminal (smartphone) analyzes the EEG data collected using the NeuroKit2 library. This analysis extracts the features of the EEG data. The input is the raw EEG data and the output is the features of the analyzed EEG data. Specifically, NeuroKit2 functions are invoked to analyze the EEG data and extract the features.

Step 3:

The terminal encrypts the analyzed EEG data using the Cryptography library. The input is the features of the analyzed EEG data and the output is the encrypted EEG data. The specific operation is to generate an encryption key and encrypt the EEG data using that key.

Step 4:

The terminal uploads encrypted EEG data to the cloud using the Requests library. The input is the encrypted EEG data and the output is the encrypted data stored on the cloud. The specific operation is to send an HTTP POST request and upload the data to the cloud server.

Step 5:

The server manages the encrypted data stored on the cloud and shares the data with medical and research institutions as needed. The input is the encrypted data on the cloud and the output is the shared data. The specific operation is to decrypt the data and provide it to the designated third party with the user's permission.

Step 6:

The server maintains a data sharing history, recording who accessed what data and when. The input is the data access request information and the output is the shared history log. The specific operation is to generate an access log and store it locally or in the cloud.

In this way, the user's EEG data can be managed securely and efficiently and shared with third parties as needed.

Example 3

Next, example 3 of exemplary embodiment of implement will be described. In the following description, the data processing device 12 is referred to as the "server" and the robot 414 is referred to as the "terminal.

Conventional brain-machine interfaces (BMIs) have had difficulty effectively analyzing users' brain wave data and identifying their emotions and intentions in real time. They also lacked a platform for intuitive communication, health management, biometric authentication, and other services based on these data. Furthermore, users lacked the ability to manage their own EEG data and share it with third parties as needed. To solve these problems, a system that provides highly accurate analysis of EEG data and a variety of services based on this data is needed.

The specific processing by the specific processing unit 290 of the data processing device 12 in Example 3 is realized by the following means.

In this invention, the server has means for the user to wear an EEG measurement device and connect it to the terminal; the terminal collects EEG data from the EEG measurement device and transmits it to the server; the server receives the EEG data and performs pre-processing; the server analyzes the pre-processed data to identify emotions and intentions, means by which the server transmits the analysis results to the terminal, the terminal displays the analysis results and provides feedback to the user, means for providing a platform for disseminating the system in society, and means for providing intuitive communication using brain activity provided through the platform. services, virtual reality interface, health management services, and biometric authentication services provided through the platform. This makes it possible to analyze users' brain wave data with high precision and provide a variety of services based on such data in real time.

The term "user" refers to the individual who wears the EEG measurement device and uses the system.

The term "EEG measurement device" refers to a device used to measure a user's EEG data.

The term "terminal" refers to an electronic device that transmits the data collected from the EEG measurement device to the server and displays the analysis results to the user.

The term "server" refers to a computer system that receives EEG data, performs pre-processing and analysis, and transmits the results to the terminal.

Pre-processing" refers to data cleansing operations performed on EEG data prior to analysis, such as noise removal and filtering.

The term "analysis" refers to the processing of data to identify the user's emotions and intentions based on the preprocessed EEG data.

The term "generative AI model" refers to a machine learning model used to analyze brain wave data to identify a user's emotions and intentions.

The term "platform" refers to the infrastructure that will allow the system to be disseminated to society and for users to manage their EEG data and share it with third parties as needed.

The term "intuitive communication service" refers to a service that uses brain wave data from users to understand their emotions and intentions and communicate accordingly.

The term "virtual reality interface" refers to an interface that controls behavior in a virtual or augmented reality world based on the user's brain wave data.

The term "health management service" refers to a service that uses brain wave data to determine a user's stress level, sleep status, etc., and suggests health management based on this information.

The term "biometric authentication service" refers to a service that analyzes a user's brain wave patterns for personal authentication.

The invention begins with the user wearing an EEG measurement device and connecting it to a terminal. The user wears the EEG measurement device (e.g. EEG device) on his/her head and connects it to a terminal (e.g. smart phone or PC) using Bluetooth or USB cable.

The terminal collects EEG data from the EEG device in real time using a dedicated application. The collected data is sent to the server via the Internet. The server receives the EEG data sent from the terminal and performs pre-processing. Pre-processing includes noise removal and filtering, and uses the Python MNE library for data cleansing.

The preprocessed data is input to a machine learning model on the server (e.g., using TensorFlow or PyTorch) to analyze emotions and intentions. The analysis results are used to identify the user's emotion (e.g., joy, sadness, surprise, etc.) or intention (e.g., the intention to perform a specific action).

The analysis results are sent from the server to the terminal. The terminal displays the analysis results received from the server to the user. For example, a chat application displays a message that the user is happy. The metaverse interface also controls actions in the VR and AR worlds based on the user's intentions.

As a concrete example, consider an intuitive communication service. A user wears an EEG device and connects it to a smart phone. The smart device collects brain wave data from the EEG device in real time and sends it to the server. The server preprocesses the received data and analyzes emotions using TensorFlow. If the analysis shows that the user is "happy," this information is reflected in the smartphone's chat application and a message is sent to the other party saying that the user is happy.

Example of a Prompt Statement:

The user wears the EEG device and connects it to a smart phone. The smartphone collects EEG data in real-time and sends it to the server. The server preprocesses the data and analyzes the emotions using TensorFlow. If the analysis shows that the user is "happy," the information is reflected in the chat application and a message is sent to the other party saying that the user is happy.

In this way, the server, terminal, and user work together to realize a system that provides new services using EEG data. The flow of the identification process in Example 3 is described using FIG. 15.

Step 1:

The user wears the EEG measurement device and connects it to the terminal.

Specifically, the user wears an EEG measurement device (e.g., EEG device) on his/her head and connects it to a terminal (e.g., smart phone or PC) using Bluetooth or USB cable. The input is the user's EEG and the output device is the EEG measurement device connected to the terminal.

Step 2:

The terminal collects EEG data from the EEG measurement device and sends it to the server.

Specifically, the terminal uses a dedicated application to collect EEG data from the EEG device in real time. The collected data is sent to the server via the Internet. The input is the EEG data from the EEG measurement device and the output is the EEG data sent to the server.

Step 3:

The server receives the EEG data and performs preprocessing.

Specifically, the server receives EEG data sent from the terminal. The received data is preprocessed, including noise removal and filtering; data cleansing is performed using Python's MNE library. The input is the EEG data transmitted from the terminal and the output is the preprocessed EEG data.

Step 4:

The server analyzes the preprocessed data to identify emotions and intentions.

Specifically, the server inputs the preprocessed data into a machine learning model (e.g., using TensorFlow or PyTorch). The model identifies the user's emotions and intentions from the EEG data. The input is the preprocessed EEG data and the output is the emotion and intention information as the result of the analysis.

Step 5:

The server sends the analysis results to the terminal.

As a specific action, the server sends the analysis results to the terminal. The analysis results include the user's emotions (e.g., joy, sadness, surprise, etc.) and intentions (e.g., intention to perform a specific action). The input is the analysis result and the output is the analysis result sent to the terminal.

Step 6:

The terminal displays the analysis results and provides feedback to the user.

As a specific action, the terminal displays the analysis results received from the server to the user. For example, a chat application displays a message that the user is happy. In addition, the metaverse interface controls actions in the VR and AR worlds based on the user's intentions. The input is the analysis results received from the server and the output is the feedback displayed to the user.

Example of Application 3

Next, example 3 of application of example of implement 3 will be described. In the following description, data processing device 12 is referred to as the "server" and robot 414 is referred to as the "terminal.

Conventional brain-machine interfaces (BMIs) have limited technology for analyzing a user's brain waves, making it difficult to perform highly accurate analysis in real time. They also lacked intuitive means of navigation and interaction within the metaverse, making it difficult to perform actions that reflect the user's intentions and emotions. Furthermore, functions related to the management and sharing of EEG data were inadequate, making it less convenient for users.

The specific processing by the specific processing unit 290 of the data processing device 12 in example of application 3 is realized by the following means.

In this invention, the server provides means for generating a minimally invasive and highly accurate brain-machine interface (BMI) that combines brain waves and generative AI, means for providing a platform for disseminating the BMI in society, means for providing, through the platform, brain activity-based intuitive communication services, metaverse interface, health management services, and biometric authentication services provided through the platform; means for controlling navigation and interaction in the metaverse by analyzing the user's brain waves in real time; and means for performing actions in the metaverse based on the user's intentions and emotions. means to perform actions. This allows users to intuitively navigate and interact within the metaverse using brain waves.

EEG" is a recording of the brain's electrical activity, data that can be used to analyze a user's intentions and emotions.

Generative AI is a type of artificial intelligence that generates new information and output based on input data.

A "brain-machine interface" (BMI) is an interface that analyzes brain waves to control machines and computers.

A "platform" is a system that serves as the foundation for providing a particular service or function.

Intuitive communication service" is a service that analyzes a user's brain waves to understand their emotions and intentions, and communicates accordingly.

A "metaverse interface" is an interface for user interaction in a virtual or augmented reality world.

The "Health Management Service" is a service that analyzes users' brain waves to determine their stress levels and sleep conditions, and suggests health management based on this information.

Biometric authentication service" is a personal authentication service that analyzes a user's brain wave patterns.

The term "navigation" refers to the instructions and operations that users use to navigate within a virtual space.

Interaction" refers to the user's interaction with other objects or characters in the virtual space.

Intent" is the user's intention to perform a particular action or operation.

Emotion" refers to the psychological state or feeling of a user.

An "action" is an action or reaction performed in the virtual space based on a user's intention or emotion.

A system for implementing this invention includes means to generate a minimally invasive, highly accurate brain-machine interface (BMI) that combines electroencephalograms and generative AI; means to provide a platform for popularizing the BMI in society; means to provide intuitive communication utilizing brain activity provided through the platform, metaverse interface, health management services, and biometric authentication services using brain activity provided through the platform; means to control navigation and interaction in the metaverse by analyzing the user's brain waves in real time; and means to execute actions in the metaverse based on the user's intentions and emotions. The system includes means to execute actions in the metaverse based on the user's intentions and emotions.

System Configuration

This system uses the following hardware and software

Hardware: Brainwave sensor, head-mounted display

Software: Python, EEG sensor API, Metaverse controller API

Explanation of Program Processing

The server analyzes the EEG data acquired from the EEG sensor in real time and inputs it to the generative AI. The generative AI analyzes the user's intentions and emotions based on the input EEG data and generates output based on them. Specifically, if the user wants to move forward, the brain wave sensor detects this intention and the avatar moves forward. Also, if the user feels happy, the emotion is detected and the avatar smiles.

Concrete Example

For example, if the user wants to move forward in the metaverse, the brainwave sensor will detect that intention and the avatar will move forward. Also, if the user feels happy, the emotion will be detected and the avatar will smile.

Example of Prompt Text

Examples of prompt sentences to be input into the generative AI model are as follows If the user wants to move forward, the brainwave sensor should detect that intention and generate a program that causes the avatar to move forward. Also, if the user feels happy, the emotion should be detected and the avatar should smile.

The flow of the identification process in example of application 3 is described in FIG. 16.

Step 1:

The server acquires EEG data from the EEG sensor.

Input: Raw data from EEG sensor

Output: Acquired EEG data

Specific operation: An EEG sensor measures the user's brain waves in real time and sends the data to the server.

Step 2:

The server preprocesses the acquired EEG data.

Input: EEG data acquired

Output: preprocessed EEG data

Specific operation: Pre-processing such as noise removal and filtering is performed, and the data is converted into a format suitable for analysis.

Step 3:

The server inputs the preprocessed EEG data to the generator system AI.

Input: preprocessed EEG data

Output: Data input to the generative AI

Specific operation: Pre-processed EEG data is input into a generative AI model to analyze the user's intentions and emotions.

Step 4:

The generative AI analyzes the user's intentions and emotions based on the input brain wave data.

Input: Data input to the generative AI

Output: parsed intentions and feelings

Specific behavior: A generative AI model analyzes brain wave data to identify what the user intends and what emotion identification model the user has.

Step 5:

The server determines actions in the metaverse based on the analysis results.

Input: parsed intentions and feelings

Output: Actions performed in the metaverse

Specific actions: If the user's intention is "forward", the avatar determines the action of moving forward; if the emotion is "happy", the avatar determines the action of smiling.

Step 6:

The server sends the determined action to the Metaverse Controller.

Input: Actions to be performed in the metaverse

Output: Action instructions sent to the Metaverse Controller

Specific actions: The determined actions are sent through the Metaverse Controller's API to instruct the avatar to actually perform the action.

Step 7:

The Metaverse Controller controls the avatar based on the action instructions received.

Input: Action instructions sent to the Metaverse Controller

Output: Avatar behavior

Specific actions: The metaverse controller controls the avatar to perform actions based on the user's intentions and emotions. For example, the avatar moves forward or smiles.

Further, an emotion engine that estimates the user's emotion may be combined. In other words, the specific processing unit 290 may use the emotion identification model 59 to estimate the user's emotion and perform specific processing using the user's emotion.

Example of Implement 1

In one exemplary embodiment, the brain-machine interface (BMI) analyzes the user's brain waves in real time and inputs the results to the generative AI. In addition, by combining an emotion engine, the user's emotional state is also analyzed simultaneously. Based on the results of this analysis, the system understands the user's intentions and emotional state, and generates output based on them. For example, if a user thinks of "making coffee" with an emotion of joy, the system recognizes that joyful emotion and takes action to make coffee accordingly.

Example of Implement 2

In another exemplary embodiment of the invention, the platform has a function that allows users to manage their own EEG data and emotional states and share them with third parties as needed. For example, users can share their EEG data with medical and research institutions when they are feeling joyful emotions to obtain more accurate medical services and research results.

Example of Implement 3

In a further exemplary embodiment of the invention, the services provided through the platform have the ability to provide services that utilize the emotional state of the user. For example, an intuitive communication service analyzes the user's brain waves to understand their emotions and intentions, and communicates with them based on this information. If the user has a joyful emotion, the service recognizes that joyful emotion and provides communication accordingly.

The following is a description of the process flow for each example of implement.

Example of Implement 1

Step 1: The user thinks of a specific action. For example, think "make coffee".

Step 2: The brain-machine interface (BMI) analyzes the user's brain waves in real time.

Step 3: The emotion engine analyzes the user's emotional state. In this example, it analyzes that the user has the emotion of joy.

Step 4: Based on the analysis results, understand the user's intentions and emotional state and generate output based on them. In this example, the coffee-making action is tailored to the emotion of joy.

Example of Implement 2

Step 1: The user feels a specific emotion. For example, feel the emotion of joy.

Step 2: The platform manages the user's EEG data and emotional state.

Step 3: The user shares his/her EEG data and emotional state with third parties as needed. In this example, it is shared with a medical or research institution.

Example of Implement 3

Step 1: The user uses the service through the platform. For example, use intuitive communication services.

Step 2: The service analyzes the user's brain waves to understand their emotions and intentions.

Step 3: The service provides communication tailored to the user's emotional state based on the analysis results. In this example, if the user has a joyful emotion, the service provides communication tailored to that joyful emotion.

Example 1

Next, example 1 of exemplary embodiment of implement will be described. In the following description, data processing device 12 will be referred to as the "server" and robot 414 will be referred to as the "terminal.

Conventional brain-machine interfaces (BMI) only analyze the user's brain waves and fail to take into account the user's emotional state. This made it difficult to accurately understand the user's intentions and generate appropriate output. It also lacked a platform for managing users' EEG data and sharing it with third parties. This prevented the social diffusion of BMI and made it difficult to provide intuitive communication services, health management services, and biometric authentication services The specific processing by the specific processing unit 290 of the data processing device 12 in Example 1 is realized by the following means.

In this invention, the server includes means for acquiring the user's brain waves in real time, analyzing the acquired brain wave data to extract the user's intentions, analyzing the user's emotional state, generating and inputting prompt sentences to a generative AI based on the analysis results, and executing the output generated by the generative AI The system also includes means to execute the outputs generated by the generative AI. This enables the system to accurately understand the user's intentions and emotional state and generate appropriate outputs. The system can also provide a platform for disseminating the system in society, and provide intuitive communication services, virtual space interface, health management services, and biometric authentication services using brain activity.

A "user" is an individual who uses the system.

Brain waves" are electrical signals generated by neural activity in the brain.

Real-time" means that data is processed as soon as it is generated.

Means of acquisition" refers to devices and methods for collecting data.

Means to analyze" refers to devices and methods used to analyze acquired data and extract meaningful information.

Intent" refers to information that indicates what the user wants or is thinking about.

The term "emotional state" refers to information that indicates a user's feelings or mood.

Generative AI" refers to artificial intelligence that generates new information and output based on given data.

A "prompt sentence" is an input sentence used to give instructions or ask questions to the generative AI.

Output" refers to the results or responses generated by the generative AI based on the prompted statements.

Means of execution" refers to devices and methods used to convert output generated by the generative AI into concrete actions and operations.

The term "platform" refers to the infrastructure used to operate the system and provide services to users.

An "intuitive communication service" is one that allows users to exchange information with others in a natural way.

The term "virtual space interface" refers to an interface that allows users to operate and experience things within a virtual environment.

The term "health management services" refers to services for monitoring and managing the health status of users.

The term "biometric authentication service" refers to a service that uses a user's biometric information to verify his or her identity.

This invention is a system that analyzes a user's brain waves in real time and inputs the results to a generative AI to understand the user's intentions and emotional state and generate output based on these results. The system includes an EEG measurement device to acquire the user's EEG, software to analyze the EEG data, an emotion engine to analyze the emotional state, a generative AI, and hardware to execute the generated output.

Hardware and Software Used

1. Brain Wave Measurement Device

The user wears a special EEG measurement device. This device acquires the user's brain waves in real time.

2. Brain Wave Analysis Software

EEG analysis software (e.g., OpenBCI) is used by the terminal to analyze the EEG data acquired from the EEG measurement device. This software analyzes the EEG data and extracts the user's intentions.

3. Emotion Engine:

The terminal uses an emotion engine to analyze the user's emotional state. This engine acquires emotional data through facial recognition cameras and voice analysis to understand the user's emotional state.

4. Generative AI: The

The server generates and inputs prompt sentences to the generative AI (e.g. OpenAI GPT-4) based on the analysis results. The generative AI generates appropriate outputs based on the prompt sentences.

5. Output Execution Hardware

The server receives output from the generative AI and manipulates hardware (e.g., IoT devices) to perform specific actions.

Concrete Example

The user wakes up in the morning and puts on the EEG measurement device.

The terminal receives data from the EEG measurement device and begins analyzing it in real time.

The terminal detects the intention to "drink coffee" from brain wave data.

The terminal confirms that the user has a feeling of "joy" through the facial recognition camera.

The terminal says, "The user wants to 'have a cup of coffee' with an emotion of pleasure. Please suggest an appropriate action." The terminal generates the prompt sentence "The user wants to have a cup of coffee.

The server sends a prompt sentence to the generative AI, and the generative AI generates an output that "instructs the coffee maker to make coffee.

The server operates the coffee maker through an IoT device to make coffee.

Example of Prompt Text

EEG data of user: [data].

User's emotional state: joy

User Intent: I want a cup of coffee

Prompt for generative AI: A user wants to 'have a cup of coffee' with a joyful emotion. Please suggest an appropriate action.

In this way, the system can analyze the user's brain waves and emotional state, generate output based on the user's intentions using generative AI, and execute specific actions.

The flow of the identification process in Example 1 is described in FIG. 17.

Step 1:

The user wears a special EEG measurement device.

Input: User's brain waves

Output: Real-time EEG data

Specific operation: The user wears the EEG measurement device on his/her head and the device begins to measure brain waves. The device transmits EEG data to the terminal in real time via Bluetooth or USB connection.

Step 2:

The terminal acquires EEG data from the EEG measurement device in real time.

Input: Real-time EEG data

Output: Acquired EEG data

Specific operation: The terminal receives EEG data transmitted from the EEG measurement device and stores it in a database.

Step 3:

The EEG data acquired by the terminal is analyzed to extract the user's intention.

Input: EEG data acquired

Output: User intent

Specific operation: The terminal uses EEG analysis software (e.g. OpenBCI) to analyze EEG data. It detects specific brain wave patterns and extracts the user's intentions based on them. For example, the intention of "I want a cup of coffee" is detected.

Step 4:

The terminal analyzes the user's emotional state.

Input: User's face image and voice data

Output: User's emotional state

Specific operation: The terminal uses the emotion engine to acquire emotion data through facial recognition camera and voice analysis. As a result of the analysis, the user identifies an emotional state such as "joy" or "sadness".

Step 5:

The terminal generates and inputs prompt sentences to the generative AI based on the analysis results.

Input: user intent and emotional state

Output: Prompt statement to generative AI

Specific action: The terminal integrates the user's intention and emotional state and says, "The user wants to 'have a cup of coffee' with a feeling of joy. Please suggest an appropriate action." The prompt sentence "The user wants to drink a cup of coffee" is generated.

Step 6:

The server sends prompt sentences to the generative AI, and the generative AI generates output.

Input: Prompt statement to generative AI

Output: Output from generative AI

Specific behavior: The server sends a prompt sentence to the generative AI (e.g., OpenAI GPT-4), and the generative AI generates an output "instructing the coffee maker to make coffee" based on the prompt sentence.

Step 7:

The server receives output from the generative AI and executes specific actions.

Input: Output from generative AI

Output: Actions performed

Specific operation: The server operates the coffee maker through the IoT device to make coffee. Specifically, "make coffee" instructions are sent to the coffee maker, and coffee is actually made.

Example of Application 1

Next, example of application 1 of example of implement 1 will be described. In the following description, the data processing device 12 is referred to as the "server" and the robot 414 is referred to as the "terminal.

Conventional brain-machine interface (BMI) technology exists that analyzes the brain waves of users to understand their intentions, but the scope of its application is limited and has not been fully utilized, especially in work support in factories. In addition, the lack of a system that understands the intentions of workers in real time and automatically performs appropriate tasks has not sufficiently improved work efficiency or enabled human-machine collaboration.

The specific processing by the specific processing unit 290 of the data processing device 12 in example of application 1 is realized by the following means. In this invention, the server provides means to generate a minimally invasive and highly accurate brain-machine interface (BMI) that combines brain waves and generative AI, means to provide a platform to disseminate the BMI in society, means to provide intuitive communication services, metaverse interface, health management services, and biometric authentication services, and means to be installed in a robot performing work in a factory to analyze the worker's brain waves in real time, understand the worker's intentions, and automatically perform appropriate tasks. This makes it possible to understand the worker's intentions in real time and automatically perform appropriate tasks.

Brain waves" are electrical signals generated by neural activity in the brain.

Generative AI" is an artificial intelligence technology that generates new data and outputs based on input data.

Brain Machine Interface (BMI) is an interface technology that analyzes brain waves and uses the results to control machines and computers.

Minimally invasive" means less stressful or damaging to the body.

High precision" means extremely accurate.

A "platform" is the underlying system or environment that provides a specific service or function.

An "intuitive communication service" is one that allows users to interact with information in a natural way.

The term "metaverse interface" refers to the user interface within the virtual space.

A "health management service" is a service that monitors and manages a user's health status.

Biometric authentication service" is a service that uses an individual's biometric information for authentication.

A "robot that works in a factory" is a machine that is designed to automatically perform a specific task in a factory.

A "worker" is a person who performs work in a factory.

Real-time" means that processing and analysis occur almost simultaneously.

Intent" refers to the purpose or idea of what the user wants to do.

Output" refers to the results or actions produced by a system or machine.

The system for implementing this invention uses a minimally invasive and highly accurate brain-machine interface (BMI) that combines EEG and generative AI. The server analyzes the user's brain waves in real time and inputs the results to the generative AI, which understands the user's intentions and generates output based on them. In addition, by combining an emotion engine, the emotional state of the user is analyzed at the same time to understand the user's intentions and emotional state to generate output.

The system is installed on a robot performing a task in the factory and analyzes the worker's brain waves in real time. When a worker wants to perform a specific task, the robot understands his/her intention and automatically performs the appropriate task. For example, if the worker wants to "assemble parts," the robot understands his/her intention and starts assembling the parts.

The server uses EEG sensors to acquire EEG data. EEG data is analyzed in real-time using a Python library. An emotional engine will be used to analyze emotional states. A generative AI model (e.g., OpenAI GPT-3) understands the user's intentions based on the analyzed EEG data and emotional state, and generates appropriate output.

As a concrete example, here is a prompt sentence for a worker who wants to "assemble a part".

Example of a prompt statement: "I am a member of the EEG data of user: [0.1, 0.2, 0.3, . . . ].

User's emotional state: joy

User Intent: To assemble parts

By inputting this prompt sentence into the generative AI model, it understands the user's intention and generates appropriate actions. For example, a specific output is obtained, such as a robot starting to assemble a part.

This system enables the system to understand the intentions of workers in real time and automatically perform appropriate tasks. This improves work efficiency in the factory and realizes collaboration between man and machine.

The flow of the identification process in Example of Application 1 is described in FIG. 18.

Step 1:

The server acquires the user's EEG data in real time using EEG sensors. The input is the user's EEG signal and the output is the EEG data acquired. This data is transmitted from the EEG sensor to the server.

Step 2:

The server analyzes the acquired EEG data in real time using a Python library. The input is the acquired EEG data and the output is the analyzed EEG data. Through this analysis, EEG features and patterns are extracted.

Step 3:

The server analyzes the emotional state of the user from the analyzed EEG data using the emotion engine. The input is the analyzed EEG data and the output is the user's emotional state. This analysis determines whether the user is happy, sad, angry, etc.

Step 4:

The server uses a generative AI model (e.g., OpenAI GPT-3) to understand user intentions based on parsed EEG data and emotional states. The input is the parsed EEG data and emotional state, and the output is the user's intention. The data generation AI model inputs these data as prompts and infers what the user wants to do.

Step 5:

The server generates appropriate outputs based on user intent. The input is the user's intention and the output is a specific action. For example, if the user intends to assemble a part, the server instructs the robot to begin the process of assembling the part.

Step 6:

The robot receives instructions from the server and executes specific tasks. The input is the instructions from the server and the output is the work performed. For example, this includes a series of operations in which the robot starts and completes the assembly of a part.

Step 7:

The server monitors work progress and provides feedback as needed. The input is work progress data from the robot and the output is feedback information. This improves the accuracy and efficiency of the work.

Example 2

Next, example 2 of exemplary embodiment of implement will be described. In the following description, the data processing device 12 is referred to as the "server" and the robot 414 is referred to as the "terminal.

Conventional brain-machine interfaces (BMIs) lack the ability to effectively manage users' EEG data and share it with third parties as needed. In addition, the accuracy and real-time nature of EEG data analysis was low, making it difficult to accurately understand the user's intentions. Furthermore, the acquisition and management of EEG data was complicated, making it difficult for ordinary users to use the system.

The specific processing by the specific processing unit 290 of the data processing device 12 in Example 2 is realized by the following means. In this invention, the server includes means by which the user acquires EEG data using a dedicated EEG measurement device and uploads it to the platform through a terminal, the server receives the EEG data and stores it in a database, and the server preprocesses and analyzes the EEG data. This allows users to effectively manage their own EEG data and share it with third parties as needed. It also improves the accuracy of the analysis of the EEG data and allows for an accurate understanding of the user's intentions in real time. Furthermore, the system simplifies the acquisition and management of EEG data, providing an easy-to-use system for the general user.

Brain Machine Interface (BMI) is a technology that uses brain wave data to understand the user's intentions and intuitively interact with machines and computers.

Generative AI is an artificial intelligence technology that analyzes a user's brain wave data and generates output based on the results.

The "platform" is the system infrastructure that allows users to manage their EEG data and share it with third parties as needed.

An "EEG measurement device" is a device worn on the user's head to acquire EEG data.

A "terminal" is a device that allows users to input and upload their EEG data to the platform.

A "server" is a computer system that receives EEG data, stores it in a database, and performs pre-processing and analysis.

A "database" is an information management system for storing received EEG data.

Pre-processing" refers to data cleaning operations performed on EEG data prior to analysis, such as noise removal and completion of missing values.

Analysis" is the process of classifying and understanding the user's emotional state and intentions based on the preprocessed EEG data.

The "third party" is the party with whom the user shares EEG data, such as a medical or research institution.

Exemplary Embodiment of the Invention

This invention is a system in which users acquire EEG data using a dedicated EEG measurement device and upload it to the platform through a terminal. The server stores the received EEG data in a database for pre-processing and analysis. This allows users to effectively manage their own EEG data and share it with third parties as needed.

Hardware and Software Used

Hardware: (1)

EEG measurement device: The user uses a dedicated EEG measurement device (e.g., a common EEG measuring device) to obtain EEG data. This device is worn on the user's head and collects EEG data in real time.

Software: C

Terminal application: The terminal provides an interface for the user to receive and upload the EEG data acquired by the user to the platform. The user uploads the data through the terminal application.

Server: The server performs preprocessing and analysis of EEG data using Python. Specifically, libraries such as NumPy and Pandas are used to clean and filter the data. It also builds and analyzes machine learning models using libraries such as TensorFlow and PyTorch.

Database: The server uses a relational database such as MySQL or PostgreSQL to store EEG data.

Concrete Example

As a concrete example, consider a scenario in which EEG data is shared with a healthcare provider when a user is experiencing feelings of joy. The user acquires the data using an EEG measurement device and uploads it to the platform through a terminal. The server receives the data, analyzes it, and then sends the data to the medical institution.

Example of Prompt Sentences to be Entered into a Generative AI Model:

Describe the steps you would take to share EEG data with a medical provider when a user is experiencing feelings of joy."

Using this prompt statement, the generated AI model can provide detailed descriptions of specific procedures and necessary hardware and software.

In this way, users can effectively manage their own EEG data and share it with third parties as needed. In addition, the accuracy of EEG data analysis is improved, allowing the system to accurately understand the user's intentions in real time. Furthermore, the system simplifies the acquisition and management of EEG data, providing an easy-to-use system for the general user.

The flow of the identification process in Example 2 is described in FIG. 19.

Program Processing Flow

Step 1:

User Obtains EEG Data

Input: User's brain waves

Output: EEG data

Specific Operation: The user wears a dedicated EEG measurement device on the head to acquire EEG data in real time. The device detects the user's brain waves with sensors and stores them as digital data.

Step 2:

The Terminal Uploads EEG Data to the Platform

Input: EEG data

Output: Data uploaded to the platform

Specific operation: The user opens the application on the terminal, selects the EEG data acquired and presses the "Upload" button. The terminal sends the data to the platform.

Step 3:

Server Receives EEG Data and Stores it in a Database

Input: Uploaded EEG data

Output: Data stored in database

Specific Operation: The server receives EEG data sent from the terminal and stores it in a relational database such as MySQL or PostgreSQL. The database also stores metadata such as user IDs and time stamps.

Step 4:

Server Preprocesses EEG Data

Input: EEG data stored in database

Output: preprocessed data

Specifics: The server runs Python scripts and uses libraries such as NumPy and Pandas to clean and filter data. Specifically, it performs noise removal and missing value completion.

Step 5:

Server Analyzes EEG Data

Input: preprocessed data

Output: Analysis results (e.g. classification of emotional states)

Specific behavior: The server runs machine learning models using libraries such as TensorFlow and PyTorch to classify emotional states from EEG data. The analysis results are output as data indicating the user's emotional state and intentions.

Step 6:

User Manages EEG Data

Input: Analysis results and original EEG data

Output: Controlled data (e.g. filtered data display)

Specific behavior: users access the platform's dashboard to review analysis results. Data can be filtered and displayed for specific time periods.

Step 7:

Users Share EEG Data with Third Parties

Input: Managed data

Output: Shared data

How it specifically works: The user presses the "Share" button on the dashboard, enters the contact information of a third party (e.g., a medical institution), and gives permission to share. The server encrypts the data and sends it to the third party using HTTPS.

Thus, by performing specific actions in each step, users can effectively manage their own EEG data and share it with third parties as needed.

Example of Application 2

Next, example of application 2 of example of implement 2 will be described. In the following description, the data processing device 12 is referred to as the "server" and the robot 414 is referred to as the "terminal.

Conventional brain-machine interfaces (BMIs) can collect and analyze users' brain wave data, but lacked a means to share that data with third parties in a secure and efficient manner. In addition, no system existed to analyze the user's emotional state in real time and take appropriate action when abnormalities were detected. This made it difficult to share data with medical and research institutions, and prevented users from improving the accuracy of their health management and biometric identification.

The specific processing by the specific processing unit 290 of the data processing device 12 in example of application 2 is realized by the following means.

In this invention, the server provides means for generating a minimally invasive and highly accurate brain-machine interface (BMI) that combines brain waves and generative AI, means for providing a platform for disseminating the BMI to society, means for providing intuitive brain activity-based communication services, metaverse interface, health management services, and biometric authentication services provided through the platform; collecting users' brain wave data in real time, encrypting it, and sharing it with third parties; analyzing users' emotional states and alerting them if any abnormality is detected. The system includes the following. This enables the secure and efficient sharing of the user's EEG data and strengthens cooperation with medical and research institutions. In addition, the user's emotional state can be monitored in real time, and if an abnormality is detected, a quick response can be made to improve the accuracy of health management and biometric authentication.

Brain waves" are electrical signals generated by neural activity in the brain.

Generative AI" is a type of artificial intelligence, a system that has the ability to generate new data and information based on input data.

The term "minimally invasive" refers to less burden or damage to the body.

A "brain-machine interface" (BMI) is an interface that uses brain waves to operate a machine or computer.

A "platform" is the underlying system or environment that provides a specific function or service.

An "intuitive communication service" is one that allows users to interact with information in a natural way.

A "metaverse interface" is an interface that allows users to operate and experience things in a virtual space.

Health Management Service" is a service that monitors the health status of users and provides them with appropriate advice and support.

Biometric services" are services that use a user's biometric information to verify identity.

Encryption" is a technique whereby data is converted using a specific algorithm so that it cannot be easily deciphered by a third party.

An "emotional state" is the emotional state a user is feeling at a particular moment in time.

An "alert" is a notification or warning of an abnormality or emergency.

The following system configuration is an exemplary embodiment of this invention.

System Configuration

The system will include hardware and software to collect the user's EEG data and analyze it using a generative AI. Specifically, the system will include the following elements.

1. EEG sensor: A device that collects the user's brain waves in real time. The EEG sensor is worn on the user's head and measures the electrical activity of the brain.
2. smart device: a device used to receive, encrypt, and analyze data from the EEG sensor. A dedicated application is installed on the smartphone.
3. server: provides a platform for receiving encrypted EEG data and sharing it with third parties (medical and research institutions) as needed. The server shall include software to manage and share the data.

Program Processing

The server will perform the following processes

1. EEG data collection: EEG sensors collect the user's EEG data in real time and transmit it to the smartphone.
2. data encryption: The smartphone encrypts the received EEG data. Fernet, a cryptography library, is used for encryption.
3. data sharing: encrypted data is sent from the smartphone to the server. The server shares the received data with a designated third party (medical or research institution).
4. emotional state analysis: Smartphones analyze brain wave data to identify the user's emotional state. If an abnormality is detected, the smart phone will send out an alert.

Hardware and Software Used

EEG sensor: a device that collects the user's brain waves.

Smart devices: devices that receive, encrypt, parse, and share data.

Server: A platform for managing and sharing data.

cryptography library: Software used to encrypt data.

requests library: Software used to transmit data.

Concrete Example

For example, consider a case where brain wave data is collected when a user is stressed and sent to a medical facility. An EEG sensor collects the user's brain waves and transmits them to a smart phone. The smartphone encrypts the received data and sends it to the server. The server shares the encrypted data with the medical institution. The medical institution analyzes the received data and evaluates the user's stress state.

Example of Prompt Text

Create a Python program that collects the user's EEG data, encrypts it, and sends it to a designated medical facility. The EEG data can be virtual data. Use the cryptography library Fernet for encryption and the requests library to send the data."

The above is an exemplary embodiment of this invention.

The flow of the identification process in example of application 2 is described in FIG. 20.

Step 1:

The user wears an EEG sensor. The EEG sensor collects the user's EEG data in real time. The input is the user's EEG signal and the output is the raw data collected by the EEG sensor.

Step 2:

The terminal (smartphone) receives EEG data from the EEG sensor. The terminal acquires the data using wireless communication such as Bluetooth or Wi-Fi. The input is the raw data transmitted from the EEG sensor and the output is the EEG data stored in the terminal.

Step 3:

Encrypt the EEG data received by the terminal. The cryptography library Fernet is used for encryption. The input is the EEG data stored in the terminal and the output is the encrypted EEG data. The specific operation is to generate an encryption key and encrypt the EEG data with the key.

Step 4:

The terminal sends encrypted EEG data to the server. The requests library is used for transmission. The input is the encrypted EEG data and the output is the data sent to the server. The specific operation is to send the data using an HTTP POST request.

Step 5:

The server stores the encrypted EEG data received. The server manages the data using a database. The input is the encrypted data sent from the terminal and the output is the encrypted data stored in the database.

Step 6:

The server shares encrypted EEG data with third parties (medical and research institutions) as needed. Secure communication protocols are used for sharing. The input is the encrypted data stored in the database and the output is the data sent to the third party. The specific operation is to authenticate the third party and send the data if the authentication is successful.

Step 7:

The terminal analyzes EEG data to identify the user's emotional state. A generative AI model is used for the analysis. The input is the EEG data stored in the terminal and the output is the emotional state as the result of the analysis. Specifically, the EEG data is input to the AI generation model, and the emotional state is estimated.

Step 8:

The terminal monitors the emotional state and sends out an alert when an abnormality is detected. The input is the emotional state as an analysis result, and the output is an alert when an abnormality is detected. Specifically, when the emotional state exceeds a predefined threshold, a notification is sent to the user or a designated third party.

Example 3

Next, example 3 of exemplary embodiment of implement will be described. In the following description, the data processing device 12 is referred to as the "server" and the robot 414 is referred to as the "terminal.

Conventional brain-machine interfaces (BMI) require high accuracy in analyzing a user's brain waves, but it has been difficult to achieve high accuracy in a minimally invasive manner. In addition, there was a lack of a system to provide real-time feedback of the analysis results to the user, which could not immediately reflect the user's intentions or emotional state. Furthermore, users lacked the ability to manage their own EEG data and share it with third parties as needed.

The specific processing by the specific processing unit 290 of the data processing device 12 in Example 3 is realized by the following means. In this invention, the server includes the following means: the server measures the user's EEG data and transmits it to the server in real time; the server analyzes the EEG data and identifies the user's emotional state and intentions; and the server stores the analysis results in a database and transmits them to the terminal. This enables minimally invasive and highly accurate EEG analysis, which can reflect the user's intentions and emotional state in real time. It also allows users to manage their own EEG data and share it with third parties as needed.

Brain Machine Interface (BMI) is a technology that uses brain waves to control computers and other devices.

Generative AI" is a type of artificial intelligence that has the ability to generate new data and information based on input data.

A "platform" is the underlying system or environment that provides a specific service or function.

EEG data" is data that electrically measures the user's brain activity and reflects emotional states and intentions.

Real-time" means that data is measured and processed immediately.

Analysis" is the process of processing measured data to extract specific information or patterns.

The "emotional state" is a state that indicates the user's current emotion or mood.

Intent is what the user is trying to do or wants.

A "database" is a system that stores data in an organized manner and can be retrieved and updated as needed.

Feedback" is the response or information provided by the system to the user.

Minimally invasive" means less physical strain or discomfort to the user.

High precision" means that the measurement and analysis of data is extremely accurate.

A "virtual reality interface" is the means by which a user interacts with a virtual reality environment.

Health Management Service" is a service that monitors the user's health status and provides appropriate advice and support.

A "biometric service" is a service that uses a user's biometric information to authenticate an individual.

This invention is a system that combines EEG and generative AI to provide a minimally invasive and highly accurate brain-machine interface (BMI). The system measures and analyzes the user's EEG data in real time to identify the user's emotional state and intentions, and provides feedback based on them.

Hardware and Software Used

Hardware (esp. Computer)

- EEG measurement devices: Devices to measure the user's brain waves (e.g., EEG headsets)
- Terminal: Device (e.g., smart device, tablet, PC) that connects to the EEG measurement device and sends data to the server
- Server: Computer system for receiving and analyzing EEG data Software

- Data transmission program: A program installed in the terminal to transmit EEG data to the server
- Data analysis programs: Programs installed on the server to analyze EEG data (e.g., FFT analysis using Python)

Database management system: A system for storing analysis results and retrieving and updating them as needed.

Feedback program: A program installed on the terminal to display the results of the analysis to the user.

Specific System Operation

User Behavior

The user wears an EEG measurement device (e.g., EEG headset) and connects it to the terminal. The user performs certain actions to generate EEG data. For example, if the user is relaxed, the EEG data has a specific frequency component.

Terminal Operation

The terminal measures the user's brain waves in real time and transmits them to the server using a data transmission program. The terminal waits for a response from the server to confirm that the data transmission was successful.

Server Operation

The server receives the EEG data sent from the terminal. The received data is analyzed using a data analysis program. Specifically, the FFT (Fast Fourier Transform) is used to break down the EEG data into its frequency components and extract specific patterns. For example, the intensity of alpha and beta waves is calculated to identify the user's emotional state.

Save and Send Analysis Results

The server stores the analysis results in a database. The stored data includes user ID, measurement date and time, and analysis results (emotional state and intention). This makes it possible to refer to the data later. The server sends the analysis results to the terminal. Secure communication protocols (e.g. HTTPS) are used for transmission.

Terminal Feedback

The terminal displays the analysis results received from the server to the user. The display uses a graphical user interface (GUI). For example, if the user is relaxed, the terminal displays "relaxed state" and suggests appropriate actions (e.g., playing relaxing music).

Examples of Specific Examples and Prompt Sentences

Concrete Example

For example, when a user uses an intuitive communication service, the following steps are taken 1. the user puts on the EEG headset and connects it to the terminal.

The terminal measures EEG data in real time and sends it to the server.

3. the server receives the EEG data and analyzes it using FFT. For example, if the intensity of alpha waves is high, the server determines that the user is relaxed.

The results of the analysis are stored in a database. For example, data such as "User ID: 12345, Date: 2023 Oct. 1 10:00, State: Relaxed" will be saved.

The server sends the analysis results to the terminal. The terminal displays "Relaxed" and suggests playing relaxing music.

6. the user relaxes by playing relaxing music as suggested by the terminal.

Example of Prompt Text

The program should analyze the user's EEG data to identify their emotional state and generate a program for intuitive communication. The hardware used is an EEG headset and the software is Python. Specifically, the program will analyze EEG data using FFT and calculate the intensity of alpha and beta waves to identify emotional states."

This specific description of the operation of the entire system clearly shows the exemplary embodiment of the invention. The flow of the specific process in Example 3 is explained using FIG. 21.

Step 1: Measure the User's EEG Data

The user wears an EEG measurement device (e.g., EEG headset). The device measures the user's EEG in real time and converts it into a digital signal. The input is the user's EEG and the output is the digitized EEG data. Specifically, the device contacts the user's scalp and detects the electrical signals.

Step 2: Transmission of EEG Data

The terminal transmits the measured EEG data to the server via Bluetooth or Wi-Fi. The input is the digitized EEG data and the output is the data sent to the server. Specifically, the terminal executes a data transmission program and sends the data to the IP address of the server.

Step 3: Receive and Analyze EEG Data by Server

The server receives the EEG data sent from the terminal. The input is the EEG data transmitted from the terminal and the output is the analysis result. The server executes FFT (Fast Fourier Transform) using Python to decompose the EEG data into its frequency components. Specifically, the server runs a data analysis program to calculate the intensity of alpha and beta waves.

Step 4: Save Analysis Results

The server stores the analysis results in a database. The input is the analysis results and the output is the data stored in the database. Specifically, the server uses a database management system to store user IDs, measurement dates and times, and analysis results.

Step 5: Transmission of Analysis Results

The server sends the analysis results to the terminal. The input is the analysis results stored in the database and the output is the analysis results sent to the terminal. As a specific operation, the server sends data using a secure communication protocol (e.g., HTTPS).

Step 6: Display of Analysis Results by Terminal

The terminal displays the analysis results received from the server to the user. The input is the analysis results sent from the server and the output is the information displayed to the user. Specifically, the terminal executes a feedback program and displays the analysis results using a graphical user interface (GUI).

Step 7: Feedback to Users

The user confirms his/her own emotional state and intentions based on the feedback provided by the terminal. The input is the feedback information from the terminal and the output is the user's next action. Specifically, the user takes actions such as playing relaxing music according to the terminal's suggestions.

Example of Application 3

Next, example 3 of application of example of implement 3 will be described. In the following description, data processing device 12 is referred to as the "server" and robot 414 is referred to as the "terminal.

Conventional brain-machine interfaces (BMI) can understand intentions by analyzing the user's brain waves, but there are issues with their accuracy and real-time performance. In addition, intuitive operation and emotion-based action control within the metaverse were difficult, and there was a need to improve the user experience. Furthermore, there was a lack of a user-friendly system for managing EEG data and sharing it with third parties.

The specific processing by the specific processing unit 290 of the data processing device 12 in example of application 3 is realized by the following means.

In this invention, the server provides means for generating a minimally invasive and highly accurate brain-machine interface (BMI) that combines brain waves and generative AI, means for providing a platform for disseminating the BMI in society, means for providing, through the platform, intuitive communication services, metaverse interface, health management services, and biometric authentication services provided through the platform; means for controlling actions in the metaverse by analyzing brain waves of users in real time and understanding their emotions and intentions; and means for controlling actions in the metaverse based on the emotional state of users. means to control actions in the metaverse based on the user's emotional state. This allows the user to intuitively perform operations in the metaverse using brain waves, thereby enabling action control based on emotions. In addition, EEG data can be easily managed and shared with third parties.

Brain waves" are electrical signals generated by neural activity in the brain.

Generative AI is an artificial intelligence technology that generates new information and content based on data.

A "brain-machine interface" (BMI) is an interface that analyzes brain waves to control machines and computers.

A "platform" is the underlying system or environment that provides a specific service or function.

Intuitive Communication Service" is a service that analyzes a user's brain waves to understand their emotions and intentions, and communicates accordingly.

A "metaverse interface" is an interface for controlling behavior in virtual reality (VR) and augmented reality (AR) worlds.

The "Health Management Service" is a service that analyzes users' brain waves to determine their stress levels and sleep conditions, and suggests health management based on this information.

Biometric authentication service" is a personal authentication service that analyzes a user's brain wave patterns.

Real-time" means immediate processing and reaction without delay.

The "emotional state" is the emotional state analyzed from the user's brain waves.

The term "action control" refers to controlling the behavior of a system or avatar based on a user's intentions or emotions.

The system for implementing this invention includes: means for generating a minimally invasive and highly accurate brain-machine interface (BMI) by combining brain waves and generative AI; means for providing a platform for disseminating the BMI in society; means for providing intuitive communication services, metaverse interface, health management services, and biometric authentication services using brain activity provided through the platform; means for controlling actions in the metaverse based on the user's emotional state by analyzing the user's brain waves in real time and understanding the user's emotions and intentions; and means for controlling actions in the metaverse based on the user's emotional state. means to provide intuitive communication services, metaverse interface, health management services, and biometric authentication services using brain activity provided through the platform; means to control actions in the metaverse by analyzing the user's brain waves in real time and understanding emotions and intentions; means to control actions in the metaverse based on the user's emotional state. Means to control actions in the metaverse based on the user's emotional state, including.

System Configuration

The server will use an EEG sensor, a head-mounted display (HMD), and a generative AI to configure the system. The EEG sensor acquires the user's brain waves in real time, and the HMD provides the user with visual information in the metaverse. The generative AI analyzes the acquired EEG data to understand the user's emotions and intentions.

Program Processing

The server acquires EEG data using the BrainFlow library and filters the data to remove noise. Next, the data is analyzed using a generative AI to detect the user's emotion (e.g., joy). Based on the detected emotion, actions in the metaverse are controlled. Specifically, if the user has the emotion of joy, the avatar is controlled to dance a joyful dance.

Hardware and Software Used

Hardware: EEG sensors (e.g., BrainFlow-compatible devices), head-mounted displays (HMDs)

Software: Python, BrainFlow library

Concrete Example

For example, consider a scene where a user wears an HMD and uses brainwave sensors to control their behavior in the metaverse. If the user has the emotion of joy, the avatar will dance a joyful dance. This allows the user to intuitively operate within the metaverse and control actions based on emotions.

Example of Prompt Text

Example of prompt sentences to be entered into a generative AI model:

Create a Python program that analyzes the user's brain wave data to detect emotions and control actions in the metaverse. If the user has a joyful emotion, have the avatar perform a joyful dance.

In this way, an intuitive metaverse interface can be realized using brain waves.

The flow of the identification process in example of application 3 is described in FIG. 22.

Step 1:

The server uses EEG sensors to acquire the user's EEG data in real time.

Input: User's EEG signal

Output: Raw EEG data

Specific operation: The server collects data from EEG sensors using the BrainFlow library and stores this in memory.

Step 2:

The server filters the acquired EEG data to remove noise.

Input: Raw EEG data

Output: Filtered EEG data

Specific operation: The server uses the filtering function of the BrainFlow library to remove noise in specific frequency bands.

Step 3:

The server inputs the filtered EEG data to the generative AI to analyze the user's emotions.

Input: Filtered EEG data

Output: User's emotional state (e.g., joy, sadness)

Specific operation: The server inputs data into the data generation AI model and runs an emotion identification model to identify the user's emotion.

Step 4:

The server determines actions in the metaverse based on the analyzed emotional state.

Input: User's emotional state

Output: Action instructions in the metaverse (e.g., Dance of Joy)

Specific operation: The server determines actions according to the emotional state and sends the instructions to the metaverse system.

Step 5:

The terminal (HMD) controls avatars in the metaverse based on action instructions received from the server.

Input: Action instructions in the metaverse

Output: Avatar behavior (e.g., joyful dancing)

Specific operation: The terminal provides visual information to the user through the HMD and controls the avatar to perform the specified action.

Step 6:

Users visually see the action in the metaverse through the HMD.

Input: Avatar behavior

Output: Visual information (e.g., avatar dancing for joy scene)

Specific behavior: The user wears an HMD to visually confirm the avatar's behavior in the metaverse in real time.

The specific processing unit 290 sends the results of the specific processing to the robot 414. In robot 414, control unit 46A causes speaker 240 and control target 443 to output the results of specific processing. Microphone 238 acquires audio indicating user input to the result of the specific processing. The control unit 46A transmits the voice data indicating the user input acquired by the microphone 238 to the data processing device 12. In data processing device 12, specific processing unit 290 acquires the voice data.

The data generation model 58 is a so-called Generative AI (Artificial Intelligence). An example of a data generation model 58 is a generative AI such as ChatGPT (Internet Search <URL: https://openai.com/blog/chatgpt>). The data generation model 58 is obtained by having a neural network perform deep learning. Prompts containing instructions are input to the data generation model 58, as well as data for inference, such as voice data indicating audio, text data indicating text, and image data indicating images. The data generation model 58 infers the input data for inference according to the instructions indicated by the prompts, and outputs the results of the inference in data formats such as voice data and text data. Here, reasoning refers to, for example, analysis, classification, prediction, and/or summarization.

Another example of generative AI is Gemini (Internet search <URL: https://gemini.google.com/?hl=ja>).

In the above exemplary embodiment, an example of implement in which the specific processing is performed by the data processing device 12 is given, but the technology of the present disclosure is not limited to this, and the specific processing may be performed by the robot 414.

The emotion identification model 59, as the emotion engine, may determine the user's emotion according to a specific mapping. Specifically, the emotion identification model 59 may determine the user's emotion according to a specific mapping, the emotion map (see FIG. 9). The emotion identification model 59 may similarly determine the robot's emotion, and the specific processing unit 290 may perform the identification process using the robot's emotion.

Figure 9:
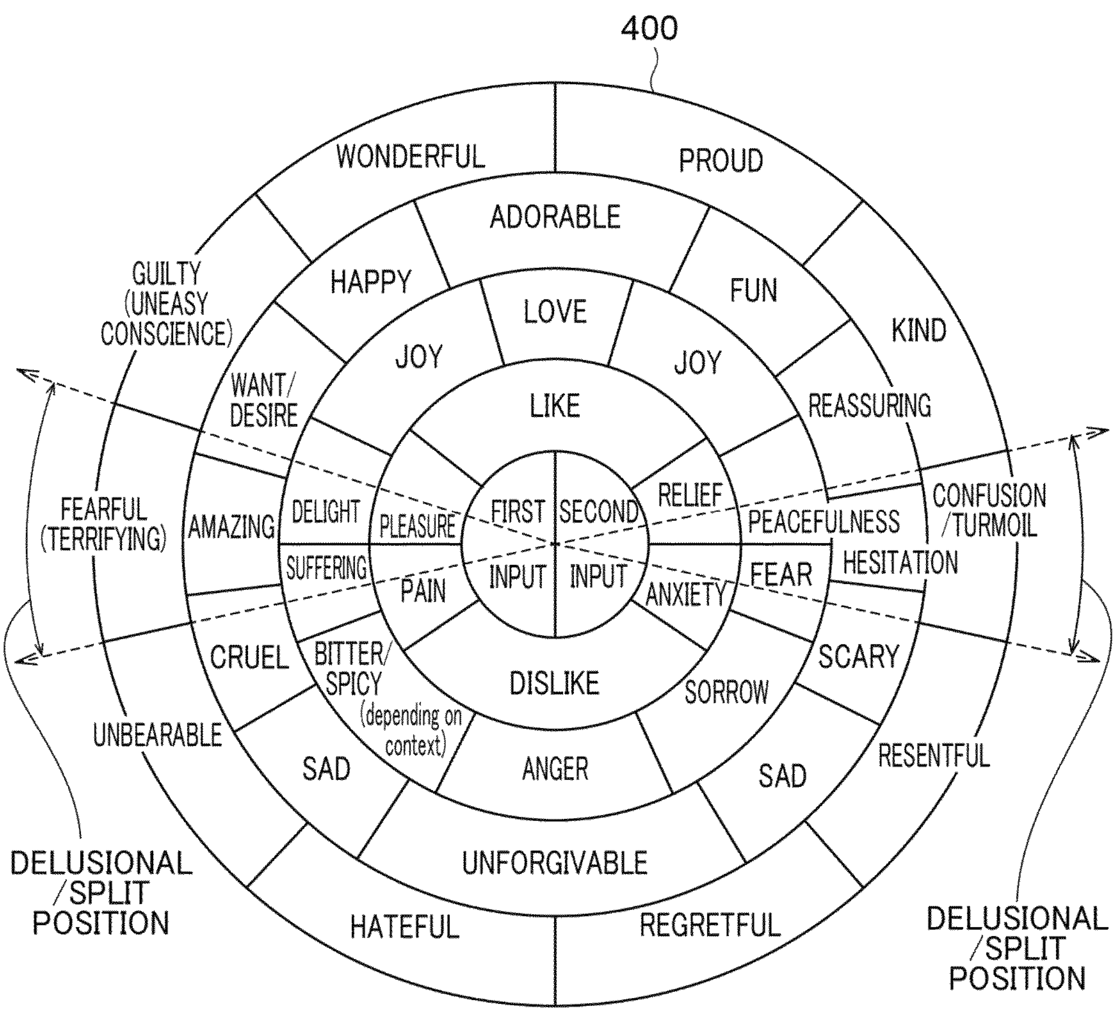
FIG. 9 shows an emotion map where multiple emotions are mapped.

FIG. 9 shows an emotion map 400 in which multiple emotions are mapped. In emotion map 400, the emotions are arranged in concentric circles radiating from the center. The closer to the center of the concentric circles, the more primitive state emotions are arranged. The more outward of the concentric circles are placed the emotions that represent states of mind and actions that arise from the state of mind. Emotion is a concept that includes emotional and mental states. On the left side of the concentric circles are the emotions that are generally generated from the reactions that occur in the brain. On the right side of the concentric circles are the emotions that are generally induced by situational judgments. On the upper and lower sides of the concentric circles are the emotions that are generally generated from the reactions that occur in the brain and are guided by situational judgments. In addition, "pleasant" emotions are placed on the upper side of the concentric circles, and "unpleasant" emotions are placed on the lower side. Thus, in emotion map 400, multiple emotions are mapped based on the structure in which emotions are generated, and emotions that tend to occur simultaneously are mapped close together.

These emotions are distributed in the 3 o'clock direction of the emotion map 400 and usually move back and forth between relief and anxiety. In the right half of the emotion map 400, situational awareness predominates over internal sensations, resulting in a calm impression.

Since the inside of the emotion map 400 represents the mind and the outside of the emotion map 400 represents behavior, the further outside of the emotion map 400, the more visible the emotion becomes (expressed in behavior).

Here, human emotions are based on various balances such as posture and blood glucose level, and when these balances move away from the ideal, they are unpleasant, and when they move closer to the ideal, they are pleasant. In robots, cars, motorcycles, etc., emotions can also be created based on various balances such as posture and battery level, with the state of discomfort when these balances move away from the ideal and pleasure when they move closer to the ideal. An emotion map may be generated based on, for example, Dr. Mitsuyoshi's emotion map (Research on Speech Emotion Recognition and Brain Physiological Signal Analysis System for Emotion, The University of Tokushima, PhD thesis: https://ci.nii.ac.jp/naid/500000375379). In the left half of the emotion map, emotions belonging to a region called "reaction," in which the senses predominate, are lined up. In the right half of the emotion map, emotions belonging to the "situation" domain, in which situational awareness predominates, are lined up.

The emotion map defines two emotions that facilitate learning: one is the emotion around the middle of negative "repentance" or "remorse" on the situational side. That is, when the robot experiences negative emotions such as "I don't want to feel this way again" or "I don't want to be scolded again. The other emotion is around the positive "greed" on the reaction side. In other words, it is when the robot has a positive feeling of "wanting more" or "wanting to know more.

Figure 10:
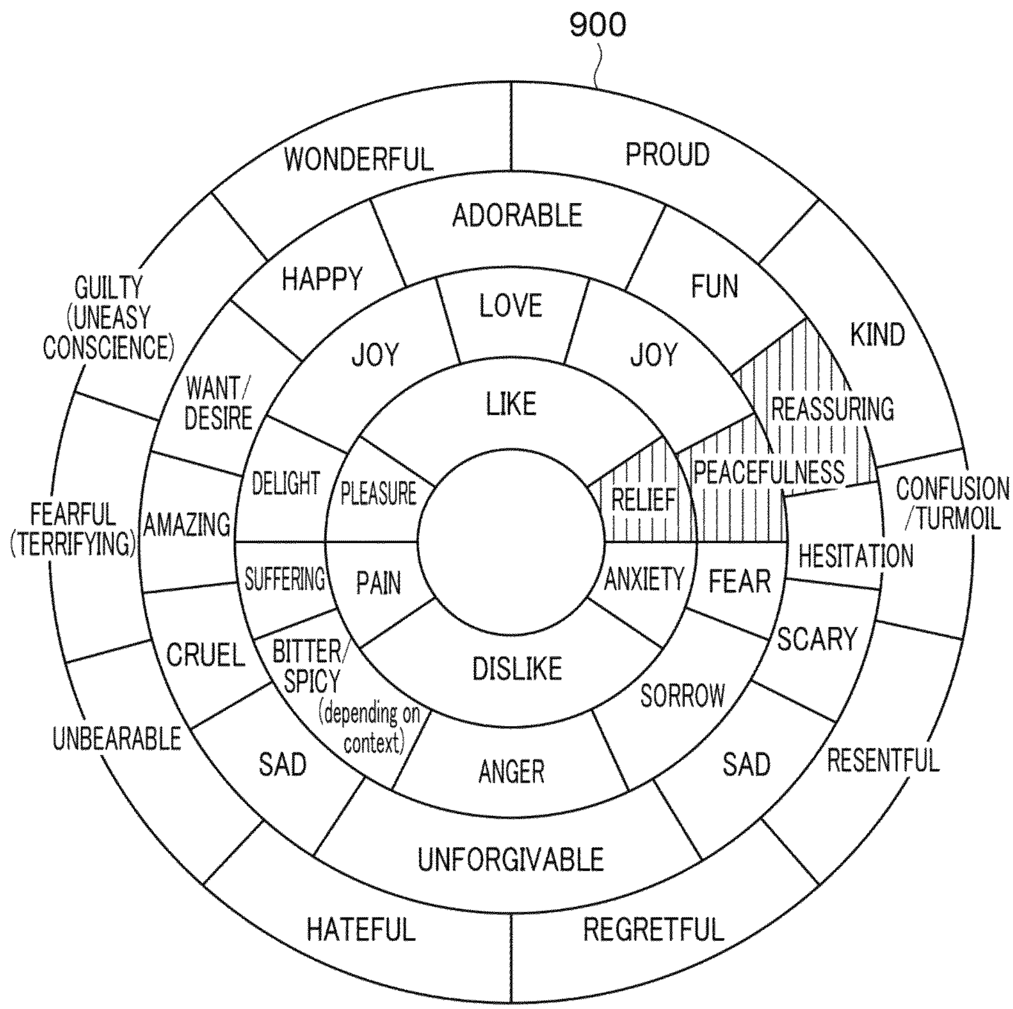
FIG. 10 shows an emotion map where multiple emotions are mapped.

The emotion identification model 59 determines the user's emotion by inputting the user input into a neural network that has been trained in advance and obtaining an emotion value indicating each emotion shown in the emotion map 400. This neural network is pre-trained based on a plurality of training data, which are combinations of user input and emotion values indicating each emotion shown in the emotion map 400. This neural network is also learned so that emotions that are placed close to each other have close values, as shown in the emotion map 900 in FIG. 10. FIG. 10 shows an example in which multiple emotions, such as "safe," "peaceful," and "reassuring," have close emotion values.

In the above exemplary embodiment, an example of implement in which specific processing is performed by one computer 22 is given, but the technology of the present disclosure is not limited to this, and distributed processing for specific processing may be performed by multiple computers including computer 22.

In the above exemplary embodiment, an example of implement in which specific processing program 56 is stored in storage 32 has been described, but the technology of the present disclosure is not limited to this. For example, the specific processing program 56 may be stored in a portable, computer-readable, non-transitory storage medium such as a USB (Universal Serial Bus) memory. The specific processing program 56 stored on the non-transitory storage medium is installed on the computer 22 of the data processing device 12. Processor 28 performs specific processing according to specific processing program 56.

The specific processing program 56 may be stored on a server or other storage device connected to the data processing device 12 via network 54, and the specific processing program 56 may be downloaded and installed on the computer 22 at the request of the data processing device 12.

It is not necessary to have all of the specific processing program 56 stored in a server or other storage device connected to the data processing device 12 via network 54, or to have all of the specific processing program 56 stored in storage 32, but a portion of the specific processing program 56 may be stored.

The following various processors can be used as hardware resources that execute the specific processing. Processors include, for example, CPUs, which are general-purpose processors that function as hardware resources that execute specific processing programs by executing software, i.e., programs. A processor can also be, for example, a field-programmable gate array (FPGA), programmable logic device (PLD), or application-specific integrated circuit (ASIC). For example, a dedicated electrical circuit, which is a processor with a circuit configuration designed specifically to perform a particular process, such as a FPGA (Field Programmable Gate Array), PLD (Programmable Logic Device), or ASIC (Application Specific Integrated Circuit). Any of these processors has a memory built in or connected to it, and any of them performs a specific process by using the memory.

The hardware resource that executes the specific processing may consist of one of these various processors or a combination of two or more processors of the same or different types (e.g., a combination of multiple FPGAs or a CPU and an FPGA). The hardware resource that performs the specific processing may be a single processor.

An example of implementing a single processor is, first, a form in which one processor is composed of a combination of one or more CPUs and software, and this processor functions as a hardware resource that executes a specific process. Second, there is a form that uses a processor that realizes the functions of the entire system, including multiple hardware resources that execute specific processing, in a single IC chip, as typified by a system-on-a-chip (SoC). Thus, the specific processing is realized using one or more of the various processors mentioned above as hardware resources.

Furthermore, the hardware structure of these various processors can be more specifically an electric circuit that combines circuit elements such as semiconductor devices. In addition, the above specific process is only an example. Therefore, it goes without saying that unnecessary steps may be deleted, new steps may be added, or the order of processing may be replaced to the extent that it does not deviate from the main purpose.

The descriptions and illustrations shown above are detailed descriptions of portions pertaining to the technology of the present disclosure and are only examples of the technology of the present disclosure. For example, the above description of the configuration, functions, actions, and effects is a description of one example of the configuration, functions, actions, and effects of the portion pertaining to the technology of the disclosure. Therefore, it goes without saying that unnecessary portions may be deleted, new elements may be added, or new elements may be substituted for the above description and illustration to the extent that it does not depart from the main purpose of the technology of the present disclosure. In addition, in order to avoid confusion and to facilitate understanding of the parts pertaining to the technology of the present disclosure, explanations regarding technical common sense, etc. that do not require particular explanation to enable implementation of the technology of the present disclosure have been omitted from the descriptions and illustrations shown above.

All references, patent applications, and technical standards described herein are incorporated by reference herein to the same extent that individual references, patent applications, and technical standards are specifically and individually noted as being incorporated by reference.

With respect to the above exemplary embodiments, the following is further disclosed (Claim 1)

A system including means to generate a minimally invasive and highly accurate brain-machine interface (BMI) combining EEG and generative AI, means to provide a platform to disseminate the BMI to society, intuitive communication services using brain activity provided through the platform The system including means to provide the BMI, the metaverse interface, health management services, and biometric authentication services.

(Claim 2)

The system of claim 1, wherein the brain-machine interface (BMI) is capable of analyzing the user's brain waves in real time and inputting the results to the generative AI to understand the user's intentions and generate output based on them.

(Claim 3)

The system of claim 1, wherein the platform has the ability for users to manage their own EEG data and share it with third parties as needed.

(Claim 4)

The system of claim 1, wherein the brain-machine interface (BMI) is further combined with an emotion engine that recognizes the user's emotions and has the ability to generate output based on the user's emotional state.

The system described in claim 1, wherein the platform has the ability to manage the user's emotional state and share it with third parties as needed.

The system of claim 1, wherein the services provided through the platform have the ability to provide services using the emotional state of the user.

Example 1

(Claim 1)

A means of collecting the user's brain waves in real time, and,

Means for analyzing the collected EEG data,

A means of inputting the analyzed EEG data into a generative AI model,

The means by which the generative AI model understands the user's intent and generates output based on it, A means of providing feedback to the user on the output generated, A means of providing a platform for the dissemination of the brain-machine interface (BMI) to society, A system that includes means to provide intuitive communication services using brain activity, virtual space interface, health management services, and biometric authentication services provided through the platform.

(Claim 2)

The system of claim 1, wherein the brain-machine interface (BMI) is capable of analyzing the user's brain waves in real time and inputting the results into a generative AI model to understand the user's intentions and generate output based thereon.

(Claim 3)

The system of claim 1, wherein the platform has the ability for users to manage their own EEG data and share it with third parties as needed.

Example of Application 1

(Claim 1)

A means of generating minimally invasive and highly accurate brain-machine interfaces (BMI) by combining EEG and generative AI, means of providing a platform for the dissemination of the BMI in society, Means to provide intuitive communication services using brain activity, metaverse interface, health management services, and biometric authentication services provided through the platform, A means for factory workers to wear head-mounted displays and control factory robots using brain waves, A means of analyzing the user's brain wave data in real time and inputting the results into a generative AI to understand the user's intentions and generate output based on them, Means of controlling factory robots based on user intent The system includes.

(Claim 2)

The system of claim 1, wherein the brain-machine interface (BMI) is capable of analyzing the user's brain waves in real time and inputting the results to the generative AI to understand the user's intentions and generate output based on them.

(Claim 3)

The system of claim 1, wherein the platform has the ability for users to manage their own EEG data and share it with third parties as needed.

Example 2

(Claim 1)

A means of generating minimally invasive and highly accurate brain-machine interfaces (BMI) by combining EEG and generative AI, means of providing a platform for the dissemination of the BMI in society, Means to provide intuitive communication services, virtual space interface, health management services, and biometric authentication services using brain activity provided through the platform, A means of uploading EEG data acquired by the user using a dedicated measurement device from the terminal to the server, means of storing the EEG data received by the server in a database, A means for users to access the platform and manage their data, A means for users to set up the sharing of data with third parties, A means by which the server encrypts data and grants access to third parties, The system includes.

(Claim 2)

The system of claim 1, wherein the brain-machine interface (BMI) is capable of analyzing the user's brain waves in real time and inputting the results to the generative AI to understand the user's intentions and generate output based thereon.

(Claim 3)

The system of claim 1, wherein the platform has the ability for users to manage their own EEG data and share it with third parties as needed.

Example of Application 2

(Claim 1)

A means of generating minimally invasive and highly accurate brain-machine interfaces (BMI) by combining EEG and generative AI, means of providing a platform for the dissemination of the BMI in society, Means to provide intuitive communication services using brain activity, metaverse interface, health management services, and biometric authentication services provided through the platform, A means of collecting users' brain wave data in real time and uploading it to the cloud in encrypted form, A means to share data with medical and research institutions and to manage data sharing history, The system includes.

(Claim 2)

The system of claim 1, wherein the brain-machine interface (BMI) is capable of analyzing the user's brain waves in real time and inputting the results to the generative AI to understand the user's intentions and generate output based on them.

(Claim 3)

The system of claim 1, wherein the platform has the ability for users to manage their own EEG data and share it with third parties as needed.

Example 3

(Claim 1)

A means for the user to wear the EEG measurement device and connect it to the terminal, A means by which the terminal collects EEG data from the EEG measurement device and transmits it to the server, A means by which the server receives and preprocesses EEG data, A means by which the server analyzes the preprocessed data and identifies emotions and intentions, A means by which the server sends the analysis results to the terminal, A means by which the terminal displays the results of the analysis and provides feedback to the user, means of providing a platform for the dissemination of the system in society, Means to provide intuitive communication services using brain activity, virtual reality interface, health care services, and biometric authentication services provided through the platform, The system includes.

(Claim 2)

The system of claim 1, wherein the system has the ability to analyze the user's brain waves in real time and input the results into a generative AI model to understand the user's intentions and generate output based thereon.

(Claim 3)

The system of claim 1, wherein the platform has the ability for users to manage their own EEG data and share it with third parties as needed.

Example of Application 3

(Claim 1)

A means of generating minimally invasive and highly accurate brain-machine interfaces (BMI) by combining EEG and generative AI, means of providing a platform for the dissemination of the BMI in society, Means to provide intuitive communication services using brain activity, metaverse interface, health management services, and biometric authentication services provided through the platform, A means of analyzing the user's brain waves in real time to control navigation and interaction in the metaverse, and A means of performing actions in the metaverse based on the user's intentions and emotions, The system includes.

(Claim 2) The system of claim 1, wherein the brain-machine interface (BMI) is capable of analyzing the user's brain waves in real time and inputting the results to the generative AI to understand the user's intentions and generate output based on them.

(Claim 3) The system of claim 1, wherein the platform has the ability for users to manage their own EEG data and share it with third parties as needed.

Example 1 for the Combined Emotional Engine (Claim 1)

A means of acquiring the user's brain waves in real time; and

A means of analyzing the acquired EEG data and extracting the user's intentions, A means of analyzing the user's emotional state, A means to generate and input prompt sentences to the generative AI based on the analysis results, A means of executing the output generated by the generative AI, means of providing a platform for the dissemination of the system in society, A system that includes means to provide intuitive communication services using brain activity, virtual space interface, health management services, and biometric authentication services provided through the platform.

(Claim 2)

The system of claim 1, wherein the brain-machine interface (BMI) has the ability to analyze the user's brain waves in real time and input the results to the generative AI to understand the user's intentions and emotional state and generate output based on them.

(Claim 3)

The system of claim 1, wherein the platform has the ability for users to manage their own EEG and emotional data and share it with third parties as needed.

Example of Application 1 when Combined with the Emotional Engine (Claim 1)

A means of generating minimally invasive and highly accurate brain-machine interfaces (BMI) by combining EEG and generative AI, means of providing a platform for the dissemination of the BMI in society, Means to provide intuitive communication services using brain activity, metaverse interface, health management services, and biometric authentication services provided through the platform, A means of automatically performing appropriate tasks by analyzing the brain waves of workers in real time and understanding their intentions, installed in robots that perform tasks in a factory, The system includes.

(Claim 2)

The system of claim 1, wherein the brain-machine interface (BMI) is capable of analyzing the user's brain waves in real time and inputting the results to the generative AI to understand the user's intentions and generate output based on them.

(Claim 3)

The system of claim 1, wherein the platform has the ability for users to manage their own EEG data and share it with third parties as needed.

Example 2 for the Combined Emotional Engine (Claim 1)

A means of generating minimally invasive and highly accurate brain-machine interfaces (BMI) by combining EEG and generative AI, means of providing a platform for the dissemination of the BMI in society, Means to provide intuitive communication services, virtual space interface, health management services, and biometric authentication services using brain activity provided through the platform, A means for users to acquire EEG data using a dedicated EEG measuring device and upload it to the platform through a terminal, A means by which the server receives the EEG data and stores it in a database, A means by which the server preprocesses and analyzes EEG data, A means for users to manage their EEG data and share it with third parties as needed, The system includes.

(Claim 2)

The system of claim 1, wherein the brain-machine interface (BMI) is capable of analyzing the user's brain waves in real time and inputting the results to the generative AI to understand the user's intentions and generate output based on them.

(Claim 3)

The system of claim 1, wherein the platform has the ability for users to manage their own EEG data and share it with third parties as needed.

Example of Application 2 when Combined with an "Emotional Engine."

(Claim 1)

A means of generating minimally invasive and highly accurate brain-machine interfaces (BMI) by combining EEG and generative AI, means of providing a platform for the dissemination of the BMI in society, Means to provide intuitive communication services using brain activity, metaverse interface, health management services, and biometric authentication services provided through the platform, A means of collecting users' brainwave data in real time, encrypting it, and sharing it with third parties, A means of analyzing the user's emotional state and issuing an alert when an abnormality is detected, The system includes.

(Claim 2)

The system of claim 1, wherein the brain-machine interface (BMI) is capable of analyzing the user's brain waves in real time and inputting the results to the generative AI to understand the user's intentions and generate output based on them.

(Claim 3)

The system of claim 1, wherein the platform has the ability for users to manage their own EEG data and share it with third parties as needed.

Example 3 for the Combined Emotional Engine (Claim 1)

A means of generating minimally invasive and highly accurate brain-machine interfaces (BMI) by combining EEG and generative AI, means of providing a platform for the dissemination of the BMI in society, Means to provide intuitive communication services using brain activity, virtual reality interface, health care services, and biometric authentication services provided through the platform, A means of measuring the user's brain wave data and transmitting it to the server in real time, A means by which the server analyzes brain wave data to identify the user's emotional state and intentions, A means of storing the analysis results in a database and transmitting them to the terminal, A means by which the terminal displays the results of the analysis and provides feedback to the user, The system includes.

(Claim 2)

The system of claim 1, wherein the brain-machine interface (BMI) is capable of analyzing the user's brain waves in real time and inputting the results to the generative AI to understand the user's intentions and generate output based on them.

(Claim 3)

The system of claim 1, wherein the platform has the ability for users to manage their own EEG data and share it with third parties as needed.

An example of application3 when combined with an "emotional engine."

(Claim 1)

A means of generating minimally invasive and highly accurate brain-machine interfaces (BMI) by combining EEG and generative AI, means of providing a platform for the dissemination of the BMI in society, Means to provide intuitive communication services using brain activity, metaverse interface, health management services, and biometric authentication services provided through the platform, A means of analyzing the user's brain waves in real time to understand their emotions and intentions and control their behavior in the metaverse, means of controlling actions in the metaverse based on the user's emotional state, The system includes.

(Claim 2)

The system of claim 1, wherein the brain-machine interface (BMI) is capable of analyzing the user's brain waves in real time and inputting the results to the generative AI to understand the user's intentions and generate output based on them.

(Claim 3)

The system of claim 1, wherein the platform has the ability for users to manage their own EEG data and share it with third parties as needed.

With respect to the combination of the above exemplary embodiments, we further disclose the following (Claim 1)

A means of acquiring EEG data of a user in real time,

Analyzing the acquired EEG data and extracting the user's intention, means of analyzing the emotional state of said user, The means of executing the output using a generative AI based on the extracted user intentions and the analyzed prompt sentences according to the emotional state of the user, The system includes.

(Claim 2)

A means of providing a platform with the ability for users to manage their own EEG and emotional data and share it with third parties as needed, Including means to provide at least any one of the following services provided through said platform: intuitive communication services using brain wave data, virtual space interface, health management services, and biometric authentication services, System according to claim 1.

(Claim 3)

A means of controlling navigation and interaction in the virtual space by analyzing the user's brain wave data in real time, means for performing actions of an avatar corresponding to said user in said virtual space based on at least one of said user's intentions and emotions.

System according to claim 1.

What is claimed is:

1. A system comprising: a processor configured to:

acquire a user's brainwave data in real time; wherein the processor analyzes the brainwave data to extract both an intention of the user and an emotional state of the user;

wherein the processor analyzes the intention of the user and the emotional state of the user;

wherein the processor generated a prompt sentence based on analysis results of the emotional state of the user and the intention of the user; and wherein the processor executes an output using a generative AI based on the intention of the user and prompt sentence analyzed according to the emotional state of the user.

2. The system of claim 1, wherein the processor is further configured to:

provide a platform enabling the user to manage the user's brainwave and emotional data and share the data with third parties as needed; and facilitate, through the platform, at least one of a communication service, a virtual space interface, a health management service, and a biometric authentication service using the brainwave data.

3. The system of claim 1, wherein the processor is further configured to:

analyze the user's brainwave data in real time to control navigation and interaction in a virtual space; and perform actions of an avatar corresponding to the user in the virtual space based on at least one of the user's intention and emotional state.

4. The system of claim 1 further comprising the processor being further configured to control a robot using the generative AI based on the analyzed brainwave data.

* * * * *